United States Patent
Ban et al.

(10) Patent No.: US 10,588,952 B2
(45) Date of Patent: Mar. 17, 2020

(54) CONJUGATE VACCINE USING TRIMMING FUNCTION OF ERAP1

(71) Applicant: SUMITOMO DAINIPPON PHARMA CO., LTD., Osaka-shi (JP)

(72) Inventors: Hitoshi Ban, Osaka (JP); Yukihiro Nishio, Osaka (JP); Masashi Goto, Osaka (JP); Yosuke Takanashi, Osaka (JP)

(73) Assignee: SUMITOMO DAINIPPON PHARMA CO., LTD., Osaka-shi (JP)

( * ) Notice: Subject to any disclaimer, the term of this patent is extended or adjusted under 35 U.S.C. 154(b) by 505 days.

(21) Appl. No.: 14/780,241

(22) PCT Filed: Mar. 28, 2014

(86) PCT No.: PCT/JP2014/059352
§ 371 (c)(1),
(2) Date: Sep. 25, 2015

(87) PCT Pub. No.: WO2014/157704
PCT Pub. Date: Oct. 2, 2014

(65) Prior Publication Data
US 2016/0045582 A1   Feb. 18, 2016

(30) Foreign Application Priority Data

Mar. 29, 2013  (JP) ................. 2013-074441
Jul. 31, 2013  (JP) ................. 2013-158386

(51) Int. Cl.
*C12N 9/12*       (2006.01)
*A61K 39/00*   (2006.01)
*A61K 47/64*   (2017.01)

(52) U.S. Cl.
CPC ........ *A61K 39/0011* (2013.01); *A61K 47/646* (2017.08); *C12N 9/12* (2013.01);
(Continued)

(58) Field of Classification Search
None
See application file for complete search history.

(56) References Cited

U.S. PATENT DOCUMENTS 7,030,212 B1   4/2006   Sugiyama et al.
7,326,767 B1   2/2008   Stauss et al.
(Continued)

FOREIGN PATENT DOCUMENTS

CA   2757764         10/2010
CA   2 846 479 A1    3/2013
(Continued)

OTHER PUBLICATIONS

WO 2004/029248 machine translation (Year: 2004).*
(Continued)

*Primary Examiner* — Sergio Coffa
(74) *Attorney, Agent, or Firm* — Oblob, McClelland, Maier & Neustadt, L.L.P.

(57) ABSTRACT

The present invention provides a compound represented by the formula (1):

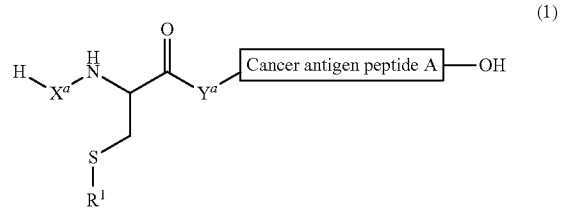

(1)

wherein $X^a$ and $Y^a$ are each a single bond or the like, cancer antigen peptide A is an MHC class I-restricted cancer antigen peptide, and
$R^1$ is a hydrogen atom; a group represented by the formula (2):

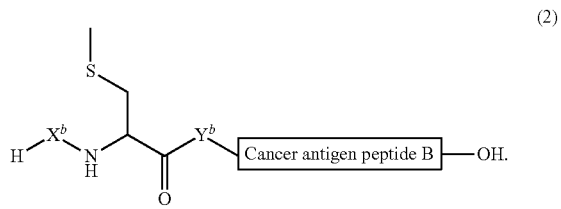

(2)

wherein $X^b$ and $Y^b$ are each a single bond or the like, and cancer antigen peptide B is different from the cancer antigen peptide A and is an MHC class I or II-restricted cancer antigen peptide; a group represented by the formula (3):

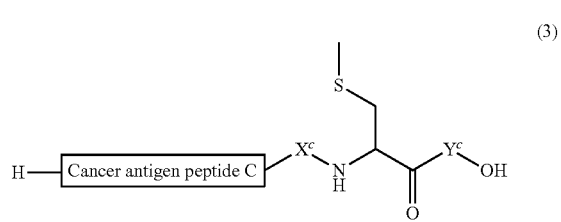

(3)

wherein $X^c$ and $Y^c$ are each a single bond or the like, and cancer antigen peptide C is an MHC class II-restricted cancer antigen peptide; or cancer antigen peptide D, wherein the cancer antigen peptide D is an MHC class I or II-restricted cancer antigen peptide containing one cysteine residue,
or a salt thereof, for example.

8 Claims, 22 Drawing Sheets

Specification includes a Sequence Listing.

(52) U.S. Cl.
CPC .. *A61K 2039/572* (2013.01); *A61K 2039/627* (2013.01); *C12Y 207/10001* (2013.01)

(56) References Cited

U.S. PATENT DOCUMENTS

| | | | |
|---|---|---|---|
| 7,547,439 B1* | 6/2009 | Huang | C07K 14/4748 424/184.1 |
| 7,608,685 B1 | 10/2009 | Sugiyama et al. | |
| 9,181,302 B2* | 11/2015 | Li | A61K 39/00 |
| 9,248,173 B2* | 2/2016 | Li | A61K 39/00 |
| 2004/0097703 A1 | 5/2004 | Sugiyama | |
| 2005/0050580 A1 | 3/2005 | Gotoh | |
| 2005/0266014 A1 | 12/2005 | Sugiyama et al. | |
| 2006/0093615 A1 | 5/2006 | Sugiyama et al. | |
| 2006/0107339 A1 | 5/2006 | Gotoh | |
| 2006/0217297 A1* | 9/2006 | Sugiyama | C07K 7/06 424/185.1 |
| 2008/0014636 A1 | 1/2008 | Sato et al. | |
| 2008/0070835 A1 | 3/2008 | Sugiyama | |
| 2008/0159993 A1 | 7/2008 | Stauss et al. | |
| 2009/0143291 A1 | 6/2009 | Sugiyama et al. | |
| 2009/0281043 A1 | 11/2009 | Sugiyama et al. | |
| 2010/0062010 A1 | 3/2010 | Nishihara et al. | |
| 2010/0255579 A1 | 10/2010 | Sato et al. | |
| 2010/0292164 A1 | 11/2010 | Sugiyama et al. | |
| 2011/0070251 A1 | 3/2011 | Sugiyama | |
| 2011/0098233 A1 | 4/2011 | Sugiyama | |
| 2011/0229506 A1 | 9/2011 | Nishihara et al. | |
| 2012/0045465 A1 | 2/2012 | Sugiyama | |
| 2012/0237569 A1 | 9/2012 | Saito et al. | |
| 2012/0301492 A1 | 11/2012 | Gaiger et al. | |
| 2014/0046036 A1 | 2/2014 | Nishihara et al. | |
| 2014/0134200 A1 | 5/2014 | Sugiyama et al. | |
| 2016/0168197 A1 | 6/2016 | Nishihara et al. | |
| 2016/0199472 A1 | 7/2016 | Sugiyama | |

FOREIGN PATENT DOCUMENTS

| | | |
|---|---|---|
| EP | 1 584 627 A1 | 10/2005 |
| EP | 1 961 761 A1 | 8/2008 |
| EP | 2 341 142 A2 | 7/2011 |
| JP | 11-504635 A | 4/1999 |
| JP | 2002-525099 | 8/2002 |
| JP | 2006-280324 A | 10/2006 |
| JP | 2009-23993 A | 2/2009 |
| JP | 2012-522513 A | 9/2012 |
| WO | WO 96/34888 A1 | 11/1996 |
| WO | WO 97/26784 * | 7/1997 |
| WO | WO 00/06602 | 2/2000 |
| WO | WO 00/18795 | 4/2000 |
| WO | WO 02/47474 A1 | 6/2002 |
| WO | WO 02/079253 A1 | 10/2002 |
| WO | WO 2004/029248 * | 4/2004 |
| WO | WO 2004/029248 A1 | 4/2004 |
| WO | WO 2004/63217 A1 | 7/2004 |
| WO | WO 2004/113530 A | 12/2004 |
| WO | WO 2005/045027 | 5/2005 |
| WO | WO 2007/047764 | 4/2007 |
| WO | WO 2007/063903 | 6/2007 |
| WO | WO 2007/120673 | 10/2007 |
| WO | WO 2008/081701 A1 | 7/2008 |
| WO | WO 2009/072610 A1 | 6/2009 |
| WO | WO 2010/037395 A2 | 4/2010 |
| WO | WO 2010/123065 A1 | 10/2010 |
| WO | WO 2011/110953 A2 | 9/2011 |
| WO | WO 2012/026309 A1 | 3/2012 |

OTHER PUBLICATIONS

Gentle et al. (Bioconjugate Chem.,2004, 15, 658-663) (Year: 2004).*
Fisk et al. (J Exp Med. Jun. 1, 1995;181(6):2109-17) (Year: 1995).*
Chianese-Bullock et al. (Vaccine. Mar. 10, 2009; 27(11): 1764-1770) (Year: 2009).*
U.S. Appl. No. 14/706,772, filed May 7, 2015, US2015/0238587 A1, Li, et al.
U.S. Appl. No. 14/549,091, filed Nov. 20, 2014, US2015/0080321 A1, Li, et al.
Supplementary Partial European Search Report dated Oct. 13, 2016 in Patent Application 14773223.4.
Extended European Search Report dated Sep. 19, 2016 in Patent Application No. 14775899.9.
Valerie Dutoit, et al., "Dissecting TCR-MHC/peptide Complex Interactions with A2/peptide Multimers Incorporating Tumor Antigen Peptide Variants: Crucial Role of Interaction Kinetics on Functional Outcomes" European Journal of Immunology, vol. 32, No. 11, XP055305530, Nov. 1, 2002, pp. 3285-3293.
Peter Van Endert, "Post-proteasomal and Proteasome-independent Generation of MHC Class I Ligands" Cellular and Molecular Life Sciences, vol. 68, No. 9, XP019894461, Mar. 10, 2011, pp. 1553-1567
U.S. Appl. No. 14/984,763, filed Dec. 30, 2015, Li et al.
Gaiger et al., Blood 96(4), 1480-1489, 2000.
Mailander et al., Leukemia 18, 165-166, 2004.
Janeway et al., Immunobiology 1997 4th Edition Garland Press 1999, pp. 121, 551 and 569 and Figures 4.3, 4.5 and 4.7.
Srivastava, Nature Immun. 1(5), 363-366, 2000.
Gaiger et al., Clin. Cancer Clin. Cancer Res. 7, 761s-765s, 2001.
Guidance for Industry—Preclinical Assessment of Investigational Cellular and Gene Therapy Products, U.S. Department of Health and Human Services Food and Drug Administration Cancer for Biologics Evaluation and research, Nov. 2013, 35 pages.
Keilholz, Leukemia (2004) 18, 165-166.
Oka et al., National Acad. Sci (2004), 101,13885-13890.
Kakugawa et al., Efficient Induction of Peptide-specific Cytotoxic T Lymphocytes by LPS-Activated Spleen Cells, Microbiol. Immunol., vol. 44(2), pp. 123-133, 2000.
Title page and pp. 551-554 of Janeway et al., Immunobiology, 1997 4th Edition Garland Press, 1999.
Interference No. 105987—Sugiyama Motion 1 (Mar. 26, 2014).
Interference No. 105987—Stauss Motion 1 (May 15, 2014).
Interference No. 105987—Stauss Motion 2 (May 15, 2014).
Interference No. 105987—Stauss Motion 3 (May 15, 2014).
Interference No. 105987—Sugiyama Substantive Motion 1 (May 15, 2014).
Interference No. 105987—Sugiyama Responsive Motion 2 (Jun. 5, 2014).
Interference No. 105987—Stauss Opposition 1 (Jul. 17, 2014).
Interference No. 105987—Stauss Opposition 2 (Jul. 17, 2014).
Interference No. 105987—Sugiyama Opposition to Stauss Motion 1 (Jul. 17, 2014).
Interference No. 105987—Sugiyama Oppiosition to Stauss Motion 2 (Jul. 17, 2014).
Interference No. 105987—Sugiyama Opposition to Stauss Motion 3 (Jul. 17, 2014).
Interference No. 105987—Sugiyama Reply 1 (Aug. 28, 2014).
Interference No. 105987—Sugiyama Reply 2 (Aug. 28, 2014).
Interference No. 105987—Stauss Reply 1 (Aug. 28, 2014).
Interference No. 105987—Stauss Reply 2 (Aug. 28, 2014).
Interference No. 105987—Stauss Reply 3 (Aug. 28, 2014).
Interference No. 105987—Sugiyama Miscellaneous Motion (Oct. 9, 2014).
Interference No. 105987—Stauss Opposition 3 (Oct. 30, 2014).
Interference No. 105987—Sugiyama Reply 3 (to Stauss Oppsition to Sugiyama Misc. Motion 1) (Nov. 20, 2014).
Yoshihiro Oka, et al., "Cancer Immunotherapy Targeting Wilms' Tumor Gene WT1 Product", The Journal of Immunology, 164(4), 2000, 1873-1880.
Ann Van Driessche, et al., "Active Specific Immunotherapy Targeting the Wilms' Tumor Protein 1 (WT1) for Patients with Hematological Malignancies and Solid Tumors: Lessons from Early Clinical Trials", The Oncologist, 17(2), 2012, pp. 250-259.
Peter G. Maslak, et al., "Vaccination with synthetic analog peptides derived from WT1 oncoprotein induces T-cell responses in patients with complete remission from acute myeloid leukemia", Clinical Trials and Observations, Blood, 116(2), 2010, pp. 171-179.

(56) References Cited

OTHER PUBLICATIONS

Paul H. Naylor, et al., "Peptide Based Vaccine Approaches for Cancer—A Novel Approach Using a WT-1 Synthetic Long Peptide and the IRX-2 Immunomodulatory Regimen", Cancers, Mar. 2011, pp. 3991-4009.

Norihiko Takahashi, et al., "First clinical trial of cancer vaccine therapy with artificially synthesized helper/killer-hybrid epitope long peptide of MAGE-A4 cancer antigen", Cancer Science, 103, 2012, pp. 150-153.

Anthony W. Purcell, et al., "More than one reason to rethink the use of peptides in vaccine design", Nature Reviews Drug Discovery, 6(5), 2007, pp. 404-414.

Katherine M. Call, "Isolation and Characterization of a Zinc Finger Polypeptide Gene at the Human Chromosome 11 Wilms' Tumor Locus", Cell, 60(3), 1990, pp. 509-520.

Akihiro Tsuboi, et al., "Cytotoxic T-Lymphocyte Responses Elicited to Wilms' Tumor Gene WT1 Product by DNA Vaccination", Journal of Clinical Immunology, 20(3), 2000, pp. 195-202.

Kenneth L. Rock, et al., "Post-proteasomal antigen processing for major histocompatibility complex class I presentation", Nature Immunology, 5(7), 2004, pp. 670-677.

Sonia A. Perez, et al., "A New Era in Anticancer Peptide Vaccines", Cancer, 116(9), 2010, pp. 2071-2080.

Lee M. Krug, et al., "WT1 peptide vaccinations induce CD4 and CD8 T cell immune responses in patients with mesothelioma and non-small cell lung cancer", Cancer Immunol Immunother, 59, 2010, pp. 1467-1479.

Grazyna Kochan, et al., "Crystal structures of the endoplasmic reticulum aminopeptidase-1 (ERAP1) reveal the molecular basis for N-terminal peptide trimming", Proceedings of the National Academy of Science of United States of America, 108(19), 2011, pp. 7745-7750.

Tomo Saric, et al., "An IFN-γ-induced aminopeptidase in the ER, ERAP I, trims precursors to MHC class I-presented peptides", Nature Immunology, 3(12), 2002, pp. 1169-1176.

Ian A. York, et al., "The ER aminopeptidase ERAP I enhances or limits antigen presentation by trimming epitopes to 8-9 residues", Nature Immunology, 3(12), 2002, pp. 1177-1184.

Efthalia Zervoudi, et al., "Probing the S1 specificity pocket of the aminopeptidases that generate antigenic peptides", Biochemical Journal, 435, 2011, pp. 411-420.

Ian E. Gentle et al., "Direct Production of Proteins with N-Terminal Cysteine for Site-Specific Conjugation", Bioconjugate Chem., vol. 15, No. 3, 2004, pp. 658-663.

Interference No. 105987—Decision on Motions BD.R. 125(a) (Feb. 20, 2015).

Interference No. 105987—Exhibit 1001—Amendment for entry in Sugiyama U.S. Appl. No. 12/181,938.

Interference No. 105987—Exhibit 1002—U.S. Pat. No. 7,030,212 B1, issued Apr. 18, 2006.

Interference No. 105987—Exhibit 1003—Terminal Disclaimer filed and approved in Sugiyama U.S. Appl. No. 12/181,938 on Dec. 4, 2013.

Interference No. 105987—Exhibit 1004—the original specification of Sugiyama U.S. Appl. No. 12/181,938, filed Jul. 29, 2008.

Interference No. 105987—Exhibit 1005—the original specification of U.S. Appl. No. 11/196,452, filed Aug. 4, 2005, issued as U.S. Pat. No. 7,608,685.

Interference No. 105987—Exhibit 1006—the original specification of U.S. Appl. No. 09/744,815, filed Jan. 30, 2001, issued as U.S. Pat. No. 7,030,212.

Interference No. 105987—Exhibit 1007—WO 00/06602 which is a publication of International Application PCT/JP99/04130, filed Jul. 30, 1999.

Interference No. 105987—Exhibit 1008—the original and the certified translation of Japanese Application JP 10-218093, filed Jul. 31, 1998.

Interference No. 105987—Exhibit 1009—the USPTO Communication dated Jan. 9, 2014, in Sugiyama U.S. Appl. No. 12/181,938.

Interference No. 105987—Exhibit 1010—U.S. Pat. No. 7,326,767 B1, issued Feb. 5, 2008.

Interference No. 105987—Exhibit 1011—U.S. Pat. No. 8,529,904 B2, issued Sep. 10, 2013.

Interference No. 105987—Exhibit 1012—Certified UK 9823897.5, filed Nov. 2, 1998, which was filed in the USPTO Apr. 12, 2002.

Interference No. 105987—Exhibit 1013—Sugiyama U.S. Appl. No. 12/181,938, published as U.S. 2009/0143291 A1.

Interference No. 105987—Exhibit 1014—PCT/GB99/03572, filed on Nov. 2, 1999, published as WO 00/26249 on May 11, 2000.

Interference No. 105987—Exhibit 1015—Non-Final Office Action dated May 5, 2003, in Stauss U.S. Appl. No. 09/625,963.

Interference No. 105987—Exhibit 1016—Non-Final Office Action dated Jan. 30, 2004, in Stauss U.S. Appl. No. 09/625,963.

Interference No. 105987—Exhibit 1017—Stauss Response filed Apr. 26, 2013, in Stauss U.S. Appl. No. 11/825,578.

Interference No. 105987—Exhibit 1018—Stauss Response filed Nov. 5, 2003, in Stauss U.S. Appl. No. 09/625,963.

Interference No. 105987—Exhibit 1019—Oka et al., J. Immunol. 164(4): 1873-1880, 2000.

Interference No. 105987—Exhibit 1020—Stauss Response filed Jul. 30, 2004, in Stauss U.S. Appl. No. 09/625,963.

Interference No. 105987—Exhibit 1021—Gaiger et al., Blood 96(4): 1480-1489, 2000.

Interference No. 105987—Exhibit 1022—Mailander et al., Leukemia 18: 165-166, 2004.

Interference No. 105987—Exhibit 1023—Non-Final Office Action dated Apr. 29, 2010, in Stauss U.S. Appl. No. 11/825,578.

Interference No. 105987—Exhibit 1024—Final Office Action dated Oct. 26, 2010, in Stauss U.S. Appl. No. 11/825,578.

Interference No. 105987—Exhibit 1025—Janeway et al., Immunobiology, 1997 4th Edition Garland Press 1999 pp. 121, 551 and 569 and Figures 4.3, 4.5 and 4.7.

Interference No. 105987—Exhibit 1026—Srivastava, P., Nature Immunology 1(5): 363-366, 2000.

Interference No. 105987—Exhibit 1027—Gaiger et al., Clin. Cancer Res. 7: 761s-765s, 2001.

Interference No. 105987—Exhibit 1028—Guidance for Industry—Preclinical Assessment of Investigational Cellular and Gene Therapy Products, U.S. Department of Health and Human Services Food and Drug Administration Center for Biologics Evaluation and Research, Nov. 2013.

Interference No. 105987—Exhibit 1029—U.S. Pat. No. 7,063,854.

Interference No. 105987—Exhibit 1031—Amendment for entry in Sugiyama U.S. Appl. No. 12/181,938.

Interference No. 105987—Exhibit 1032—Terminal Disclaimer over U.S. Pat. No. 7,030,212 filed on Feb. 4, 2010 in U.S. Appl. No. 12/366,200.

Interference No. 105987—Exhibit 1033—USPTO notice dated Mar. 10, 2010, showing the approval of the Terminal Disclaimer filed on Feb. 4, 2010.

Interference No. 105987—Exhibit 1034—Amendment filed Sep. 17, 2004, in U.S. Appl. No. 09/744,815.

Interference No. 105987—Exhibit 1035—Preliminary Amendment filed Jul. 2, 2009, in Sugiyama U.S. Appl. No. 12/181,938.

Interference No. 105987—Exhibit 1036—U.S. Patent Application Publication US 2008/0159993, published Jul. 3, 2008.

Interference No. 105987—Exhibit 1038—Response to Formalities Letter and Preliminary Amendment filed Mar. 31, 2014 in Stauss U.S. Appl. No. 13/966,454.

Interference No. 105987—Exhibit 1039—Chart comparing Sugiyama current claims with pre-critical date claims in Sugiyama U.S. Appl. No. 12/181,938 and U.S. Appl. No. 09/744,815.

Interference No. 105987—Exhibit 1040—the Preliminary Amendment filed on Jul. 29, 2008, in Sugiyama U.S. Appl. No. 12/181,938.

Interference No. 105987—Exhibit 1041—Preliminary Amendment filed on Feb. 2, 2009, in Sugiyama U.S. Appl. No. 12/181,938.

Interference No. 105987—Exhibit 1042—Preliminary Amendment filed on Aug. 4, 2005, in U.S. Appl. No. 11/196,452.

Interference No. 105967—Exhibit 1043—Amendment filed on Mar. 20, 2008, in U.S. Appl. No. 11/196,452.

Interference No. 105987—Exhibit 1044—Preliminary Amendment filed on Jan. 30, 2001, in U.S. Appl. No. 09/744,815.

(56) References Cited

OTHER PUBLICATIONS

Interference No. 105987—Exhibit 1045—Amendment filed on Aug. 1, 2005, in U.S. Appl. No. 09/744,815.
Interference No. 105987—Exhibit 1046—Amendment filed on Jun. 29, 2011, in Sugiyama U.S. Appl. No. 12/181,938.
Interference No. 105987—Exhibit 1047—Office Action dated Dec. 29, 2010, in Sugiyama U.S. Appl. No. 12/181,938.
Interference No. 105987—Exhibit 1048—Amendment filed on Dec. 4, 2013, in Sugiyama U.S. Appl. No. 12/181,938.
Interference No. 105987—Exhibit 1049—Amendment filed on Nov. 9, 2012, in Sugiyama U.S. Appl. No. 12/181,938.
Interference No. 105987—Exhibit 1050—Deposition Transcript of Dr. Özlem Türeci taken Jun. 30, 2014.
Interference No. 105987—Exhibit 1051—Keilholz, Leukemia, (2004) 18, 165-166.
Interference No. 105987—Exhibit 1052—Oka et al, Proc. Natl. Acad. Sci., (2004) 101, 13885-13890.
Interference No. 105987—Exhibit 1053—Amendment filed Mar. 14, 2006, in Stauss U.S. Appl. No. 09/625,963.
Interference No. 105987—Exhibit 1054—Appeal Brief filed Nov. 22, 2006, in Stauss U.S. Appl. No. 09/625,963.
Interference No. 105987—Exhibit 1055—Amendment filed Aug. 27, 2010, in Stauss U.S. Appl. No. 11/825,578.
Interference No. 105987—Exhibit 1056—Claim Chart Showing Support for the Claimed Invention in the '938 Application.
Interference No. 105987—Exhibit 1057—Declaration for Utility or Design Patent Application filed on Jul. 6, 2007 during examination of the '904 patent.
Interference No. 105987—Exhibit 1058—Sugiyama's Objections to Stauss's Exhibits.
Interference No. 105987—Exhibit 2001—U.S. Pat. No. 7,326,767 (Stauss '767).
Interference No. 105987—Exhibit 2002—Sugiyama Preliminary Amendment dated Jul. 29, 2008 to U.S. Appl. No. 12/181,938, cancelling claims 1-7, adding new claims 8-19.
Interference No. 105987—Exhibit 2003—Sugiyama Preliminary Amendment dated Feb. 2, 2009 to U.S. Appl. No. 12/181,938, cancelling claims 1-19, adding new claims 20-23.
Interference No. 105987—Exhibit 2004—Sugiyama Preliminary Amendment dated Jul. 2, 2009 to U.S. Appl. No. 12/181,938, amending claims 21, 22, adding new claims 24-67.
Interference No. 105987—Exhibit 2005—Office Action dated Dec. 29, 2010 rejecting Sugiyama claims 20-24, and 27-28 as unpatentable under 35 USC § 112 and for nonstatutory double patenting over claims 1-5 of U.S. Pat. No. 7,030,212 and claims 1-5 of U.S. Pat. No. 7,608,685.
Interference No. 105987—Exhibit 2006—U.S. Pat. No. 7,608,685 (Sugiyama '685).
Interference No. 105987—Exhibit 2007—Sugiyama Amendment dated Jun. 29, 2011 amending the numeric range and size 14 limitations of the amino acids in claims 20, and 21.
Interference No. 105987—Exhibit 2008—Final Office Action dated Oct. 7, 2011 rejecting Sugiyama claim 28 as unpatentable under 35 USC §112 and claims 20-24, and 27-28 as unpatentable for nonstatutory double patenting over claims 1-5 of U.S. Pat. No. 7,030,212 and claims 1-5 of U.S. Pat. No. 7,608,685.
Interference No. 105987—Exhibit 2009—Sugiyama Amendment dated Nov. 9, 2012 adding involved new claims 68-75.
Interference No. 105987—Exhibit 2010—Office Action dated Jul. 24, 2013 rejecting Sugiyama claims 20-24, 27-28, 72-73 as being unpatentable for nonstatutory obviousness-type double patenting over claims 1-5 of now U.S. Pat. No. 7,030,212 and claims 1-5 of U.S. Pat. No. 7,608,685.
Interference No. 105987—Exhibit 2011—Sugiyama Amendment dated Dec. 4, 2013 amending limitations of claims 27-28.
Interference No. 105987—Exhibit 2012—Application Data Sheet from file history of the '938 application filed on Jul. 29, 2008.
Interference No. 105987—Exhibit 2013—Declaration of Dr. Özlem Türeci.
Interference No. 105987—Exhibit 2014—Chart of Sugiyama's Pre-and Post-critical Date Claims.
Interference No. 105987—Exhibit 2015—Kakugawa et al "Efficient Induction of Peptide-specific Cytotoxic T Lymphocytes by LPS-Activated Spleen Cells", Microbiol. Immunnol., vol. 44(2), pp. 123-133, (2000).
Interference No. 105987—Exhibit 2016—the Decision dated Jan. 17, 2014 of the Board of Patent Appeals of the European Patent Office rendered in Case No. T1457/09-3.3.04, entitled "Immunotherapeutic methods using epitopes of WT-1 and GATA-1", Patent Proprietor: Ganymed Pharmaceuticals AG and Opponent Dainippon Sumitomo Pharma Co., Ltd., issued Mar. 6, 2014.
Interference No. 105987—Exhibit 2017—Transcript of Deposition of Dr. Türeci taken on Jun. 30, 2014.
Interference No. 105987—Exhibit 2018—Supplemental Application Data Sheet filed Mar. 31, 2014 in Response to Formalities Letter and Preliminary Amendment to U.S. Appl. No. 13/966,454 (the '454 application).
Interference No. 105987—Exhibit 2019—Office Action dated Sep. 14, 2012 from the file history of involved Stauss U.S. Pat. No. 8,529,904.
Interference No. 105987—Exhibit 2020—the Notice of Allowability dated May 6, 2013 from the file history of involved Stauss U.S. Pat. No. 8,529,904.
Interference No. 105987—Exhibit 2021—Office Action Response dated Apr. 26, 2013 from the file history of involved Stauss U.S. Pat. No. 8,529,904.
Interference No. 105987—Exhibit 2022—title page and pp. 551 to 554 of Janeway et al., Immunobiology, 1997 4th Edition Garland Press 1999.
International Search Report dated Jul. 8, 2014 in PCT/JP2014/059352 filed Mar. 28, 2014.
International Preliminary Report on Patentability dated Oct. 8, 2015 in PCT/JP2014/059352 filed Mar. 28, 2014 (English translation only).
Francesca Di Modugno, et al., MHC-Peptide Binding: Dimers of Cysteine-Containing Nonapeptides Bind with High Affinity to HLA-A2.1 Class I Molecule, Journal of Immunotherapy, 1997, vol. 20, No. 6, pp. 431-436.
Nature Reviews Drug Discovery, Sep. 2009, vol. 8, pp. 685-686.
Craig L. Slingluff Jr., M.D., "The Present and Future of Peptide Vaccines for Cancer: Single or Multiple, Long or Short, Alone or in Combination?", Cancer Journal, 2011, 17(5), pp. 343-350.
Shih-Chung Chang, "The ER aminopeptidase, ERAP1, trims precursors to lengths of MHC class I peptides by a "molecular ruler" mechanism", Proceedings of the National Academy of Sciences of United States of America, 2005, vol. 102, No. 47, pp. 17107-17112.
Irini Evnouchidou, "The Internal Sequence of the Peptide-Substrate Determines Its N-Terminus Trimming by ERAP1", PLoS One, 2008; vol. 3, Issue 11, e3658; pp. 1-12.
Arron Hearn, et al., "The Specificity of Trimming of MHC Class I-Presented Peptides in the Endoplasmic Reticulum", The Journal of Immunology, 2009, 183, pp. 5526-5536.
Arron Hearn, et al., "Characterizing the Specificity and Cooperation of Aminopeptidases in the Cytosol and Endoplasmic Reticulum during MHC Class I Antigen Presentation", Journal of Immunology, 2010, 184; pp. 4725-4732.
Office Action dated Oct. 3, 2017 in JP 2015-508814, filed Sep. 25, 2015 (with English translation).
Extended European Search Report dated Feb. 8, 2017 in Patent Application No. 14773223.4.
Katayoun Rezvani,et al., "Leukemia-associated antigen-specific T-cell responses following combined PR1 and WT1 peptide vaccination in patients with myeloid malignancies" Immunobiology, Blood, vol. 111, No. 1, XP055339775, Jan. 1, 2008, From www.bloodjournal. org by guest on Jan. 27, 2017, pp. 236-242.
Jeffrey J. Molldrem, et al., "Cytotoxic T Lymphocytes Specific for a Nonpolymorphic Proteinase 3 Peptide Preferentially Inhibit Chronic Myeloid Leukemia Colony-Forming Units" Rapid Communication, Blood, vol. 90, No. 7, XP002300135, Oct. 1, 1997, pp. 2529-2534.
Gomez-Nunez et al., "Non-Natural and Photo-Reactive Amino Acids as Biochemical Probes of Immune Function", PLoS One, vol. 3, Issue 12, e3938, Dec. 2008, 9 pages.

(56) References Cited

OTHER PUBLICATIONS

U.S. Appl. No. 16/163,067, filed Oct. 17, 2018, US 2019-0030149 A1, Li et al.

* cited by examiner

SEQUENCE LISTING

```
<160> NUMBER OF SEQ ID NOS: 249

<210> SEQ ID NO 1
<211> LENGTH: 9
<212> TYPE: PRT
<213> ORGANISM: Artificial Sequence
<220> FEATURE:
<223> OTHER INFORMATION: Peptide

<400> SEQUENCE: 1

Glu Ala Asp Pro Thr Gly His Tyr Ser
1               5

<210> SEQ ID NO 2
<211> LENGTH: 9
<212> TYPE: PRT
<213> ORGANISM: Artificial Sequence
<220> FEATURE:
<223> OTHER INFORMATION: Peptide

<400> SEQUENCE: 2

Ser Leu Phe Arg Ala Val Ile Thr Lys
1               5

<210> SEQ ID NO 3
<211> LENGTH: 9
<212> TYPE: PRT
<213> ORGANISM: Artificial Sequence
<220> FEATURE:
<223> OTHER INFORMATION: Peptide

<400> SEQUENCE: 3

Asn Tyr Lys His Cys Phe Pro Glu Ile
1               5

<210> SEQ ID NO 4
<211> LENGTH: 10
<212> TYPE: PRT
<213> ORGANISM: Artificial Sequence
<220> FEATURE:
<223> OTHER INFORMATION: Peptide

<400> SEQUENCE: 4
```

Glu Val Tyr Asp Gly Arg Glu His Ser Ala
1               5                  10

<210> SEQ ID NO 5
<211> LENGTH: 10
<212> TYPE: PRT
<213> ORGANISM: Artificial Sequence
<220> FEATURE:
<223> OTHER INFORMATION: Peptide

<400> SEQUENCE: 5

Arg Glu Pro Val Thr Lys Ala Glu Met Leu
1               5                  10

<210> SEQ ID NO 6
<211> LENGTH: 9
<212> TYPE: PRT
<213> ORGANISM: Artificial Sequence
<220> FEATURE:
<223> OTHER INFORMATION: Peptide

<400> SEQUENCE: 6

Asp Pro Ala Arg Tyr Glu Phe Leu Trp
1               5

<210> SEQ ID NO 7
<211> LENGTH: 9
<212> TYPE: PRT
<213> ORGANISM: Artificial Sequence
<220> FEATURE:
<223> OTHER INFORMATION: Peptide

<400> SEQUENCE: 7

Ser Ala Phe Pro Thr Thr Ile Asn Phe
1               5

<210> SEQ ID NO 8
<211> LENGTH: 9
<212> TYPE: PRT
<213> ORGANISM: Artificial Sequence
<220> FEATURE:
<223> OTHER INFORMATION: Peptide

<400> SEQUENCE: 8

Ser Ala Tyr Gly Glu Pro Arg Lys Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Peptide

<400> SEQUENCE: 9

Ser Ala Tyr Gly Glu Pro Arg Lys Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Peptide

<400> SEQUENCE: 10

Lys Met Val Glu Leu Val His Phe Leu

```
1               5

<210> SEQ ID NO 11
<211> LENGTH: 9
<212> TYPE: PRT
<213> ORGANISM: Artificial Sequence
<220> FEATURE:
<223> OTHER INFORMATION: Peptide

<400> SEQUENCE: 11

Glu Tyr Leu Gln Leu Val Phe Gly Ile
1               5

<210> SEQ ID NO 12
<211> LENGTH: 9
<212> TYPE: PRT
<213> ORGANISM: Artificial Sequence
<220> FEATURE:
<223> OTHER INFORMATION: Peptide

<400> SEQUENCE: 12

Glu Ala Asp Pro Ile Gly His Leu Tyr
1               5

<210> SEQ ID NO 13
<211> LENGTH: 9
<212> TYPE: PRT
<213> ORGANISM: Artificial Sequence
<220> FEATURE:
<223> OTHER INFORMATION: Peptide

<400> SEQUENCE: 13

Phe Leu Trp Gly Pro Arg Ala Leu Val
1               5

<210> SEQ ID NO 14
<211> LENGTH: 9
<212> TYPE: PRT
<213> ORGANISM: Artificial Sequence
<220> FEATURE:
<223> OTHER INFORMATION: Peptide

<400> SEQUENCE: 14

Thr Phe Pro Asp Leu Glu Ser Glu Phe
1               5

<210> SEQ ID NO 15
<211> LENGTH: 10
<212> TYPE: PRT
<213> ORGANISM: Artificial Sequence
<220> FEATURE:
<223> OTHER INFORMATION: Peptide

<400> SEQUENCE: 15

Met Glu Val Asp Pro Ile Gly His Leu Tyr
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Peptide

<400> SEQUENCE: 16

Trp Gln Tyr Phe Phe Pro Val Ile Phe
1               5
```

```
<210> SEQ ID NO 17
<211> LENGTH: 10
<212> TYPE: PRT
<213> ORGANISM: Artificial Sequence
<220> FEATURE:
<223> OTHER INFORMATION: Peptide

<400> SEQUENCE: 17

Gly Val Tyr Asp Gly Arg Glu His Thr Val
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Peptide

<400> SEQUENCE: 18

Met Val Lys Ile Ser Gly Gly Pro Arg
1               5

<210> SEQ ID NO 19
<211> LENGTH: 9
<212> TYPE: PRT
<213> ORGANISM: Artificial Sequence
<220> FEATURE:
<223> OTHER INFORMATION: Peptide

<400> SEQUENCE: 19

Gly Leu Tyr Asp Gly Met Glu His Leu
1               5

<210> SEQ ID NO 20
<211> LENGTH: 9
<212> TYPE: PRT
<213> ORGANISM: Artificial Sequence
<220> FEATURE:
<223> OTHER INFORMATION: Peptide

<400> SEQUENCE: 20

Val Arg Ile Gly His Leu Tyr Ile Leu
1               5

<210> SEQ ID NO 21
<211> LENGTH: 9
<212> TYPE: PRT
<213> ORGANISM: Artificial Sequence
<220> FEATURE:
<223> OTHER INFORMATION: Peptide

<400> SEQUENCE: 21

Ala Ala Arg Ala Val Phe Leu Ala Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Peptide

<400> SEQUENCE: 22

Phe Leu Trp Gly Pro Arg Ala Tyr Ala
1               5
```

<210> SEQ ID NO 23
<211> LENGTH: 8
<212> TYPE: PRT
<213> ORGANISM: Artificial Sequence
<220> FEATURE:
<223> OTHER INFORMATION: Peptide

<400> SEQUENCE: 23

```
Tyr Arg Pro Arg Pro Arg Arg Tyr
1               5
```

<210> SEQ ID NO 24
<211> LENGTH: 9
<212> TYPE: PRT
<213> ORGANISM: Artificial Sequence
<220> FEATURE:
<223> OTHER INFORMATION: Peptide

<400> SEQUENCE: 24

```
Tyr Tyr Trp Pro Arg Pro Arg Arg Tyr
1               5
```

<210> SEQ ID NO 25
<211> LENGTH: 11
<212> TYPE: PRT
<213> ORGANISM: Artificial Sequence
<220> FEATURE:
<223> OTHER INFORMATION: Peptide

<400> SEQUENCE: 25

```
Met Thr Gln Gly Gln His Phe Leu Gln Lys Val
1               5                   10
```

<210> SEQ ID NO 26
<211> LENGTH: 11
<212> TYPE: PRT
<213> ORGANISM: Artificial Sequence
<220> FEATURE:
<223> OTHER INFORMATION: Peptide

<400> SEQUENCE: 26

```
Ser Leu Leu Met Trp Ile Thr Gln Cys Phe Leu
1               5                   10
```

<210> SEQ ID NO 27
<211> LENGTH: 9
<212> TYPE: PRT
<213> ORGANISM: Artificial Sequence
<220> FEATURE:
<223> OTHER INFORMATION: Peptide

<400> SEQUENCE: 27

```
Gln Leu Ser Leu Leu Met Trp Ile Thr
1               5
```

<210> SEQ ID NO 28
<211> LENGTH: 10
<212> TYPE: PRT
<213> ORGANISM: Artificial Sequence
<220> FEATURE:
<223> OTHER INFORMATION: Peptide

<400> SEQUENCE: 28

```
Ala Ser Gly Pro Gly Gly Gly Ala Pro Arg
1               5                   10
```

```
<210> SEQ ID NO 29
<211> LENGTH: 9
<212> TYPE: PRT
<213> ORGANISM: Artificial Sequence
<220> FEATURE:
<223> OTHER INFORMATION: Peptide

<400> SEQUENCE: 29

Ala Ala Gly Ile Gly Ile Leu Thr Val
1               5

<210> SEQ ID NO 30
<211> LENGTH: 10
<212> TYPE: PRT
<213> ORGANISM: Artificial Sequence
<220> FEATURE:
<223> OTHER INFORMATION: Peptide

<400> SEQUENCE: 30

Ala Glu Glu Ala Ala Gly Ile Gly Ile Leu
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Peptide

<400> SEQUENCE: 31

Thr Ile Leu Leu Gly Ile Phe Phe Leu
1               5

<210> SEQ ID NO 32
<211> LENGTH: 9
<212> TYPE: PRT
<213> ORGANISM: Artificial Sequence
<220> FEATURE:
<223> OTHER INFORMATION: Peptide

<400> SEQUENCE: 32

Lys Thr Trp Gly Gln Tyr Trp Gln Val
1               5

<210> SEQ ID NO 33
<211> LENGTH: 9
<212> TYPE: PRT
<213> ORGANISM: Artificial Sequence
<220> FEATURE:
<223> OTHER INFORMATION: Peptide

<400> SEQUENCE: 33

Leu Ile Tyr Arg Arg Arg Leu Met Lys
1               5

<210> SEQ ID NO 34
<211> LENGTH: 9
<212> TYPE: PRT
<213> ORGANISM: Artificial Sequence
<220> FEATURE:
<223> OTHER INFORMATION: Peptide

<400> SEQUENCE: 34

Val Tyr Phe Phe Leu Pro Asp His Leu
1               5

<210> SEQ ID NO 35
```

```
<211> LENGTH: 8
<212> TYPE: PRT
<213> ORGANISM: Artificial Sequence
<220> FEATURE:
<223> OTHER INFORMATION: Peptide

<400> SEQUENCE: 35

Ser Asn Asp Gly Pro Thr Leu Ile
1               5

<210> SEQ ID NO 36
<211> LENGTH: 10
<212> TYPE: PRT
<213> ORGANISM: Artificial Sequence
<220> FEATURE:
<223> OTHER INFORMATION: Peptide

<400> SEQUENCE: 36

Val Ser His Ser Phe Pro His Pro Leu Tyr
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Peptide

<400> SEQUENCE: 37

Phe Leu Thr Pro Lys Lys Leu Gln Cys Val
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Peptide

<400> SEQUENCE: 38

His Ser Thr Asn Gly Val Thr Arg Ile Tyr
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Peptide

<400> SEQUENCE: 39

Lys Cys Asp Ile Cys Thr Asp Glu Tyr
1               5

<210> SEQ ID NO 40
<211> LENGTH: 9
<212> TYPE: PRT
<213> ORGANISM: Artificial Sequence
<220> FEATURE:
<223> OTHER INFORMATION: Peptide

<400> SEQUENCE: 40

Tyr Met Asp Gly Thr Met Ser Gln Val
1               5

<210> SEQ ID NO 41
<211> LENGTH: 9
```

```
<212> TYPE: PRT
<213> ORGANISM: Artificial Sequence
<220> FEATURE:
<223> OTHER INFORMATION: Peptide

<400> SEQUENCE: 41

Ala Phe Leu Pro Trp His Arg Leu Phe
1               5

<210> SEQ ID NO 42
<211> LENGTH: 9
<212> TYPE: PRT
<213> ORGANISM: Artificial Sequence
<220> FEATURE:
<223> OTHER INFORMATION: Peptide

<400> SEQUENCE: 42

Ser Glu Ile Trp Arg Asp Ile Asp Phe
1               5

<210> SEQ ID NO 43
<211> LENGTH: 9
<212> TYPE: PRT
<213> ORGANISM: Artificial Sequence
<220> FEATURE:
<223> OTHER INFORMATION: Peptide

<400> SEQUENCE: 43

Val Leu Gln Glu Leu Asn Val Thr Val
1               5

<210> SEQ ID NO 44
<211> LENGTH: 9
<212> TYPE: PRT
<213> ORGANISM: Artificial Sequence
<220> FEATURE:
<223> OTHER INFORMATION: Peptide

<400> SEQUENCE: 44

Met Ser Leu Gln Arg Gln Phe Leu Arg
1               5

<210> SEQ ID NO 45
<211> LENGTH: 9
<212> TYPE: PRT
<213> ORGANISM: Artificial Sequence
<220> FEATURE:
<223> OTHER INFORMATION: Peptide

<400> SEQUENCE: 45

Ser Val Tyr Asp Phe Phe Val Trp Leu
1               5

<210> SEQ ID NO 46
<211> LENGTH: 9
<212> TYPE: PRT
<213> ORGANISM: Artificial Sequence
<220> FEATURE:
<223> OTHER INFORMATION: Peptide

<400> SEQUENCE: 46

Leu Leu Gly Pro Gly Arg Pro Tyr Arg
1               5

<210> SEQ ID NO 47
<211> LENGTH: 9
<212> TYPE: PRT
```

```
<213> ORGANISM: Artificial Sequence
<220> FEATURE:
<223> OTHER INFORMATION: Peptide

<400> SEQUENCE: 47

Ala Asn Asp Pro Ile Phe Val Val Leu
1               5

<210> SEQ ID NO 48
<211> LENGTH: 8
<212> TYPE: PRT
<213> ORGANISM: Artificial Sequence
<220> FEATURE:
<223> OTHER INFORMATION: Peptide

<400> SEQUENCE: 48

Ala Phe Leu Arg His Ala Ala Leu
1               5

<210> SEQ ID NO 49
<211> LENGTH: 11
<212> TYPE: PRT
<213> ORGANISM: Artificial Sequence
<220> FEATURE:
<223> OTHER INFORMATION: Peptide

<400> SEQUENCE: 49

Met Leu Met Ala Gln Glu Ala Leu Ala Phe Leu
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Peptide

<400> SEQUENCE: 50

Tyr Leu Ser Gly Ala Asn Leu Asn Leu
1               5

<210> SEQ ID NO 51
<211> LENGTH: 9
<212> TYPE: PRT
<213> ORGANISM: Artificial Sequence
<220> FEATURE:
<223> OTHER INFORMATION: Peptide

<400> SEQUENCE: 51

His Leu Phe Gly Tyr Ser Trp Tyr Lys
1               5

<210> SEQ ID NO 52
<211> LENGTH: 9
<212> TYPE: PRT
<213> ORGANISM: Artificial Sequence
<220> FEATURE:
<223> OTHER INFORMATION: Peptide

<400> SEQUENCE: 52

Lys Phe His Arg Val Ile Lys Asp Phe
1               5

<210> SEQ ID NO 53
<211> LENGTH: 9
<212> TYPE: PRT
<213> ORGANISM: Artificial Sequence
```

```
<220> FEATURE:
<223> OTHER INFORMATION: Peptide

<400> SEQUENCE: 53

Lys Ile Phe Gly Ser Leu Ala Phe Leu
1               5

<210> SEQ ID NO 54
<211> LENGTH: 9
<212> TYPE: PRT
<213> ORGANISM: Artificial Sequence
<220> FEATURE:
<223> OTHER INFORMATION: Peptide

<400> SEQUENCE: 54

Val Leu Arg Glu Asn Thr Ser Pro Lys
1               5

<210> SEQ ID NO 55
<211> LENGTH: 9
<212> TYPE: PRT
<213> ORGANISM: Artificial Sequence
<220> FEATURE:
<223> OTHER INFORMATION: Peptide

<400> SEQUENCE: 55

Ile Leu Ala Lys Phe Leu His Trp Leu
1               5

<210> SEQ ID NO 56
<211> LENGTH: 9
<212> TYPE: PRT
<213> ORGANISM: Artificial Sequence
<220> FEATURE:
<223> OTHER INFORMATION: Peptide

<400> SEQUENCE: 56

Ser Pro Arg Trp Trp Pro Thr Cys Leu
1               5

<210> SEQ ID NO 57
<211> LENGTH: 9
<212> TYPE: PRT
<213> ORGANISM: Artificial Sequence
<220> FEATURE:
<223> OTHER INFORMATION: Peptide

<400> SEQUENCE: 57

Ser Thr Ala Pro Pro Ala His Gly Val
1               5

<210> SEQ ID NO 58
<211> LENGTH: 9
<212> TYPE: PRT
<213> ORGANISM: Artificial Sequence
<220> FEATURE:
<223> OTHER INFORMATION: Peptide

<400> SEQUENCE: 58

Ser Thr Ala Pro Pro Val His Asn Val
1               5

<210> SEQ ID NO 59
<211> LENGTH: 9
<212> TYPE: PRT
<213> ORGANISM: Artificial Sequence
<220> FEATURE:
```

<223> OTHER INFORMATION: Peptide

<400> SEQUENCE: 59

Leu Leu Asn Gln Leu Gln Val Asn Leu
1               5

<210> SEQ ID NO 60
<211> LENGTH: 9
<212> TYPE: PRT
<213> ORGANISM: Artificial Sequence
<220> FEATURE:
<223> OTHER INFORMATION: Peptide

<400> SEQUENCE: 60

Leu Tyr Val Asp Ser Leu Phe Phe Leu
1               5

<210> SEQ ID NO 61
<211> LENGTH: 9
<212> TYPE: PRT
<213> ORGANISM: Artificial Sequence
<220> FEATURE:
<223> OTHER INFORMATION: Peptide

<400> SEQUENCE: 61

Ala Tyr Gly Leu Asp Phe Tyr Ile Leu
1               5

<210> SEQ ID NO 62
<211> LENGTH: 9
<212> TYPE: PRT
<213> ORGANISM: Artificial Sequence
<220> FEATURE:
<223> OTHER INFORMATION: Peptide

<400> SEQUENCE: 62

Val Pro Tyr Gly Ser Phe Lys His Val
1               5

<210> SEQ ID NO 63
<211> LENGTH: 9
<212> TYPE: PRT
<213> ORGANISM: Artificial Sequence
<220> FEATURE:
<223> OTHER INFORMATION: Peptide

<400> SEQUENCE: 63

Leu Pro Arg Trp Pro Pro Pro Gln Leu
1               5

<210> SEQ ID NO 64
<211> LENGTH: 9
<212> TYPE: PRT
<213> ORGANISM: Artificial Sequence
<220> FEATURE:
<223> OTHER INFORMATION: Peptide

<400> SEQUENCE: 64

Glu Tyr Arg Gly Phe Thr Gln Asp Phe
1               5

<210> SEQ ID NO 65
<211> LENGTH: 9
<212> TYPE: PRT
<213> ORGANISM: Artificial Sequence
<220> FEATURE:
<223> OTHER INFORMATION: Peptide

```
<400> SEQUENCE: 65

Asp Tyr Ser Ala Arg Trp Asn Glu Ile
1               5

<210> SEQ ID NO 66
<211> LENGTH: 9
<212> TYPE: PRT
<213> ORGANISM: Artificial Sequence
<220> FEATURE:
<223> OTHER INFORMATION: Peptide

<400> SEQUENCE: 66

Ala Tyr Ile Asp Phe Glu Met Lys Ile
1               5

<210> SEQ ID NO 67
<211> LENGTH: 9
<212> TYPE: PRT
<213> ORGANISM: Artificial Sequence
<220> FEATURE:
<223> OTHER INFORMATION: Peptide

<400> SEQUENCE: 67

Gly Val Ala Leu Gln Thr Met Lys Gln
1               5

<210> SEQ ID NO 68
<211> LENGTH: 9
<212> TYPE: PRT
<213> ORGANISM: Artificial Sequence
<220> FEATURE:
<223> OTHER INFORMATION: Peptide

<400> SEQUENCE: 68

Ser Tyr Leu Asp Ser Gly Ile His Phe
1               5

<210> SEQ ID NO 69
<211> LENGTH: 9
<212> TYPE: PRT
<213> ORGANISM: Artificial Sequence
<220> FEATURE:
<223> OTHER INFORMATION: Peptide

<400> SEQUENCE: 69

Phe Pro Ser Asp Ser Trp Cys Tyr Phe
1               5

<210> SEQ ID NO 70
<211> LENGTH: 10
<212> TYPE: PRT
<213> ORGANISM: Artificial Sequence
<220> FEATURE:
<223> OTHER INFORMATION: Peptide

<400> SEQUENCE: 70

Ala Cys Asp Pro His Ser Gly His Phe Val
1               5                   10

<210> SEQ ID NO 71
<211> LENGTH: 9
<212> TYPE: PRT
<213> ORGANISM: Artificial Sequence
<220> FEATURE:
<223> OTHER INFORMATION: Peptide
```

```
<400> SEQUENCE: 71

Glu Thr Val Ser Glu Gln Ser Asn Val
1               5

<210> SEQ ID NO 72
<211> LENGTH: 9
<212> TYPE: PRT
<213> ORGANISM: Artificial Sequence
<220> FEATURE:
<223> OTHER INFORMATION: Peptide

<400> SEQUENCE: 72

Val Leu Pro Asp Val Phe Ile Arg Cys
1               5

<210> SEQ ID NO 73
<211> LENGTH: 9
<212> TYPE: PRT
<213> ORGANISM: Artificial Sequence
<220> FEATURE:
<223> OTHER INFORMATION: Peptide

<400> SEQUENCE: 73

His Leu Ser Thr Ala Phe Ala Arg Val
1               5

<210> SEQ ID NO 74
<211> LENGTH: 9
<212> TYPE: PRT
<213> ORGANISM: Artificial Sequence
<220> FEATURE:
<223> OTHER INFORMATION: Peptide

<400> SEQUENCE: 74

Ser Leu Phe Glu Gly Ile Asp Ile Tyr
1               5

<210> SEQ ID NO 75
<211> LENGTH: 10
<212> TYPE: PRT
<213> ORGANISM: Artificial Sequence
<220> FEATURE:
<223> OTHER INFORMATION: Peptide

<400> SEQUENCE: 75

Tyr Ser Trp Met Asp Ile Ser Cys Trp Ile
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Peptide

<400> SEQUENCE: 76

Glu Glu Lys Leu Ile Val Val Leu Phe
1               5

<210> SEQ ID NO 77
<211> LENGTH: 10
<212> TYPE: PRT
<213> ORGANISM: Artificial Sequence
<220> FEATURE:
<223> OTHER INFORMATION: Peptide

<400> SEQUENCE: 77
```

Ser Glu Leu Phe Arg Ser Gly Leu Asp Tyr
1               5                   10

<210> SEQ ID NO 78
<211> LENGTH: 9
<212> TYPE: PRT
<213> ORGANISM: Artificial Sequence
<220> FEATURE:
<223> OTHER INFORMATION: Peptide

<400> SEQUENCE: 78

Phe Arg Ser Gly Leu Asp Ser Tyr Val
1               5

<210> SEQ ID NO 79
<211> LENGTH: 9
<212> TYPE: PRT
<213> ORGANISM: Artificial Sequence
<220> FEATURE:
<223> OTHER INFORMATION: Peptide

<400> SEQUENCE: 79

Glu Ala Phe Ile Gln Pro Ile Thr Arg
1               5

<210> SEQ ID NO 80
<211> LENGTH: 9
<212> TYPE: PRT
<213> ORGANISM: Artificial Sequence
<220> FEATURE:
<223> OTHER INFORMATION: Peptide

<400> SEQUENCE: 80

Lys Ile Asn Lys Asn Pro Lys Tyr Lys
1               5

<210> SEQ ID NO 81
<211> LENGTH: 10
<212> TYPE: PRT
<213> ORGANISM: Artificial Sequence
<220> FEATURE:
<223> OTHER INFORMATION: Peptide

<400> SEQUENCE: 81

Ser Pro Ser Ser Asn Arg Ile Arg Asn Thr
1               5                   10

<210> SEQ ID NO 82
<211> LENGTH: 9
<212> TYPE: PRT
<213> ORGANISM: Artificial Sequence
<220> FEATURE:
<223> OTHER INFORMATION: Peptide

<400> SEQUENCE: 82

Arg Val Ala Ala Leu Ala Arg Asp Ala
1               5

<210> SEQ ID NO 83
<211> LENGTH: 9
<212> TYPE: PRT
<213> ORGANISM: Artificial Sequence
<220> FEATURE:
<223> OTHER INFORMATION: Peptide

<400> SEQUENCE: 83

```
Ala Tyr Ala Cys Asn Thr Ser Thr Leu
1               5
```

<210> SEQ ID NO 84
<211> LENGTH: 10
<212> TYPE: PRT
<213> ORGANISM: Artificial Sequence
<220> FEATURE:
<223> OTHER INFORMATION: Peptide

<400> SEQUENCE: 84

```
Lys Trp Phe Pro Ser Cys Gln Phe Leu Leu
1               5                   10
```

<210> SEQ ID NO 85
<211> LENGTH: 9
<212> TYPE: PRT
<213> ORGANISM: Artificial Sequence
<220> FEATURE:
<223> OTHER INFORMATION: Peptide

<400> SEQUENCE: 85

```
Gly Tyr Asp Gln Ile Met Pro Lys Lys
1               5
```

<210> SEQ ID NO 86
<211> LENGTH: 11
<212> TYPE: PRT
<213> ORGANISM: Artificial Sequence
<220> FEATURE:
<223> OTHER INFORMATION: Peptide

<400> SEQUENCE: 86

```
Cys Lys Lys Ile Phe Gly Ser Leu Ala Phe Leu
1               5                   10
```

<210> SEQ ID NO 87
<211> LENGTH: 9
<212> TYPE: PRT
<213> ORGANISM: Artificial Sequence
<220> FEATURE:
<223> OTHER INFORMATION: Peptide

<400> SEQUENCE: 87

```
Val Tyr Gly Phe Val Arg Ala Cys Leu
1               5
```

<210> SEQ ID NO 88
<211> LENGTH: 9
<212> TYPE: PRT
<213> ORGANISM: Artificial Sequence
<220> FEATURE:
<223> OTHER INFORMATION: Peptide

<400> SEQUENCE: 88

```
Ser Leu Leu Met Trp Ile Thr Gln Cys
1               5
```

<210> SEQ ID NO 89
<211> LENGTH: 11
<212> TYPE: PRT
<213> ORGANISM: Artificial Sequence
<220> FEATURE:
<223> OTHER INFORMATION: Peptide

<400> SEQUENCE: 89

```
Cys Ala Gly Leu Tyr Asp Gly Met Glu His Leu
```

<210> SEQ ID NO 90
<211> LENGTH: 11
<212> TYPE: PRT
<213> ORGANISM: Artificial Sequence
<220> FEATURE:
<223> OTHER INFORMATION: Peptide

<400> SEQUENCE: 90

Cys Leu Gly Leu Tyr Asp Gly Met Glu His Leu
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Peptide

<400> SEQUENCE: 91

Cys Met Gly Leu Tyr Asp Gly Met Glu His Leu
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Peptide

<400> SEQUENCE: 92

Cys Ala Val Leu Gln Glu Leu Asn Val Thr Val
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Peptide

<400> SEQUENCE: 93

Cys Leu Val Leu Gln Glu Leu Asn Val Thr Val
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Peptide

<400> SEQUENCE: 94

Cys Met Val Leu Gln Glu Leu Asn Val Thr Val
1               5                   10

<210> SEQ ID NO 95
<211> LENGTH: 11
<212> TYPE: PRT
<213> ORGANISM: Artificial Sequence
<220> FEATURE:
<223> OTHER INFORMATION: Peptide

<400> SEQUENCE: 95

Cys Ala Lys Ile Phe Gly Ser Leu Ala Phe Leu
1               5                   10

```
<210> SEQ ID NO 96
<211> LENGTH: 11
<212> TYPE: PRT
<213> ORGANISM: Artificial Sequence
<220> FEATURE:
<223> OTHER INFORMATION: Peptide

<400> SEQUENCE: 96

Cys Leu Lys Ile Phe Gly Ser Leu Ala Phe Leu
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Peptide

<400> SEQUENCE: 97

Cys Met Lys Ile Phe Gly Ser Leu Ala Phe Leu
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Peptide

<400> SEQUENCE: 98

Cys Gly Leu Tyr Asp Gly Met Glu His Leu
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Peptide

<400> SEQUENCE: 99

Cys Val Leu Gln Glu Leu Asn Val Thr Val
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Peptide

<400> SEQUENCE: 100

Cys Lys Ile Phe Gly Ser Leu Ala Phe Leu
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Peptide

<400> SEQUENCE: 101

Ala Lys Phe Val Ala Ala Trp Thr Leu Lys Ala Ala Ala
1               5                   10
```

```
<210> SEQ ID NO 102
<211> LENGTH: 13
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa stands for D-Alanine
<220> FEATURE:
<221> NAME/KEY: MISC_FEATURE
<222> LOCATION: (13)..(13)
<223> OTHER INFORMATION: Xaa stands for D-Alanine

<400> SEQUENCE: 102

Xaa Lys Phe Val Ala Ala Trp Thr Leu Lys Ala Ala Xaa
1               5                   10

<210> SEQ ID NO 103
<211> LENGTH: 15
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa stands for D-Alanine
<220> FEATURE:
<221> NAME/KEY: MISC_FEATURE
<222> LOCATION: (3)..(3)
<223> OTHER INFORMATION: Xaa stands for Cyclohexylalanine
<220> FEATURE:
<221> NAME/KEY: MISC_FEATURE
<222> LOCATION: (13)..(13)
<223> OTHER INFORMATION: Xaa stands for D-Alanine
<220> FEATURE:
<221> NAME/KEY: MISC_FEATURE
<222> LOCATION: (14)..(14)
<223> OTHER INFORMATION: Xaa stands for 2-Aminohexanoic acid

<400> SEQUENCE: 103

Xaa Lys Xaa Val Ala Ala Trp Thr Leu Lys Ala Ala Xaa Xaa Cys
1               5                   10                  15

<210> SEQ ID NO 104
<211> LENGTH: 18
<212> TYPE: PRT
<213> ORGANISM: Artificial Sequence
<220> FEATURE:
<223> OTHER INFORMATION: Peptide

<400> SEQUENCE: 104

Ala Ala Asp His Arg Gln Leu Gln Leu Ser Ile Ser Ser Cys Leu Gln
1               5                   10                  15

Gln Leu

<210> SEQ ID NO 105
<211> LENGTH: 23
<212> TYPE: PRT
<213> ORGANISM: Artificial Sequence
<220> FEATURE:
<223> OTHER INFORMATION: Peptide

<400> SEQUENCE: 105

Arg Asn Gly Tyr Arg Ala Leu Met Asp Lys Ser Leu His Val Gly Thr
1               5                   10                  15

Gln Cys Ala Leu Thr Arg Arg
```

<210> SEQ ID NO 106
<211> LENGTH: 13
<212> TYPE: PRT
<213> ORGANISM: Artificial Sequence
<220> FEATURE:
<223> OTHER INFORMATION: Peptide

<400> SEQUENCE: 106

Lys Lys Leu Gln Cys Val Gln Leu His Val Ile Ser Met
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Peptide

<400> SEQUENCE: 107

Gly Ser Tyr Val Ser Arg Leu Leu Gly Ile Cys Leu
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Peptide

<400> SEQUENCE: 108

Cys Arg Lys Ile Phe Gly Ser Leu Ala Phe Leu
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Peptide

<400> SEQUENCE: 109

Cys Asn Lys Ile Phe Gly Ser Leu Ala Phe Leu
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Peptide

<400> SEQUENCE: 110

Cys Asp Lys Ile Phe Gly Ser Leu Ala Phe Leu
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Peptide

<400> SEQUENCE: 111

Cys Cys Lys Ile Phe Gly Ser Leu Ala Phe Leu
1               5                   10

```
<210> SEQ ID NO 112
<211> LENGTH: 11
<212> TYPE: PRT
<213> ORGANISM: Artificial Sequence
<220> FEATURE:
<223> OTHER INFORMATION: Peptide

<400> SEQUENCE: 112

Cys Gln Lys Ile Phe Gly Ser Leu Ala Phe Leu
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Peptide

<400> SEQUENCE: 113

Cys Gly Lys Ile Phe Gly Ser Leu Ala Phe Leu
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Peptide

<400> SEQUENCE: 114

Cys His Lys Ile Phe Gly Ser Leu Ala Phe Leu
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Peptide

<400> SEQUENCE: 115

Cys Glu Lys Ile Phe Gly Ser Leu Ala Phe Leu
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Peptide

<400> SEQUENCE: 116

Cys Ile Lys Ile Phe Gly Ser Leu Ala Phe Leu
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Peptide

<400> SEQUENCE: 117

Cys Phe Lys Ile Phe Gly Ser Leu Ala Phe Leu
1               5                   10
```

<210> SEQ ID NO 118
<211> LENGTH: 11
<212> TYPE: PRT
<213> ORGANISM: Artificial Sequence
<220> FEATURE:
<223> OTHER INFORMATION: Peptide

<400> SEQUENCE: 118

Cys Pro Lys Ile Phe Gly Ser Leu Ala Phe Leu
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Peptide

<400> SEQUENCE: 119

Cys Ser Lys Ile Phe Gly Ser Leu Ala Phe Leu
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Peptide

<400> SEQUENCE: 120

Cys Thr Lys Ile Phe Gly Ser Leu Ala Phe Leu
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Peptide

<400> SEQUENCE: 121

Cys Trp Lys Ile Phe Gly Ser Leu Ala Phe Leu
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Peptide

<400> SEQUENCE: 122

Cys Tyr Lys Ile Phe Gly Ser Leu Ala Phe Leu
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Peptide

<400> SEQUENCE: 123

Cys Val Lys Ile Phe Gly Ser Leu Ala Phe Leu
1               5                   10

```
<210> SEQ ID NO 124
<211> LENGTH: 11
<212> TYPE: PRT
<213> ORGANISM: Artificial Sequence
<220> FEATURE:
<223> OTHER INFORMATION: Peptide

<400> SEQUENCE: 124

Ala Cys Lys Ile Phe Gly Ser Leu Ala Phe Leu
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Synthtic

<400> SEQUENCE: 125

Arg Cys Lys Ile Phe Gly Ser Leu Ala Phe Leu
1               5                   10

<210> SEQ ID NO 126
<211> LENGTH: 11
<212> TYPE: PRT
<213> ORGANISM: Artificial Sequence
<220> FEATURE:
<223> OTHER INFORMATION: Synthtic

<400> SEQUENCE: 126

Asn Cys Lys Ile Phe Gly Ser Leu Ala Phe Leu
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Synthtic

<400> SEQUENCE: 127

Asp Cys Lys Ile Phe Gly Ser Leu Ala Phe Leu
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Synthtic

<400> SEQUENCE: 128

Gln Cys Lys Ile Phe Gly Ser Leu Ala Phe Leu
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Peptide

<400> SEQUENCE: 129

Glu Cys Lys Ile Phe Gly Ser Leu Ala Phe Leu
1               5                   10

<210> SEQ ID NO 130
```

```
<211> LENGTH: 11
<212> TYPE: PRT
<213> ORGANISM: Artificial Sequence
<220> FEATURE:
<223> OTHER INFORMATION: Peptide

<400> SEQUENCE: 130

Gly Cys Lys Ile Phe Gly Ser Leu Ala Phe Leu
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Peptide

<400> SEQUENCE: 131

His Cys Lys Ile Phe Gly Ser Leu Ala Phe Leu
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Peptide

<400> SEQUENCE: 132

Ile Cys Lys Ile Phe Gly Ser Leu Ala Phe Leu
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Peptide

<400> SEQUENCE: 133

Leu Cys Lys Ile Phe Gly Ser Leu Ala Phe Leu
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Peptide

<400> SEQUENCE: 134

Lys Cys Lys Ile Phe Gly Ser Leu Ala Phe Leu
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Peptide

<400> SEQUENCE: 135

Met Cys Lys Ile Phe Gly Ser Leu Ala Phe Leu
1               5                   10

<210> SEQ ID NO 136
<211> LENGTH: 11
```

```
<212> TYPE: PRT
<213> ORGANISM: Artificial Sequence
<220> FEATURE:
<223> OTHER INFORMATION: Peptide

<400> SEQUENCE: 136

Phe Cys Lys Ile Phe Gly Ser Leu Ala Phe Leu
1               5                   10

<210> SEQ ID NO 137
<211> LENGTH: 11
<212> TYPE: PRT
<213> ORGANISM: Artificial Sequence
<220> FEATURE:
<223> OTHER INFORMATION: Peptide

<400> SEQUENCE: 137

Pro Cys Lys Ile Phe Gly Ser Leu Ala Phe Leu
1               5                   10

<210> SEQ ID NO 138
<211> LENGTH: 11
<212> TYPE: PRT
<213> ORGANISM: Artificial Sequence
<220> FEATURE:
<223> OTHER INFORMATION: Peptide

<400> SEQUENCE: 138

Ser Cys Lys Ile Phe Gly Ser Leu Ala Phe Leu
1               5                   10

<210> SEQ ID NO 139
<211> LENGTH: 11
<212> TYPE: PRT
<213> ORGANISM: Artificial Sequence
<220> FEATURE:
<223> OTHER INFORMATION: Peptide

<400> SEQUENCE: 139

Thr Cys Lys Ile Phe Gly Ser Leu Ala Phe Leu
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Peptide

<400> SEQUENCE: 140

Trp Cys Lys Ile Phe Gly Ser Leu Ala Phe Leu
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Peptide

<400> SEQUENCE: 141

Tyr Cys Lys Ile Phe Gly Ser Leu Ala Phe Leu
1               5                   10

<210> SEQ ID NO 142
<211> LENGTH: 11
<212> TYPE: PRT
```

```
<213> ORGANISM: Artificial Sequence
<220> FEATURE:
<223> OTHER INFORMATION: Peptide

<400> SEQUENCE: 142

Val Cys Lys Ile Phe Gly Ser Leu Ala Phe Leu
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Peptide

<400> SEQUENCE: 143

Ala Cys Val Leu Gln Glu Leu Asn Val Thr Val
1               5                   10

<210> SEQ ID NO 144
<211> LENGTH: 11
<212> TYPE: PRT
<213> ORGANISM: Artificial Sequence
<220> FEATURE:
<223> OTHER INFORMATION: Peptide

<400> SEQUENCE: 144

Arg Cys Val Leu Gln Glu Leu Asn Val Thr Val
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Peptide

<400> SEQUENCE: 145

Asn Cys Val Leu Gln Glu Leu Asn Val Thr Val
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Peptide

<400> SEQUENCE: 146

Asp Cys Val Leu Gln Glu Leu Asn Val Thr Val
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Peptide

<400> SEQUENCE: 147

Gln Cys Val Leu Gln Glu Leu Asn Val Thr Val
1               5                   10

<210> SEQ ID NO 148
<211> LENGTH: 11
<212> TYPE: PRT
<213> ORGANISM: Artificial Sequence
```

```
<220> FEATURE:
<223> OTHER INFORMATION: Peptide

<400> SEQUENCE: 148

Glu Cys Val Leu Gln Glu Leu Asn Val Thr Val
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Peptide

<400> SEQUENCE: 149

Gly Cys Val Leu Gln Glu Leu Asn Val Thr Val
1               5                   10

<210> SEQ ID NO 150
<211> LENGTH: 11
<212> TYPE: PRT
<213> ORGANISM: Artificial Sequence
<220> FEATURE:
<223> OTHER INFORMATION: Peptide

<400> SEQUENCE: 150

His Cys Val Leu Gln Glu Leu Asn Val Thr Val
1               5                   10

<210> SEQ ID NO 151
<211> LENGTH: 11
<212> TYPE: PRT
<213> ORGANISM: Artificial Sequence
<220> FEATURE:
<223> OTHER INFORMATION: Peptide

<400> SEQUENCE: 151

Ile Cys Val Leu Gln Glu Leu Asn Val Thr Val
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Peptide

<400> SEQUENCE: 152

Leu Cys Val Leu Gln Glu Leu Asn Val Thr Val
1               5                   10

<210> SEQ ID NO 153
<211> LENGTH: 11
<212> TYPE: PRT
<213> ORGANISM: Artificial Sequence
<220> FEATURE:
<223> OTHER INFORMATION: Peptide

<400> SEQUENCE: 153

Lys Cys Val Leu Gln Glu Leu Asn Val Thr Val
1               5                   10

<210> SEQ ID NO 154
<211> LENGTH: 11
<212> TYPE: PRT
<213> ORGANISM: Artificial Sequence
<220> FEATURE:
```

<223> OTHER INFORMATION: Peptide

<400> SEQUENCE: 154

Met Cys Val Leu Gln Glu Leu Asn Val Thr Val
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Peptide

<400> SEQUENCE: 155

Phe Cys Val Leu Gln Glu Leu Asn Val Thr Val
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Peptide

<400> SEQUENCE: 156

Pro Cys Val Leu Gln Glu Leu Asn Val Thr Val
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Peptide

<400> SEQUENCE: 157

Ser Cys Val Leu Gln Glu Leu Asn Val Thr Val
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Peptide

<400> SEQUENCE: 158

Thr Cys Val Leu Gln Glu Leu Asn Val Thr Val
1               5                   10

<210> SEQ ID NO 159
<211> LENGTH: 11
<212> TYPE: PRT
<213> ORGANISM: Artificial Sequence
<220> FEATURE:
<223> OTHER INFORMATION: Peptide

<400> SEQUENCE: 159

Trp Cys Val Leu Gln Glu Leu Asn Val Thr Val
1               5                   10

<210> SEQ ID NO 160
<211> LENGTH: 11
<212> TYPE: PRT
<213> ORGANISM: Artificial Sequence
<220> FEATURE:
<223> OTHER INFORMATION: Peptide

<400> SEQUENCE: 160

Tyr Cys Val Leu Gln Glu Leu Asn Val Thr Val
1               5                   10

<210> SEQ ID NO 161
<211> LENGTH: 11
<212> TYPE: PRT
<213> ORGANISM: Artificial Sequence
<220> FEATURE:
<223> OTHER INFORMATION: Peptide

<400> SEQUENCE: 161

Val Cys Val Leu Gln Glu Leu Asn Val Thr Val
1               5                   10

<210> SEQ ID NO 162
<211> LENGTH: 11
<212> TYPE: PRT
<213> ORGANISM: Artificial Sequence
<220> FEATURE:
<223> OTHER INFORMATION: Peptide

<400> SEQUENCE: 162

Cys Gln Gly Leu Tyr Asp Gly Met Glu His Leu
1               5                   10

<210> SEQ ID NO 163
<211> LENGTH: 11
<212> TYPE: PRT
<213> ORGANISM: Artificial Sequence
<220> FEATURE:
<223> OTHER INFORMATION: Peptide

<400> SEQUENCE: 163

Cys Glu Gly Leu Tyr Asp Gly Met Glu His Leu
1               5                   10

<210> SEQ ID NO 164
<211> LENGTH: 11
<212> TYPE: PRT
<213> ORGANISM: Artificial Sequence
<220> FEATURE:
<223> OTHER INFORMATION: Peptide

<400> SEQUENCE: 164

Cys Gly Gly Leu Tyr Asp Gly Met Glu His Leu
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Peptide

<400> SEQUENCE: 165

Cys His Gly Leu Tyr Asp Gly Met Glu His Leu
1               5                   10

<210> SEQ ID NO 166
<211> LENGTH: 11
<212> TYPE: PRT
<213> ORGANISM: Artificial Sequence
<220> FEATURE:
<223> OTHER INFORMATION: Peptide

<400> SEQUENCE: 166

Cys Ile Gly Leu Tyr Asp Gly Met Glu His Leu
1               5                   10

<210> SEQ ID NO 167
<211> LENGTH: 11
<212> TYPE: PRT
<213> ORGANISM: Artificial Sequence
<220> FEATURE:
<223> OTHER INFORMATION: Peptide

<400> SEQUENCE: 167

Cys Lys Gly Leu Tyr Asp Gly Met Glu His Leu
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Peptide

<400> SEQUENCE: 168

Cys Phe Gly Leu Tyr Asp Gly Met Glu His Leu
1               5                   10

<210> SEQ ID NO 169
<211> LENGTH: 11
<212> TYPE: PRT
<213> ORGANISM: Artificial Sequence
<220> FEATURE:
<223> OTHER INFORMATION: Peptide

<400> SEQUENCE: 169

Cys Pro Gly Leu Tyr Asp Gly Met Glu His Leu
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Peptide

<400> SEQUENCE: 170

Cys Thr Gly Leu Tyr Asp Gly Met Glu His Leu
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Peptide

<400> SEQUENCE: 171

Cys Trp Gly Leu Tyr Asp Gly Met Glu His Leu
1               5                   10

<210> SEQ ID NO 172
<211> LENGTH: 11
<212> TYPE: PRT
<213> ORGANISM: Artificial Sequence
<220> FEATURE:
<223> OTHER INFORMATION: Peptide

<400> SEQUENCE: 172

Cys Tyr Gly Leu Tyr Asp Gly Met Glu His Leu
1               5                   10

<210> SEQ ID NO 173
<211> LENGTH: 11
<212> TYPE: PRT
<213> ORGANISM: Artificial Sequence
<220> FEATURE:
<223> OTHER INFORMATION: Peptide

<400> SEQUENCE: 173

Cys Val Gly Leu Tyr Asp Gly Met Glu His Leu
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Peptide

<400> SEQUENCE: 174

Cys Arg Gly Leu Tyr Asp Gly Met Glu His Leu
1               5                   10

<210> SEQ ID NO 175
<211> LENGTH: 11
<212> TYPE: PRT
<213> ORGANISM: Artificial Sequence
<220> FEATURE:
<223> OTHER INFORMATION: Peptide

<400> SEQUENCE: 175

Cys Asn Gly Leu Tyr Asp Gly Met Glu His Leu
1               5                   10

<210> SEQ ID NO 176
<211> LENGTH: 11
<212> TYPE: PRT
<213> ORGANISM: Artificial Sequence
<220> FEATURE:
<223> OTHER INFORMATION: Peptide

<400> SEQUENCE: 176

Cys Asp Gly Leu Tyr Asp Gly Met Glu His Leu
1               5                   10

<210> SEQ ID NO 177
<211> LENGTH: 11
<212> TYPE: PRT
<213> ORGANISM: Artificial Sequence
<220> FEATURE:
<223> OTHER INFORMATION: Peptide

<400> SEQUENCE: 177

Cys Ser Gly Leu Tyr Asp Gly Met Glu His Leu
1               5                   10

<210> SEQ ID NO 178
<211> LENGTH: 11
<212> TYPE: PRT
<213> ORGANISM: Artificial Sequence
<220> FEATURE:
<223> OTHER INFORMATION: Peptide

<400> SEQUENCE: 178

Gln Cys Gly Leu Tyr Asp Gly Met Glu His Leu
1               5                   10

<210> SEQ ID NO 179
<211> LENGTH: 11
<212> TYPE: PRT
<213> ORGANISM: Artificial Sequence
<220> FEATURE:
<223> OTHER INFORMATION: Peptide

<400> SEQUENCE: 179

Pro Cys Gly Leu Tyr Asp Gly Met Glu His Leu
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Peptide

<400> SEQUENCE: 180

Ser Cys Gly Leu Tyr Asp Gly Met Glu His Leu
1               5                   10

<210> SEQ ID NO 181
<211> LENGTH: 11
<212> TYPE: PRT
<213> ORGANISM: Artificial Sequence
<220> FEATURE:
<223> OTHER INFORMATION: Peptide

<400> SEQUENCE: 181

Thr Cys Gly Leu Tyr Asp Gly Met Glu His Leu
1               5                   10

<210> SEQ ID NO 182
<211> LENGTH: 11
<212> TYPE: PRT
<213> ORGANISM: Artificial Sequence
<220> FEATURE:
<223> OTHER INFORMATION: Peptide

<400> SEQUENCE: 182

Trp Cys Gly Leu Tyr Asp Gly Met Glu His Leu
1               5                   10

<210> SEQ ID NO 183
<211> LENGTH: 11
<212> TYPE: PRT
<213> ORGANISM: Artificial Sequence
<220> FEATURE:
<223> OTHER INFORMATION: Peptide

<400> SEQUENCE: 183

Tyr Cys Gly Leu Tyr Asp Gly Met Glu His Leu
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Peptide

<400> SEQUENCE: 184

Val Cys Gly Leu Tyr Asp Gly Met Glu His Leu

```
1               5                   10

<210> SEQ ID NO 185
<211> LENGTH: 11
<212> TYPE: PRT
<213> ORGANISM: Artificial Sequence
<220> FEATURE:
<223> OTHER INFORMATION: Peptide

<400> SEQUENCE: 185

Ala Cys Gly Leu Tyr Asp Gly Met Glu His Leu
1               5                   10

<210> SEQ ID NO 186
<211> LENGTH: 11
<212> TYPE: PRT
<213> ORGANISM: Artificial Sequence
<220> FEATURE:
<223> OTHER INFORMATION: Peptide

<400> SEQUENCE: 186

Arg Cys Gly Leu Tyr Asp Gly Met Glu His Leu
1               5                   10

<210> SEQ ID NO 187
<211> LENGTH: 11
<212> TYPE: PRT
<213> ORGANISM: Artificial Sequence
<220> FEATURE:
<223> OTHER INFORMATION: Peptide

<400> SEQUENCE: 187

Asn Cys Gly Leu Tyr Asp Gly Met Glu His Leu
1               5                   10

<210> SEQ ID NO 188
<211> LENGTH: 11
<212> TYPE: PRT
<213> ORGANISM: Artificial Sequence
<220> FEATURE:
<223> OTHER INFORMATION: Peptide

<400> SEQUENCE: 188

Asp Cys Gly Leu Tyr Asp Gly Met Glu His Leu
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Peptide

<400> SEQUENCE: 189

Glu Cys Gly Leu Tyr Asp Gly Met Glu His Leu
1               5                   10

<210> SEQ ID NO 190
<211> LENGTH: 11
<212> TYPE: PRT
<213> ORGANISM: Artificial Sequence
<220> FEATURE:
<223> OTHER INFORMATION: Peptide

<400> SEQUENCE: 190

Gly Cys Gly Leu Tyr Asp Gly Met Glu His Leu
1               5                   10
```

```
<210> SEQ ID NO 191
<211> LENGTH: 11
<212> TYPE: PRT
<213> ORGANISM: Artificial Sequence
<220> FEATURE:
<223> OTHER INFORMATION: Peptide

<400> SEQUENCE: 191

His Cys Gly Leu Tyr Asp Gly Met Glu His Leu
1               5                   10

<210> SEQ ID NO 192
<211> LENGTH: 11
<212> TYPE: PRT
<213> ORGANISM: Artificial Sequence
<220> FEATURE:
<223> OTHER INFORMATION: Peptide

<400> SEQUENCE: 192

Ile Cys Gly Leu Tyr Asp Gly Met Glu His Leu
1               5                   10

<210> SEQ ID NO 193
<211> LENGTH: 11
<212> TYPE: PRT
<213> ORGANISM: Artificial Sequence
<220> FEATURE:
<223> OTHER INFORMATION: Peptide

<400> SEQUENCE: 193

Leu Cys Gly Leu Tyr Asp Gly Met Glu His Leu
1               5                   10

<210> SEQ ID NO 194
<211> LENGTH: 11
<212> TYPE: PRT
<213> ORGANISM: Artificial Sequence
<220> FEATURE:
<223> OTHER INFORMATION: Peptide

<400> SEQUENCE: 194

Lys Cys Gly Leu Tyr Asp Gly Met Glu His Leu
1               5                   10

<210> SEQ ID NO 195
<211> LENGTH: 11
<212> TYPE: PRT
<213> ORGANISM: Artificial Sequence
<220> FEATURE:
<223> OTHER INFORMATION: Peptide

<400> SEQUENCE: 195

Met Cys Gly Leu Tyr Asp Gly Met Glu His Leu
1               5                   10

<210> SEQ ID NO 196
<211> LENGTH: 11
<212> TYPE: PRT
<213> ORGANISM: Artificial Sequence
<220> FEATURE:
<223> OTHER INFORMATION: Peptide

<400> SEQUENCE: 196

Phe Cys Gly Leu Tyr Asp Gly Met Glu His Leu
1               5                   10
```

```
<210> SEQ ID NO 197
<211> LENGTH: 14
<212> TYPE: PRT
<213> ORGANISM: Artificial Sequence
<220> FEATURE:
<223> OTHER INFORMATION: peptide

<400> SEQUENCE: 197

Cys Ala Lys Phe Val Ala Ala Trp Thr Leu Lys Ala Ala Ala
1               5                   10

<210> SEQ ID NO 198
<211> LENGTH: 14
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa stands for D-Alanine
<220> FEATURE:
<221> NAME/KEY: MISC_FEATURE
<222> LOCATION: (14)..(14)
<223> OTHER INFORMATION: Xaa stands for D-Alanine

<400> SEQUENCE: 198

Cys Xaa Lys Phe Val Ala Ala Trp Thr Leu Lys Ala Ala Xaa
1               5                   10

<210> SEQ ID NO 199
<211> LENGTH: 14
<212> TYPE: PRT
<213> ORGANISM: Artificial Sequence
<220> FEATURE:
<223> OTHER INFORMATION: peptide

<400> SEQUENCE: 199

Ala Lys Phe Val Ala Ala Trp Thr Leu Lys Ala Ala Ala Cys
1               5                   10

<210> SEQ ID NO 200
<211> LENGTH: 14
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa stands for D-Alanine
<220> FEATURE:
<221> NAME/KEY: MISC_FEATURE
<222> LOCATION: (13)..(13)
<223> OTHER INFORMATION: Xaa stands for D-Alanine

<400> SEQUENCE: 200

Xaa Lys Phe Val Ala Ala Trp Thr Leu Lys Ala Ala Xaa Cys
1               5                   10

<210> SEQ ID NO 201
<211> LENGTH: 10
<212> TYPE: PRT
<213> ORGANISM: Artificial Sequence
<220> FEATURE:
<223> OTHER INFORMATION: peptide

<400> SEQUENCE: 201

Cys Gly Tyr Asp Gln Ile Met Pro Lys Ile
```

```
1               5                   10
```

<210> SEQ ID NO 202
<211> LENGTH: 10
<212> TYPE: PRT
<213> ORGANISM: Artificial Sequence
<220> FEATURE:
<223> OTHER INFORMATION: peptide

<400> SEQUENCE: 202

```
Cys Gly Tyr Asp Gln Ile Met Pro Lys Lys
1               5                   10
```

<210> SEQ ID NO 203
<211> LENGTH: 12
<212> TYPE: PRT
<213> ORGANISM: Artificial Sequence
<220> FEATURE:
<223> OTHER INFORMATION: peptide

<400> SEQUENCE: 203

```
Cys Ser Leu Leu Met Trp Ile Thr Gln Cys Phe Leu
1               5                   10
```

<210> SEQ ID NO 204
<211> LENGTH: 10
<212> TYPE: PRT
<213> ORGANISM: Artificial Sequence
<220> FEATURE:
<223> OTHER INFORMATION: peptide

<400> SEQUENCE: 204

```
Cys Glu Tyr Leu Gln Leu Val Phe Gly Ile
1               5                   10
```

<210> SEQ ID NO 205
<211> LENGTH: 10
<212> TYPE: PRT
<213> ORGANISM: Artificial Sequence
<220> FEATURE:
<223> OTHER INFORMATION: peptide

<400> SEQUENCE: 205

```
Cys Leu Ile Tyr Arg Arg Arg Leu Met Lys
1               5                   10
```

<210> SEQ ID NO 206
<211> LENGTH: 10
<212> TYPE: PRT
<213> ORGANISM: Artificial Sequence
<220> FEATURE:
<223> OTHER INFORMATION: peptide

<400> SEQUENCE: 206

```
Cys Ala Phe Leu Pro Trp His Arg Leu Phe
1               5                   10
```

<210> SEQ ID NO 207
<211> LENGTH: 10
<212> TYPE: PRT
<213> ORGANISM: Artificial Sequence
<220> FEATURE:
<223> OTHER INFORMATION: peptide

<400> SEQUENCE: 207

```
Cys Tyr Met Asp Gly Thr Met Ser Gln Val
1               5                   10
```

```
<210> SEQ ID NO 208
<211> LENGTH: 10
<212> TYPE: PRT
<213> ORGANISM: Artificial Sequence
<220> FEATURE:
<223> OTHER INFORMATION: peptide

<400> SEQUENCE: 208

Cys Ala Ala Gly Ile Gly Ile Leu Thr Val
1               5                   10

<210> SEQ ID NO 209
<211> LENGTH: 10
<212> TYPE: PRT
<213> ORGANISM: Artificial Sequence
<220> FEATURE:
<223> OTHER INFORMATION: peptide

<400> SEQUENCE: 209

Cys Phe Leu Trp Gly Pro Arg Ala Leu Val
1               5                   10

<210> SEQ ID NO 210
<211> LENGTH: 10
<212> TYPE: PRT
<213> ORGANISM: Artificial Sequence
<220> FEATURE:
<223> OTHER INFORMATION: peptide

<400> SEQUENCE: 210

Cys Ala Tyr Ala Cys Asn Thr Ser Thr Leu
1               5                   10

<210> SEQ ID NO 211
<211> LENGTH: 11
<212> TYPE: PRT
<213> ORGANISM: Artificial Sequence
<220> FEATURE:
<223> OTHER INFORMATION: peptide

<400> SEQUENCE: 211

Cys Lys Trp Phe Pro Ser Cys Gln Phe Leu Leu
1               5                   10

<210> SEQ ID NO 212
<211> LENGTH: 10
<212> TYPE: PRT
<213> ORGANISM: Artificial Sequence
<220> FEATURE:
<223> OTHER INFORMATION: peptide

<400> SEQUENCE: 212

Cys Asn Tyr Lys His Cys Phe Pro Glu Ile
1               5                   10

<210> SEQ ID NO 213
<211> LENGTH: 10
<212> TYPE: PRT
<213> ORGANISM: Artificial Sequence
<220> FEATURE:
<223> OTHER INFORMATION: peptide

<400> SEQUENCE: 213

Cys Tyr Leu Ser Gly Ala Asn Leu Asn Leu
1               5                   10
```

```
<210> SEQ ID NO 214
<211> LENGTH: 10
<212> TYPE: PRT
<213> ORGANISM: Artificial Sequence
<220> FEATURE:
<223> OTHER INFORMATION: peptide

<400> SEQUENCE: 214

Cys Ala Tyr Ile Asp Phe Glu Met Lys Ile
1               5                   10

<210> SEQ ID NO 215
<211> LENGTH: 10
<212> TYPE: PRT
<213> ORGANISM: Artificial Sequence
<220> FEATURE:
<223> OTHER INFORMATION: peptide

<400> SEQUENCE: 215

Cys Gln Leu Ser Leu Leu Met Trp Ile Thr
1               5                   10

<210> SEQ ID NO 216
<211> LENGTH: 11
<212> TYPE: PRT
<213> ORGANISM: Artificial Sequence
<220> FEATURE:
<223> OTHER INFORMATION: peptide

<400> SEQUENCE: 216

Cys Ala Glu Glu Ala Ala Gly Ile Gly Ile Leu
1               5                   10

<210> SEQ ID NO 217
<211> LENGTH: 9
<212> TYPE: PRT
<213> ORGANISM: Artificial Sequence
<220> FEATURE:
<223> OTHER INFORMATION: peptide

<400> SEQUENCE: 217

Cys Ser Asn Asp Gly Pro Thr Leu Ile
1               5

<210> SEQ ID NO 218
<211> LENGTH: 10
<212> TYPE: PRT
<213> ORGANISM: Artificial Sequence
<220> FEATURE:
<223> OTHER INFORMATION: peptide

<400> SEQUENCE: 218

Cys Lys Cys Asp Ile Cys Thr Asp Glu Tyr
1               5                   10

<210> SEQ ID NO 219
<211> LENGTH: 10
<212> TYPE: PRT
<213> ORGANISM: Artificial Sequence
<220> FEATURE:
<223> OTHER INFORMATION: peptide

<400> SEQUENCE: 219

Cys His Leu Phe Gly Tyr Ser Trp Tyr Lys
1               5                   10
```

```
<210> SEQ ID NO 220
<211> LENGTH: 10
<212> TYPE: PRT
<213> ORGANISM: Artificial Sequence
<220> FEATURE:
<223> OTHER INFORMATION: peptide

<400> SEQUENCE: 220

Cys Trp Gln Tyr Phe Phe Pro Val Ile Phe
1               5                   10

<210> SEQ ID NO 221
<211> LENGTH: 10
<212> TYPE: PRT
<213> ORGANISM: Artificial Sequence
<220> FEATURE:
<223> OTHER INFORMATION: peptide

<400> SEQUENCE: 221

Cys Lys Thr Trp Gly Gln Tyr Trp Gln Val
1               5                   10

<210> SEQ ID NO 222
<211> LENGTH: 10
<212> TYPE: PRT
<213> ORGANISM: Artificial Sequence
<220> FEATURE:
<223> OTHER INFORMATION: peptide

<400> SEQUENCE: 222

Cys Ser Glu Ile Trp Arg Asp Ile Asp Phe
1               5                   10

<210> SEQ ID NO 223
<211> LENGTH: 10
<212> TYPE: PRT
<213> ORGANISM: Artificial Sequence
<220> FEATURE:
<223> OTHER INFORMATION: peptide

<400> SEQUENCE: 223

Cys Val Leu Arg Glu Asn Thr Ser Pro Lys
1               5                   10

<210> SEQ ID NO 224
<211> LENGTH: 10
<212> TYPE: PRT
<213> ORGANISM: Artificial Sequence
<220> FEATURE:
<223> OTHER INFORMATION: peptide

<400> SEQUENCE: 224

Cys Ser Thr Ala Pro Pro Ala His Gly Val
1               5                   10

<210> SEQ ID NO 225
<211> LENGTH: 10
<212> TYPE: PRT
<213> ORGANISM: Artificial Sequence
<220> FEATURE:
<223> OTHER INFORMATION: peptide

<400> SEQUENCE: 225

Cys Ser Thr Ala Pro Pro Val His Asn Val
1               5                   10

<210> SEQ ID NO 226
```

```
<211> LENGTH: 10
<212> TYPE: PRT
<213> ORGANISM: Artificial Sequence
<220> FEATURE:
<223> OTHER INFORMATION: peptide

<400> SEQUENCE: 226

Cys Val Tyr Phe Phe Leu Pro Asp His Leu
1               5                   10

<210> SEQ ID NO 227
<211> LENGTH: 11
<212> TYPE: PRT
<213> ORGANISM: Artificial Sequence
<220> FEATURE:
<223> OTHER INFORMATION: peptide

<400> SEQUENCE: 227

Cys Ala Ser Gly Pro Gly Gly Gly Ala Pro Arg
1               5                   10

<210> SEQ ID NO 228
<211> LENGTH: 11
<212> TYPE: PRT
<213> ORGANISM: Artificial Sequence
<220> FEATURE:
<223> OTHER INFORMATION: peptide

<400> SEQUENCE: 228

Cys Met Glu Val Asp Pro Ile Gly His Leu Tyr
1               5                   10

<210> SEQ ID NO 229
<211> LENGTH: 10
<212> TYPE: PRT
<213> ORGANISM: Artificial Sequence
<220> FEATURE:
<223> OTHER INFORMATION: peptide

<400> SEQUENCE: 229

Cys Thr Phe Pro Asp Leu Glu Ser Glu Phe
1               5                   10

<210> SEQ ID NO 230
<211> LENGTH: 10
<212> TYPE: PRT
<213> ORGANISM: Artificial Sequence
<220> FEATURE:
<223> OTHER INFORMATION: peptide

<400> SEQUENCE: 230

Cys Glu Ala Asp Pro Ile Gly His Leu Tyr
1               5                   10

<210> SEQ ID NO 231
<211> LENGTH: 18
<212> TYPE: PRT
<213> ORGANISM: Artificial Sequence
<220> FEATURE:
<223> OTHER INFORMATION: peptide

<400> SEQUENCE: 231

Gly Leu Tyr Asp Gly Met Glu His Leu Lys Ile Phe Gly Ser Leu Ala
1               5                   10                  15

Phe Leu
```

<210> SEQ ID NO 232
<211> LENGTH: 18
<212> TYPE: PRT
<213> ORGANISM: Artificial Sequence
<220> FEATURE:
<223> OTHER INFORMATION: peptide

<400> SEQUENCE: 232

Lys Ile Phe Gly Ser Leu Ala Phe Leu Gly Leu Tyr Asp Gly Met Glu
1               5                   10                  15

His Leu

<210> SEQ ID NO 233
<211> LENGTH: 24
<212> TYPE: PRT
<213> ORGANISM: Artificial Sequence
<220> FEATURE:
<223> OTHER INFORMATION: peptide

<400> SEQUENCE: 233

Gly Leu Tyr Asp Gly Met Glu His Leu Gly Gly Gly Gly Gly Gly Lys
1               5                   10                  15

Ile Phe Gly Ser Leu Ala Phe Leu
            20

<210> SEQ ID NO 234
<211> LENGTH: 24
<212> TYPE: PRT
<213> ORGANISM: Artificial Sequence
<220> FEATURE:
<223> OTHER INFORMATION: peptide

<400> SEQUENCE: 234

Lys Ile Phe Gly Ser Leu Ala Phe Leu Gly Gly Gly Gly Gly Gly Gly
1               5                   10                  15

Leu Tyr Asp Gly Met Glu His Leu
            20

<210> SEQ ID NO 235
<211> LENGTH: 18
<212> TYPE: PRT
<213> ORGANISM: Artificial Sequence
<220> FEATURE:
<223> OTHER INFORMATION: peptide

<400> SEQUENCE: 235

Val Tyr Gly Phe Val Arg Ala Cys Leu Gly Leu Tyr Asp Gly Met Glu
1               5                   10                  15

His Leu

<210> SEQ ID NO 236
<211> LENGTH: 18
<212> TYPE: PRT
<213> ORGANISM: Artificial Sequence
<220> FEATURE:
<223> OTHER INFORMATION: peptide

<400> SEQUENCE: 236

Gly Leu Tyr Asp Gly Met Glu His Leu Val Tyr Gly Phe Val Arg Ala
1               5                   10                  15

Cys Leu

<210> SEQ ID NO 237
<211> LENGTH: 24

```
<212> TYPE: PRT
<213> ORGANISM: Artificial Sequence
<220> FEATURE:
<223> OTHER INFORMATION: peptide

<400> SEQUENCE: 237

Val Tyr Gly Phe Val Arg Ala Cys Leu Gly Gly Gly Gly Gly Gly
1               5                   10                  15

Leu Tyr Asp Gly Met Glu His Leu
            20

<210> SEQ ID NO 238
<211> LENGTH: 24
<212> TYPE: PRT
<213> ORGANISM: Artificial Sequence
<220> FEATURE:
<223> OTHER INFORMATION: peptide

<400> SEQUENCE: 238

Gly Leu Tyr Asp Gly Met Glu His Leu Gly Gly Gly Gly Gly Val
1               5                   10                  15

Tyr Gly Phe Val Arg Ala Cys Leu
            20

<210> SEQ ID NO 239
<211> LENGTH: 22
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (10)..(10)
<223> OTHER INFORMATION: Xaa stands for D-Alanine
<220> FEATURE:
<221> NAME/KEY: MISC_FEATURE
<222> LOCATION: (22)..(22)
<223> OTHER INFORMATION: Xaa stands for D-Alanine

<400> SEQUENCE: 239

Lys Ile Phe Gly Ser Leu Ala Phe Leu Xaa Lys Phe Val Ala Ala Trp
1               5                   10                  15

Thr Leu Lys Ala Ala Xaa
            20

<210> SEQ ID NO 240
<211> LENGTH: 28
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (16)..(16)
<223> OTHER INFORMATION: Xaa stands for D-Alanine
<220> FEATURE:
<221> NAME/KEY: MISC_FEATURE
<222> LOCATION: (28)..(28)
<223> OTHER INFORMATION: Xaa stands for D-Alanine

<400> SEQUENCE: 240

Lys Ile Phe Gly Ser Leu Ala Phe Leu Gly Gly Gly Gly Gly Xaa
1               5                   10                  15

Lys Phe Val Ala Ala Trp Thr Leu Lys Ala Ala Xaa
            20                  25

<210> SEQ ID NO 241
```

```
<211> LENGTH: 22
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa stands for D-Alanine
<220> FEATURE:
<221> NAME/KEY: MISC_FEATURE
<222> LOCATION: (13)..(13)
<223> OTHER INFORMATION: Xaa stands for D-Alanine

<400> SEQUENCE: 241

Xaa Lys Phe Val Ala Ala Trp Thr Leu Lys Ala Ala Xaa Lys Ile Phe
1               5                   10                  15

Gly Ser Leu Ala Phe Leu
            20

<210> SEQ ID NO 242
<211> LENGTH: 28
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa stands for D-Alanine
<220> FEATURE:
<221> NAME/KEY: MISC_FEATURE
<222> LOCATION: (13)..(13)
<223> OTHER INFORMATION: Xaa stands for D-Alanine

<400> SEQUENCE: 242

Xaa Lys Phe Val Ala Ala Trp Thr Leu Lys Ala Ala Xaa Gly Gly Gly
1               5                   10                  15

Gly Gly Gly Lys Ile Phe Gly Ser Leu Ala Phe Leu
            20                  25

<210> SEQ ID NO 243
<211> LENGTH: 9
<212> TYPE: PRT
<213> ORGANISM: Artificial Sequence
<220> FEATURE:
<223> OTHER INFORMATION: Peptide
<220> FEATURE:
<221> NAME/KEY: MOD_RES
<222> LOCATION: (1)..(1)
<223> OTHER INFORMATION: Lysine is protected by Fmoc and Boc groups
<220> FEATURE:
<221> NAME/KEY: MOD_RES
<222> LOCATION: (5)..(5)
<223> OTHER INFORMATION: Serine is protected by a tBu group
<220> FEATURE:
<221> NAME/KEY: MOD_RES
<222> LOCATION: (9)..(9)
<223> OTHER INFORMATION: Leucine is bonded to Alko-resin

<400> SEQUENCE: 243

Lys Ile Phe Gly Ser Leu Ala Phe Leu
1               5

<210> SEQ ID NO 244
<211> LENGTH: 10
<212> TYPE: PRT
<213> ORGANISM: Artificial Sequence
<220> FEATURE:
<223> OTHER INFORMATION: Peptide
<220> FEATURE:
```

```
<221> NAME/KEY: MOD_RES
<222> LOCATION: (1)..(1)
<223> OTHER INFORMATION: Cysteine is protected by a tBu group
<220> FEATURE:
<221> NAME/KEY: MOD_RES
<222> LOCATION: (2)..(2)
<223> OTHER INFORMATION: Lysine is protected by a Boc group
<220> FEATURE:
<221> NAME/KEY: MOD_RES
<222> LOCATION: (6)..(6)
<223> OTHER INFORMATION: Serine is protected by a tBu group
<220> FEATURE:
<221> NAME/KEY: MOD_RES
<222> LOCATION: (10)..(10)
<223> OTHER INFORMATION: Leucine is bonded to Alko-resin

<400> SEQUENCE: 244

Cys Lys Ile Phe Gly Ser Leu Ala Phe Leu
1               5                   10

<210> SEQ ID NO 245
<211> LENGTH: 9
<212> TYPE: PRT
<213> ORGANISM: Artificial Sequence
<220> FEATURE:
<223> OTHER INFORMATION: Peptide
<220> FEATURE:
<221> NAME/KEY: MOD_RES
<222> LOCATION: (1)..(1)
<223> OTHER INFORMATION: Lysine is protected by a Boc group
<220> FEATURE:
<221> NAME/KEY: MOD_RES
<222> LOCATION: (5)..(5)
<223> OTHER INFORMATION: Serine is protected by a tBu group
<220> FEATURE:
<221> NAME/KEY: MOD_RES
<222> LOCATION: (9)..(9)
<223> OTHER INFORMATION: Leucine is bonded to Alko-resin

<400> SEQUENCE: 245

Lys Ile Phe Gly Ser Leu Ala Phe Leu
1               5

<210> SEQ ID NO 246
<211> LENGTH: 10
<212> TYPE: PRT
<213> ORGANISM: Artificial Sequence
<220> FEATURE:
<223> OTHER INFORMATION: Peptide
<220> FEATURE:
<221> NAME/KEY: MOD_RES
<222> LOCATION: (1)..(1)
<223> OTHER INFORMATION: Cysteine has a disulfide bond to
      2-mercaptopyridine

<400> SEQUENCE: 246

Cys Gly Leu Tyr Asp Gly Met Glu His Leu
1               5                   10

<210> SEQ ID NO 247
<211> LENGTH: 10
<212> TYPE: PRT
<213> ORGANISM: Artificial Sequence
<220> FEATURE:
<223> OTHER INFORMATION: Peptide
<220> FEATURE:
<221> NAME/KEY: MOD_RES
<222> LOCATION: (1)..(1)
<223> OTHER INFORMATION: Cysteine has a disulfide bond to
      2-mercaptopyridine

<400> SEQUENCE: 247
```

```
<210> SEQ ID NO 248
<211> LENGTH: 12
<212> TYPE: PRT
<213> ORGANISM: Artificial Sequence
<220> FEATURE:
<223> OTHER INFORMATION: Peptide
<220> FEATURE:
<221> NAME/KEY: MOD_RES
<222> LOCATION: (1)..(1)
<223> OTHER INFORMATION: Cysteine is protected by a 4-methoxytrityl
      group

<400> SEQUENCE: 248

Cys Ala Cys Gly Leu Tyr Asp Gly Met Glu His Leu
1               5                   10

<210> SEQ ID NO 249
<211> LENGTH: 14
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa stands for D-Alanine
<220> FEATURE:
<221> NAME/KEY: MISC_FEATURE
<222> LOCATION: (13)..(13)
<223> OTHER INFORMATION: Xaa stands for D-Alanine
<220> FEATURE:
<221> NAME/KEY: MOD_RES
<222> LOCATION: (14)..(14)
<223> OTHER INFORMATION: Cysteine has a disulfide bond to
      2-mercaptopyridine

<400> SEQUENCE: 249

Xaa Lys Phe Val Ala Ala Trp Thr Leu Lys Ala Ala Xaa Cys
1               5                   10
```

CONJUGATE VACCINE USING TRIMMING FUNCTION OF ERAP1

TECHNICAL FIELD

The present invention belongs to the field of cancer immunotherapy, and relates to a conjugate vaccine wherein cancer antigen peptide precursors are conjugated via a sulfur-sulfur covalent bond, which can be subjected to trimming by a particular peptidase and efficiently induces cytotoxic T cells.

BACKGROUND ART

For eradication of cancer cells in the body, cellular immunity, particularly cytotoxic T cells (cytotoxic T-lymphocytes, Cytotoxic T-cells, hereinafter to be referred to as CTLs) mainly play an important role. CTLs are produced by differentiation and proliferation of precursor T cells that have recognized a complex formed by an antigen peptide derived from a cancer antigen protein (cancer antigen peptide) and an MHC class I molecule, and attacks cancer cells. MHC in human is called human leukocyte-type antigen (HLA), and HLA subtypes such as HLA-A, B, Cw, F and G are known.

A cancer antigen peptide is produced through degradation (processing) of a cancer antigen protein synthesized in cancer cells, i.e., protein denaturation by reduction of a sulfur-sulfur covalent bond, degradation by proteosome or protease, cleavage into an optimum length by a trimming enzyme in the endoplasmic reticulum of the protein. The cancer antigen protein generally consists of 8-12 amino acid residues.

In cancer immunotherapy, activation of helper T cells is also important for activating other T cells including CTLs. In general, an antigen protein is degraded by intracellular lysosome, and a part of the peptide fragments, each of which is a peptide consisting of about 13-17 amino acid residues, binds as an antigen peptide to MHC class II molecule and is presented to helper T cell-TCR.CD3 complex to activate helper T cells. In human, HLA subtypes such as HLA-DR, DQ and DP are known.

As an antigen of a cancer vaccine, a cancer antigen protein itself or an antigen peptide derived from a cancer antigen protein is mainly used (see Non Patent Literature 1). Since a cancer vaccine using a protein generally contains various cancer antigen peptides, it can simultaneously induce a plurality of CTLs and helper T cells. However, the cancer protein vaccine possesses problems in stable supply and quality control. On the other hand, a cancer vaccine using a peptide can be conveniently produced or quality-controlled, but is mainly constituted by a single MHC class I-presented peptide antigen. Thus, it has been pointed out in recent years that efficient induction of CTLs requires further improvement (see Non Patent Literature 2).

One of the solutions for such problems is a multivalent antigen peptide-presenting peptide cancer vaccine. As such peptide cancer vaccines, a cocktail vaccine containing a mixture of a plurality of peptide antigens to be presented by MHC class I and class II, a long chain peptide vaccine containing peptide antigens to be presented by MHC class I and class II which are bound by an amide bond, and the like have been reported (see Non Patent Literature 2). In the case of a cocktail vaccine, however, since each peptide antigen composed of various amino acids shows various physical properties, the development of an optimal formulation capable of efficiently inducing CTLs corresponding thereto is often problematic. In the case of a long chain peptide vaccine, its production sometimes has problems similar to those of production of a protein. Furthermore, since the peptide antigens to be presented by class I and class II are bonded via a peptide spacer in a long chain peptide vaccine, it is difficult to control and predict the cleavage sites by intracellular enzyme. In the meantime, a peptide dimer wherein two peptide monomers are mutually bonded by a disulfide bond has been reported (see Patent Literature 1). Different from cocktail vaccine, a homodimer has two single peptides being bonded, and therefore, they have single physical property and can be produced conveniently. On the other hand, cancer antigen peptides are required to contain cysteine in their amino acid sequences, and therefore, applicable peptides are limited.

The process of presentation of a cancer antigen peptide on MHC class I involves a plurality of peptidases. Of such peptidases, Endoplasmic reticulum aminopeptidase 1 (hereinafter to be referred to as ERAP1) is one of the trimming enzymes in the endoplasmic reticulum (hereinafter to be referred to as ER), and has been reported to recognize a particular antigen peptide sequence and peptide length, and cleaves a cancer antigen peptide precursor from the N-terminal to control the length to be optimal for binding to MHC class I (see Non Patent Literature 3). However, there is no report to date on a conjugate vaccine using the trimming function of ERAP1. Moreover, although ERAP1 has been reported to convert a precursor peptide to a cancer antigen peptide by cleaving dicysteine from the N-terminal, it has been unclear whether the trimming is affected when an amino acid sequence containing cysteine is introduced to the N-terminal (see non-patent documents 3-6).

CITATION LIST

Patent Literature

Patent Literature 1: WO 2004/063217

Non Patent Literature

Non Patent Literature 1: Nature Reviews Drug Discovery, 2009; 8; 685-686
Non Patent Literature 2: Cancer Journal, 2011; 17(5); 343-350
Non Patent Literature 3: Proceedings of the National Academy of Sciences of United States of America, 2005; 102(47); 17107-17112
Non Patent Literature 4: PLoS One, 2008; 3(11); e3658; 1-12
Non Patent Literature 5: The Journal of Immunology, 2009; 183; 5526-5536
Non Patent Literature 6: The Journal of Immunology, 2010; 184; 4725-4732

SUMMARY OF INVENTION

Technical Problem

The problem to be solved by the present invention is to provide a conjugate vaccine that induces CTLs efficiently.

Solution to Problem

The present inventors have conducted intensive studies in an attempt to solve the aforementioned problem, and conceived, when considering adopting conjugate vaccine, an idea of adding cysteine in a cancer antigen peptide, and further confirmed that the results of pharmacological tests using in vivo animal model or other tests strongly suggest that ERAP1 cleaves amino acids residues including cysteine extended from the N-terminal in diverse cancer antigen peptides generated by intracellular reductive cleavage of disulfide bond, and efficiently converts those peptides to cancer antigen peptides, which in turn led to the finding of preparation of a multivalent antigen peptide-presenting conjugate vaccine capable of inducing CTLs in the body, and the completion of the present invention.

To be specific, during the process of studying the solving means to the above-mentioned problem, the present inventors have obtained an idea of a method for introducing cysteine, which is necessary for forming a conjugate of two different cancer antigen peptides, into a desired position of the N-terminal or C-terminal, without influencing the antigen presentation by MHC class I. As a result of further study, the present inventors have created a peptide by introducing 0-5 amino acids containing cysteine into the N terminal of a cancer antigen peptide, and a conjugate of the peptides containing a disulfide bond via cysteine. Furthermore, the present inventors have confirmed for the first time that such peptides and conjugates are susceptible to trimming by ERAP1 in vitro and/or in vivo, which in turn results in the formation of a cancer antigen peptide, and thereby, completed the present invention.

It has been desired to develop a novel multivalent antigen peptide-presenting peptide cancer vaccine that can be produced easily, is applicable to various peptides, and induces CTLs with high efficiency. The conjugate invented by the present inventors has enabled the development of a multivalent antigen peptide-presenting peptide cancer vaccine that induces CTLs efficiently, has superior physicochemical properties, can be produced easily, facilitates production management, and is applicable to various peptides.

Accordingly, the present invention relates to the following.
1. A compound represented by formula (1):

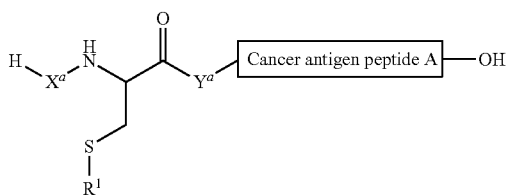

or a pharmaceutically acceptable salt thereof,
wherein $X^a$ and $Y^a$ are each independently a single bond or a divalent peptide group consisting of 1-4 amino acid residues, and a total of the amino acid residue number for $X^a$ and the amino acid residue number for $Y^a$ is an integer of 0-4,
cancer antigen peptide A is an MHC class I-restricted cancer antigen peptide consisting of 7-30 amino acid residues, an amino group of an N-terminal amino acid of the cancer antigen peptide A binds to $Y^a$ in the formula (1), and a carbonyl group of a C-terminal amino acid of the cancer antigen peptide A binds to a hydroxyl group in the formula (1), and $R^1$ is a hydrogen atom; a group represented by formula (2):

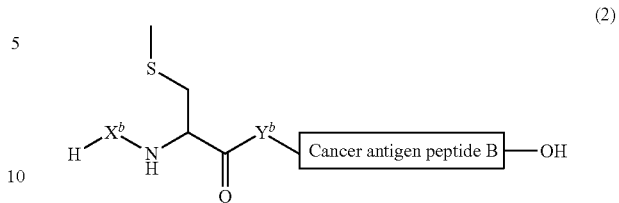

wherein $X^b$ and $Y^b$ are each independently a single bond or a divalent peptide group consisting of 1-4 amino acid residues, and a total of the amino acid residue number for $X^b$ and the amino acid residue number for $Y^b$ is an integer of 0-4,
cancer antigen peptide B is different in sequence from the cancer antigen peptide A, and is an MHC class I-restricted cancer antigen peptide consisting of 7-30 amino acid residues or an MHC class II-restricted cancer antigen peptide consisting of 7-30 amino acid residues, an amino group of an N-terminal amino acid of the cancer antigen peptide B binds to $Y^b$ in the formula (2), and a carbonyl group of a C-terminal amino acid of the cancer antigen peptide B binds to a hydroxyl group in the formula (2), and a thioether group in the formula (2) binds to a thioether group in the formula (1);
a group represented by formula (3):

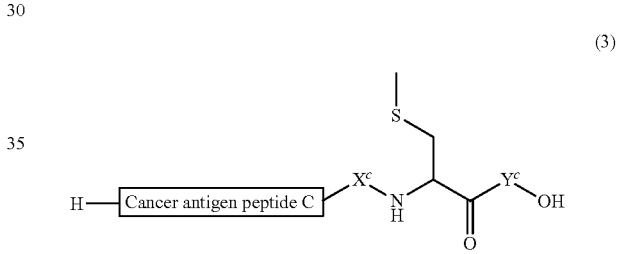

wherein $X^c$ and $Y^c$ are each independently a single bond or a divalent peptide group consisting of 1-4 amino acid residues, and a total of the amino acid residue number for $X^c$ and the amino acid residue number for $Y^c$ is an integer of 0-4,
cancer antigen peptide C is an MHC class II-restricted cancer antigen peptide consisting of 7-30 amino acid residues, a carbonyl group of a C-terminal amino acid of the cancer antigen peptide C binds to $X^c$ in the formula (3), and an amino group of an N-terminal amino acid of the cancer antigen peptide C binds to a hydrogen atom in the formula (3), and
a thioether group in the formula (3) binds to a thioether group in the formula (1);
or cancer antigen peptide D, wherein the cancer antigen peptide D is an MHC class I-restricted cancer antigen peptide consisting of 7-30 amino acid residues containing one cysteine residue or an MHC class II-restricted cancer antigen peptide consisting of 7-30 amino acid residues containing one cysteine residue, and a thioether group of the cysteine residue of the cancer antigen peptide D binds to a thioether group in the formula (1),
provided when $R^1$ is a hydrogen atom, the sequence of the compound represented by the formula (1) is not identical to the partial sequence of a cancer antigen protein;
2. the compound according to 1, wherein $X^a$ is a divalent peptide group consisting of 2 amino acid residues and $Y^a$ is a single bond, or X$^a$ and Y$^a$ are each independently a divalent peptide group consisting of 1 amino acid residue, or X$^a$ is a single bond and Y$^a$ is a divalent peptide group consisting of 2 amino acid residues, or X$^a$ is a divalent peptide group consisting of 1 amino acid residue and Y$^a$ is a single bond, or X$^a$ is a single bond and Y$^a$ is a divalent peptide group consisting of 1 amino acid residue, or X$^a$ and Y$^a$ are each a single bond, or a pharmaceutically acceptable salt thereof;

3. the compound according to 1 or 2, wherein X$^a$ is a single bond, and Y$^a$ is a single bond, an alanine residue, a leucine residue or a methionine residue, or a pharmaceutically acceptable salt thereof;

4. the compound according to 1 or 2, wherein X$^a$ is a single bond, an alanine residue, a glycine residue, a serine residue or a tyrosine residue, and Y$^a$ is a single bond, or a pharmaceutically acceptable salt thereof;

5. the compound according to any one of 1-4, wherein X$^a$ and Y$^a$ are each a single bond, or a pharmaceutically acceptable salt thereof;

6. the compound according to any one of 1-5, wherein the cancer antigen peptide A consists of 7-15 amino acid residues and is an HLA-A, HLA-B or HLA-Cw-restricted cancer antigen peptide, or a pharmaceutically acceptable salt thereof;

7. the compound according to any one of 1-6, wherein the cancer antigen peptide A consists of 7-15 amino acid residues and is an HLA-A1, HLA-A2, HLA-A3, HLA-A11, HLA-A24, HLA-A28, HLA-A29, HLA-A31, HLA-A33, HLA-A34, HLA-A68, HLA-B7, HLA-B13, HLA-B35, HLA-B37, HLA-B44, HLA-B45, HLA-B51, HLA-B52, HLA-B53, HLA-Cw2, HLA-Cw3, HLA-Cw6, HLA-Cw7, HLA-Cw8 or HLA-Cw16-restricted cancer antigen peptide, or a pharmaceutically acceptable salt thereof;

8. the compound according to any one of 1-7, wherein the cancer antigen peptide A is an MHC class I cancer antigen peptide derived from a cancer antigen protein selected from the group consisting of MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-3, GAGE-4, GAGE-5, GAGE-6, GAGE-7B, GAGE-8, NA88-A, NY-ESO-1, NY-ESO-1a, MART-1/Melan-A, MC1R, Gp100, PSA, PSM, Tyrosinase, Proteinase 3, TRP-1, TRP-2, ART-4, CAMEL, CEA, Ep-CAM, Cyp-B, Her2/neu, VEGFR, hTERT, hTRT, iCE, MUC1, MUC2, PRAME, P15, RU1, RU2, SART-1, SART-2, SART-3, AFP, β-Catenin, Caspase-8, CDK-4, ELF2, GnT-V, G250, HSP70-2M, HST-2, KIAA0205, MUM-1, MUM-2, MUM-3, Myosin, RAGE, SART-2, TRP-2, 707-AP, Survivin, Livin and SYT-SSX, or a pharmaceutically acceptable salt thereof;

9. the compound according to any one of 1-8, wherein the cancer antigen peptide A is a peptide comprising an amino acid sequence selected from the following amino acid sequences:

```
                                    (SEQ ID NO: 3)
NYKHCFPEI, (SEQ ID NO: 11)
EYLQLVFGI, (SEQ ID NO: 13)
FLWGPRALV, (SEQ ID NO: 19)
GLYDGMEHL,
```

```
                                    (SEQ ID NO: 26)
SLLMWITQCFL, (SEQ ID NO: 27)
QLSLLMWIT, (SEQ ID NO: 29)
AAGIGILTV, (SEQ ID NO: 33)
LIYRRRLMK, (SEQ ID NO: 40)
YMDGTMSQV, (SEQ ID NO: 41)
AFLPWHRLF, (SEQ ID NO: 43)
VLQELNVTV, (SEQ ID NO: 50)
YLSGANLNL, (SEQ ID NO: 53)
KIFGSLAFL, (SEQ ID NO: 66)
AYIDFEMKI, (SEQ ID NO: 83)
AYACNTSTL, (SEQ ID NO: 84)
KWFPSCQFLL
and (SEQ ID NO: 85)
GYDQIMPKK,
``` or a peptide comprising an altered amino acid sequence which is an amino acid sequence selected from SEQ ID NOs: 3, 11, 13, 19, 26, 27, 29, 33, 40, 41, 43, 50, 53, 66, 83, 84 and 85 but containing alteration of amino acid residue(s), and having a CTL induction activity, or a pharmaceutically acceptable salt thereof;

10. the compound according to any one of 1-9, wherein the cancer antigen peptide A is a peptide consisting of an amino acid sequence selected from the following amino acid sequences:

```
                                    (SEQ ID NO: 19)
GLYDGMEHL, (SEQ ID NO: 43)
VLQELNVTV
and (SEQ ID NO: 53)
KIFGSLAFL,
``` or a pharmaceutically acceptable salt thereof;

11. the compound according to any one of 1-10, wherein R$^1$ is a hydrogen atom, or a pharmaceutically acceptable salt thereof;

12. the compound according to any one of 1-3 and 6-11, wherein the compound represented by the formula (1) is a peptide consisting of an amino acid sequence selected from the following amino acid sequences:

CAGLYDGMEHL, (SEQ ID NO: 89)

CLGLYDGMEHL, (SEQ ID NO: 90)

CMGLYDGMEHL, (SEQ ID NO: 91)

CAVLQELNVTV, (SEQ ID NO: 92)

CLVLQELNVTV, (SEQ ID NO: 93)

CMVLQELNVTV, (SEQ ID NO: 94)

CAKIFGSLAFL, (SEQ ID NO: 95)

CLKIFGSLAFL (SEQ ID NO: 96)
and

CMKIFGSLAFL, (SEQ ID NO: 97)

or a pharmaceutically acceptable salt thereof;
13. the compound according to any one of 1-11, wherein the compound represented by the formula (1) is a peptide consisting of an amino acid sequence selected from the following amino acid sequences:

CGLYDGMEHL, (SEQ ID NO: 98)

CVLQELNVTV (SEQ ID NO: 99)
and

CKIFGSLAFL, (SEQ ID NO: 100)

or a pharmaceutically acceptable salt thereof;
14. the compound according to any one of 1-10, wherein $R^1$ is a group represented by the formula (2), or a pharmaceutically acceptable salt thereof;
15. the compound according to any one of 1-10 and 14, wherein $X^b$ is a divalent peptide group consisting of 2 amino acid residues and $Y^b$ is a single bond, or $X^b$ and $Y^b$ are each independently a divalent peptide group consisting of 1 amino acid residue, or $X^b$ is a single bond and $Y^b$ is a divalent peptide group consisting of 2 amino acid residues, or $X^b$ is a divalent peptide group consisting of 1 amino acid residue and $Y^b$ is a single bond, or $X^b$ is a single bond and $Y^b$ is a divalent peptide group consisting of 1 amino acid residue, or $X^b$ and $Y^b$ are each a single bond, or a pharmaceutically acceptable salt thereof;
16. the compound according to any one of 1-10 and 14-15, wherein $X^b$ is a single bond, and $Y^b$ is a single bond, an alanine residue, a leucine residue or a methionine residue, or a pharmaceutically acceptable salt thereof;
17. the compound according to any one of 1-10 and 14-15, wherein $X^b$ is a single bond or a divalent peptide group consisting of 1 amino acid residue, and $Y^b$ is a single bond, or a pharmaceutically acceptable salt thereof;
18. the compound according to any one of 1-10 and 14-17, wherein $X^b$ and $Y^b$ are each a single bond, or a pharmaceutically acceptable salt thereof;
19. the compound according to any one of 1-10 and 14-18, wherein the cancer antigen peptide B is an MHC class I-restricted cancer antigen peptide consisting of 7-15 amino acid residues, or a pharmaceutically acceptable salt thereof;
20. the compound according to any one of 1-10 and 14-19, wherein the cancer antigen peptide B consists of 7-15 amino acid residues and is an HLA-A, HLA-B or HLA-Cw-restricted cancer antigen peptide, or a pharmaceutically acceptable salt thereof;
21. the compound according to any one of 1-10 and 14-20, wherein the cancer antigen peptide B consists of 7-15 amino acid residues and is an HLA-A1, HLA-A2, HLA-A3, HLA-A11, HLA-A24, HLA-A28, HLA-A29, HLA-A31, HLA-A33, HLA-A34, HLA-A68, HLA-B7, HLA-B13, HLA-B35, HLA-B37, HLA-B44, HLA-B45, HLA-B51, HLA-B52, HLA-B53, HLA-Cw2, HLA-Cw3, HLA-Cw6, HLA-Cw7, HLA-Cw8 or HLA-Cw16-restricted cancer antigen peptide, or a pharmaceutically acceptable salt thereof;
22. the compound according to any one of 1-10 and 14-21, wherein the cancer antigen peptide B is an MHC class I cancer antigen peptide derived from a cancer antigen protein selected from the group consisting of MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-3, GAGE-4, GAGE-5, GAGE-6, GAGE-7B, GAGE-8, NA88-A, NY-ESO-1, NY-ESO-1a, MART-1/Melan-A, MC1R, Gp100, PSA, PSM, Tyrosinase, Proteinase 3, TRP-1, TRP-2, ART-4, CAMEL, CEA, Ep-CAM, Cyp-B, Her2/neu, VEGFR, hTERT, hTRT, iCE, MUC1, MUC2, PRAME, P15, RU1, RU2, SART-1, SART-2, SART-3, AFP, β-Catenin, Caspase-8, CDK-4, ELF2, GnT-V, G250, HSP70-2M, HST-2, KIAA0205, MUM-1, MUM-2, MUM-3, Myosin, RAGE, SART-2, TRP-2, 707-AP, Survivin, Livin and SYT-SSX, or a pharmaceutically acceptable salt thereof;
23. the compound according to any one of 1-10 and 14-22, wherein the cancer antigen peptide B is a peptide comprising an amino acid sequence selected from the following amino acid sequences:

NYKHCFPEI, (SEQ ID NO: 3)

EYLQLVFGI, (SEQ ID NO: 11)

FLWGPRALV, (SEQ ID NO: 13)

GLYDGMEHL, (SEQ ID NO: 19)

SLLMWITQCFL, (SEQ ID NO: 26)

QLSLLMWIT, (SEQ ID NO: 27)

AAGIGILTV, (SEQ ID NO: 29)

LIYRRRLMK, (SEQ ID NO: 33)

YMDGTMSQV, (SEQ ID NO: 40)

AFLPWHRLF, (SEQ ID NO: 41)

VLQELNVTV, (SEQ ID NO: 43)

YLSGANLNL, (SEQ ID NO: 50)

-continued

```
                   (SEQ ID NO: 53)
KIFGSLAFL, (SEQ ID NO: 66)
AYIDFEMKI, (SEQ ID NO: 83)
AYACNTSTL, (SEQ ID NO: 84)
KWFPSCQFLL
and (SEQ ID NO: 85)
GYDQIMPKK,
``` or a peptide comprising an altered amino acid sequence which is an amino acid sequence selected from SEQ ID NOs: 3, 11, 13, 19, 26, 27, 29, 33, 40, 41, 43, 50, 53, 66, 83, 84 and 85 but containing alteration of amino acid residue(s), and having a CTL induction activity, or a pharmaceutically acceptable salt thereof;

24. the compound according to any one of 1-10 and 14-23, wherein the cancer antigen peptide B is a peptide consisting of an amino acid sequence selected from the following amino acid sequences:

```
                   (SEQ ID NO: 19)
GLYDGMEHL, (SEQ ID NO: 43)
VLQELNVTV
and (SEQ ID NO: 53)
KIFGSLAFL,
``` or a pharmaceutically acceptable salt thereof;

25. the compound according to any one of 1-10 and 14-24, wherein the compound represented by the formula (1) is a compound represented by the formula (4):

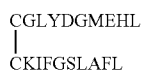

(4)

wherein the bond between C and C is a disulfide bond, or a compound represented by the formula (5):

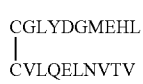

(5)

wherein the bond between C and C is a disulfide bond, or a pharmaceutically acceptable salt thereof;

26. the compound according to any one of 1-10, 14 and 15, wherein when $X^b$ is a divalent peptide group consisting of 2 amino acid residues containing a cysteine residue and $Y^b$ is a single bond, or $X^b$ is a single bond and $Y^b$ is a divalent peptide group consisting of 2 amino acid residues containing a cysteine residue, a thioether group in the cysteine residue of $X^b$ or a thioether group in the cysteine residue of $Y^b$ binds to a thioether group in the formula (20):

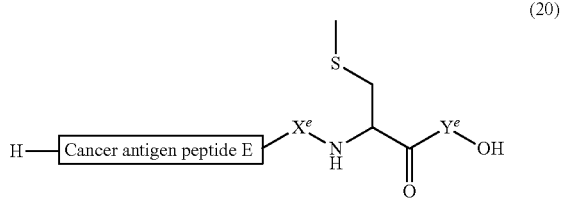

(20)

wherein $X^e$ and $Y^e$ are each independently a single bond or a divalent peptide group consisting of 1-4 amino acid residues, and a total of the amino acid residue number for $X^e$ and the amino acid residue number for $Y^e$ is an integer of 0-4, cancer antigen peptide E is an MHC class II-restricted cancer antigen peptide consisting of 7-30 amino acid residues, a carbonyl group of a C-terminal amino acid of the cancer antigen peptide E binds to $X^e$ in the formula (20), and an amino group of an N-terminal amino acid of the cancer antigen peptide E binds to a hydrogen atom in the formula (20), or a pharmaceutically acceptable salt thereof;

27. the compound according to 26, wherein $X^b$ is a divalent dipeptide group consisting of CA and $Y^b$ is a single bond, or $X^b$ is a single bond and $Y^b$ is a divalent dipeptide group consisting of CA, or a pharmaceutically acceptable salt thereof;

28. the compound according to 26 or 27, wherein the cancer antigen peptide B is an MHC class I-restricted cancer antigen peptide consisting of 7-15 amino acid residues, or a pharmaceutically acceptable salt thereof;

29. the compound according to any one of 26-28, wherein the cancer antigen peptide B consists of 7-15 amino acid residues and is an HLA-A, HLA-B or HLA-Cw-restricted cancer antigen peptide, or a pharmaceutically acceptable salt thereof;

30. the compound according to any one of 26-29, wherein the cancer antigen peptide B consists of 7-15 amino acid residues and is an HLA-A1, HLA-A2, HLA-A3, HLA-A11, HLA-A24, HLA-A28, HLA-A29, HLA-A31, HLA-A33, HLA-A34, HLA-A68, HLA-B7, HLA-B13, HLA-B35, HLA-B37, HLA-B44, HLA-B45, HLA-B51, HLA-B52, HLA-B53, HLA-Cw2, HLA-Cw3, HLA-Cw6, HLA-Cw7, HLA-Cw8 or HLA-Cw16-restricted cancer antigen peptide, or a pharmaceutically acceptable salt thereof;

31. the compound according to any one of 26-30, wherein the cancer antigen peptide B is an MHC class I cancer antigen peptide derived from a cancer antigen protein selected from the group consisting of MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-3, GAGE-4, GAGE-5, GAGE-6, GAGE-7B, GAGE-8, NA88-A, NY-ESO-1, NY-ESO-1a, MART-1/Melan-A, MC1R, Gp100, PSA, PSM, Tyrosinase, Proteinase 3, TRP-1, TRP-2, ART-4, CAMEL, CEA, Ep-CAM, Cyp-B, Her2/neu, VEGFR, hTERT, hTRT, iCE, MUC1, MUC2, PRAME, P15, RU1, RU2, SART-1, SART-2, SART-3, AFP, β-Catenin, Caspase-8, CDK-4, ELF2, GnT-V, G250, HSP70-2M, HST-2, KIAA0205, MUM-1, MUM-2, MUM-3, Myosin, RAGE, SART-2, TRP-2, 707-AP, Survivin, Livin and SYT-SSX, or a pharmaceutically acceptable salt thereof;

32. the compound according to any one of 26-31, wherein the cancer antigen peptide B is a peptide comprising an amino acid sequence selected from the following amino acid sequences:

```
NYKHCFPEI,      (SEQ ID NO: 3)

EYLQLVFGI,      (SEQ ID NO: 11)

FLWGPRALV,      (SEQ ID NO: 13)

GLYDGMEHL,      (SEQ ID NO: 19)

SLLMWITQCFL,    (SEQ ID NO: 26)

QLSLLMWIT,      (SEQ ID NO: 27)

AAGIGILTV,      (SEQ ID NO: 29)

LIYRRRLMK,      (SEQ ID NO: 33)

YMDGTMSQV,      (SEQ ID NO: 40)

AFLPWHRLF,      (SEQ ID NO: 41)

VLQELNVTV,      (SEQ ID NO: 43)

YLSGANLNL,      (SEQ ID NO: 50)

KIFGSLAFL,      (SEQ ID NO: 53)

AYIDFEMKI,      (SEQ ID NO: 66)

AYACNTSTL,      (SEQ ID NO: 83)

KWFPSCQFLL      (SEQ ID NO: 84)
and

GYDQIMPKK,      (SEQ ID NO: 85)
``` or a peptide comprising an altered amino acid sequence which is an amino acid sequence selected from SEQ ID NOs: 3, 11, 13, 19, 26, 27, 29, 33, 40, 41, 43, 50, 53, 66, 83, 84 and 85 but containing alteration of amino acid residue(s), and having a CTL induction activity, or a pharmaceutically acceptable salt thereof;

33. the compound according to any one of 26-32, wherein the cancer antigen peptide B is a peptide consisting of an amino acid sequence selected from the following amino acid sequences:

```
GLYDGMEHL,      (SEQ ID NO: 19)

VLQELNVTV       (SEQ ID NO: 43)
and

KIFGSLAFL,      (SEQ ID NO: 53)
``` or a pharmaceutically acceptable salt thereof;

34. the compound according to any one of 26-33, wherein $X^e$ is a divalent peptide group consisting of 2 amino acid residues and $Y^e$ is a single bond, $X^e$ and $Y^e$ are each independently a divalent peptide group consisting of 1 amino acid residue, $X^e$ is a single bond and $Y^e$ is a divalent peptide group consisting of 2 amino acid residues, $X^e$ is a divalent peptide group consisting of 1 amino acid residue and $Y^e$ is a single bond, $X^e$ is a single bond and $Y^e$ is a divalent peptide group consisting of 1 amino acid residue, or $X^e$ and $Y^e$ are each a single bond, or a pharmaceutically acceptable salt thereof;

35. the compound according to any one of 26-34, wherein $X^e$ is a single bond, and $Y^e$ is a single bond, an alanine residue, a leucine residue or a methionine residue, or a pharmaceutically acceptable salt thereof;

36. the compound according to any one of 26-34, wherein $X^e$ is a single bond or a divalent peptide group consisting of 1 amino acid residue, and $Y^e$ is a single bond, or a pharmaceutically acceptable salt thereof;

37. the compound according to any one of 26-36, wherein $X^e$ and $Y^e$ are each a single bond, or a pharmaceutically acceptable salt thereof;

38. the compound according to any one of 26-37, wherein the cancer antigen peptide E is an MHC class II-restricted cancer antigen peptide consisting of 7-15 amino acid residues, or a pharmaceutically acceptable salt thereof;

39. the compound according to any one of 26-38, wherein the cancer antigen peptide E consists of 7-15 amino acid residues and is an HLA-DR, HLA-DQ or HLA-DP-restricted cancer antigen peptide, or a pharmaceutically acceptable salt thereof;

40. the compound according to any one of 26-39, wherein the cancer antigen peptide E is an HLA-DR-restricted universal cancer antigen peptide consisting of 13-15 amino acid residues, or a pharmaceutically acceptable salt thereof;

41. the compound according to any one of 26-40, wherein the cancer antigen peptide E is a peptide comprising an amino acid sequence selected from the following amino acid sequences:

```
AKFVAAWTLKAAA   (SEQ ID NO: 101)
and aKFVAAWTLKAAa,  (SEQ ID NO: 102)
``` or a peptide comprising an altered amino acid sequence which is an amino acid sequence selected from SEQ ID NOs: 101 and 102 but containing alteration of amino acid residue(s), and having a helper T cell induction activity, or a pharmaceutically acceptable salt thereof;

42. the compound according to any one of 26-41, wherein the cancer antigen peptide E is a peptide consisting of an amino acid sequence selected from the following amino acid sequences:

```
AKFVAAWTLKAAA   (SEQ ID NO: 101)
and aKFVAAWTLKAAa,  (SEQ ID NO: 102)
``` or a pharmaceutically acceptable salt thereof;

43. the compound according to any one of 1-10, 14, 15 and 26-42, wherein the compound represented by the formula (1) is a compound represented by the formula (19):

```
      CKIFGSLAFL                                          (19)
       |
      CACGLYDGMEHL
              |
  aKFVAAWTLKAAaC
``` wherein the bond between C and C is a disulfide bond,
or a compound represented by the formula (21):

```
      CKIFGSLAFL                                          (21)
       |
      CACGLYDGMEHL
              |
  aKFVAAWTLKAAaC
``` wherein the bond between C and C is a disulfide bond,
or a pharmaceutically acceptable salt thereof;

44. the compound according to any one of 1-10 and 14-18, wherein the cancer antigen peptide B is an MHC class II-restricted cancer antigen peptide consisting of 7-15 amino acid residues, or a pharmaceutically acceptable salt thereof;

45. the compound according to any one of 1-10, 14-18 and 26, wherein the cancer antigen peptide B consists of 7-15 amino acid residues and is an HLA-DR, HLA-DQ or HLA-DP-restricted cancer antigen peptide, or a pharmaceutically acceptable salt thereof;

46. the compound according to any one of 1-10, 14-18, 44 and 45, wherein the cancer antigen peptide B is an HLA-DR-restricted universal cancer antigen peptide consisting of 13-15 amino acid residues, or a pharmaceutically acceptable salt thereof;

47. the compound according to any one of 1-10, 14-18 and 44-46, wherein the cancer antigen peptide B is a peptide comprising an amino acid sequence selected from the following amino acid sequences:

```
                                                    (SEQ ID NO: 101)
AKFVAAWTLKAAA
and
                                                    (SEQ ID NO: 102)
aKFVAAWTLKAAa,
``` or a peptide comprising an altered amino acid sequence which is an amino acid sequence selected from SEQ ID NOs: 101 and 102 but containing alteration of amino acid residue(s), and having a helper T cell induction activity, or a pharmaceutically acceptable salt thereof;

48. the compound according to any one of 1-10, 14-18 and 44-47, wherein the cancer antigen peptide B is a peptide consisting of an amino acid sequence selected from the following amino acid sequences:

```
                                                    (SEQ ID NO: 101)
AKFVAAWTLKAAA
and
                                                    (SEQ ID NO: 102)
aKFVAAWTLKAAa,
``` or a pharmaceutically acceptable salt thereof;

49. the compound according to any one of 1-10, 14-18 and 44-48, wherein the compound represented by the formula (1) is a compound represented by the formula (6):

```
      CGLYDGMEHL                                          (6)
       |
      CAKFVAAWTLKAAA
``` wherein the bond between C and C is a disulfide bond,
a compound represented by the formula (7):

```
      CGLYDGMEHL                                          (7)
       |
      CaKFVAAWTLKAAa.
``` wherein the bond between C and C is a disulfide bond, a compound represented by the formula (15):

```
      CKIFGSLAFL                                         (15)
       |
      CAKFVAAWTLKAAA
``` wherein the bond between C and C is a disulfide bond,
or a compound represented by the formula (16):

```
      CKIFGSLAFL                                         (16)
       |
      CaKFVAAWTLKAAa
``` wherein the bond between C and C is a disulfide bond,
or a pharmaceutically acceptable salt thereof;

50. the compound according to any one of 1-10, wherein $R^1$ is a group represented by the formula (3), or a pharmaceutically acceptable salt thereof;

51. the compound according to any one of 1-10 and 50, wherein $X^c$ is a divalent peptide group consisting of 2 amino acid residues and $Y^c$ is a single bond, $X^c$ and $Y^c$ are each independently a divalent peptide group consisting of 1 amino acid residue, $X^c$ is a single bond and $Y^c$ is a divalent peptide group consisting of 2 amino acid residues, $X^c$ is a divalent peptide group consisting of 1 amino acid residue and $Y^c$ is a single bond, $X^c$ is a single bond and $Y^c$ is a divalent peptide group consisting of 1 amino acid residue, or $X^c$ and $Y^c$ are each a single bond, or a pharmaceutically acceptable salt thereof;

52. the compound according to any one of 1-10, 50 and 51, wherein $X^c$ is a single bond, and $Y^c$ is a single bond, an alanine residue, a leucine residue or a methionine residue, or a pharmaceutically acceptable salt thereof;

53. the compound according to any one of 1-10, 50 and 51, wherein $X^c$ is a single bond or a divalent peptide group consisting of 1 amino acid residue, and $Y^c$ is a single bond, or a pharmaceutically acceptable salt thereof;

54. the compound according to any one of 1-10 and 50-53, wherein $X^c$ and $Y^c$ are each a single bond, or a pharmaceutically acceptable salt thereof;

55. the compound according to any one of 1-10 and 50-54, wherein the cancer antigen peptide C is an MHC class II-restricted cancer antigen peptide consisting of 7-15 amino acid residues, or a pharmaceutically acceptable salt thereof;

56. the compound according to any one of 1-10 and 50-55, wherein the cancer antigen peptide C consists of 7-15 amino acid residues and is an HLA-DR, HLA-DQ or HLA-DP-restricted cancer antigen peptide, or a pharmaceutically acceptable salt thereof;

57. the compound according to any one of 1-10 and 50-56, wherein the cancer antigen peptide C is an HLA-DR-restricted universal cancer antigen peptide consisting of 13-15 amino acid residues, or a pharmaceutically acceptable salt thereof;

58. the compound according to any one of 1-10 and 50-57, wherein the cancer antigen peptide C is a peptide comprising an amino acid sequence selected from the following amino acid sequences:

```
                                    (SEQ ID NO: 101)
AKFVAAWTLKAAA
and (SEQ ID NO: 102)
aKFVAAWTLKAAa,
``` or a peptide comprising an altered amino acid sequence which is an amino acid sequence selected from SEQ ID NOs: 101 and 102 but containing alteration of amino acid residue(s), and having a helper T cell induction activity, or a pharmaceutically acceptable salt thereof;

59. the compound according to any one of 1-10 and 50-58, wherein the cancer antigen peptide C is a peptide consisting of an amino acid sequence selected from the following amino acid sequences:

```
                                    (SEQ ID NO: 101)
AKFVAAWTLKAAA
and (SEQ ID NO: 102)
aKFVAAWTLKAAa,
``` or a pharmaceutically acceptable salt thereof;

60. the compound according to any one of 1-10, and 50-59, wherein the compound represented by the formula (1) is a compound represented by the formula (8):

$$\begin{array}{c} \text{CGLYDGMEHL} \\ | \\ \text{AKFVAAWTLKAAAC} \end{array} \quad (8)$$

wherein the bond between C and C is a disulfide bond, a compound represented by the formula (9):

$$\begin{array}{c} \text{CGLYDGMEHL} \\ | \\ \text{aKFVAAWTLKAAaC} \end{array} \quad (9)$$

wherein the bond between C and C is a disulfide bond, a compound represented by the formula (18):

$$\begin{array}{c} \text{CKIFGSLAFL} \\ | \\ \text{AKFVAAWTLKAAAC} \end{array} \quad (18)$$

wherein the bond between C and C is a disulfide bond, or a compound represented by the formula (17):

$$\begin{array}{c} \text{CKIFGSLAFL} \\ | \\ \text{aKFVAAWTLKAAaC} \end{array} \quad (17)$$

wherein the bond between C and C is a disulfide bond, or a pharmaceutically acceptable salt thereof;

61. the compound according to any one of 1-10, wherein $R^1$ is cancer antigen peptide D, or a pharmaceutically acceptable salt thereof;

62. the compound according to any one of 1-10 and 61, wherein the cancer antigen peptide D is an MHC class I-restricted cancer antigen peptide consisting of 7-15 amino acid residues, or a pharmaceutically acceptable salt thereof;

63. the compound according to any one of 1-10, 61 and 62, wherein the cancer antigen peptide D consists of 7-15 amino acid residues and is an HLA-A, HLA-B or HLA-Cw-restricted cancer antigen peptide, or a pharmaceutically acceptable salt thereof;

64. the compound according to any one of 1-10 and 61-63, wherein the cancer antigen peptide D consists of 7-15 amino acid residues and is an HLA-A1, HLA-A2, HLA-A3, HLA-A11, HLA-A24, HLA-A28, HLA-A29, HLA-A31, HLA-A33, HLA-A34, HLA-A68, HLA-B7, HLA-B13, HLA-B35, HLA-B37, HLA-B44, HLA-B45, HLA-B51, HLA-B52, HLA-B53, HLA-Cw2, HLA-Cw3, HLA-Cw6, HLA-Cw7, HLA-Cw8 or HLA-Cw16-restricted cancer antigen peptide, or a pharmaceutically acceptable salt thereof;

65. the compound according to any one of 1-10 and 61-64, wherein the cancer antigen peptide D is an MHC class I cancer antigen peptide derived from a cancer antigen protein selected from the group consisting of MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-3, GAGE-4, GAGE-5, GAGE-6, GAGE-7B, GAGE-8, NA88-A, NY-ESO-1, NY-ESO-1a, MART-1/Melan-A, MC1R, Gp100, PSA, PSM, Tyrosinase, Proteinase 3, TRP-1, TRP-2, ART-4, CAMEL, CEA, Ep-CAM, Cyp-B, Her2/neu, VEGFR, hTERT, hTRT, iCE, MUC1, MUC2, PRAME, P15, RU1, RU2, SART-1, SART-2, SART-3, AFP, β-Catenin, Caspase-8, CDK-4, ELF2, GnT-V, G250, HSP70-2M, HST-2, KIAA0205, MUM-1, MUM-2, MUM-3, Myosin, RAGE, SART-2, TRP-2, 707-AP, Survivin, Livin and SYT-SSX, or a pharmaceutically acceptable salt thereof;

66. the compound according to any one of 1-10 and 61-65, wherein the cancer antigen peptide D is a peptide comprising an amino acid sequence selected from the following amino acid sequences:

```
                                    (SEQ ID NO: 87)
VYGFVRACL
and (SEQ ID NO: 88)
SLLMWITQC,
``` or a peptide comprising an altered amino acid sequence which is an amino acid sequence selected from SEQ ID NOs: 87 and 88 but containing alteration of amino acid residue(s), and having a CTL induction activity, or a pharmaceutically acceptable salt thereof;

67. the compound according to any one of 1-10 and 61-66, wherein the cancer antigen peptide D is a peptide consisting of an amino acid sequence selected from the following amino acid sequences:

```
                              (SEQ ID NO: 87)
        VYGFVRACL
        and
                              (SEQ ID NO: 88)
        SLLMWITQC,
``` or a pharmaceutically acceptable salt thereof;

68. the compound according to any one of 1-10 and 61-67, wherein the compound represented by the formula (1) is a compound represented by the formula (10):

(10)

wherein the bond between C and C is a disulfide bond, or a compound represented by the formula (11):

(11)

wherein the bond between C and C is a disulfide bond, or a pharmaceutically acceptable salt thereof;

69. the compound according to any one of 1-10 and 61, wherein the cancer antigen peptide D is an MHC class II-restricted cancer antigen peptide consisting of 7-30 amino acid residues, or a pharmaceutically acceptable salt thereof;

70. the compound according to any one of 1-10, 61 and 69, wherein the cancer antigen peptide D consists of 13-15 amino acid residues and is an HLA-DR, HLA-DQ or HLA-DP-restricted cancer antigen peptide, or a pharmaceutically acceptable salt thereof;

71. the compound according to any one of 1-10, 61, 69 and 70, wherein the cancer antigen peptide D is an HLA-DR-restricted universal cancer antigen peptide consisting of 13-15 amino acid residues, or a pharmaceutically acceptable salt thereof;

72. the compound according to any one of 1-10, 61 and 69-71, wherein the cancer antigen peptide D is a peptide comprising the following amino acid sequence:

```
                              (SEQ ID NO: 103)
        aK-Cha-VAAWTLKAAa-Ahx-C,
``` or a peptide comprising an altered amino acid sequence which is the amino acid sequence of SEQ ID NO: 103 but containing alteration of amino acid residue(s), and having a helper T cell induction activity, or a pharmaceutically acceptable salt thereof;

73. the compound according to any one of 1-10, 61 and 69-72, wherein the cancer antigen peptide D is a peptide consisting of the following amino acid sequence:

```
                              (SEQ ID NO: 103)
        aK-Cha-VAAWTLKAAa-Ahx-C,
``` or a pharmaceutically acceptable salt thereof;

74. the compound according to any one of 1-10, 61 and 69-73, wherein the compound represented by the formula (1) is a compound represented by the formula (12):

```
                                      (12)
        CGLYDGMEHL,
        |
        aK-Cha-VAAWTLKAAa-Ahx-C
``` wherein the bond between C and C is a disulfide bond, or a pharmaceutically acceptable salt thereof;

75. the compound according to any one of 1-10, 61, 69 and 70, wherein the cancer antigen peptide D is an MHC class II cancer antigen peptide derived from a cancer antigen protein selected from the group consisting of MAGE-A1, MAGE-A2, MAGE-A3, MAGE-A6, NY-ESO-1, MART-1/Melan-A, Gp100, PSA, Tyrosinase, CEA, HER-2/neu, hTERT, MUC1 and SART-3, or a pharmaceutically acceptable salt thereof;

76. the compound according to any one of 1-10, 61, 69, 70 and 75, wherein the cancer antigen peptide D is a peptide comprising an amino acid sequence selected from the following amino acid sequences:

```
                              (SEQ ID NO: 104)
        AADHRQLQLSISSCLQQL, (SEQ ID NO: 105)
        RNGYRALMDKSLHVGTQCALTRR, (SEQ ID NO: 106)
        KKLQCVQLHVISM
        and
                              (SEQ ID NO: 107)
        GSYVSRLLGICL,
``` or a peptide comprising an altered amino acid sequence which is an amino acid sequence selected from SEQ ID NOs: 104, 105, 106 and 107 but containing alteration of amino acid residue(s), and having a helper T cell induction activity, or a pharmaceutically acceptable salt thereof;

77. the compound according to any one of 1-10, 61, 69, 70, and 76, wherein the cancer antigen peptide D is a peptide consisting of an amino acid sequence selected from the following amino acid sequences:

```
                              (SEQ ID NO: 104)
        AADHRQLQLSISSCLQQL, (SEQ ID NO: 105)
        RNGYRALMDKSLHVGTQCALTRR, (SEQ ID NO: 106)
        KKLQCVQLHVISM
        and
                              (SEQ ID NO: 107)
        GSYVSRLLGICL,
``` or a pharmaceutically acceptable salt thereof;

78. the compound according to any one of 1-77, wherein the cancer antigen peptide A, the cancer antigen peptide B, the cancer antigen peptide C, or/and the cancer antigen peptide D is not a WT1 protein-derived cancer antigen peptide, or a pharmaceutically acceptable salt thereof;

79. a pharmaceutical composition comprising the compound according to any one of 1-78, or a pharmaceutically acceptable salt thereof and a pharmaceutically acceptable carrier;

80. the pharmaceutical composition according to 79, which is used as a cancer vaccine;

81. use of the compound according to any one of 1-78, or a pharmaceutically acceptable salt thereof for the production of a cancer vaccine;

82. a method of treating or preventing cancer, comprising administering a therapeutically or prophylactically effective amount of the compound of any one of 1-78 or a pharmaceutically acceptable salt thereof to a cancer patient positive for a cancer antigen protein in need thereof;

83. a method of obtaining two different MHC class I-restricted epitopes, or an MHC class I-restricted epitope and an MHC class II-restricted epitope, comprising reacting the compound according to any one of 1-78 or a pharmaceutically acceptable salt thereof with ERAP1; and 84. a method of synthesizing a compound, comprising the following steps:

(1) a step of synthesizing, by using Fmoc-C(Mmt)A-SBn and cancer antigen peptide B wherein one cysteine residue is bonded to the N-terminal, a peptide wherein a carbonyl group of the C-terminal amino acid of C(Mmt)A and an amino group of an N-terminal amino acid bonded to the N-terminal of the cancer antigen peptide B are bonded, wherein the cancer antigen peptide B is an MHC class I-restricted cancer antigen peptide consisting of 7-15 amino acid residues, (2) a step of synthesizing, by using the peptide obtained in the step (1) and cancer antigen peptide A wherein one cysteine residue protected by SPy group is bonded to the N-terminal, a peptide wherein a thioether group of the cysteine residue bonded to the N-terminal of the cancer antigen peptide B in the peptide obtained in the step (1), and a thioether group of the cysteine residue bonded to the N-terminal of the cancer antigen peptide A are bonded, wherein the cancer antigen peptide A is an MHC class I-restricted cancer antigen peptide consisting of 7-30 amino acid residues, and (3) a step of synthesizing, by using the peptide obtained in the step (2) and cancer antigen peptide E wherein one cysteine residue protected by Spy group is bonded to the C-terminal, a peptide wherein a thioether group of the cysteine residue bonded to the N-terminal of the cancer antigen peptide A in the peptide obtained in the step (2), and a thioether group of the cysteine residue bonded to the C-terminal of the cancer antigen peptide E are bonded, wherein the cancer antigen peptide E is an MHC class II-restricted cancer antigen peptide consisting of 7-30 amino acid residues.

Effect of the Invention

According to the present invention, it becomes possible to provide the aforementioned compound represented by the formula (1) useful as a cancer immunotherapeutic agent (hereinafter sometimes to be referred to as the compound of the present invention). The compound of the present invention can provide cancer vaccines and cancer immunotherapeutic agents that efficiently induce CTLs in vivo and in vitro. To be specific, the compound of the present invention enables production of two MHC class I-restricted cancer antigen peptides having different sequences or two MHC class I-restricted cancer antigen epitopes having different sequences; an MHC class I-cancer antigen restricted peptide and an MHC class II-restricted cancer antigen peptide; or an MHC class I-cancer antigen restricted cancer antigen epitope and an MHC class II-restricted cancer antigen epitope, in vivo and in vitro, and efficient induction of CTLs.

As for the HLA subtypes of two MHC class I-restricted peptides having different sequences, the compound (conjugate) of the present invention obtained by combining A02 type (such as A-0201 and A0206) peptide and A24 type (such as A-2402) peptide is particularly preferable. In Europeans and Americans (Caucasian), the population of HLA-A0201 subtype or HLA-A0206 subtype is the highest and about 47%, then HLA-A2402 subtype is about 13%, and the total of these subtypes occupies about 56%, excluding duplicates (i.e., duplicate calculation of humans having both subtypes) (Human Immunol. 62:1009; 2001). In Japanese people and the like, the population of HLA-A2402 is the highest and about 60%, then HLA-A0201 or HLA-A0206 is about 39%, and the total of these subtypes occupies about 81%, excluding duplicates (i.e., duplicate calculation of humans having both subtypes) (www.bmdc.irc.or.jp/GF-A.htm). Therefore, one of the advantages of the compound of the present invention is, specifically, that a larger population is covered by a single compound of the present invention, and selection of the HLA subtype of the patients before administration is not always essential.

Moreover, the compound of the present invention can provide an active ingredient of a cancer vaccine that is superior in physicochemical properties and stability and easily produced. As a result, formulation of cancer vaccines has been facilitated.

Specifically, examples of the physicochemical properties include solubility, viscosity of solution, easy purification resulting from such properties, easy handling after freeze-drying, and easy purification resulting from such properties. The stability includes stability after salt substitution, hygroscopicity, thermal stability, and stability after emulsion formation. Further, examples of pharmacological activities include efficacy as a cancer vaccine, difference depending on API (Active Pharmaceutical Ingredient), and interaction with additives in the preparation. Of these, the difference depending on API is a difference as a cancer vaccine due to API. Specifically, when two APIs having vastly different solubilities are used, API with smaller solubility is prone to precipitate, and it is easily expected that a sterilization treatment by filtration with a membrane filter, which is an essential requirement for pharmaceutical products, cannot be performed. Even if a sterilization treatment by filtration of API with small solubility is barely possible, it is considered that the amount of API contained in the filtrate markedly decreases and CTL induction ability essential for a cancer vaccine markedly decreases. Therefore, it is easily predicted that API with small solubility has a demerit of markedly decreased production efficiency.

DESCRIPTION OF EMBODIMENTS

Figure 1:
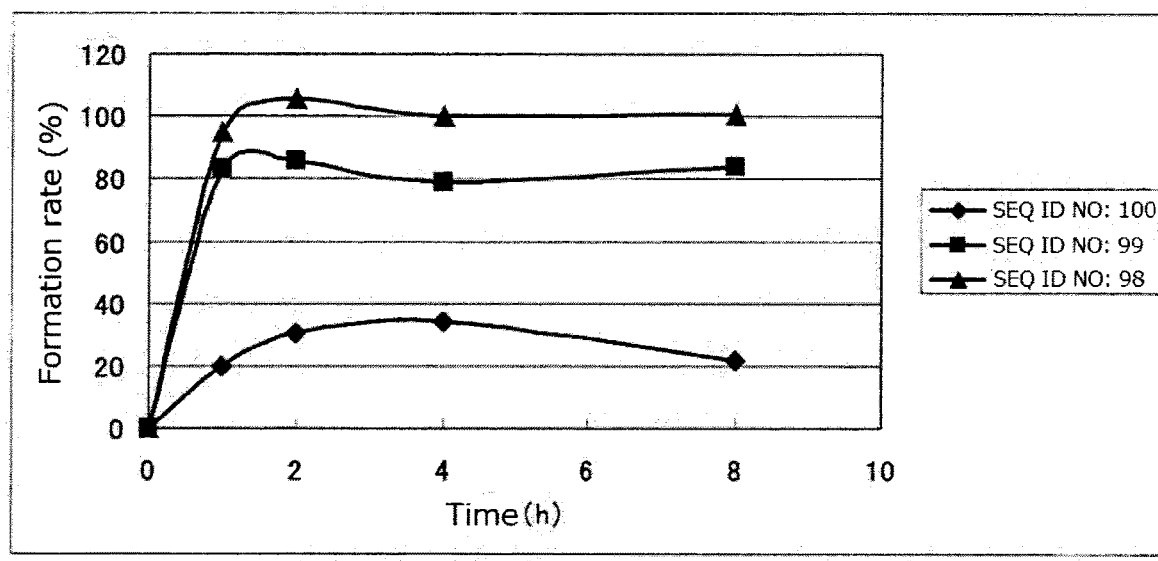
FIG. 1 is a Figure showing the test results of Experimental Example 2 that examined the time-dependent change of N-terminal amino acid trimming by ERAP1 of each peptide of SEQ ID NOs: 100, 99 and 98 synthesized in Examples 1, 21 and 25.
Figure 2:
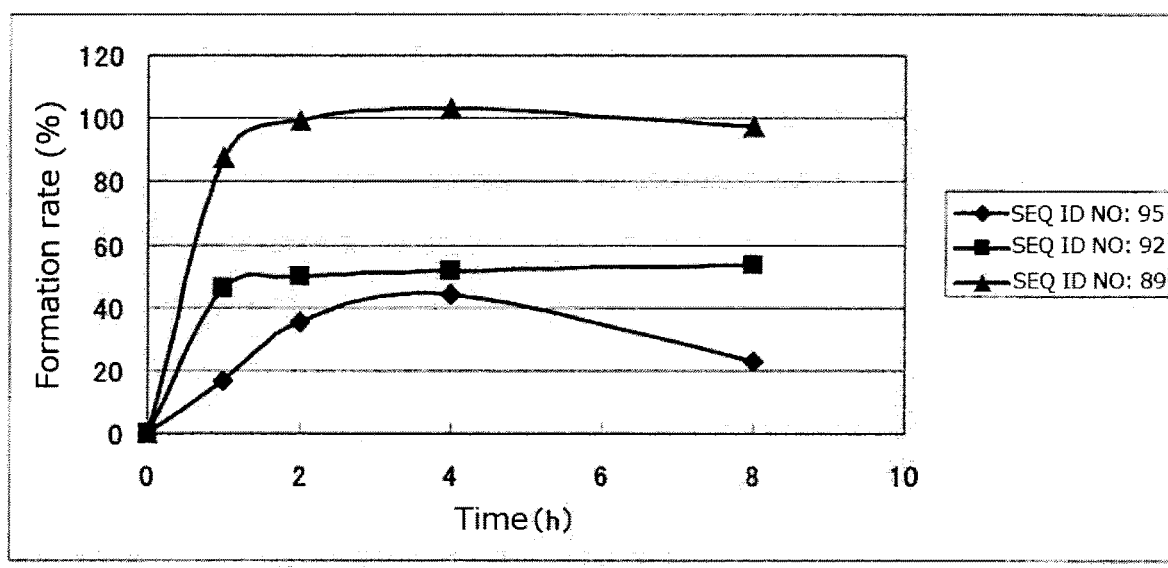
FIG. 2 is a Figure showing the test results of Experimental Example 2 that examined the time-dependent change of N-terminal amino acid trimming by ERAP1 of each peptide of SEQ ID NOs: 95, 92 and 89 synthesized in Examples 2, 22 and 26.
Figure 3:
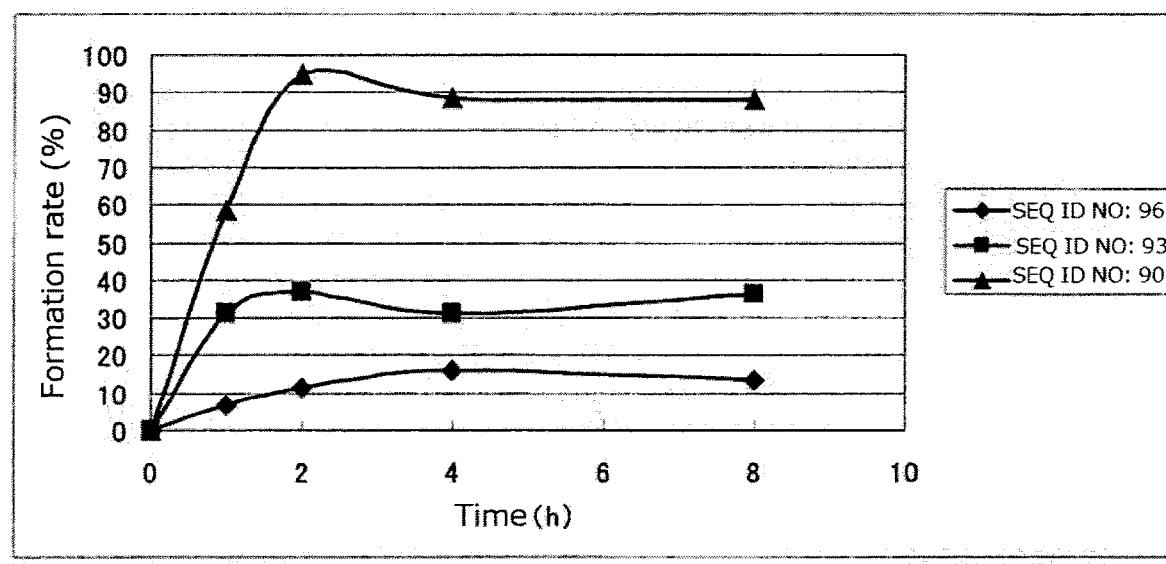
FIG. 3 is a Figure showing the test results of Experimental Example 2 that examined the time-dependent change of N-terminal amino acid trimming by ERAP1 of each peptide of SEQ ID NOs: 96, 93 and 90 synthesized in Examples 11, 23 and 27.
Figure 4:
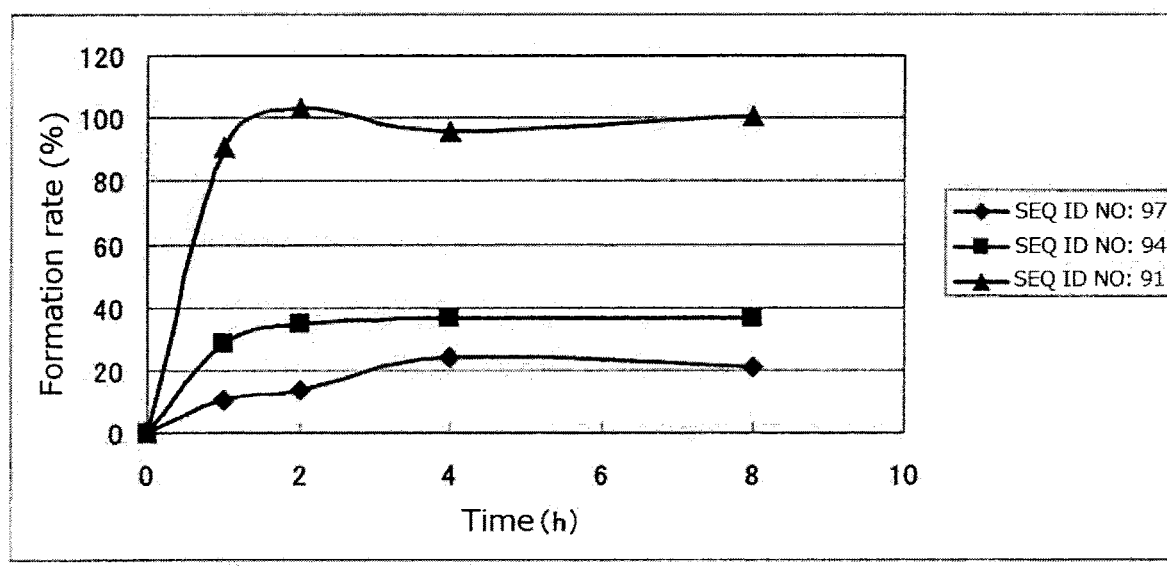
FIG. 4 is a Figure showing the test results of Experimental Example 2 that examined the time-dependent change of N-terminal amino acid trimming by ERAP1 of each peptide of SEQ ID NOs: 97, 94 and 91 synthesized in Examples 12, 24 and 28.

Embodiments of the present invention are explained in detail in the following.

The "amino acid residue" in the present invention means a region corresponding to one unit of amino acids constituting a peptide or protein in a peptide or protein molecule. Examples of the "amino acid residue" include natural or non-natural α-amino acid residue, β-amino acid residue, γ-amino acid residue or δ-amino acid residue. Specific examples thereof include natural α-amino acid residue, ornithine residue, homoserine residue, homocysteine residue, β-alanine, γ-aminobutanoic acid and δ-aminopentanoic acid. When the "amino acid residue" can be an optically active substance, it may be any of an L-form and a D-form, and an L-form is preferable.

When the "amino acid residue" in the present invention is shown in abbreviation, the following abbreviations are used.

Ala or A: alanine residue
a: D-alanine residue
Arg or R: arginine residue
Asn or N: asparagine residue
Asp or D: aspartic acid residue
Cys or C: cysteine residue
Gln or Q: glutamine residue
Glu or E: glutamic acid residue
Gly or G: glycine residue
His or H: histidine residue
Ile or I: isoleucine residue
Leu or L: leucine residue
Lys or K: lysine residue
Met or M: methionine residue
Phe or F: phenylalanine residue
Pro or P: proline residue
Ser or S: serine residue
Thr or T: threonine residue
Trp or W: tryptophan residue
Tyr or Y: tyrosine residue
Val or V: valine residue Abu: 2-aminobutyric acid residue (to be also referred to as α-aminobutyric acid residue)
Orn: ornithine residue
Cit: citrulline residue
Cha: cyclohexylalanine residue
Ahx: 2-aminohexanoic acid residue The amino acid sequence of the "peptide" in the present invention is described according to the conventional method, wherein the amino acid residue of the N-terminal amino acid is positioned on the left side, and the amino acid residue of the C-terminal amino acid is positioned on the right side. In the "peptide", unless particularly indicated, the amino group of the amino acid residue of the N-terminal amino acid is bonded to hydrogen atom, and the carbonyl group of the amino acid residue of the C-terminal amino acid is bonded to hydroxyl group. The divalent group of peptide means a group bonding via the amino group of the amino acid residue of the N-terminal amino acid and the carbonyl group of the amino acid residue of the C-terminal amino acid.

Also in the peptide that is a partial structure of the compound of the present invention, for example, the compounds represented by the formulae (4)-(12), unless particularly indicated, the amino group of the amino acid residue of the N-terminal amino acid is bonded to hydrogen atom, and the carbonyl group of the amino acid residue of the C-terminal amino acid is bonded to hydroxyl group.

"$X^a$" and "$Y^a$" in the present invention mean, independently, a single bond or a divalent group of peptides consisting of 1-4 amino acid residues. The sum of the amino acid residue number of $X^a$ and that of $Y^a$ is an integer of 0-4. For example, an integer of the sum being 0 means that $X^a$ and $Y^a$ are each a single bond. When the sum is an integer of 4, examples of $X^a$ and $Y^a$ include $X^a$ and $Y^a$ independently being divalent groups of peptide consisting of 2 amino acid residues, $X^a$ being a divalent group of peptide consisting of 3 amino acid residues and $Y^a$ being a divalent group of peptide consisting of 1 amino acid residue, and $X^a$ being a divalent group of peptide consisting of 4 amino acid residues and $Y^a$ being a single bond.

The integer of the sum is preferably 0-2, more preferably 0-1, most preferably 0. That is, $X^a$ and $Y^a$ are most preferably single bonds.

When the sum is an integer of 2, examples of $X^a$ and $Y^a$ include $X^a$ being a divalent group of peptide consisting of 2 amino acid residues and $Y^a$ being a single bond, $X^a$ and $Y^a$ independently being divalent groups of peptide consisting of 1 amino acid residue, and $X^a$ being a single bond and $Y^a$ being a divalent group of peptide consisting of 2 amino acid residues.

When the sum is an integer of 1, examples of $X^a$ and $Y^a$ include $X^a$ being a divalent group of peptide consisting of 1 amino acid residue and $Y^a$ being a single bond, and $X^a$ being a single bond and $Y^a$ being a divalent group of peptide consisting of 1 amino acid residue. Of these, preferred is $X^a$ being a single bond and $Y^a$ being an alanine residue, a leucine residue or a methionine residue, or $X^a$ being an alanine residue, a glycine residue, a serine residue or a tyrosine residue and $Y^a$ being a single bond.

The "cancer antigen peptide A" in the present invention is an MHC class I-restricted cancer antigen peptide consisting of 7-30 amino acid residues. In cancer antigen peptide A in the formula (1), the amino group of the N-terminal amino acid is bonded to $Y^a$ in the formula (1) and the carbonyl group of the C-terminal amino acid is bonded to the hydroxyl group in the formula (1).

The term "MHC class I-restricted" in the present invention means the property to induce CTLs by binding to an MHC class I molecule, which is class I of the major histocompatibility complex (MHC).

MHC in human is called human leukocyte-type antigen (HLA). HLA corresponding to the MHC class I-molecule is classified into subtypes such as HLA-A, B, Cw, F and G. Preferable examples of the "MHC class I-restricted" peptides include HLA-A-restricted peptides, HLA-B-restricted peptides, and HLA-Cw-restricted peptides.

Polymorphism (allele) of each subtype of HLA is known. Examples of the polymorphism of HLA-A include not less than 27 kinds such as HLA-A1, HLA-A0201, and HLA-A24, examples of the polymorphism of HLA-B include not less than 59 kinds such as HLA-B7, HLA-B40, and HLA-B4403, and examples of the polymorphism of HLA-Cw include not less than 10 kinds such as HLA-Cw0301, HLA-Cw0401, and HLA-Cw0602. Among these polymorphisms, HLA-A0201 and HLA-A24 are preferable.

As the cancer antigen peptide A, an HLA-A, HLA-B or HLA-Cw-restricted cancer antigen peptide consisting of 7-15 amino acid residues is preferable, and an HLA-A1, HLA-A2, HLA-A3, HLA-A11, HLA-A24, HLA-A28, HLA-A29, HLA-A31, HLA-A33, HLA-A34, HLA-A68, HLA-B7, HLA-B13, HLA-B35, HLA-B37, HLA-B44, HLA-B45, HLA-B51, HLA-B52, HLA-B53, HLA-Cw2, HLA-Cw3, HLA-Cw6, HLA-Cw7, HLA-Cw8 or HLA-Cw16-restricted cancer antigen peptide consisting of 7-15 amino acid residues is more preferable.

The "cancer antigen peptide" in the present invention means a partial peptide of a known human cancer antigen protein. Specifically, the cancer antigen peptide is a partial peptide consisting of continuous 7-30 amino acid residues in the amino acid sequence of a cancer antigen protein selected from the group consisting of MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-3, GAGE-4, GAGE-5, GAGE-6, GAGE-7B, GAGE-8, NA88-A, NY-ESO-1, NY-ESO-1a, MART-1/Melan-A, MC1R, Gp100, PSA, PSM, Tyrosinase, Proteinase 3, TRP-1, TRP-2, ART-4, CAMEL, CEA, Ep-CAM, Cyp-B, Her2/neu, VEGFR, hTERT, hTRT, iCE, MUC1, MUC2, PRAME, P15, RU1, RU2, SART-1, SART-2, SART-3, AFP, 13-Catenin, Caspase-8, CDK-4, ELF2, GnT-V, G250, HSP70-2M, HST-2, KIAA0205, MUM-1, MUM-2, MUM-3, Myosin, RAGE, SART-2, TRP-2, 707-AP, Survivin, Livin and SYT-SSX.

However, human WT1 protein (Cell, 60: 509, 1990, GenBank Acc. No. A38080) is not included in the "cancer antigen peptide" in the present invention. That is, in the compound of the present invention, the cancer antigen peptide A, the cancer antigen peptide B, the cancer antigen peptide C, or/and the cancer antigen peptide D are not WT1 protein-derived cancer antigen peptides. It is more preferable that the cancer antigen peptide A, the cancer antigen peptide B, the cancer antigen peptide C or the cancer antigen peptide D is not a WT1 protein-derived cancer antigen peptide. It is further preferable that the cancer antigen peptide A, the cancer antigen peptide B, the cancer antigen peptide C and the cancer antigen peptide D are not WT1 protein-derived cancer antigen peptides.

Specifically, in the compound represented by the formula (1) shown in item 1 above, it is preferable that: the cancer antigen peptide A is an MHC class I-restricted cancer antigen peptide consisting of continuous 7-30 amino acid residues in the amino acid sequence of a cancer antigen protein and different from a WT1 protein-derived cancer antigen peptide; and when R¹ is a group represented by the formula (2), the cancer antigen peptide B is an MHC class I or MHC class II-restricted cancer antigen peptide consisting of continuous 7-30 amino acid residues in the amino acid sequence of a cancer antigen protein and different from a WT1 protein-derived cancer antigen peptide; when R¹ is a group represented by the formula (3), the cancer antigen peptide C is an MHC class II-restricted cancer antigen peptide consisting of continuous 7-30 amino acid residues in the amino acid sequence of a cancer antigen protein and different from a WT1 protein-derived cancer antigen peptide; and when R¹ is cancer antigen peptide D, the cancer antigen peptide D is an MHC class I or MHC class II-restricted cancer antigen peptide consisting of continuous 7-30 amino acid residues in the amino acid sequence of a cancer antigen protein and different from a WT1 protein-derived cancer antigen peptide.

Therefore, the "MHC class I-restricted cancer antigen peptide" in the present invention is a peptide that binds to an MHC class I antigen in vitro and/or in vivo and is presented as a complex, and induces CTLs as a result of recognition of the complex by precursor T cells. The number of the amino acid residues of the "MHC class I-restricted cancer antigen peptide" is 7-30, preferably 7-15, more preferably 8-12, further preferably 8-11, most preferably 8 or 9.

The "MHC class I-restricted cancer antigen peptide" consisting of 7-12 or preferably 9 amino acid residues is also called "an MHC class I-restricted cancer antigen epitope". The "MHC class I-restricted cancer antigen epitope" in the present invention means a peptide per se that binds to an MHC class I antigen and is presented as a complex. That is, "MHC class I-restricted cancer antigen peptide" produces "MHC class I-restricted cancer antigen epitope" in vitro and/or in vivo, from intracellular degradation of the compound of the present invention by proteosome and/or protease such as Gamma-Interferon-inducible Lysosomal Thiol Reductase (GILT, GLT) (proteolysis, reductive cleavage of disulfide bond), and/or cleavage into the optimal residue number (also called trimming) by Endoplasmic reticulum aminopeptidase (ERAP1, ER-aminopeptidase 1). This production is mainly considered to comprise a production process wherein the C-terminal amino acid of the "MHC class I-restricted cancer antigen epitope" first results from the degradation by proteosome and/or protease, after which N-terminal amino acid of the "MHC class I-restricted cancer antigen epitope" results from trimming (cleavage) by ERAP1. In this production, however, a process other than this production process is also possible. At present, ERAP1 is also referred to as ERAAP (ER aminopeptidase associated with antigen presentation), and used to be also called A-LAP, PILS-AP or ARTS-1.

Therefore, the "MHC class I-restricted cancer antigen peptide" is preferably a peptide consisting of 7-30 amino acid residues produced by adding 1-23 amino acid residues to the carbonyl group of the C-terminal amino acid of the "MHC class I-restricted cancer antigen epitope" consisting of 7-12 amino acid residues.

Examples of the "MHC class I-restricted cancer antigen peptide" include peptides described in Tables 1-9.

The peptide of SEQ ID NO: 8 and the peptide of SEQ ID NO: 9 in Table 1 consist of the same amino acid sequence and are identical to each other. The peptide is an HLA-Cw3-restricted cancer antigen peptide, and also an HLA-Cw16-restricted cancer antigen peptide.

TABLE 1

| cancer antigen protein | HLA type | amino acid sequence | SEQ ID NO: |
|---|---|---|---|
| MAGE-A1 | A1 | EADPTGHYS | 1 |
| MAGE-A1 | A3 | SLFRAVITK | 2 |
| MAGE-A1 | A24 | NYKHCFPEI | 3 |
| MAGE-A1 | A28 | EVYDGREHSA | 4 |
| MAGE-A1, 2, 3, 6 | B37 | REPVTKAEML | 5 |
| MAGE-A1 | B53 | DPARYEFLW | 6 |
| MAGE-A1 | Cw2 | SAFPTTINF | 7 |
| MAGE-A1 | Cw3 | SAYGEPRKL | 8 |
| MAGE-A1 | Cw16 | SAYGEPRKL | 9 |
| MAGE-A2 | A2 | KMVELVHFL | 10 |

TABLE 2

| cancer antigen protein | HLA type | amino acid sequence | SEQ ID NO: |
|---|---|---|---|
| MAGE-A2 | A24 | EYLQLVFGI | 11 |
| MAGE-A3 | A1 | EADPIGHLY | 12 |
| MAGE-A3 | A2 | FLWGPRALV | 13 |
| MAGE-A3 | A24 | TFPDLESEF | 14 |
| MAGE-A3 | B44 | MEVDPIGHLY | 15 |
| MAGE-A3 | B52 | WQYFFPVIF | 16 |
| MAGE-A4 | A2 | GVYDGREHTV | 17 |
| MAGE-A6 | A34 | MVKISGGPR | 18 |
| MAGE-A10 | A2 | GLYDGMEHL | 19 |
| MAGE-A12 | Cw7 | VRIGHLYIL | 20 |

TABLE 3

| cancer antigen protein | HLA type | amino acid sequence | SEQ ID NO: |
|---|---|---|---|
| BAGE | Cw16 | AARAVFLAL | 21 |
| DAM-6, 10 | A2 | FLWGPRAYA | 22 |
| GAGE-1, 2, 8 | Cw6 | YRPRPRRY | 23 |
| GAGE-3, 4, 5, 6, 7B | A29 | YYWPRPRRY | 24 |
| NA88-A | B13 | MTQGQHFLQKV | 25 |
| NY-ESO-1 | A2 | SLLMWITQCFL | 26 |
| NY-ESO-1a | A2 | QLSLLMWIT | 27 |
| NY-ESO-1a | A31 | ASGPGGGAPR | 28 |
| MART-1/Melan-A | A2 | AAGIGILTV | 29 |

TABLE 3-continued

| cancer antigen protein | HLA type | amino acid sequence | SEQ ID NO: |
|---|---|---|---|
| MART-1/Melan-A | B45 | AEEAAGIGIL | 30 |

TABLE 4

| cancer antigen protein | HLA type | amino acid sequence | SEQ ID NO: |
|---|---|---|---|
| MC1R | A2 | TILLGIFFL | 31 |
| Gp100 | A2 | KTWGQYWQV | 32 |
| Gp100 | A3 | LIYRRRLMK | 33 |
| Gp100 | A24 | VYFFLPDHL | 34 |
| Gp100 | Cw8 | SNDGPTLI | 35 |
| PSA | A1 | VSHSFPHPLY | 36 |
| PSA | A2 | FLTPKKLQCV | 37 |
| PSM | A1 | HSTNGVTRIY | 38 |
| Tyrosinase | A1 | KCDICTDEY | 39 |
| Tyrosinase | A2 | YMDGTMSQV | 40 |

TABLE 5

| cancer antigen protein | HLA type | amino acid sequence | SEQ ID NO: |
|---|---|---|---|
| Tyrosinase | A24 | AFLPWHRLF | 41 |
| Tyrosinase | B44 | SEIWRDIDF | 42 |
| Proteinase-3 | | VLQELNVTV | 43 |
| TRP-1 | A31 | MSLQRQFLR | 44 |
| TRP-2 | A2 | SVYDFFVWL | 45 |
| TRP-2 | A31, 33 | LLGPGRPYR | 46 |
| TRP-2 | Cw8 | ANDPIFVVL | 47 |
| ART-4 | A24 | AFLRHAAL | 48 |
| CAMEL | A2 | MLMAQEALAFL | 49 |
| CEA | A2 | YLSGANLNL | 50 |

TABLE 6

| cancer antigen protein | HLA type | amino acid sequence | SEQ ID NO: |
|---|---|---|---|
| CEA | A3 | HLFGYSWYK | 51 |
| Cyp-B | A24 | KFHRVIKDF | 52 |
| HER2/neu | A2 | KIFGSLAFL | 53 |
| HER2/neu | A3 | VLRENTSPK | 54 |
| hTERT | A2 | ILAKFLHWL | 55 |
| iCE | B7 | SPRWWPTCL | 56 |

TABLE 6-continued

| cancer antigen protein | HLA type | amino acid sequence | SEQ ID NO: |
|---|---|---|---|
| MUC1 | A11 | STAPPAHGV | 57 |
| MUC1 | A2 | STAPPVHNV | 58 |
| MUC2 | A2 | LLNQLQVNL | 59 |
| PRAME | A24 | LYVDSLFFL | 60 |

TABLE 7

| cancer antigen protein | HLA type | amino acid sequence | SEQ ID NO: |
|---|---|---|---|
| P15 | A24 | AYGLDFYIL | 61 |
| RU1 | B51 | VPYGSFKHV | 62 |
| RU2 | B7 | LPRWPPPQL | 63 |
| SART-1 | A24 | EYRGFTQDF | 64 |
| SART-2 | A24 | DYSARWNEI | 65 |
| SART-3 | A24 | AYIDFEMKI | 66 |
| AFP | A2 | GVALQTMKQ | 67 |
| b-Catenin | A24 | SYLDSGIHF | 68 |
| Caspase-8 | B35 | FPSDSWCYF | 69 |
| CDK-4 | A2 | ACDPHSGHFV | 70 |

TABLE 8

| cancer antigen protein | HLA type | amino acid sequence | SEQ ID NO: |
|---|---|---|---|
| ELF2M | A68 | ETVSEQSNV | 71 |
| GnT-V | A2 | VLPDVFIRC | 72 |
| G250 | A2 | HLSTAFARV | 73 |
| HSP70-2M | A2 | SLFEGIDIY | 74 |
| HST-2 | A31 | YSWMDISCWI | 75 |
| MUM-1 | B44 | EEKLIVVLF | 76 |
| MUM-2 | B44 | SELFRSGLDY | 77 |
| MUM-2 | Cw6 | FRSGLDSYV | 78 |
| MUM-3 | A28 | EAFIQPITR | 79 |
| Myosin/m | A3 | KINKNPKYK | 80 |

TABLE 9

| cancer antigen protein | HLA type | amino acid sequence | SEQ ID NO: |
|---|---|---|---|
| RAGE | B7 | SPSSNRIRNT | 81 |
| 707-AP | A2 | RVAALARDA | 82 |
| survivin | A24 | AYACNTSTL | 83 |

TABLE 9-continued

| cancer antigen protein | HLA type | amino acid sequence | SEQ ID NO: |
|---|---|---|---|
| livin | A24 | KWFPSCQFLL | 84 |
| SYT-SSX | A24 | GYDQIPKK | 85 |
| hTERT | A24 | VYGFVRACL | 87 |
| NY-ESO-1 | A2 | SLLMWITQC | 88 |

Preferable examples of the "MHC class I-restricted cancer antigen peptide" include a peptide comprising an amino acid sequence selected from the following amino acid sequences:

NYKHCFPEI, (SEQ ID NO: 3)

EYLQLVFGI, (SEQ ID NO: 11)

FLWGPRALV, (SEQ ID NO: 13)

GLYDGMEHL, (SEQ ID NO: 19)

SLLMWITQCFL, (SEQ ID NO: 26)

QLSLLMWIT, (SEQ ID NO: 27)

AAGIGILTV, (SEQ ID NO: 29)

LIYRRRLMK, (SEQ ID NO: 33)

YMDGTMSQV, (SEQ ID NO: 40)

AFLPWHRLF, (SEQ ID NO: 41)

VLQELNVTV, (SEQ ID NO: 43)

YLSGANLNL, (SEQ ID NO: 50)

KIFGSLAFL, (SEQ ID NO: 53)

AYIDFEMKI, (SEQ ID NO: 66)

AYACNTSTL, (SEQ ID NO: 83)

KWFPSCQFLL, (SEQ ID NO: 84)

GYDQIMPKK, (SEQ ID NO: 85)

VYGFVRACL (SEQ ID NO: 87)
and

SLLMWITQC, (SEQ ID NO: 88)

or a peptide comprising an altered amino acid sequence which is an amino acid sequence selected from SEQ ID NOs: 3, 11, 13, 19, 26, 27, 29, 33, 40, 41, 43, 50, 53, 66, 83, 84, 85, 87 and 88 but contains alteration of amino acid residue(s) in the amino acid sequence, and having a CTL induction activity. As the "MHC class I-restricted cancer antigen peptide", a peptide consisting of an amino acid sequence selected from SEQ ID NOs: 3, 11, 13, 19, 26, 27, 29, 33, 40, 41, 43, 50, 53, 66, 83, 84, 85, 87 and 88 is more preferable, and a peptide consisting of an amino acid sequence selected from SEQ ID NOs: 19, 43 and 53 is further preferable.

The "peptide comprising an amino acid sequence" in the present invention means, as usual, a peptide whose amino acid sequence comprises a further amino acid added to the N-terminal amino acid and/or C-terminal amino acid of the amino acid sequence. When the further amino acid is added to the "MHC class I-restricted cancer antigen peptide" for the "cancer antigen peptide A" and "cancer antigen peptide B", the further amino acid is preferably added to the C-terminal side of the peptide.

The "peptide comprising an altered amino acid sequence that contains alteration of amino acid residue(s) in the amino acid sequence, and having a CTL induction activity" in the present invention is also called an "altered killer peptide". The altered killer peptide means a peptide that consists of an amino acid sequence wherein 1 to 3 amino acids are deleted from, substituted in, and/or added to the original amino acid sequence, and binds to MHC class I to induce CTLs. The position of the amino acid to be substituted includes position 1 (N-terminal), position 2, position 3 or position 9 for a peptide consisting of 9 amino acid residues. The number of amino acids to be added (or inserted, since "addition" encompasses "insertion") is preferably 1 or 2, more preferably 1. A preferable position for addition is the C-terminal. The number of amino acids to be deleted is preferably 1. In the alteration, the amino acid to be added or substituted may be a non-natural amino acid other than the 20 kinds of amino acids encoded by the gene.

"$R^1$" in the present invention is a hydrogen atom, a group represented by the formula (2), a group represented by the formula (3) or cancer antigen peptide D; preferably, a group represented by the formula (2), a group represented by the formula (3) or cancer antigen peptide D.

When $R^1$ is a hydrogen atom, the compound of the formula (1) is a compound represented by the formula (1-1):

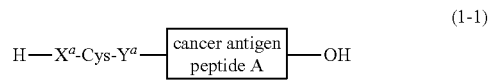

(1-1)

wherein $X^a$, $Y^a$ and cancer antigen peptide A are as defined in the above for the formula (1), and Cys is a cysteine residue,
namely, a peptide.

The compound of the formula (1) wherein $R^1$ is a hydrogen atom, namely, a peptide represented by the formula (1-1), has a sequence not identical to a partial sequence of a cancer antigen protein. The requirement that the sequence of the formula (1) "is not identical to a partial sequence of a cancer antigen protein" means that a peptide represented by the formula (1-1) is not a partial peptide consisting of continuous 8-35 amino acid residues in the amino acid sequence of a cancer antigen protein selected from the group consisting of MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-3, GAGE-4, GAGE-5, GAGE-6, GAGE-7B, GAGE-8, NA88-A, NY-ESO-1, NY-ESO-1a, MART-1/Melan-A, MC1R, Gp100, PSA, PSM, Tyrosinase, Proteinase 3, TRP-1, TRP-2, ART-4, CAMEL, CEA, Ep-CAM, Cyp-B, Her2/neu, VEGFR, hTERT, hTRT, iCE, MUC1, MUC2, PRAME, P15, RU1, RU2, SART-1, SART-2, SART-3, AFP, β-Catenin, Caspase-8, CDK-4, ELF2, GnT-V, G250, HSP70-2M, HST-2, KIAA0205, MUM-1, MUM-2, MUM-3, Myosin, RAGE, SART-2, TRP-2, 707-AP, Survivin, Livin and SYT-SSX.

That is, the compound of the formula (1) wherein $R^1$ is a hydrogen atom is not a partial peptide consisting of continuous 8-35 amino acid residues in the amino acid sequence of the aforementioned cancer antigen protein. A specific explanation is given by taking a case when the cancer antigen peptide A is a HER2/neu$_{369-377}$ peptide as an example. HER2/neu$_{369-377}$ peptide is a partial peptide consisting of continuous 9 amino acid residues at positions 369-377 of the amino acid sequence of human HER2/neu protein, and has an amino acid sequence of KIFGSLAFL (SEQ ID NO: 53). In the amino acid sequence of HER2/neu protein, the amino acid residue at position 368 continuing from the N-terminal side of HER2/neu$_{369-377}$ peptide is K, and the amino acid residue at position 367 further continuing therefrom is C. Therefore, HER2/neu$_{367-377}$ peptide (CK-KIFGSLAFL) (SEQ ID NO: 86) corresponds to a partial peptide consisting of continuous 11 amino acid residues of the amino acid sequence of HER2/neu protein. On the other hand, based on the requirement of the present invention that the compound of the formula (1) wherein $R^1$ is a hydrogen atom is not a partial peptide consisting of continuous 8-35 amino acid residues in the amino acid sequence of a cancer antigen protein, HER2/neu$_{367-377}$ peptide (CKKIFGSLAFL) is excluded from the compound of the present invention. Thus, when $R^1$ is a hydrogen atom and the cancer antigen peptide A is HER2/neu$_{369-377}$KIFGSLAFL (SEQ ID NO: 53) in the compound of the formula (1), $X^a$ is not a single bond and $Y^a$ is not a lysine residue. HER2/neu$_{367-377}$ peptide (CKKIFGSLAFL) (SEQ ID NO: 86) is not Example but is Reference Example of the present invention, as mentioned later.

For each of the peptides of SEQ ID NOs: 3, 11, 13, 19, 26, 27, 29, 33, 40, 41, 43, 50, 53, 66, 83, 84 and 85, which are preferable examples of the "MHC class I-restricted cancer antigen epitope" of the present invention, Tables 10-11 show the 5 amino acid residues continuing from the N-terminal side of the peptide in the amino acid sequence of the corresponding cancer antigen protein.

TABLE 10

| cancer antigen protein | amino acid sequence | SEQ ID NO: | 5 amino acid residues continuing from N-terminal side |
|---|---|---|---|
| MAGE-A1 | NYKHCFPEI | 3 | ESVIK |
| MAGE-A2 | EYLQLVFGI | 11 | FSKAS |
| MAGE-A3 | FLWGPRALV | 13 | PACYE |
| MAGE-A10 | GLYDGMEHL | 19 | ALNMM |
| NY-ESO-1 | SLLMWITQCFL | 26 | CLQQL |
| NY-ESO-1a | QLSLLMWIT | 27 | SSCLQ |

TABLE 10-continued

| cancer antigen protein | amino acid sequence | SEQ ID NO: | 5 amino acid residues continuing from N-terminal side |
|---|---|---|---|
| MART-1/Melan-A | AAGIGILTV | 29 | TTAEE |
| Gp100 | LIYRRRLMK | 33 | VVLAS |
| Tyrosinase | YMDGTMSQV | 40 | NALHI |

TABLE 11

| cancer antigen protein | amino acid sequence | SEQ ID NO: | 5 amino acid residues continuing from N-terminal side |
|---|---|---|---|
| Tyrosinase | AFLPWHRLF | 41 | AHEAP |
| Proteinase-3 | VLQELNVTV | 43 | DPPAQ |
| CEA | YLSGANLNL | 50 | PPDSS |
| HER2/neu | KIFGSLAFL | 53 | FAGCK |
| SART-3 | AYIDFEMKI | 66 | LAEYQ |
| survivin | AYACNTSTL | 83 | GPGTV |
| livin | KWFPSCQFLL | 84 | WTEHA |
| SYT-SSX | GYDQIMPKK | 85 | QQRPY |

Since a total of the amino acid residue number for $X^a$ and the amino acid residue number for $Y^a$ is an integer of 0-4, the peptide of the formula (1-1) that meets the requirement of the present invention that "the compound of the formula (1) wherein $R^1$ is a hydrogen atom is not a partial peptide consisting of continuous 8-35 amino acid residues in the amino acid sequence of a cancer antigen protein" can be determined easily by comparing $X^a$-Cys-$Y^a$ in the formula (1-1) with, for example, the 5 amino acid residues continuing from the N-terminal side of the peptide in the amino acid sequence of the corresponding cancer antigen protein shown in Tables 10 and 11.

The compound of the formula (1) wherein $R^1$ is a hydrogen atom is preferably a peptide consisting of an amino acid sequence selected from the following amino acid sequences:

CAGLYDGMEHL, (SEQ ID NO: 89)

CLGLYDGMEHL, (SEQ ID NO: 90)

CMGLYDGMEHL, (SEQ ID NO: 91)

CAVLQELNVTV, (SEQ ID NO: 92)

CLVLQELNVTV, (SEQ ID NO: 93)

CMVLQELNVTV, (SEQ ID NO: 94)

CAKIFGSLAFL, (SEQ ID NO: 95)

```
                                            (SEQ ID NO: 96)
CLKIFGSLAFL
and (SEQ ID NO: 97)
CMKIFGSLAFL,
``` and further preferably a peptide consisting of an amino acid sequence selected from SEQ ID NOs: 89-91.

The compound of the formula (1) wherein $R^1$ is a hydrogen atom is also preferably a peptide consisting of an amino acid sequence selected from the following amino acid sequences:

```
                                            (SEQ ID NO: 98)
CGLYDGMEHL, (SEQ ID NO: 99)
CVLQELNVTV
and (SEQ ID NO: 100)
CKIFGSLAFL,
``` and further preferably a peptide consisting of the amino acid sequence of SEQ ID NO: 98.

When "$R^1$" is a group represented by the formula (2), the compound of the formula (1) is a compound represented by the formula (1-2):

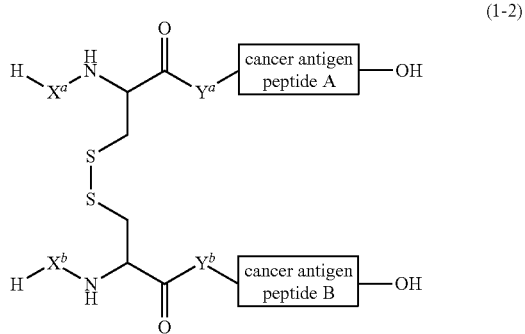

wherein $X^a$, $Y^a$ and cancer antigen peptide A are as defined in the above for the formula (1), and $X^b$, $Y^b$ and cancer antigen peptide B are as defined in the above for the formula (2).

"$X^b$" and "$Y^b$" in the present invention mean, independently, a single bond or a divalent group of peptides consisting of 1-4 amino acid residues. The sum of the amino acid residue number of $X^b$ and that of $Y^b$ is an integer of 0-4. For example, an integer of the sum being 0 means that $X^b$ and $Y^b$ are each a single bond. When the sum is an integer of 4, examples of $X^b$ and $Y^b$ include $X^b$ and $Y^b$ independently being divalent groups of peptide consisting of 2 amino acid residues, $X^b$ being a divalent group of peptide consisting of 3 amino acid residues and $Y^b$ being a divalent group of peptide consisting of 1 amino acid residue, and $X^b$ being a divalent group of peptide consisting of 4 amino acid residues and $Y^b$ being a single bond.

The integer of the sum is preferably 0-2, more preferably 0-1, most preferably 0. That is, $X^b$ and $Y^b$ are most preferably single bonds.

When the sum is an integer of 2, examples of $X^b$ and $Y^b$ include $X^b$ being a divalent group of peptide consisting of 2 amino acid residues and $Y^b$ being a single bond, $X^b$ and $Y^b$ independently being divalent groups of peptide consisting of 1 amino acid residue, and $X^b$ being a single bond and $Y^b$ being a divalent group of peptide consisting of 2 amino acid residues.

When the sum is an integer of 1, examples of $X^b$ and $Y^b$ include $X^b$ being a divalent group of peptide consisting of 1 amino acid residue and $Y^b$ being a single bond, and $X^b$ being a single bond and $Y^b$ being a divalent group of peptide consisting of 1 amino acid residue. Of these, preferred is $X^b$ being a single bond and $Y^b$ being an alanine residue, leucine residues or methionine residue.

The "cancer antigen peptide B" in the present invention is an MHC class I-restricted cancer antigen peptide consisting of 7-30 amino acid residues, or an MHC class II-restricted cancer antigen peptide consisting of 7-30 amino acid residues. In the meantime, in the compound represented by the formula (1), cancer antigen peptide A and cancer antigen peptide B are not the same peptide. That is, cancer antigen peptide B is limited by the requirement that it is "different from cancer antigen peptide A".

Since cancer antigen peptide A and cancer antigen peptide B are not the same peptide, the compound of the formula (1) wherein $R^1$ is a group represented by the formula (2) is not a homodimer but a heterodimer, even when $X^a$ and $X^b$ are the same and $Y^a$ and $Y^b$ are the same. Homodimer means a dimer wherein the same peptide monomers are dimerized, and heterodimer means a dimer wherein different peptide monomers are dimerized.

In the cancer antigen peptide B, the amino group of the N-terminal amino acid is bonded to $Y^b$ in the formula (2) (i.e., also bonded to $Y^b$ in the formula (1-2)), and the carbonyl group of the C-terminal amino acid is bonded to the hydroxyl group in the formula (2) (i.e., also bonded to the hydroxyl group in the formula (1-2)).

When the "cancer antigen peptide B" in the present invention is an MHC class I-restricted cancer antigen peptide consisting of 7-30 amino acid residues, the "MHC class I-restricted cancer antigen peptide" is as defined above.

The compound of the formula (1) wherein $R^1$ is a group represented by the formula (2) and cancer antigen peptide B is an MHC class I-restricted cancer antigen peptide consisting of 7-30 amino acid residues is preferably a compound represented by the formula (4):

wherein the bond between C and C is a disulfide bond, or a compound represented by the formula (5):

wherein the bond between C and C is a disulfide bond.

When $X^b$ is a divalent peptide group consisting of 2 amino acid residues containing a cysteine residue and $Y^b$ is a single bond, or $X^b$ is a single bond and $Y^b$ is a divalent peptide group consisting of 2 amino acid residues containing a cysteine residue, more preferably when $X^b$ is a divalent dipeptide group consisting of CA and $Y^b$ is a single bond, or $X^b$ is a single bond and $Y^b$ is a divalent dipeptide group consisting of CA, the compound of the formula (1) may be a compound wherein a thioether group in the cysteine residue of $X^b$ or a thioether group in the cysteine residue of $Y^b$ is bonded to a thioether group in the formula (20):

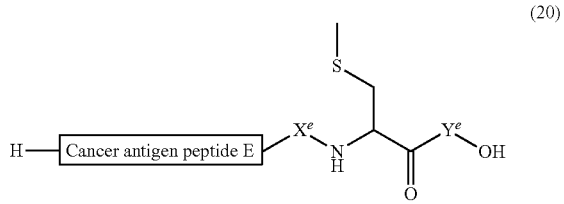

(20)

"$X^e$" and "$Y^e$" in the present invention mean, independently, a single bond or a divalent group of peptides consisting of 1-4 amino acid residues. The sum of the amino acid residue number of $X^e$ and that of $Y^e$ is an integer of 0-4. For example, an integer of the sum being 0 means that $X^e$ and $Y^e$ are each a single bond. When the sum is an integer of 4, examples of $X^e$ and $Y^e$ include $X^e$ and $Y^e$ independently being divalent groups of peptide consisting of 2 amino acid residues, $X^e$ being a divalent group of peptide consisting of 3 amino acid residues and $Y^e$ being a divalent group of peptide consisting of 1 amino acid residue, and $X^e$ being a divalent group of peptide consisting of 4 amino acid residues and $Y^e$ being a single bond.

The integer of the sum is preferably 0-2, more preferably 0-1, most preferably 0. That is, $X^e$ and $Y^e$ are most preferably single bonds.

When the sum is an integer of 2, examples of $X^e$ and $Y^e$ include $X^e$ being a divalent group of peptide consisting of 2 amino acid residues and $Y^e$ being a single bond, $X^e$ and $Y^e$ independently being divalent groups of peptide consisting of 1 amino acid residue, or $X^e$ being a single bond and $Y^e$ being a divalent group of peptide consisting of 2 amino acid residues.

When the sum is an integer of 1, examples of $X^e$ and $Y^e$ include $X^e$ being a divalent group of peptide consisting of 1 amino acid residue and $Y^e$ being a single bond, and $X^e$ being a single bond and $Y^e$ being a divalent group of peptide consisting of 1 amino acid residue. Of these, preferred is $X^e$ being a single bond and $Y^e$ being an alanine residue, leucine residues or methionine residue.

The "cancer antigen peptide E" in the present invention is an MHC class II-restricted cancer antigen peptide consisting of 7-30 amino acid residues. In the formula (20), the carbonyl group of the C-terminal amino acid of the cancer antigen peptide E is bonded to $X^e$ in the formula (20), and the amino group of the N-terminal amino acid of the cancer antigen peptide E is bonded to the hydrogen atom in the formula (20).

The "MHC class II-restricted cancer antigen peptide" in the present invention is as defined for the "MHC class II-restricted cancer antigen peptide" in the below-mentioned "cancer antigen peptide B".

HLA corresponding to the MHC class II-molecule is classified into subtypes such as HLA-DR, DQ and DP. Preferable examples of the "MHC class II-restricted" peptides include HLA-DR-restricted peptides, HLA-DQ-restricted peptides and HLA-DP-restricted peptides.

Therefore, the "MHC class II-restricted cancer antigen peptide" in the present invention is a peptide that binds to an MHC class II antigen in vitro and/or in vivo and induces helper T cells. The number of the amino acid residues of the "MHC class II-restricted cancer antigen peptide" is 7-30, preferably 14-30.

When the "cancer antigen peptide E" in the present invention is an MHC class II-restricted cancer antigen peptide consisting of 7-30 amino acid residues, the number of the amino acid residues is preferably 9-15, more preferably 13-15. As the cancer antigen peptide E, an HLA-DR-restricted universal cancer antigen peptide consisting of 13-15 amino acid residues is further preferable.

The "universal cancer antigen peptide" in the present invention means a cancer antigen peptide or an epitope that binds to plural kinds of MHC class II molecules, regardless of the subtype of MHC class II or the kind of polymorphism, and induces helper T cells. The "HLA-DR-restricted universal cancer antigen peptide" is also referred to as a pan DR pan HLA-DR binding peptide.

Examples of the "cancer antigen peptide E" include, similar to the below-mentioned "cancer antigen peptide B", a peptide consisting of an amino acid sequence selected from the following amino acid sequences:

```
                                    (SEQ ID NO: 101)
AKFVAAWTLKAAA,
and aKFVAAWTLKAAa.
                                    (SEQ ID NO: 102)
```

In the compound of the formula (1-2), when $X^b$ is a divalent peptide group consisting of 2 amino acid residues containing a cysteine residue and $Y^b$ is a single bond, or $X^b$ is a single bond and $Y^b$ is a divalent peptide group consisting of 2 amino acid residues containing a cysteine residue, more preferably when $X^b$ is a divalent dipeptide group consisting of CA and $Y^b$ is a single bond, or $X^b$ is a single bond and $Y^b$ is a divalent dipeptide group consisting of CA, the compound of the formula (1-2) wherein a thioether group in the cysteine residue of $X^b$ or a thioether group in the cysteine residue of $Y^b$ is bonded to a thioether group in the formula (20) is preferably a compound represented by the formula (19):

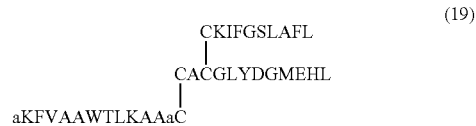

(19)

wherein the bond between C and C is a disulfide bond, or a compound represented by the formula (21):

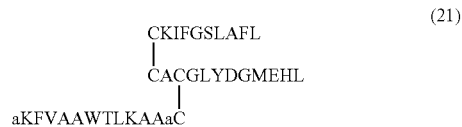

(21)

wherein the bond between C and C is a disulfide bond.

The "MHC class II-restricted cancer antigen peptide" for the "cancer antigen peptide B" in the present invention is explained in the following.

In the present invention, "MHC class II-restricted" means the property to induce helper T cells by binding to an MHC class II molecule.

HLA corresponding to the MHC class II-molecule is classified into subtypes such as HLA-DR, DQ and DP. Preferable examples of the "MHC class II-restricted" peptides include HLA-DR-restricted peptides, HLA-DQ-restricted peptides, and HLA-DP-restricted peptides.

Therefore, the "MHC class II-restricted cancer antigen peptide" in the present invention is a peptide that binds to an MHC class II antigen in vitro and/or in vivo and induces helper T cells. The number of the amino acid residues of the "MHC class II-restricted cancer antigen peptide" is 7-30, preferably 14-30.

When the "cancer antigen peptide B" in the present invention is an MHC class II-restricted cancer antigen peptide consisting of 7-30 amino acid residues, the number of the amino acid residues is preferably 9-15, more preferably 13-15. As the cancer antigen peptide B, an HLA-DR-restricted universal cancer antigen peptide consisting of 13-15 amino acid residues is further preferable.

The "universal cancer antigen peptide" in the present invention means a cancer antigen peptide or an epitope that binds to plural kinds of MHC class II molecules, regardless of the subtype of MHC class II or the kind of polymorphism, and induces helper T cells. The "HLA-DR-restricted universal cancer antigen peptide" is also referred to as a pan HLA-DR binding peptide.

Examples of the "HLA-DR-restricted universal cancer antigen peptide" include peptides described in Table 12.

TABLE 12

| amino acid sequence | SEQ ID NO: |
|---|---|
| AKFVAAWTLKAAA | 101 |
| aKFVAAWTLKAAa | 102 |

The "universal cancer antigen peptide" is preferably a peptide comprising an amino acid sequence selected from SEQ ID NOs: 101 and 102, or a peptide comprising an altered amino acid sequence which is an amino acid sequence selected from SEQ ID NOs: 101 and 102 but containing alteration of amino acid residue(s), and having a helper T cell induction activity, and more preferably a peptide consisting of an amino acid sequence selected from SEQ ID NOs: 101 and 102.

The definition "comprising the amino acid sequence" is as defined above. The "peptide comprising an altered amino acid sequence containing alteration of amino acid residue(s) in an amino acid sequence, and having a helper T cell induction activity" is also referred to as an "altered helper peptide". The altered helper peptide means a peptide that consists of an amino acid sequence wherein 1 to 3 amino acids are deleted from, substituted in, and/or added to the original sequence and binds to MHC class II to induce helper T cells. The number of the amino acids to be added (or inserted, since "addition" encompasses "insertion") is preferably 1-3. The number of the amino acids to be deleted is preferably 1-5. In the alteration, the amino acid to be added or amino acid to be substituted may be a non-natural amino acid other than the 20 kinds of amino acids encoded by the gene.

The compound of the formula (1) wherein $R^1$ is a group represented by the formula (2) and cancer antigen peptide B is an MHC class II-restricted cancer antigen peptide consisting of 7-30 amino acid residues is preferably a compound represented by the formula (6):

wherein the bond between C and C is a disulfide bond, a compound represented by the formula (7):

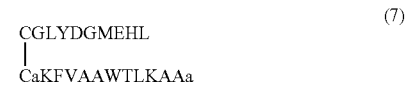

wherein the bond between C and C is a disulfide bond, a compound represented by the formula (15):

wherein the bond between C and C is a disulfide bond, or a compound represented by the formula (16):

wherein the bond between C and C is a disulfide bond.

When "$R^1$" is a group represented by the formula (3), the compound of the formula (1) is a compound represented by the formula (1-3):

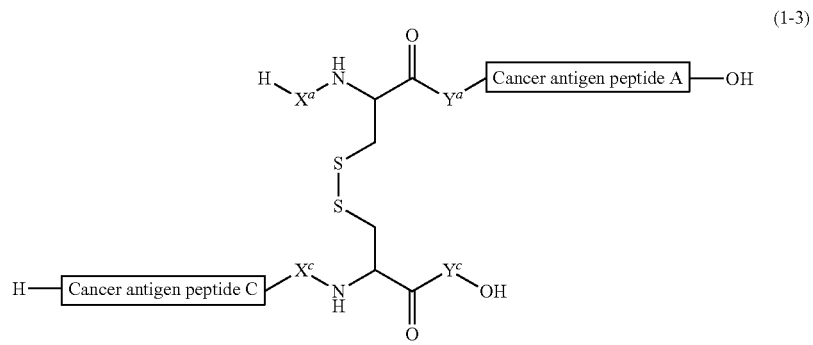

wherein $X^a$, $Y^a$ and cancer antigen peptide A are as defined in the above for the formula (1), and $X^c$, $Y^c$ and cancer antigen peptide C are as defined in the above for the formula (3).

"$X^c$" and "$Y^c$" in the present invention are each independently a single bond or a divalent peptide group consisting of 1-4 amino acid residues. The sum of the amino acid residue number of $X^c$ and the amino acid residue number of $Y^c$ is an integer of 0-4. For example, an integer of the sum being 0 means that $X^c$ and $Y^c$ are each a single bond. When the sum is an integer of 4, examples of $X^c$ and $Y^c$ include $X^c$ and $Y^c$ independently being divalent groups of peptide consisting of 2 amino acid residues, $X^c$ being a divalent group of peptide consisting of 3 amino acid residues and $Y^c$ being a divalent group of peptide consisting of 1 amino acid residue, and $X^c$ being a divalent group of peptide consisting of 4 amino acid residues and $Y^c$ being a single bond.

The integer of the sum is preferably 0-2, more preferably 0-1, most preferably 0. That is, $X^c$ and $Y^c$ are most preferably single bonds.

When the sum is an integer of 2, examples of $X^c$ and $Y^c$ include $X^c$ being a divalent group of peptide consisting of 2 amino acid residues and $Y^c$ being a single bond, $X^c$ and $Y^c$ independently being divalent groups of peptide consisting of 1 amino acid residue, and $X^c$ being a single bond and $Y^c$ being a divalent group of peptide consisting of 2 amino acid residues.

When the sum is an integer of 1, examples of $X^c$ and $Y^c$ include $X^c$ being a divalent group of peptide consisting of amino acid residue and $Y^c$ being a single bond, and $X^c$ being a single bond and $Y^c$ being a divalent group of peptide consisting of 1 amino acid residue. Of these, preferred is $X^c$ being a single bond and $Y^c$ being an alanine residue, leucine residues or methionine residue.

The "cancer antigen peptide C" in the present invention is an MHC class II-restricted cancer antigen peptide consisting of 7-30 amino acid residues. The "MHC class II-restricted cancer antigen peptide" is as defined above.

When the "cancer antigen peptide C" in the present invention is an MHC class II-restricted cancer antigen peptide consisting of 7-30 amino acid residues, the number of the amino acid residues is preferably 9-15, more preferably 13-15. As the cancer antigen peptide C, an HLA-DR-restricted universal cancer antigen peptide consisting of 13-15 amino acid residues is further preferable. The "HLA-DR-restricted universal cancer antigen peptide" is as defined above.

In the cancer antigen peptide C, the carbonyl group of the C-terminal amino acid is bonded to $X^c$ in the formula (3) (i.e., also bonded to $X^c$ in the formula (1-3)), and the amino group of the N-terminal amino acid is bonded to the hydrogen atom in the formula (3) (i.e., also bonded to the hydrogen atom in the formula (1-3)).

The compound of the formula (1) wherein $R^1$ is a group represented by the formula (3) and cancer antigen peptide C is an MHC class II-restricted cancer antigen peptide consisting of 7-30 amino acid residues is preferably a compound represented by the formula (8):

(8)

wherein the bond between C and C is a disulfide bond, a compound represented by the formula (9):

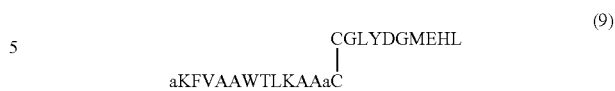
(9)

wherein the bond between C and C is a disulfide bond, a compound represented by the formula (18):

(18)

wherein the bond between C and C is a disulfide bond, or a compound represented by the formula (17):

(17)

wherein the bond between C and C is a disulfide bond.

When $R^1$ is cancer antigen peptide D, the thioether group of the cysteine residue of the cancer antigen peptide D is bonded to the thioether group in the formula (1). In the cancer antigen peptide D, the amino group of the N-terminal amino acid is bonded to the hydrogen atom, and the carbonyl group of the C-terminal amino acid is bonded to the hydroxyl group.

The cancer antigen peptide D is an MHC class I-restricted cancer antigen peptide consisting of 7-30 amino acid residues containing one cysteine residue or an MHC class II-restricted cancer antigen peptide consisting of 7-30 amino acid residues containing one cysteine residue.

The "MHC class I-restricted cancer antigen peptide consisting of 7-30 amino acid residues containing one cysteine residue" in the present invention is required to contain at least one cysteine residue in the amino acid sequence of the peptide. The number of the cysteine residues to be contained is preferably 1-3, more preferably 1-2, most preferably 1. The "MHC class I-restricted cancer antigen peptide" is as defined above. Also, the compound of the formula (1) wherein $R^1$ is "an MHC class I-restricted cancer antigen peptide consisting of 7-30 amino acid residues containing one cysteine residue" is not a homodimer but a heterodimer.

Examples of the "MHC class I-restricted cancer antigen peptide consisting of 7-30 amino acid residues containing one cysteine residue" include peptides described in Table 13.

TABLE 13

| cancer antigen protein | HLA type | amino acid sequence | SEQ ID NO: |
|---|---|---|---|
| MAGE-A1 | A24 | NYKHCFPEI | 3 |
| NY-ESO-1 | A2 | SLLMWITQCFL | 26 |
| PSA | A2 | FLTPKKLQCV | 37 |
| Tyrosinase | A1 | KCDICTDEY | 39 |
| iCE | B7 | SPRWWPTCL | 56 |
| Caspase-8 | B35 | FPSDSWCYF | 69 |
| CDK-4 | A2 | ACDPHSGHFV | 70 |

TABLE 13-continued

| cancer antigen protein | HLA type | amino acid sequence | SEQ ID NO: |
|---|---|---|---|
| GnT-V | A2 | VLPDVFIRC | 72 |
| HST-2 | A31 | YSWMDISCWI | 75 |
| survivin | A24 | AYACNTSTL | 83 |
| livin | A24 | KWFPSCQFLL | 84 |
| hTERT | A24 | VYGFVRACL | 87 |
| NY-ESO-1 | A2 | SLLMWITQC | 88 |

More preferable examples of the "MHC class I-restricted cancer antigen peptide consisting of 7-30 amino acid residues containing one cysteine residue" include a peptide comprising an amino acid sequence selected from the following amino acid sequences:
VYGFVRACL (SEQ ID NO: 87) and
SLLMWITQC (SEQ ID NO: 88)
and a peptide comprising an altered amino acid sequence which is an amino acid sequence selected from SEQ ID NOs: 87 and 88 but containing alteration of amino acid residue(s), and having a CTL induction activity. Most preferably, a peptide consisting of an amino acid sequence selected from SEQ ID NOs: 87 and 88 is mentioned. The definitions "comprising the amino acid sequence" and "peptide comprising an altered amino acid sequence containing alteration of amino acid residue(s) in an amino acid sequence, and having a CTL induction activity" are as defined above.

The compound of the formula (1) wherein R¹ is an "MHC class I-restricted cancer antigen peptide consisting of 7-30 amino acid residues containing one cysteine residue" is preferably a compound represented by the formula (10):

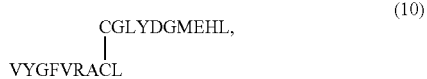
(10)

wherein the bond between C and C is a disulfide bond, or a compound represented by the formula (11):

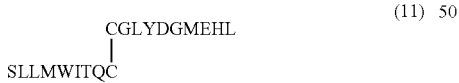
(11)

wherein the bond between C and C is a disulfide bond.

The "MHC class II-restricted cancer antigen peptide consisting of 7-30 amino acid residues containing one cysteine residue" in the present invention is required to contain at least one cysteine residue in the amino acid sequence of the peptide. The number of the cysteine residues to be contained is preferably 1-3, more preferably 1-2, most preferably 1. The "MHC class II-restricted cancer antigen peptide" is as defined above.

In the "MHC class II-restricted cancer antigen peptide consisting of 7-30 amino acid residues containing one cysteine residue", the number of the amino acid residues is preferably 9-15, more preferably 13-15. The MHC class II-restricted peptide is preferably an HLA-DR-restricted peptide, an HLA-DQ-restricted peptide, or an HLA-DP-restricted peptide.

When the cancer antigen peptide D is an "MHC class II-restricted cancer antigen peptide consisting of 13-15 amino acid residues containing one cysteine residue", the "MHC class II-restricted cancer antigen peptide" is preferably an HLA-DR-restricted universal cancer antigen peptide, or a cancer antigen peptide derived from a cancer antigen protein selected from the group consisting of MAGE-A1, MAGE-A2, MAGE-A3, MAGE-A6, NY-ESO-1, MART-1/Melan-A, Gp100, PSA, Tyrosinase, CEA, HER-2/neu, hTERT, MUC1 and SART-3.

Examples of the "HLA-DR-restricted universal cancer antigen peptide consisting of 13-15 amino acid residues containing one cysteine residue" include peptides described in Table 14.

TABLE 14

| amino acid sequence | SEQ ID NO: |
|---|---|
| aK-Cha-VAAWTLKAAa-Ahx-C | 103 |

The "HLA-DR-restricted universal cancer antigen peptide consisting of 13-15 amino acid residues containing one cysteine residue" is preferably a peptide comprising the amino acid sequence of SEQ ID NO: 103, or a peptide comprising an altered amino acid sequence which is the amino acid sequence of SEQ ID NO: 103 but containing alteration of amino acid residue(s), and having a helper T cell induction activity, and more preferably a peptide consisting of the amino acid sequence of SEQ ID NO: 103. The definitions "comprising the amino acid sequence" and "peptide comprising an altered amino acid sequence containing alteration of amino acid residue(s) in an amino acid sequence, and having a helper T cell induction activity" are as defined above.

The compound of the formula (1) wherein R¹ is an "HLA-DR-restricted universal cancer antigen peptide consisting of 13-15 amino acid residues containing one cysteine residue" is preferably a compound represented by the formula (12):

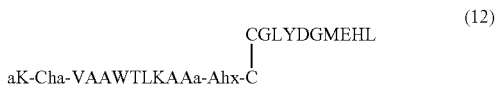
(12)

wherein the bond between C and C is a disulfide bond.

Examples of the "cancer antigen peptide derived from a cancer antigen protein selected from the group consisting of MAGE-A1, MAGE-A2, MAGE-A3, MAGE-A6, NY-ESO-1, MART-1/Melan-A, Gp100, PSA, Tyrosinase, CEA, HER-2/neu, hTERT, MUC1 and SART-3 and consisting of 13-15 amino acid residues containing one cysteine residue" include peptides described in Table 15.

TABLE 15

| amino acid sequence | SEQ ID NO: |
|---|---|
| AADHRQLQLSISSCLQQL | 104 |
| RNGYRALMDKSHVGTQCALTRR | 105 |

TABLE 15-continued

| amino acid sequence | SEQ ID NO: |
|---|---|
| KKLQCVQLHVISM | 106 |
| GSYVSRLLGICL | 107 |

The "cancer antigen peptide derived from a cancer antigen protein selected from the group consisting of MAGE-A1, MAGE-A2, MAGE-A3, MAGE-A6, NY-ESO-1, MART-1/Melan-A, Gp100, PSA, Tyrosinase, CEA, HER-2/neu, hTERT, MUC1 and SART-3 and consisting of 13-15 amino acid residues containing one cysteine residue" is preferably a peptide comprising an amino acid sequence selected from SEQ ID NOs: 104-107, or a peptide comprising an altered amino acid sequence which is an amino acid sequence selected from SEQ ID NOs: 104-107 but containing alteration of amino acid residue(s), and having a helper T cell induction activity, and more preferably a peptide consisting of an amino acid sequence selected from SEQ ID NOs: 104-107. The definitions "containing the amino acid sequence" and "peptide comprising an altered amino acid sequence containing alteration of amino acid residue(s) in an amino acid sequence, and having a helper T cell induction activity" are as defined above.

The present invention also provides a synthesis method of a compound wherein two different MHC class I-restricted cancer antigen peptide and MHC class II-restricted cancer antigen peptide, or two different MHC class I-restricted cancer antigen epitope and MHC class II-restricted cancer antigen epitope are each bonded via a disulfide bond. The method of the present invention includes the following steps (1)-(3).

In step (1) of the present invention, Fmoc-C(Mmt)A-SBn and cancer antigen peptide B wherein one cysteine residue is bonded to the N-terminal are used to synthesize a peptide wherein a carbonyl group of the C-terminal amino acid of C(Mmt)A and an amino group of an N-terminal amino acid bonded to the N-terminal of the cancer antigen peptide B are bonded.

The "cancer antigen peptide B" is as defined for the aforementioned "cancer antigen peptide B". "Fmoc" is a 9-fluorenylmethoxycarbonyl group. "Mmt" is a monomethoxytrityl group. "SBn" is a thiobenzyl group.

In step (2) of the present invention, the peptide obtained in the step (1) and cancer antigen peptide A wherein one cysteine residue protected by Spy group is bonded to the N-terminal are used to synthesize a peptide wherein a thioether group of the cysteine residue bonded to the N-terminal of the cancer antigen peptide B in the peptide obtained in the step (1) and a thioether group of the cysteine residue bonded to the N-terminal of cancer antigen peptide A are bonded.

The "cancer antigen peptide A" is as defined for the aforementioned "cancer antigen peptide A". "Spy" is a 2-pyridylsulfide group.

In step (3) of the present invention, the peptide obtained in the step (2) and cancer antigen peptide E wherein one cysteine residue protected by Spy group is bonded to the C-terminal are used to synthesize a peptide wherein a thioether group of the cysteine residue bonded to the N-terminal of the cancer antigen peptide A in the peptide obtained in the step (2) and a thioether group of the cysteine residue bonded to the C-terminal of the cancer antigen peptide E are bonded.

The "cancer antigen peptide E" is as defined for the aforementioned "cancer antigen peptide E".

The compound and peptide of the present invention, and peptides to be intermediates therefor can be produced according to the method described in the Examples of the present specification or a method to be generally used for the peptide synthesis. Examples of the production method include the methods described in the documents such as Peptide Synthesis, Interscience, New York, 1966; The Proteins, Vol. 2, Academic Press Inc., New York, 1976; peptide synthesis, Maruzen Co., LTD., 1975; Basics and Experiment of Peptide Synthesis, Maruzen Co., LTD., 1985; and Development of Pharmaceutical Product subsequent vol. 14, Peptide Synthesis, Hirokawa Shoten, 1991).

Examples of the production method include a method using a solid phase synthesizer by Fmoc method or Boc method, and a method by sequential condensation of Boc-amino acid or Z-amino acid by liquid phase synthesis process (Fmoc is a 9-fluorenylmethoxycarbonyl group, Boc is a t-butoxycarbonyl group, and Z is a benzyloxycarbonyl group).

In the intermediate for the production of the compound of the present invention, a functional group such as an amino group, a carboxy group, and a mercapto group can be protected by a suitable protecting group or deprotected as necessary using protection and deprotection techniques. Preferable protecting groups, protection method, and deprotection method are described in detail, for example, in "Protective Groups in Organic Synthesis 2nd Edition (John Wiley & Sons, Inc.; 1990)". Examples of the mercapto-protecting group include an acetamidomethyl group and a trityl group.

When the compound of the present invention has a disulfide bond, the disulfide bond can be formed between two different peptides each containing a cysteine residue or between a peptide containing a cysteine residue and cysteine according to a method generally used for peptide chemistry. Examples of the formation method of the disulfide bond include the methods described in the documents such as Peptide Synthesis, Interscience, New York, 1966; The Proteins, Vol. 2, Academic Press Inc., New York, 1976; peptide synthesis, Maruzen Co., LTD., 1975; Basics and Experiment of peptide synthesis, Maruzen Co., LTD., 1985; and Development of Pharmaceutical Product sequential vol. 14, Peptide Synthesis, Hirokawa Shoten, 1991).

Specifically, when a peptide contains one cysteine residue, a compound having a disulfide bond (disulfide compound) can be produced by removing all protecting groups including the mercapto-protecting group on the cysteine side chain and oxidizing the peptide in an inert solvent. In addition, a disulfide compound can be produced by mixing two intermediates having a mercapto group in a suitable solvent and oxidizing the mixture. The method for the oxidation may be selected as appropriate from known methods for disulfide bond formation in usual peptide synthesis. For example, iodine oxidation, a method using air oxidation reaction under alkali conditions, and a method for forming a disulfide bond by adding an oxidant under alkaline or acidic conditions can be mentioned. Here, examples of the oxidant include iodine, dimethyl sulfoxide (DMSO), and potassium ferricyanide. Examples of the solvent include water, acetic acid, methanol, chloroform, DMF, and DMSO, or a mixture thereof. The oxidation reaction often affords a mixture of symmetric and asymmetric disulfide compounds. A desired asymmetric disulfide compound can be obtained by purification using techniques such as various types of chromatography and recrystallization. Alternatively, a selective disulfide bond may be formed by mixing an intermediate having an activated mercapto group and another intermediate having a mercapto group. Examples of the intermediate having an activated mercapto group include a mercapto group bonded with an Npys group (3-nitro-2-pyridinesulphenyl group). Alternatively, one intermediate is mixed with an agent to activate the mercapto group, for example, 2,2'-dithiobis(5-nitropyridine), and then the other intermediate is added thereto, whereby a selective disulfide bond can be formed (Tetrahedron Letters. Vol. 37. No. 9, pp. 1347-1350).

Also, when two or more cysteine residues are contained in the peptide, a method similar to the aforementioned method can be used. In this case, an isomer with a different manner of disulfide bond is obtained. A dimer wherein a disulfide bond is formed between desired cysteine residues can be obtained by using a particular combination of the cysteine side chain-protecting groups. Examples of the combination of protecting groups include MeBzl (methylbenzyl) group and Acm (acetamidomethyl) group, Trt (trityl) group and Acm group, Npys (3-nitro-2-pyridylthio) group and Acm group, and S-Bu-t (S-tert-butyl) group and Acm group. For example, in the case of a combination of MeBzl group and Acm group, a method of forming disulfide bonds between cysteine residues may comprise the steps of removing MeBzl groups and protecting groups other than those of cysteine side chain, subjecting a solution containing the peptide monomers to air oxidation reaction to form a disulfide bond between the deprotected cysteine residues, and then performing deprotection with iodine and oxidation to form a disulfide bond between the cysteine residues protected with Acm groups.

The obtained compound, peptide and intermediate of the present invention can be purified according to a method known to those of ordinary skill in the art and a method generally used for peptide chemistry. For example, they can be purified by techniques such as various types of chromatography (e.g., silica gel column chromatography, ion exchange column chromatography, gel filtration or reversed-phase chromatography) and recrystallization. For example, the recrystallization solvent may be alcohol solvents such as methanol, ethanol, and 2-propanol, ether solvents such as diethyl ether, ester solvents such as ethyl acetate, aromatic hydrocarbon solvents such as benzene and toluene, ketone solvents such as acetone, hydrocarbon solvents such as hexane, aprotonic solvents such as dimethylformamide and acetonitrile, water, or a mixed solvent thereof. Different purification methods described in Jikken Kagaku Kouza (The Chemical Society of Japan ed., Maruzen) vol. 1 or other documents also may be used.

Purification methods for disulfide compounds are described in the documents such as Peptide Synthesis, Interscience, New York, 1966; The Proteins, Vol. 2, Academic Press Inc., New York, 1976; peptide synthesis, Maruzen Co., LTD., 1975; Basics and Experiment of Peptide Synthesis, Maruzen Co., LTD., 1985; and Development of Pharmaceutical Product sequential vol. 14•peptide synthesis, Hirokawa Shoten, 1991. Among these, HPLC is preferable.

When the compound of the present invention has one or more asymmetric points, the compound can be produced according to a general method and using a starting material (amino acid) having the asymmetric points. To increase the optical purity of the compound of the present invention, processes such as optical resolution may be performed at a suitable stage of the production step. Examples of the optical resolution method include a diastereomer method that forms a salt of the compound of the present invention or an intermediate thereof with an optically active acid (e.g., monocarboxylic acids such as mandelic acid, N-benzyloxyalanine, and lactic acid, dicarboxylic acids such as tartaric acid, o-diisopropylidenetartaric acid, and malic acid, or sulfonic acids such as camphorsulfonic acid and bromocamphorsulfonic acid) in an inert solvent (e.g., alcohol solvents such as methanol, ethanol, and 2-propanol, ether solvents such as diethyl ether, ester solvents such as ethyl acetate, hydrocarbon solvents such as toluene, aprotonic solvents such as acetonitrile, or a mixed solvent thereof). When the compound of the present invention or intermediate has an acidic functional group such as carboxy group, optical resolution can also be performed by forming a salt with an optically active amine (e.g., organic amine such as α-phenethylamine, kinin, quinidine, cinchonidine, cinchonine, and strychnine).

The temperature for forming a salt is selected from the range of room temperature to the boiling point of the solvent. To improve the optical purity, it is desirable to once raise the temperature to around the boiling point of the solvent. When the precipitated salt is collected by filtration, it can be cooled as necessary to increase the yield. A suitable amount of the optically active acid or amine to be used is within the range of about 0.5-about 2.0 equivalents, preferably about 1 equivalent, relative to the substrate. Where necessary, the crystals may be recrystallized in an inert solvent (e.g., alcohol solvents such as methanol, ethanol, and 2-propanol, ether solvents such as diethyl ether, ester solvents such as ethyl acetate, hydrocarbon solvents such as toluene, aprotonic solvents such as acetonitrile, or a mixed solvent thereof) to afford an optically active salt with high purity. Where necessary, an optically resolved salt may be treated with an acid or base by a general method to give a free form.

Examples of the "pharmaceutically acceptable salt" in the present invention include acid addition salt and base addition salt. Examples of the acid addition salt include inorganic acid salts such as hydrochloride, hydrobromide, sulfate, hydroiodide, nitrate, and phosphate, and organic acid salts such as citrate, oxalate, acetate, formate, propionate, benzoate, trifluoroacetate, maleate, tartrate, methanesulfonate, benzenesulfonate, and p-toluenesulfonate. Examples of the base addition salt include salts with inorganic base such as sodium salt, potassium salt, calcium salt, magnesium salt, and ammonium salt, salts with organic base such as triethylammonium salt, triethanolammonium salt, pyridinium salt, and diisopropylammonium salt, and furthermore, amino acid salts of basic or acidic amino acids such as arginine, aspartic acid, and glutamic acid.

The present invention also encompasses hydrates, solvates such as ethanol solvate of the compound of the present invention or a pharmaceutically acceptable salt thereof. Furthermore, the present invention encompasses any stereoisomers that can be present such as any diastereomer and enantiomer, and any crystals in any forms, of the compound represented by the formula (1).

In general, in the production of peptides, various byproducts such as peptides lacking amino acid residues, peptides degraded by hydrolysis, oxidation, or other reactions, and peptides with racemized amino acid residues occur in the steps such as a step of condensing an optically active α-amino acid, a step of removing various protecting groups, and a step of cleaving a peptide from a resin. At a laboratory scale, various types of chromatography (e.g., silica gel column chromatography, ion exchange column chromatography, gel filtration, and reversed-phase chromatography)

are combined to remove such impurities, whereby a peptide or compound with high purity can be obtained. However, it is not easy to obtain a peptide or compound with high purity at an industrial scale to provide pharmaceutical products.

The compound of the present invention has physicochemical properties to allow mass production of a drug substance for pharmaceutical products. Specifically, the compound of the present invention has properties such as high solubility and superior stability in a solution and it does not easily turn into a gel when concentrated, and the compound can be produced easily as a drug substance with high purity in a purification step using column chromatography such as reversed-phase HPLC even at a large scale.

The compound of the present invention thus produced is superior in stability against agents such as oxidant in a solution because the cysteine residues form a disulfide bond, for example, and retains a given quality as a drug substance of medicaments and an efficient CTL induction activity.

The compound of the present invention is useful as an active ingredient of a composition for inducing CTLs for cancer immunotherapy, an active ingredient of a cancer vaccine, or an active ingredient of a pharmaceutical composition. That is, the compound of the present invention has, as shown in the Examples of the present specification, superior immunogenicity and can efficiently show a superior CTL induction activity. In addition, CTLs induced by the compound of the present invention can surprisingly recognize a naturally-occurring partial peptide of a cancer antigen protein inherently present in cancer cells.

The CTL induction activity can be detected by measuring the number of CTLs by the HLA tetramer method (Int. J. Cancer: 100, 565-570 (2002)) or limiting dilution method (Nat. Med.: 4, 321-327 (1998)). Alternatively, HLA-A24-restricted CTL induction activity can be examined by using the HLA-A24 model mouse described in WO 02/47474 and Int. J. Cancer: 100, 565-570 (2002), for example.

Therefore, the compound of the present invention can be used as a therapeutic drug or prophylactic drug (recurrence preventive drug) for cancer expressing a cancer antigen protein or cancer associated with an increased level of gene expression of a cancer antigen protein. Examples of the cancer include hematologic cancer such as leukemia, myelodysplastic syndrome, multiple myeloma, and malignant lymphoma, and solid tumor such as gastric cancer, colorectal cancer, lung cancer, breast cancer, germ cell cancer, liver cancer, skin cancer, urinary bladder cancer, prostate cancer, uterine cancer, cervical cancer, ovarian cancer, and brain tumor.

The compound of the present invention or a pharmaceutically acceptable salt thereof can be an active ingredient of a composition of inducing CTLs for cellular immunotherapy of cancer, an active ingredient of a cancer vaccine or/and an active ingredient of a pharmaceutical composition, in a form suitable for each compound or salt.

The compound of the present invention can be administered together with a carrier acceptable as a medicament such as a suitable adjuvant so that its cellular immunity will be established effectively. Adjuvants such as those described in a document (Clin. Microbiol. Rev., 7: 277-289, 1994) may be applicable. Specifically, fungus-derived components, GM-CSF, cytokines such as interleukin-2, interleukin-7, and interleukin-12, plant-derived components, marine organism-derived components, mineral gel such as aluminum hydroxide, lysolecithin, surfactants such as pluronic polyol, polyanion, peptide, and oil emulsion (emulsion preparation) may be mentioned. Examples of the fungus-derived components include lipid A, monophosphoryl lipid A, which is a derivative of lipid A, dead bacteria (*Mycobacterium* bacteria such as BCG bacteria), bacterium-derived proteins, polynucleotides, Freund's Incomplete Adjuvant, Freund's Complete Adjuvant, cell wall skeleton components (e.g., BCG-CWS), trehalose dimycolate (TDM).

In addition, the compound of the present invention also can be administered in the form of a liposome preparation, a particulate preparation comprising the compound bound to a bead with a diameter of several μm, or a preparation comprising the compound bound to a lipid, for example.

Furthermore, the compound of the present invention (conjugate) can be administered together with an MHC class II-restricted peptide (namely, helper peptide). While the conjugate and a helper peptide may be individually administered, a cocktail preparation (also called as cocktail composition or cocktail) containing the conjugate and a helper peptide in a single pharmaceutical composition is more preferable. The cocktail preparation contains an MHC class II-restricted peptide (namely, helper peptide) in addition to a conjugate capable of producing an MHC class I-restricted peptide (i.e., killer peptide). Therefore, when administered as a cancer vaccine for cancer immunotherapy, the cocktail preparation containing a helper peptide can also activate helper T cells, which are important for functional promotion of other T cells including CTLs, and improve function and efficacy of the conjugate such as cellular immunogenicity.

The MHC class II-restricted peptide (namely, helper peptide) is as described herein. The improved efficacy of the cocktail preparation as a cancer vaccine such as cellular immunogenicity have been confirmed as shown in Examples and Experimental Examples, for example.

While the dose of the compound of the present invention in the preparation may be appropriately controlled depending on factors such as the disease to be treated or age and body weight of the patient, it is generally 0.0001 mg-1000 mg, preferably 0.001 mg-1000 mg, more preferably 0.1 mg-10 mg.

Examples of administration methods include intradermal administration, subcutaneous administration, intramuscular administration, intravenous administration, and transdermal administration. Intradermal administration and subcutaneous administration are preferable because they efficiently induce CTLs. While the administration frequency and administration intervals may be appropriately controlled depending on the disease to be prevented or treated and individual difference in patients, the compound is generally administered more than once, and preferably once per several days to several months.

Administration of a pharmaceutical composition comprising the compound of the present invention as described above as an active ingredient to patients positive for a cancer antigen protein achieves prophylaxis or treatment of cancer.

EXAMPLES

The present invention is specifically explained in the following by referring to Examples, to which, however, the invention is not limited.

Example 1

Synthesis of the Peptide Consisting of the Following Amino Acid Sequence:

```
                                        (SEQ ID NO: 100)
CKIFGSLAFL
```

1. Synthesis of the protected peptide resin Fmoc-Lys(Boc)-Ile-Phe-Gly-Ser(tBu)-Leu-Ala-Phe-Leu-Alko-Resin (SEQ ID NO: 243)

8.25 g of Fmoc-Leu-Alko-resin (Alko is p-alkoxybenzylalcohol) (manufactured by Watanabe Chemical; 0.77 mmol/g) was placed in a 1.0 L glass reaction vessel and treated with 150 mL of 30% Pip (piperidine)/DMF (dimethylformamide) solution (10 min×1, 5 min×2: a total of 450 mL) to remove Fmoc group (step 1). After washing of the resin with DMF and diethyl ether, 6.2 g (5 equivalents) of Fmoc-Phe-OH, 6.04 g (5 equivalents) of HBTU (O-benzotriazol-1-yl-N,N,N',N'-tetramethyluronium hexafluorophosphate) and 2.46 g (5 equivalents) of HOBT (1-hydroxybenzotriazole) were added, subsequently 150 ml of DMF and 5.52 ml (5 equivalents) of DIEA (N,N-diisopropylethylamine) were added, and the mixture was stirred at room temperature for 3 hr (step 2). The resin was washed with DMF twice to synthesize Fmoc-Phe-Leu-Alko resin.

Step 1 and step 2 were sequentially performed by using each of the amino acids shown below.

5.14 g of Fmoc-Ala-OH, 5.69 g of Fmoc-Leu-OH, 6.18 g of Fmoc-Ser(tBu)-OH, 4.97 g of Fmoc-Gly-OH, 6.63 g of Fmoc-Phe-OH, 5.98 g of Fmoc-Ile-OH, and 7.83 g of Fmoc-Lys(Boc)-OH.

For Fmoc-Ser(tBu)-OH, step 2 was repetitively performed three times. After washing of the obtained resin with DMF, an unreacted amino group was capped using 25% $Ac_2O$ (acetic anhydride) (15 min×2). Finally, washing with DMF was carried out to give 14.14 g of Fmoc-Lys(Boc)-Ile-Phe-Gly-Ser(tBu)-Leu-Ala-Phe-Leu-Alko-Resin (SEQ ID NO: 243).

2. Synthesis of the protected peptide resin H-Cys(tBu)-Lys(Boc)-Ile-Phe-Gly-Ser(tBu)-Leu-Ala-Phe-Leu-Alko-Resin (SEQ ID NO: 244)

503 mg of the protected peptide resin Fmoc-Lys(Boc)-Ile-Phe-Gly-Ser(tBu)-Leu-Ala-Phe-Leu-Alko-Resin (SEQ ID NO: 243) obtained by the aforementioned operation was placed in a 25 ml glass reaction vessel, and subjected to the deprotection operation of step 1 while being shaken in a rotary shaker N-500 manufactured by Kokusan Chemical, to give H-Lys(Boc)-Ile-Phe-Gly-Ser(tBu)-Leu-Ala-Phe-Leu-Alko-Resin (SEQ ID NO: 245). A solution of 340.4 mg of Fmoc-Cys(tBu)-OH, 248.2 mg of HBTU and 92.9 mg of HOBT dissolved in 10 ml of DMF was added, further 0.2 ml of DIEA was added, and the mixture was shaken at room temperature for 3 hr, whereby the coupling reaction of step 2 was performed. After washing with 10 ml of DMF 4 times, Fmoc group was cleaved by treatment with 30% Pip/DMF 10 ml (10 min×1 and 5 min×2). 100 ml of TFA cocktail (2.5% tetraisopropylsilane/2.5% dodecanethiol/2.5% $H_2O$/92.5% TFA solution) was added, and the mixture was stirred at room temperature for 2.0 hr. Thereafter, diethyl ether was added, and filtration through a glass filter was performed to remove TFA cocktail and diethyl ether as a filtrate. The residue was washed with diethyl ether to give 269.5 mg of crude peptide (CKIFGSLAFL (SEQ ID NO: 100)).

3. Purification of the Crude Peptide

The obtained crude peptide (269.5 mg) was charged into HPLC (manufactured by Shimadzu; LC8AD) loaded with a Daiso-Pak ODS 30 I.D.×250 mm column (manufactured by Daiso) equilibrated with eluting solution 1 ($H_2O$/0.1% TFA) and eluting solution 2 ($CH_3CN$/0.1% TFA) with the concentration of eluting solution 2 ($CH_3CN$/0.1% TFA) set to 24.3%. While monitoring the eluate of the peptide of interest by 220 nm UV, the concentration of eluting solution 2 was raised to 44.3% in 80 min, and the fractions containing the peptide of interest were collected. The obtained solution was freeze dried to give 49 mg of the desired purified product.

pump: manufactured by Shimadzu; LC-8A
column: ODS Daiso-Pak ODS 30 I.D. cmφ×cmL
eluting solution 1: $H_2O$/0.1% TFA
eluting solution 2: $CH_3CN$/0.1% TFA
flow rate: 20 ml/min
column temperature: 40° C.
detection: UV 220 nm
mass spectrometry: LC-ESI/MS m/z=1098.9 $[M+1]^+$ (Calculated=1098.4)

Examples 2-20

By a method similar to that in Example 1, respective peptides consisting of the amino acid sequences of SEQ ID NOs: 95-97 and 108-123 were synthesized. Tables 16 and 17 show the result of mass spectrometry of each synthesized peptide.

All of the peptides in Tables 16 and 17 are the compounds of the present invention of the formula (1) wherein $R^1$ is a hydrogen atom, $X^a$ is a single bond, $Y^a$ is a divalent peptide group consisting of 1 amino acid residue, and cancer antigen peptide A is HER2/neu$_{369-377}$ peptide (KIFGSLAFL) (SEQ ID NO: 53), which is a partial peptide of the cancer antigen protein HER2/neu.

TABLE 16

| Ex. No. | amino acid sequence | SEQ ID NO: | mass spectrometry: LC-ESI/ Ms m/z | mass spectrometry: Calculated |
|---|---|---|---|---|
| 2 | CAKIFGSLAFL | 95 | 1169.8 $[M + 1]^+$ | 1169.4 |
| 3 | CRKIFGSLAFL | 108 | 628.3 $[M + 2H]^{2+}$ | 1254.5 |
| 4 | CNKIFGSLAFL | 109 | 1212.9 $[M + 1]^+$ | 1212.5 |
| 5 | CDKIFGSLAFL | 110 | 1214.0 $[M + 1]^+$ | 1213.4 |
| 6 | CCKIFGSLAFL | 111 | 1201.9 $[M + 1]^+$ | 1201.5 |
| 7 | CQKIFGSLAFL | 112 | 1227.0 $[M + 1]^+$ | 1226.5 |
| 8 | CGKIFGSLAFL | 113 | 1155.9 $[M + 1]^+$ | 1155.4 |
| 9 | CHKIFGSLAFL | 114 | 618.8 $[M + 2H]^{2+}$ | 1235.5 |
| 10 | CEKIFGSLAFL | 115 | 1228.0 $[M + 1]^+$ | 1227.5 |

TABLE 17

| Ex. No. | amino acid sequence | SEQ ID NO: | mass spectrometry: LC-ESI/ Ms m/z | mass spectrometry: Calculated |
|---|---|---|---|---|
| 11 | CLKIFGSLAFL | 96 | 1212.0 $[M + 1]^+$ | 1211.5 |
| 12 | CMKIFGSLAFL | 97 | 1223.0 $[M + 1]^+$ | 1229.6 |

TABLE 17-continued

| Ex. No. | amino acid sequence | SEQ ID NO: | mass spectrometry: LC-ESI/ Ms m/z | mass spectrometry: Calculated |
|---|---|---|---|---|
| 13 | CIKIFGSLAFL | 116 | 1212.0 [M + 1]$^+$ | 1211.5 |
| 14 | CFKIFGSLAFL | 117 | 1246.0 [M + 1]$^+$ | 1245.5 |
| 15 | CPKIFGSLAFL | 118 | 1196.0 [M + 1]$^+$ | 1195.5 |
| 16 | CSKIFGSLAFL | 119 | 1186.0 [M + 1]$^+$ | 1185.4 |
| 17 | CTKIFGSLAFL | 120 | 1199.9 [M + 1]$^+$ | 1199.5 |
| 18 | CWKIFGSAFL | 121 | 1285.0 [M + 1]$^+$ | 1284.6 |
| 19 | CYKIFGSLAFL | 122 | 1261.9 [M + 1]$^+$ | 1261.5 |
| 20 | CVKIFGSLAFL | 123 | 1198.0 [M + 1]$^+$ | 1197.5 |

Reference Example 1

By a method similar to that in Example 1, a peptide consisting of the amino acid sequence of SEQ ID NO: 86 was synthesized. Table 18 shows the result of mass spectrometry of the synthesized peptide.

The peptide of SEQ ID NO: 86 is not the compound of the present invention as mentioned above and is therefore described as Reference Example 1.

TABLE 18

| Ref. Ex. No. | amino acid sequence | SEQ ID NO: | mass spectrometry: LC-ESI/ Ms m/z | mass spectrometry: Calculated |
|---|---|---|---|---|
| 1 | CKKIFGSLAFL | 86 | 614.4 [M + 2H]$^{2+}$ | 1226.5 |

Examples 21-24

By a method similar to that in Example 1, respective peptides consisting of the amino acid sequences of SEQ ID Nos: 92-94 and 99 were synthesized. Table 19 shows the result of mass spectrometry of each synthesized peptide.

All of the peptides in Table 19 are the compounds of the present invention of the formula (1) wherein R$^1$ is a hydrogen atom, X$^a$ is a single bond, Y$^a$ is a single bond or a divalent peptide group consisting of 1 amino acid residue, and cancer antigen peptide A is Proteinase-3$_{169-177}$ peptide (VLQELNVTV) (SEQ ID NO: 43), which is a partial peptide of the cancer antigen protein Proteinase-3.

TABLE 19

| Ex. No. | amino acid sequence | SEQ ID NO: | mass spectrometry: LC-ESI/ Ms m/z [M +1]$^+$ | mass spectrometry: Calculated |
|---|---|---|---|---|
| 21 | CVLQELNVTV | 99 | 1117.9 | 1118.3 |
| 22 | CAVLQELNVTV | 92 | 1189.0 | 1189.4 |
| 23 | CLVLQELNVTV | 93 | 1231.0 | 1231.5 |
| 24 | CMVLQELNVTV | 94 | 1249.0 | 1249.5 |

Examples 25-28

By a method similar to that in Example 1, respective peptides consisting of the amino acid sequences of SEQ ID NOs: 98, 89-91 were synthesized. Table 20 shows the result of mass spectrometry of each synthesized peptide.

All of the peptides in Table 20 are the compounds of the present invention of the formula (1) wherein R$^1$ is a hydrogen atom, X$^a$ is a single bond, Y$^a$ is a single bond or a divalent peptide group consisting of 1 amino acid residue, and cancer antigen peptide A is MAGE-A10$_{254-262}$ peptide (GLYDGMEHL) (SEQ ID NO: 19), which is a partial peptide of the cancer antigen protein MAGE-A10.

TABLE 20

| Ex. No. | amino acid sequence | SEQ ID NO: | mass spectrometry: LC-ESI/ Ms m/z | mass spectrometry: Calculated |
|---|---|---|---|---|
| 25 | CGLYDGMEHL | 98 | 569.5 [M + 2H]$^{2+}$ | 1137.5 |
| 26 | CAGLYDGMEHL | 89 | 1209.0 [M + 1]$^+$ | 1208.5 |
| 27 | CLGLYDGMEHL | 90 | 1250.9 [M + 1]$^+$ | 1250.5 |
| 28 | CMGLYDGMEHL | 91 | 1269.0 [M + 1]$^+$ | 1268.5 |

Experimental Example 1

Test of Trimming of N-Terminal Amino Acid by ERAP1

The peptides synthesized in Examples 1-20 were evaluated for N-terminal amino acid trimming efficiency using ERAP1 (PLoS One November 2008, vol. 3, Issue 11, e3658). 50 µl of ERAP1 solution (50 ng/ml) in pH 8.0, 20 mM Tris.HCl-100 mM NaCl buffer (Tris.HCl buffer) was added to 142 µl of Tris.HCl buffer. An aqueous solution of 2.5 mM each peptide (8.0 µl) was added to the aforementioned ERAP1 solution, and the mixture was blended well and stood at room temperature. 1.0 hr later, 50 µl of the mixture was injected into UFLC (under the analysis conditions shown below), and AUC of the peptide of interest was determined. The peptide to be obtained by trimming was chemically synthesized separately, and analyzed under similar conditions in the absence of the enzyme. The formation ratio of the peptide [HER2/neu$_{369-377}$ peptide (KIFG-SLAFL) (SEQ ID NO: 53)] obtained by trimming was determined based on the obtained AUC, and is shown in Table 21.

Analysis Conditions
pump: UFLC manufactured by Shimadzu
column: Shim-pack XR-ODS 3.0 mmi.d.×75 mm
solution: 0.05% TFA $H_2O$(A)-0.05% TFA $CH_3CN$(B)
oven temperature: 40° C.
flow rate: 1.0 ml/min
detection wavelength: λ=220 nm
gradient: concentration of SOLUTION B was raised from 10% to 60% from 0.0 min to 5.0 min

TABLE 21

| Example | amino acid sequence | SEQ ID NO: | formation rate of KIFGSLAFL (SEQ ID NO: 53)(%) |
|---|---|---|---|
| 1 | CKIFGSLAFL | 100 | 27.6 |
| 2 | CAKIFGSLAFL | 95 | 49.7 |
| 3 | CRKIFGSLAFL | 108 | 5.7 |
| 4 | CNKIFGSLAFL | 109 | 0 |
| 5 | CDKIFGSLAFL | 110 | 0 |
| 6 | CCKIFGSLAFL | 111 | 2.1 |
| 7 | CQKIFGSLAFL | 112 | 69.4 |
| 8 | CGKIFGSLAFL | 113 | 0 |
| 9 | CHKIFGSLAFL | 114 | 5.6 |
| 10 | CEKIFGSLAFL | 115 | 20.3 |
| 11 | CLKIFGSLAFL | 96 | 13.5 |
| 12 | CMKIFGSLAFL | 97 | 26.7 |
| 13 | CIKIFGSLAFL | 116 | 31.7 |
| 14 | CFKIFGSLAFL | 117 | 13.4 |
| 15 | CPKIFGSLAFL | 118 | 0 |
| 16 | CSKIFGSLAFL | 119 | 51.2 |
| 17 | CTKIFGSLAFL | 120 | 13.1 |
| 18 | CWKIFGSLAFL | 121 | 3.92 |
| 19 | CYKIFGSLAFL | 122 | 5.3 |
| 20 | CVKIFGSLAFL | 123 | 36.6 |

Experimental Example 2

Time-course changes of trimming of N-terminal amino acid by ERAP1

The peptides synthesized in Examples 1-2, 11-12, and 21-28 were evaluated for time-course changes of the trimming of the N-terminal amino acid(s) by ERAP1. 20 μl of ERAP1 solution (0.5 mg/ml) in Tris.HCl buffer was added to 172 μl of Tris.HCl buffer. 10 mM peptide solution in DMSO (8.0 μl) was added to the aforementioned ERAP1 solution, and the mixture was blended well and stood at room temperature. 1.0, 2.0, 4.0, and 8.0 hr later, 50 μl of the sample was added to 150 μl of MeOH to terminate the reaction, 25 μl of the resulting solution was injected into UFLC (under the analysis conditions shown below), and AUC of the peptide of interest was determined. The peptide to be obtained by trimming was chemically synthesized separately, and analyzed under similar conditions in the absence of the enzyme. The formation ratio of the peptide obtained by trimming was determined based on the obtained AUC, and is shown in Table 22.

Analysis Conditions
pump: UFLC manufactured by Shimadzu
column: Shim-pack XR-ODS 3.0 mmi.d.×75 mm
solution: 0.05% TFA $H_2O$(A)-0.05% TFA $CH_3CN$(B)
oven temperature: 40° C.
flow rate: 1.0 ml/min
detection wavelength: λ=220 nm
gradient: Concentration of SOLUTION B was raised from 1.0% 70% from 0.0 min to 5.0 min
peptide of interest:

The peptide to be obtained by the trimming of the N-terminal amino acid(s) by ERAP1 is,
in the case of each peptide of SEQ ID NOs: 100 and 95-97, HER2/neu$_{369-377}$ peptide (KIFGSLAFL) (SEQ ID NO: 53),
in the case of each peptide of SEQ ID NOs: 99 and 92-94, Proteinase-3$_{169-177}$ peptide (VLQELNVTV) (SEQ ID NO: 43), or
in the case of peptide of SEQ ID NOs: 98 and 89-91, MAGE-A10$_{254-262}$ peptide (GLYDGMEHL) (SEQ ID NO: 19).

TABLE 22

| Ex. No. | SEQ ID NO: | formation rate(%) | | | |
|---|---|---|---|---|---|
| | | 1 hr later | 2 hr later | 4 hr later | 8 hr later |
| 1 | 100 | 20.0 | 30.7 | 33.9 | 22.0 |
| 2 | 95 | 17.0 | 35.5 | 44.3 | 23.0 |
| 11 | 96 | 6.9 | 11.3 | 16.0 | 13.3 |
| 12 | 97 | 10.5 | 13.4 | 24.1 | 20.9 |
| 21 | 99 | 83.4 | 85.6 | 78.8 | 83.9 |
| 22 | 92 | 46.1 | 49.9 | 51.3 | 53.5 |
| 23 | 93 | 31.1 | 36.9 | 38.1 | 36.1 |
| 24 | 94 | 28.7 | 34.5 | 36.5 | 36.8 |
| 25 | 98 | 95.1 | 106 | 100 | 101 |
| 26 | 89 | 87.8 | 99.4 | 103 | 97.5 |
| 27 | 90 | 58.3 | 94.9 | 88.4 | 88.3 |
| 28 | 91 | 90.6 | 103 | 96.0 | 101 |

Experimental Example 3

Evaluation of In Vivo CTL Induction Ability Using HLA-A0201 Transgenic Mouse

The CTL induction ability of each peptide extended by cysteine (Cys) (Cys-extended peptide) shown in Table 23 was evaluated by in vivo CTL induction test using an HLA-A0201 transgenic mouse.

TABLE 23

| Example | amino acid sequence | SEQ ID NO: |
|---|---|---|
| 1 | CKIFGSLAFL | 100 |
| 21 | CVLQELNVTV | 99 |
| 25 | CGLYDGMEHL | 98 |

HLA-A0201 transgenic mouse (C57BL/6CrHLA-A2.1DR1) is a mouse which is defective in mouse MHC, and expresses a chimera HLA of human MHC HLA-A0201 and mouse MHC H-2D$^b$, and HLA-DRB1*0101. Using this mouse, peptides capable of inducing CTLs in HLA-A02 positive humans can be selected (Eur J Immunol. 2004; 34: 3060-9).

Whether the administration of the peptide extended by Cys (SEQ ID NO: 100, 99 or 98) results in the induction of CTLs to a peptide (SEQ ID NO: 53, 43 or 19) endogenously presented by cancer cells was determined based on the measurement of IFNγ production by re-stimulation, with the peptide (SEQ ID NO: 53, 43 or 19), of the splenocyte derived from the above-mentioned mouse administered with the peptide extended by Cys (SEQ ID NO: 100, 99 or 98). The peptide (SEQ ID NO: 53, 43 or 19) endogenously presented by cancer cells shown in Table 24 is also referred to as a Cys non-extended peptide in this Experimental Example.

TABLE 24

| amino acid sequence | SEQ ID NO: |
|---|---|
| KIFGSLAFL | 53 |
| VLQELNVTV | 43 |
| GLYDGMEHL | 19 |

Specifically, each peptide (SEQ ID NO: 19, 43, 53, 98, 99 or 100) was dissolved in dimethyl sulfoxide (DMSO) at 200 mg/mL, further diluted with phosphate buffered saline (PBS, pH 5) to 2 mg/mL, and emulsified by mixing with an equal amount of incomplete Freund's adjuvant (IFA). The emulsified peptide was intradermally administered to 2 sites at the base of tail of the mouse at 50 μg/site. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated at $2.5 \times 10^5$ cells/well on the blocked ELISPOT plate. Each peptide (SEQ ID NO: 19, 43, 53, 98, 99 or 100) was dissolved in DMSO at 40 mg/mL, and further diluted with RPMI1640 medium containing 10% FBS to 40 μg/mL. The splenocytes derived from the mouse administered with the peptide represented by SEQ ID NO: 53 or 100 were pulsed with each of the diluted peptides represented by SEQ ID NO: 53 and 100 (final concentration: 10 μg/mL). The splenocytes derived from the mouse administered with the peptide represented by SEQ ID NO: 43 or 99 were pulsed with each of the diluted peptides represented by SEQ ID NOs: 43 and 99 (final concentration: 10 μg/mL). The splenocytes derived from the mouse administered with the peptide represented by SEQ ID NO: 19 or 98 were pulsed with each of the diluted peptides represented by SEQ ID NOs: 19 and 98 (final concentration: 10 μg/mL). These splenocytes were cultivated for 20 hr at 37° C., 5% $CO_2$, whereby peptide re-stimulation in vitro was performed. Thereafter, the supernatant was removed, and the ELISPOT plate was allowed to develop color according to the attached protocol. The number of spots that developed color was measured by KS ELISPOT.

Figure 5:
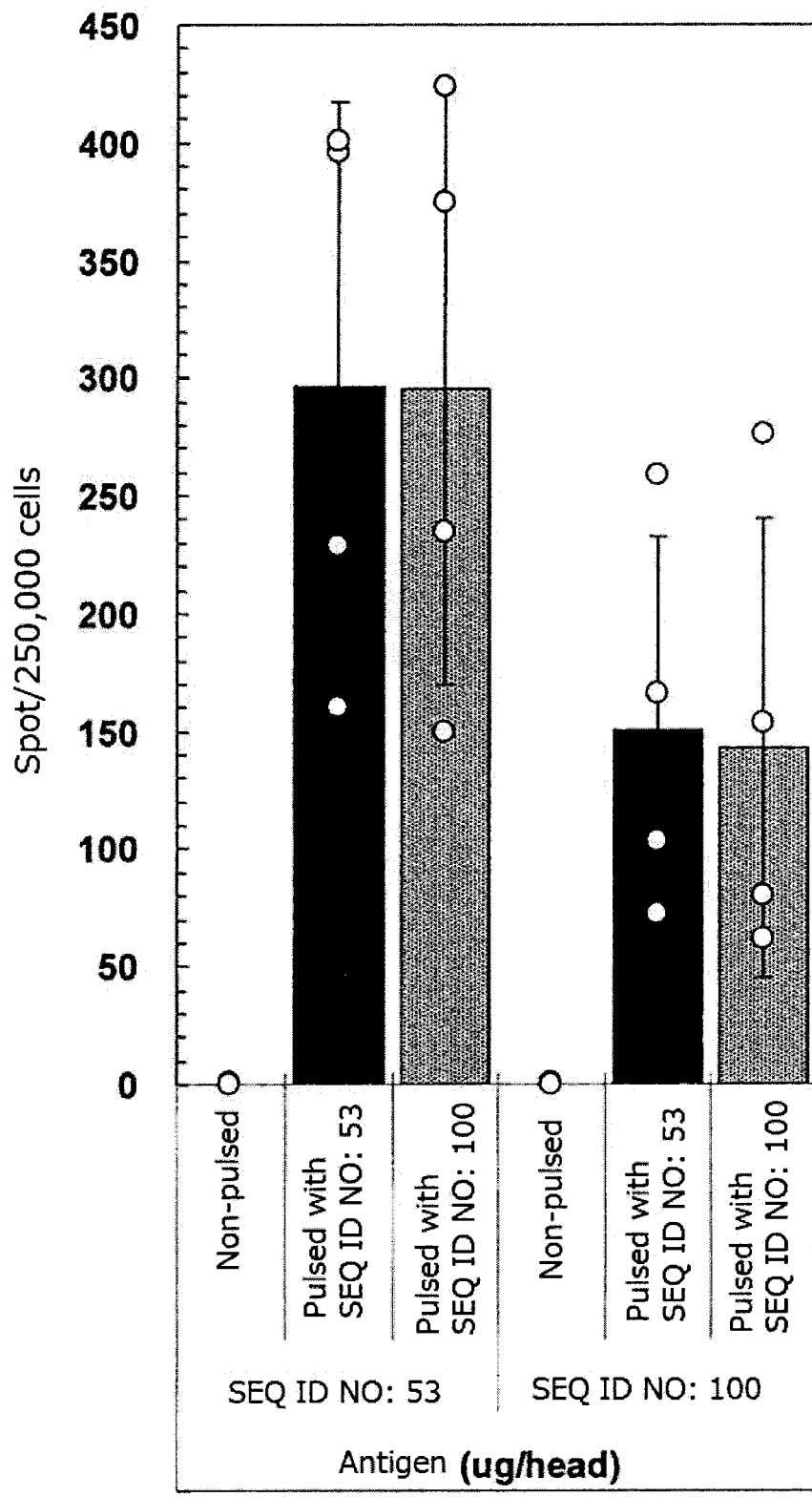
FIG. 5 is a Figure showing the test results of Experimental Example 3 that examined the in vivo CTL induction ability of peptide of SEQ ID NO: 100 synthesized in Example 1, by IFNγ ELISPOT assay using HLA-A0201 transgenic mouse.
Figure 6:
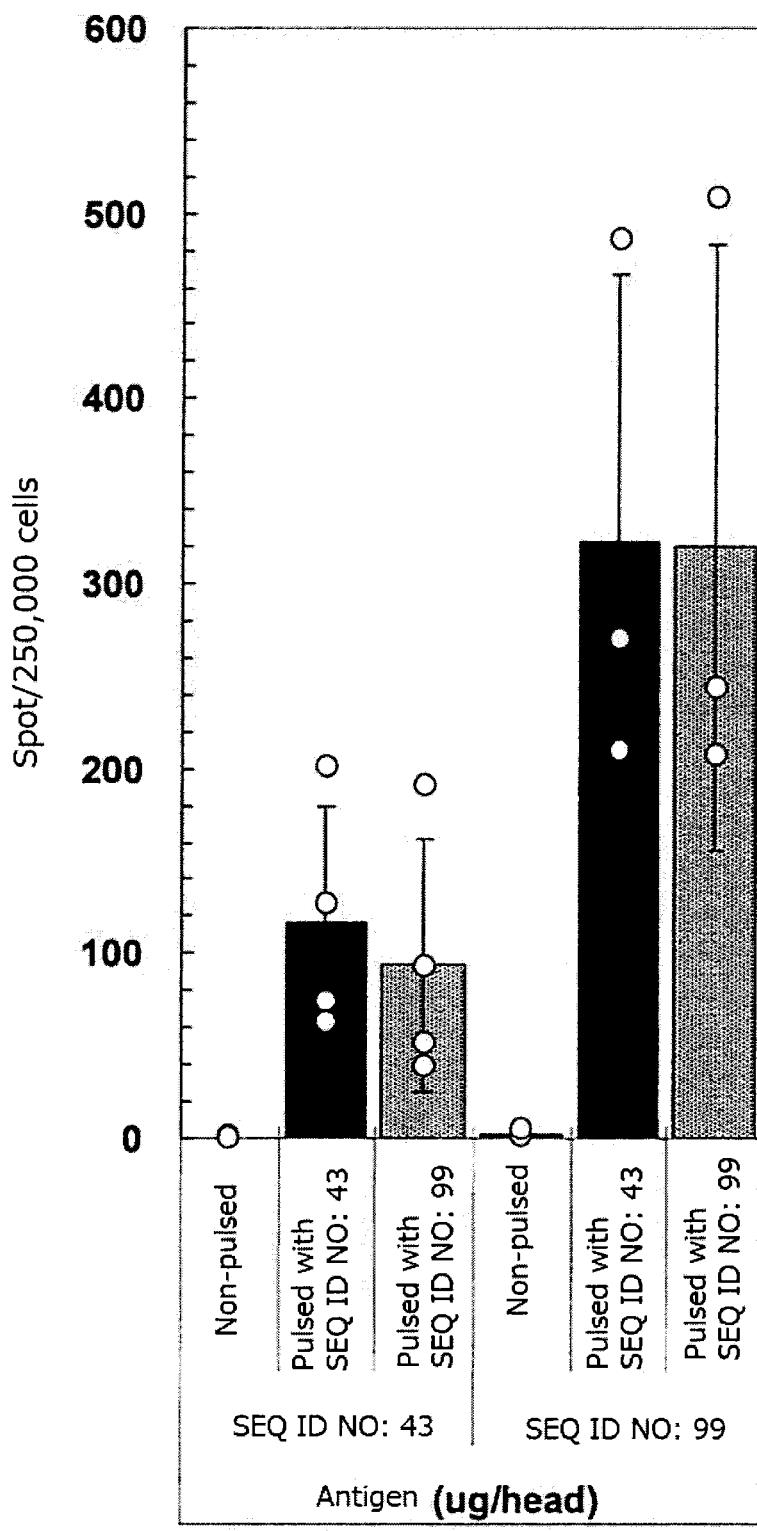
FIG. 6 is a Figure showing the test results of Experimental Example 3 that examined the in vivo CTL induction ability of peptide of SEQ ID NO: 99 synthesized in Example 21, by IFNγ ELISPOT assay using HLA-A0201 transgenic mouse.
Figure 7:
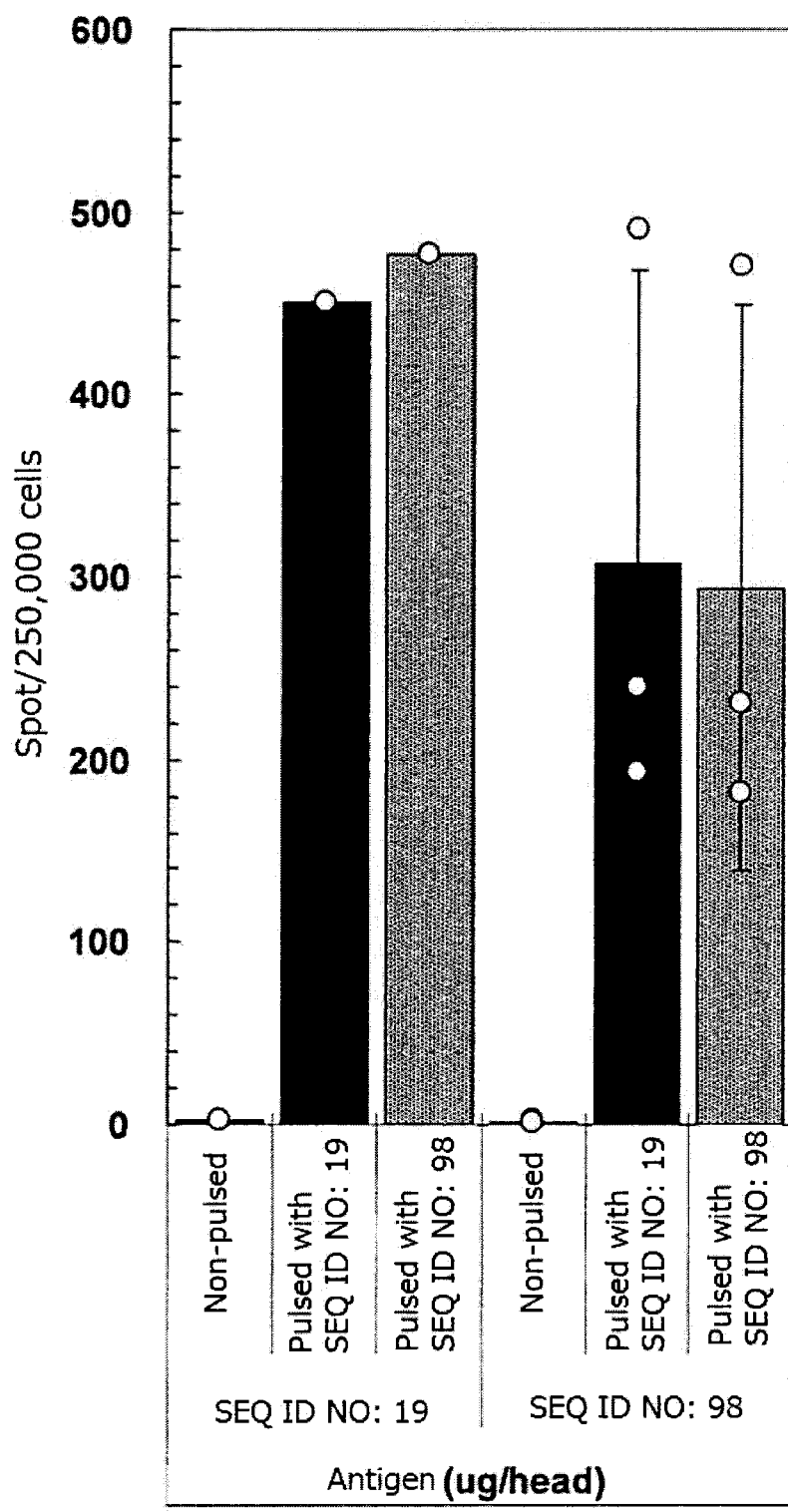
FIG. 7 is a Figure showing the test results of Experimental Example 3 that examined the in vivo CTL induction ability of peptide of SEQ ID NO: 98 synthesized in Example 25, by IFNγ ELISPOT assay using HLA-A0201 transgenic mouse.

The results of IFNγ ELISPOT assay are shown in FIGS. 5-7. In each Figure, the vertical axis shows the number of cells that responded among the plated cells. In any of Figures, the value of the white bar showing the result in the non-pulsed state is hardly detected. This means that the splenocytes of respective transgenic mice did not react at all in the absence of peptide re-stimulation. That is, the difference in the values of the color bar and the white bar shows the number of CTLs specific to the peptide used in in vitro re-stimulation, and that CTLs were induced in the mouse in vivo by the administration of each peptide. Here, the color bar means the black bar showing the result in the pulsed state with the Cys non-extended peptide, or the gray bar showing the result in the pulsed state with the Cys-extended peptide. FIG. 5 shows the results of administration of the peptide represented by SEQ ID NO: 53 or 100. FIG. 6 shows the results of administration of the peptide represented by SEQ ID NO: 43 or 99. FIG. 7 shows the results of administration of the peptide represented by SEQ ID NO: 19 or 98. From the above, a similar level of IFNγ production was confirmed by in vitro stimulation with the Cys non-extended peptide or the Cys-extended peptide in the HLA-A0201 transgenic mouse-derived splenocytes, regardless of the presence or absence of Cys extension of the peptide administered in vivo, and it was demonstrated that the Cys-extended peptide (SEQ ID NO: 100, 99 and 98) has an in vivo CTL induction ability. That is, it was demonstrated that the administration of the Cys-extended peptide (SEQ ID NO: 100, 99 or 98) can induce CTLs that can recognize the Cys non-extended peptide (SEQ ID NO: 53, 43 or 19). This means that the Cys-extended peptide can induce CTLs recognizing a peptide (Cys non-extended peptide) endogenously presented by cancer cells. It was strongly suggested that the Cys-extended peptide undergoes appropriate trimming by ERAP1 in mice in vivo and is indeed processed into the Cys non-extended peptide.

Example 29

Synthesis of the Compound Represented by the Formula (4)

wherein the bond between C and C is a disulfide bond
Step 1. Synthesis of H-Cys(Pys)-Gly-Leu-Tyr-Asp-Gly-Met-Glu-His-Leu-OH) (SEQ ID NO: 246)
[i.e., Synthesis of the compound represented by the formula (13):

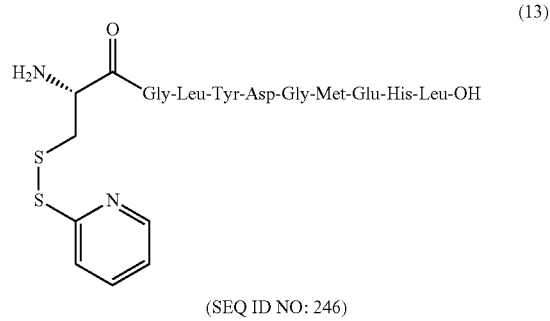

(SEQ ID NO: 246)

1.20 mL of an isopropanol solution of 2,2'-bispyridyl disulfide (0.2 M) was added to 2.74 mL of 20% (w/w) acetic acid aqueous solution of H-Cys-Gly-Leu-Tyr-Asp-Gly-Met-Glu-His-Leu-OH (SEQ ID NO: 98) (274 mg) obtained in Example 25, and the mixture was stirred at room temperature for 30 min. The reaction mixture was purified by reversed-phase HPLC.

pump: manufactured by Shimadzu; LC-8A
column: YMC ODS-A 3 cmϕ×25 cmL, 10 μm
eluting solution 1: H₂O/0.1% TFA
eluting solution 2: CH₃CN/0.1% TFA
flow rate: 20 ml/min
detection: UV 220 nm The reaction solution was injected to a column equilibrated with 10% eluting solution 2. Thereafter, the concentration of eluting solution 2 was raised to 32% over 10 min and then raised at a rate of 0.25% per minute. Fractions containing the desired product were collected and freeze dried to give 230 mg of H-Cys(Pys)-Gly-Leu-Tyr-Asp-Gly-Met-Glu-His-Leu-OH (SEQ ID NO: 246) (i.e., the compound represented by the formula (13)).

mass spectrometry: LC-ESI/MS m/z=1246.7 [M+H]¹⁺ (Calculated=1246.5)

Step 2. Synthesis of (H-Cys-Gly-Leu-Tyr-Asp-Gly-Met-Glu-His-Leu-OH)(H-Cys-Lys-Ile-Phe-Gly-Ser-Leu-Ala-Phe-Leu-OH)disulfide bond
[i.e., Synthesis of the compound represented by the formula (4):

(4)

wherein the bond between C and C is a disulfide bond]

27 mg of H-Cys(Pys)-Gly-Leu-Tyr-Asp-Gly-Met-Glu-His-Leu-OH (SEQ ID NO: 246) (i.e., the compound represented by the formula (13)) obtained in step 1 and 23 mg of H-Cys-Lys-Ile-Phe-Gly-Ser-Leu-Ala-Phe-Leu-OH (SEQ ID NO: 100) obtained in Example 1 were mixed, 2 mL of 20% (v/v) acetic acid aqueous solution was added, and the mixture was stirred at room temperature for 30 min. The reaction mixture was purified by reversed-phase HPLC.
pump: manufactured by Shimadzu; LC-8A
column: YMC ODS-A 3 cmϕ×25 cmL, 10 μm
eluting solution 1: H₂O/0.1% TFA
eluting solution 2: CH₃CN/0.1% TFA
flow rate: 20 ml/min
detection: UV 220 nm The reaction solution was injected to a column equilibrated with 10% eluting solution 2. Thereafter, the concentration of eluting solution 2 was raised to 34% over 10 min and then raised at a rate of 0.25% per minute. Fractions containing the desired product were collected and freeze dried to give 21 mg of the desired compound represented by the formula (4).

mass spectrometry: LC-EST/MS m/z=1118.0 [M+2H]² (Calculated=1117.8)

Example 30

Synthesis of the Compound Represented by the Formula (10):

(10)

wherein the bond between C and C is a disulfide bond

By a method similar to that in Example 29, the compound represented by the formula (10) was synthesized.

mass spectrometry: LC-ESI/MS m/z=1082.2 [M+2H]²⁺ (Calculated=1082.3)

Experimental Example 4

Evaluation of In Vivo CTL Induction Ability Using HLA-A0201 Transgenic Mouse

The compound represented by the formula (4) synthesized in Example 29 was evaluated for the CTL induction ability by an in vivo CTL induction test using an HLA-A0201 transgenic mouse. The compound represented by the formula (4):

(4)

wherein the bond between C and C is a disulfide bond, is, in particular, a compound of the aforementioned formula (1) wherein cancer antigen peptide A is GLYDGMEHL (SEQ ID NO: 19) and cancer antigen peptide B is KIFGSLAFL (SEQ ID NO: 53). GLYDGMEHL (SEQ ID NO: 19) and KIFGSLAFL (SEQ ID NO: 53) are HLA-A0201-restricted cancer antigen peptides.

The HLA-A0201 transgenic mouse (C57BL/6CrHLA-A2.1DR1) is a mouse which is defective in mouse MHC, and expresses a chimera HLA of human MHC HLA-A0201 and mouse MHC H-2D$^b$, and HLA-DRB1*0101. Using this mouse, peptides capable of inducing CTLs in HLA-A02 positive humans can be selected (Eur J Immunol. 2004; 34: 3060-9).

To evaluate whether CTLs to each of the peptides (SEQ ID NOs: 19 and 53) endogenously presented by cancer cells was induced, the compound represented by the formula (4) was administered to the HLA-A0201 transgenic mouse. That is, it was determined whether IFNγ production was observed by re-stimulation, with the peptide (SEQ ID NO: 19 or 53), of the splenocyte derived from the above-mentioned mouse administered with the compound represented by the formula (4).

Specifically, the compound represented by the formula (4) was diluted with water for injection to 10 mg/mL, and emulsified by mixing with an equal amount of incomplete Freund's adjuvant (IFA). The emulsified compound was intradermally administered to 2 sites at the base of tail of the mouse at 250 μg/site. One week later, the mouse was euthanized with CO₂ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated at 0.25×10⁶ cells/well on the blocked ELISPOT plate. Each of the peptide (SEQ ID NOs: 19 and 53) was dissolved in DMSO at 40 mg/mL, and further diluted with RPMI1640 medium containing 10% FBS to 40 μg/mL. The HLA-A0201 transgenic mouse-derived splenocytes were pulsed with the diluted peptide represented by SEQ ID NO: 19 or SEQ ID NO: 53 (final concentration: 10 μg/mL), and cultivated for 20 hr at 37° C., 5% CO₂, whereby peptide re-stimulation in vitro was performed. After the culture, the supernatant was removed, and the ELISPOT plate was allowed to develop color according to the attached protocol. The number of spots that developed color was measured by ImmunoSpot Analyzer (manufactured by C.T.L.).

Figure 8:
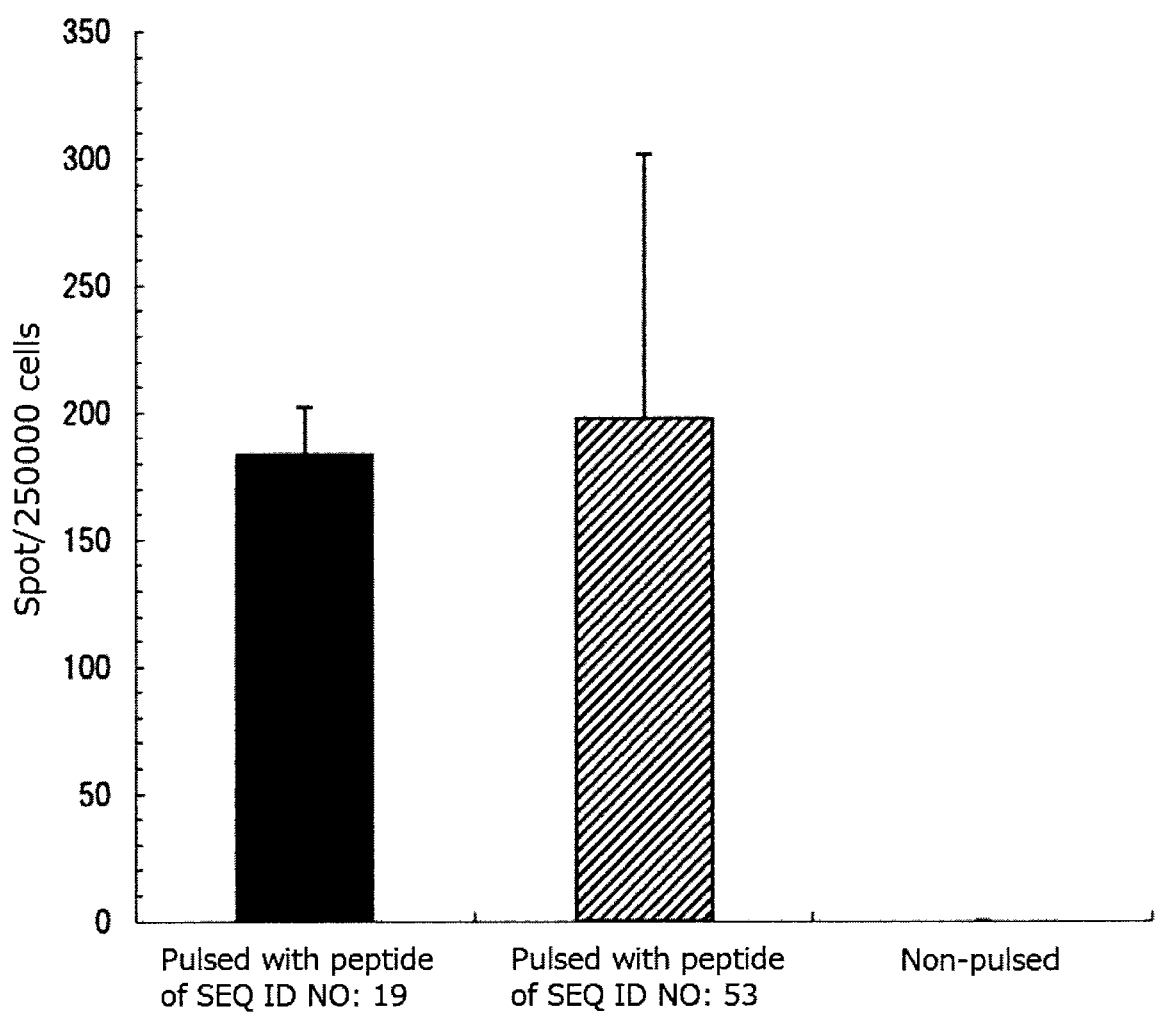
FIG. 8 is a Figure showing the test results of Experimental Example 4 that examined the in vivo CTL induction ability of a compound represented by the formula (4) synthesized in Example 29, by IFNγ ELISPOT assay using HLA-A0201 transgenic mouse.

The results of IFNγ ELISPOT assay using the HLA-A0201 transgenic mouse are shown in FIG. 8.

In FIG. 8, the vertical axis shows the number of cells that responded among the plated cells. In FIG. 8, the black bar and the shaded bar show the results of culture of HLA-A0201 transgenic mouse-derived splenocytes while being pulsed with the peptides shown by SEQ ID NOs: 19 and 53, respectively, and the white bar show the result of culture without pulsing. That is, the difference in the values of the black or shaded bar and the white bar shows the number of peptide-specific CTLs, and that the administration of the compound represented by the formula (4) resulted in the induction of CTLs specific to each of the peptides shown by SEQ ID NOs: 19 and 53 in vivo in the mouse.

In FIG. 8, the value of the white bar is not detected. This means that the splenocytes of the HLA-A0201 transgenic mouse did not react at all in the absence of pulsing with the peptide of interest. As a result of this test, IFNγ production specific to each of the peptides shown by SEQ ID NOs: 19 and 53 was detected in the HLA-A0201 transgenic mouse-derived splenocytes.

From the above, it was demonstrated that the compound represented by the formula (4) can induce CTLs specific to each of the peptides shown by SEQ ID NOs: 19 and 53. It was strongly suggested that the compound represented by the formula (4) undergoes cleavage of disulfide bond and appropriate trimming by ERAP-1 in mice in vivo and is indeed processed into the peptides shown by SEQ ID NOs: 19 and 53.

That is, it was demonstrated that the compound represented by the formula (4), which is one embodiment of the compound of the present invention, is a conjugate wherein two different peptides form a composite via the disulfide bond shown in the formula (1), and is a cancer antigen peptide conjugate vaccine that indeed can induce different two types of CTLs in vivo.

Experimental Example 5

Evaluation of In Vivo CTL Induction Ability Using HLA-A0201 Transgenic Mouse and HLA-A2402 Transgenic Mouse The compound represented by the formula (10) synthesized in Example 30 was evaluated for the CTL induction ability by an in vivo CTL induction test using an HLA-A0201 transgenic mouse and an HLA-A2402 transgenic mouse. The compound represented by the formula (10):

(10)

wherein the bond between C and C is a disulfide bond, is, in particular, a compound of the aforementioned formula (1) wherein cancer antigen peptide A is GLYDGMEHL (SEQ ID NO: 19) and cancer antigen peptide D is VYGFVRACL (SEQ ID NO: 87). GLYDGMEHL (SEQ ID NO: 19) is an HLA-A0201-restricted cancer antigen peptide, and VYGFVRACL (SEQ ID NO: 87) is an HLA-A24-restricted cancer antigen peptide.

The HLA-A0201 transgenic mouse is as described in Experimental Example 4. On the other hand, the HLA-A2402 transgenic mouse (C57BL/6CrHLA-A2402/K$^b$) is a mouse that expresses a chimera HLA of human MHC HLA-A2402 and mouse MHC H-2K$^b$. Using this mouse, peptides capable of inducing CTLs in HLA-A24 positive humans can be selected (Int J Cancer. 2002; 100: 565-70).

To evaluate whether CTLs to each of the peptides (SEQ ID NOs: 19 and 87) endogenously presented by cancer cells was induced, the compound represented by the formula (10) was administered to the HLA-A0201 transgenic mouse and the HLA-A2402 transgenic mouse. That is, it was determined whether IFNγ production was observed by re-stimulation, with the peptide (SEQ ID NO: 19 or 87), of the splenocyte derived from the above-mentioned mouse administered with the compound represented by the formula (10).

Specifically, the compound represented by the formula (10) was dissolved in dimethyl sulfoxide (DMSO) at 80 mg/mL, further diluted with water for injection to 10 mg/mL, and emulsified by mixing with an equal amount of incomplete Freund's adjuvant (IFA). The emulsified compound was intradermally administered to 2 sites at the base of tail of the mouse at 250 μg/site. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated at 0.25×10$^6$ cells/well, and HLA-A2402 transgenic mouse-derived splenocytes were plated at 0.5×10$^6$ cells/well, on the blocked ELISPOT plate. Each of the peptide (SEQ ID NOs: 19 and 87) was dissolved in DMSO at 40 mg/mL, and further diluted with RPMI1640 medium containing 10% FBS to 40 μg/mL. The HLA-A0201 transgenic mouse-derived splenocytes were pulsed with the diluted peptide represented by SEQ ID NO: 19 (final concentration: 10 μg/mL), and the HLA-A2402 transgenic mouse-derived splenocytes were pulsed with the diluted peptide represented by SEQ ID NO: 87 (final concentration: 10 μg/mL). These splenocytes were cultivated for 20 hr at 37° C., 5% $CO_2$, whereby peptide re-stimulation in vitro was performed. After the culture, the supernatant was removed, and the ELISPOT plate was allowed to develop color according to the attached protocol. The number of spots that developed color was measured by ImmunoSpot Analyzer (manufactured by C.T.L.).

Figure 9:
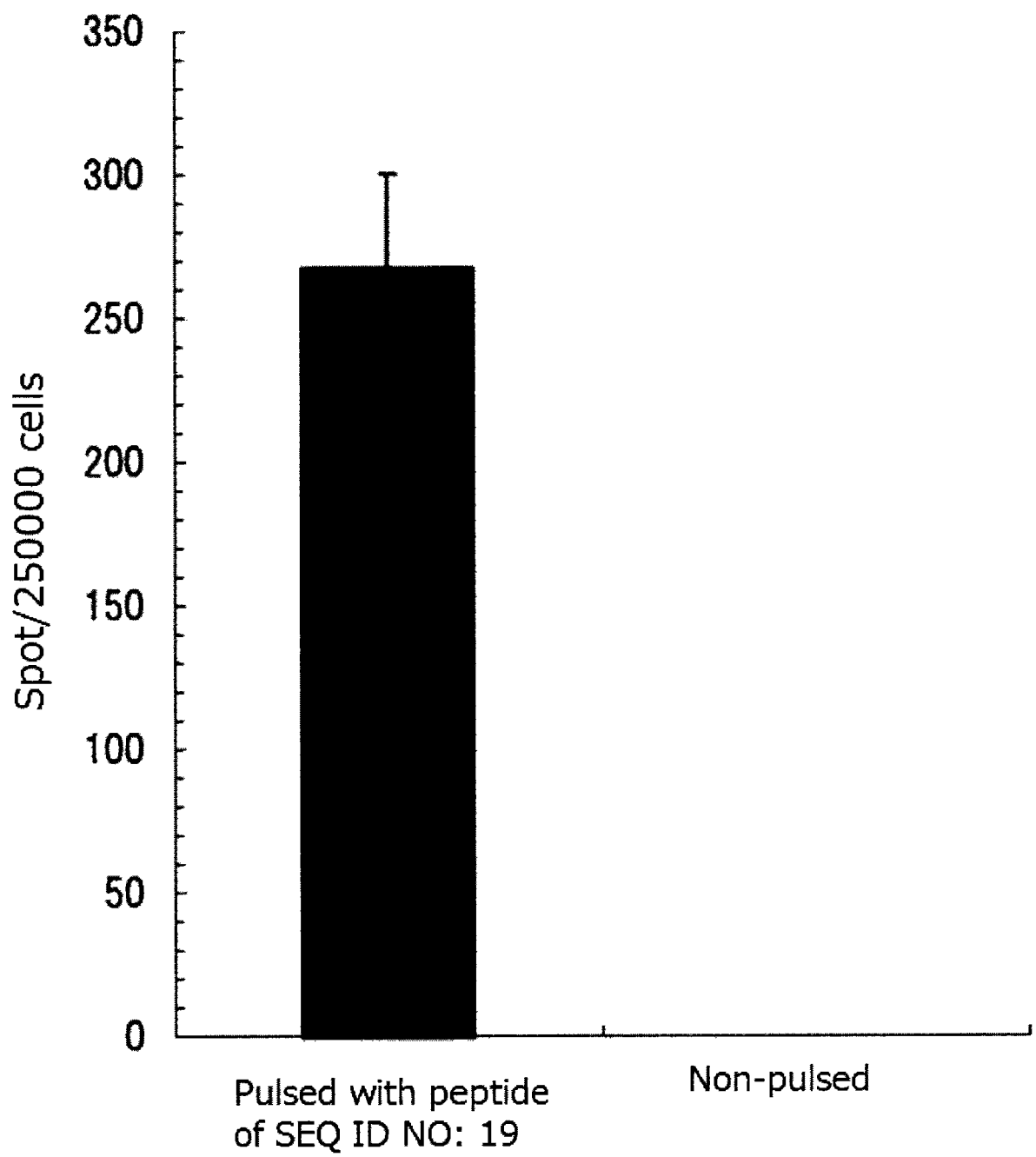
FIG. 9 is a Figure showing the test results of Experimental Example 5 that examined the in vivo CTL induction ability of a compound represented by the formula (10) synthesized in Example 30, by IFNγ ELISPOT assay using HLA-A0201 transgenic mouse.
Figure 10:
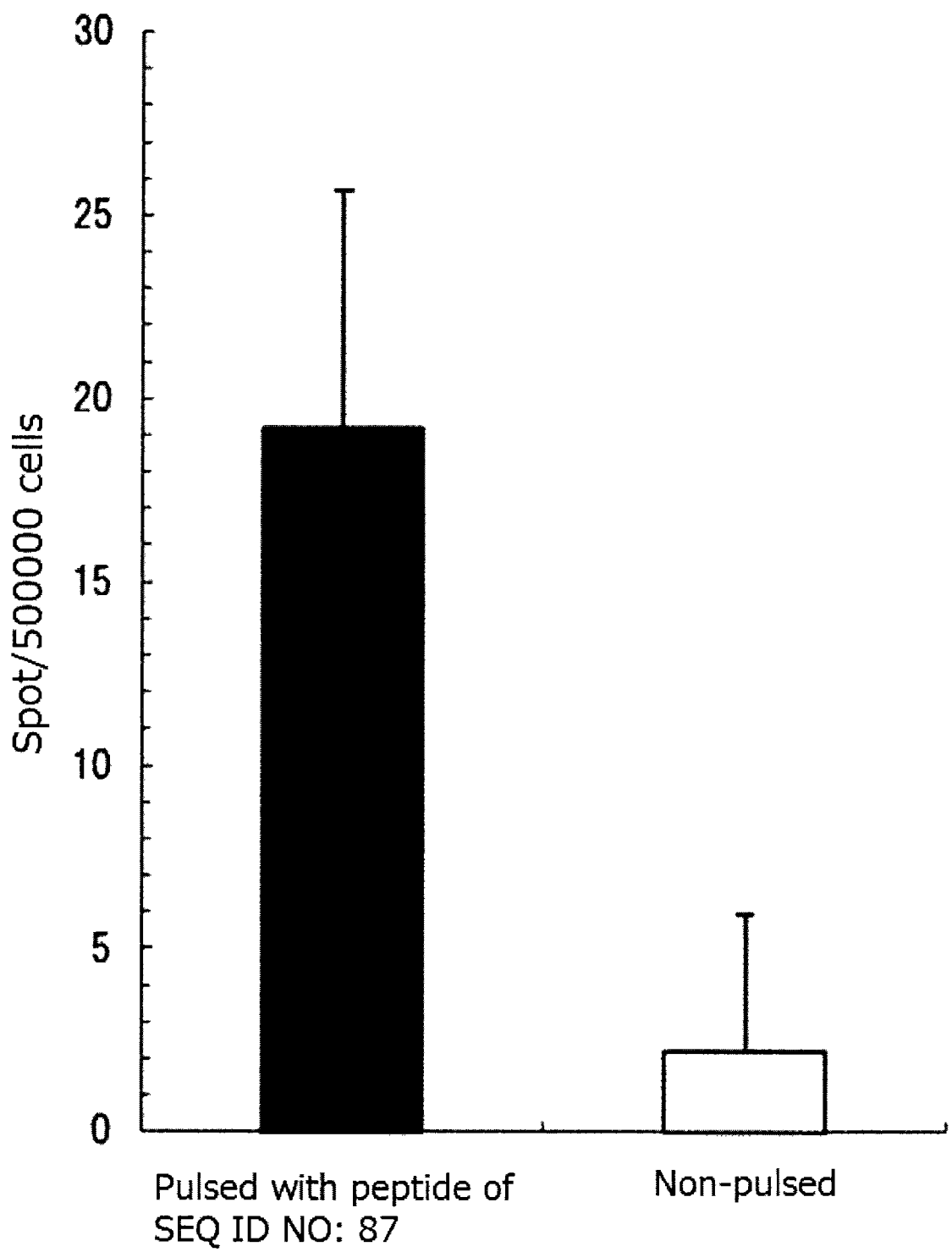
FIG. 10 is a Figure showing the test results of Experimental Example 5 that examined the in vivo CTL induction ability of a compound represented by the formula (10) synthesized in Example 30, by IFNγ ELISPOT assay using HLA-A2402 transgenic mouse.

The results of IFNγ ELISPOT assay using HLA-A0201 transgenic mouse are shown in FIG. 9, and the results of IFNγ ELISPOT assay using HLA-A2402 transgenic mouse are shown in FIG. 10.

In each Figure, the vertical axis shows the number of cells that responded among the plated cells. In FIG. 9, the black bar and the white bar show the results of culture of HLA-A0201 transgenic mouse-derived splenocytes while being pulsed and non-pulsed with the peptide represented by SEQ ID NO: 19, respectively, and in FIG. 10, the black bar and the white bar show the results of culture of HLA-A2402 transgenic mouse-derived splenocytes while being pulsed and non-pulsed with the peptide represented by SEQ ID NO: 87, respectively. That is, the difference in the values of the black bar and the white bar shows the number of peptide-specific CTLs, and that the administration of the compound represented by the formula (10) resulted in the induction of CTLs specific to each of the peptides shown by SEQ ID NO: 19 and 87 in vivo in the mouse.

In particular, in FIG. 9, the value of the white bar is not detected. This means that the splenocytes of the HLA-A0201 transgenic mouse did not react at all in the absence of the peptide of interest. As a result of this test, IFNγ production specific to the peptide shown by SEQ ID NO: 19 was detected in the HLA-A0201 transgenic mouse-derived splenocytes, and IFNγ production specific to the peptide shown by SEQ ID NO: 87 was detected in the HLA-A2402 transgenic mouse-derived splenocytes.

From the above, it was demonstrated that the compound represented by the formula (10) can induce CTLs specific to each of the peptide shown by SEQ ID NO: 19 or 87. It was strongly suggested that the compound represented by the formula (10) undergoes cleavage of disulfide bond and appropriate trimming by ERAP-1 in mice in vivo and is indeed processed into the peptides shown by SEQ ID NOs: 19 and 87.

That is, it was demonstrated that the compound represented by the formula (10), which is one embodiment of the compound of the present invention, is a conjugate wherein two different peptides form a composite via the disulfide bond shown in the formula (1), and is a cancer antigen peptide conjugate vaccine that indeed can induce different two types of CTLs in vivo.

Examples 31-49

By a method similar to that in Example 1, respective peptides consisting of the amino acid sequences of SEQ ID NOs: 124-142 were synthesized. Tables 25-26 show the result of mass spectrometry of each synthesized peptide.

All of the peptides in Tables 25 and 26 are the compounds of the present invention of the formula (1) wherein $R^1$ is a hydrogen atom, $X^a$ is a divalent peptide group consisting of 1 amino acid residue, $Y^a$ is a single bond, and cancer antigen peptide A is HER2/neu$_{369-377}$ peptide (KIFGSLAFL) (SEQ ID NO: 53), which is a partial peptide of the cancer antigen protein HER2/neu.

TABLE 25

| Ex. No. | amino acid sequence | SEQ ID NO: | mass spectrometry: LC-ESI/MS m/z | mass spectrometry: Calculated |
|---|---|---|---|---|
| 31 | ACKIFGSLAFL | 124 | 585.6 $[M + 2H]^{2+}$ | 585.7 |
| 32 | RCKIFGSLAFL | 125 | 628.3 $[M + 2H]^{2+}$ | 628.3 |
| 33 | NCKIFGSLAFL | 126 | 607.3 $[M + 2H]^{2+}$ | 607.2 |
| 34 | DCKIFGSLAFL | 127 | 607.9 $[M + 2H]^{2+}$ | 607.7 |
| 35 | QCKIFGSLAFL | 128 | 614.4 $[M + 2H]^{2+}$ | 614.2 |
| 36 | ECKIFGSLAFL | 129 | 614.9 $[M + 2H]^{2+}$ | 614.7 |
| 37 | GCKIFGSLAFL | 130 | 578.8 $[M + 2H]^{2+}$ | 578.7 |
| 38 | HCKIFGSLAFL | 131 | 618.9 $[M + 2H]^{2+}$ | 618.7 |
| 39 | ICKIFGSLAFL | 132 | 606.9 $[M + 2H]^{2+}$ | 606.8 |

TABLE 25-continued

| Ex. No. | amino acid sequence | SEQ ID NO: | mass spectrometry: LC-ESI/MS m/z | mass spectrometry: Calculated |
|---|---|---|---|---|
| 40 | LCKIFGSLAFL | 133 | 606.8 $[M + 2H]^{2+}$ | 606.8 |

TABLE 26

| Ex. No. | amino acid sequence | SEQ ID NO: | mass spectrometry: LC-ESI/MS m/z | mass spectrometry: Calculated |
|---|---|---|---|---|
| 41 | KCKIFGSLAFL | 134 | 614.4 $[M + 2H]^{2+}$ | 614.3 |
| 42 | MCKIFGSLAFL | 135 | 615.9 $[M + 2H]^{2+}$ | 615.8 |
| 43 | FCKIFGSLAFL | 136 | 623.8 $[M + 2H]^{2+}$ | 623.8 |
| 44 | PCKIFGSLAFL | 137 | 598.8 $[M + 2H]^{2+}$ | 598.7 |
| 45 | SCKIFGSLAFL | 138 | 593.8 $[M + 2H]^{2+}$ | 593.7 |
| 46 | TCKIFGSLAFL | 139 | 600.9 $[M + 2H]^{2+}$ | 600.7 |
| 47 | WCKIFGSLAFL | 140 | 643.4 $[M + 2H]^{2+}$ | 643.3 |
| 48 | YCKIFGSLAFL | 141 | 631.9 $[M + 2H]^{2+}$ | 631.8 |
| 49 | VCKIFGSLAFL | 142 | 599.8 $[M + 2H]^{2+}$ | 599.7 |

Examples 50-68

By a method similar to that in Example 1, respective peptides consisting of the amino acid sequences of SEQ ID NOs: 143-161 were synthesized. Tables 27 and 28 show the result of mass spectrometry of each synthesized peptide.

All of the peptides in Tables 27 and 28 are the compounds of the present invention of the formula (1) wherein $R^1$ is a hydrogen atom, $X^a$ is a divalent peptide group consisting of 1 amino acid residue, $Y^a$ is a single bond, and cancer antigen peptide A is Proteinase-3$_{169-177}$ peptide (VLQELNVTV) (SEQ ID NO: 43), which is a partial peptide of the cancer antigen protein Proteinase-3.

TABLE 27

| Ex. No. | amino acid sequence | SEQ ID NO: | mass spectrometry: LC-ESI/MS m/z | mass spectrometry: Calculated |
|---|---|---|---|---|
| 50 | ACVLQELNVTV | 143 | 595.1 $[M + 2H]^{2+}$ | 595.2 |
| 51 | RCVLQELNVTV | 144 | 637.9 $[M + 2H]^{2+}$ | 637.8 |
| 52 | NCVLQELNVTV | 145 | 616.5 $[M + 2H]^{2+}$ | 616.7 |
| 53 | DCVLQELNVTV | 146 | 617.1 $[M + 2H]^{2+}$ | 617.2 |

TABLE 27-continued

| Ex. No. | amino acid sequence | SEQ ID NO: | mass spectrometry: LC-ESI/MS m/z | mass spectrometry: Calculated |
|---|---|---|---|---|
| 54 | QCVLQELNVTV | 147 | 623.6 $[M + 2H]^{2+}$ | 623.7 |
| 55 | ECVLQELNVTV | 148 | 624.1 $[M + 2H]^{2+}$ | 624.2 |
| 56 | GCVLQELNVTV | 149 | 588.0 $[M + 2H]^{2+}$ | 588.2 |
| 57 | HCVLQELNVTV | 150 | 628.4 $[M + 2H]^{2+}$ | 628.2 |
| 58 | ICVLQELNVTV | 151 | 616.4 $[M + 2H]^{2+}$ | 616.2 |
| 59 | LCVLQELNVTV | 152 | 616.1 $[M + 2H]^{2+}$ | 616.2 |

TABLE 28

| Ex. No. | amino acid sequence | SEQ ID NO: | mass spectrometry: LC-ESI/MS m/z | mass spectrometry: Calculated |
|---|---|---|---|---|
| 60 | KCVLQELNVTV | 153 | 623.8 $[M + 2H]^{2+}$ | 623.7 |
| 61 | MCVLQELNVTV | 154 | 625.2 $[M + 2H]^{2+}$ | 625.3 |
| 62 | FCVLQELNVTV | 155 | 633.3 $[M + 2H]^{2+}$ | 633.2 |
| 63 | PCVLQELNVTV | 156 | 608.0 $[M + 2H]^{2+}$ | 608.2 |
| 64 | SCVLQELNVTV | 157 | 603.0 $[M + 2H]^{2+}$ | 603.2 |
| 65 | TCVLQELNVTV | 158 | 610.1 $[M + 2H]^{2+}$ | 610.2 |
| 66 | WCVLQELNVTV | 159 | 652.8 $[M + 2H]^{2+}$ | 652.8 |
| 67 | YCVLQELNVTV | 160 | 641.3 $[M + 2H]^{2+}$ | 641.2 |
| 68 | VCVLQELNVTV | 161 | 609.3 $[M + 2H]^{2+}$ | 609.2 |

TABLE 29

| Ex. No. | amino acid sequence | SEQ ID NO: | mass spectrometry: LC-ESI/MS m/z | mass spectrometry: Calculated |
|---|---|---|---|---|
| 69 | CQGLYDGMEHL | 162 | 633.6 $[M + 2H]^{2+}$ | 633.7 |
| 70 | CEGLYDGMEHL | 163 | 634.3 $[M + 2H]^{2+}$ | 634.2 |
| 71 | CGGLYDGMEHL | 164 | 598.3 $[M + 2H]^{2+}$ | 598.2 |
| 72 | CHGLYDGMEHL | 165 | 638.3 $[M + 2H]^{2+}$ | 638.2 |
| 73 | CIGLYDGMEHL | 166 | 626.3 $[M + 2H]^{2+}$ | 626.2 |
| 74 | CKGLYDGMEHL | 167 | 633.9 $[M + 2H]^{2+}$ | 633.7 |
| 75 | CFGLYDGMEHL | 168 | 643.3 $[M + 2H]^{2+}$ | 643.2 |
| 76 | CPGLYDGMEHL | 169 | 618.3 $[M + 2H]^{2+}$ | 618.2 |

TABLE 30

| Ex. No. | amino acid sequence | SEQ ID NO: | mass spectrometry: LC-ESI/MS m/z | mass spectrometry: Calculated |
|---|---|---|---|---|
| 77 | CTGLYDGMEHL | 170 | 620.4 $[M + 2H]^{2+}$ | 620.2 |
| 78 | CWGLYDGMEHL | 171 | 662.8 $[M + 2H]^{2+}$ | 662.7 |
| 79 | CYGLYDGMEHL | 172 | 651.3 $[M + 2H]^{2+}$ | 651.2 |
| 80 | CVGLYDGMEHL | 173 | 619.3 $[M + 2H]^{2+}$ | 619.2 |
| 81 | CRGLYDGMEHL | 174 | 647.8 $[M + 2H]^{2+}$ | 647.7 |
| 82 | CNGLYDGMEHL | 175 | 626.8 $[M + 2H]^{2+}$ | 626.7 |
| 83 | CDGLYDGMEHL | 176 | 627.3 $[M + 2H]^{2+}$ | 627.2 |
| 84 | CSGLYDGMEHL | 177 | 613.3 $[M + 2H]^{2+}$ | 613.2 |

Examples 69-84

By a method similar to that in Example 1, respective peptides consisting of the amino acid sequences of SEQ ID NOs: 162-177 were synthesized. Tables 29 and 30 show the result of mass spectrometry of each synthesized peptide.

All of the peptides in Tables 29 and 30 are the compounds of the present invention of the formula (1) wherein $R^1$ is a hydrogen atom, $X^a$ is a single bond, $Y^a$ is a divalent peptide group consisting of 1 amino acid residue, and cancer antigen peptide A is MAGE-A10$_{254\text{-}262}$ peptide (GLYDGMEHL) (SEQ ID NO: 19), which is a partial peptide of the cancer antigen protein MAGE-A10.

Examples 85-103

By a method similar to that in Example 1, respective peptides consisting of the amino acid sequences of SEQ ID NOs: 178-196 were synthesized. Tables 31 and 32 show the result of mass spectrometry of each synthesized peptide.

All of the peptides in Tables 31 and 32 are the compounds of the present invention of the formula (1) wherein $R^1$ is a hydrogen atom, $X^a$ is a divalent peptide group consisting of 1 amino acid residue, $Y^a$ is a single bond, and cancer antigen peptide A is MAGE-A10$_{254\text{-}262}$ peptide (GLYDGMEHL) (SEQ ID NO: 19), which is a partial peptide of the cancer antigen protein MAGE-A10.

TABLE 31

| Ex. No. | amino acid sequence | SEQ ID NO: | mass spectrometry: LC-ESI/MS m/z | mass spectrometry: Calculated |
|---|---|---|---|---|
| 85 | QCGLYDGMEHL | 178 | 633.8 $[M + 2H]^{2+}$ | 633.7 |
| 86 | PCGLYDGMEHL | 179 | 618.3 $[M + 2H]^{2+}$ | 618.2 |
| 87 | SCGLYDGMEHL | 180 | 613.2 $[M + 2H]^{2+}$ | 613.2 |
| 88 | TCGLYDGMEHL | 181 | 620.3 $[M + 2H]^{2+}$ | 620.2 |
| 89 | WCGLYDGMEHL | 182 | 662.8 $[M + 2H]^{2+}$ | 662.7 |
| 90 | YCGLYDGMEHL | 183 | 651.4 $[M + 2H]^{2+}$ | 651.2 |
| 91 | VCGLYDGMEHL | 184 | 619.3 $[M + 2H]^{2+}$ | 619.2 |
| 92 | ACGLYDGMEHL | 185 | 605.3 $[M + 2H]^{2+}$ | 605.2 |
| 93 | RCGLYDGMEHL | 186 | 647.9 $[M + 2H]^{2+}$ | 647.7 |
| 94 | NCGLYDGMEHL | 187 | 626.8 $[M + 2H]^{2+}$ | 626.7 |

TABLE 32

| Ex. No. | amino acid sequence | SEQ ID NO: | mass spectrometry: LC-ESI/MS m/z | mass spectrometry: Calculated |
|---|---|---|---|---|
| 95 | DCGLYDGMEHL | 188 | 627.2 $[M + 2H]^{2+}$ | 627.2 |
| 96 | ECGLYDGMEHL | 189 | 634.3 $[M + 2H]^{2+}$ | 634.2 |
| 97 | GCGLYDGMEHL | 190 | 598.1 $[M + 2H]^{2+}$ | 598.2 |
| 98 | HCGLYDGMEHL | 191 | 638.4 $[M + 2H]^{2+}$ | 638.2 |
| 99 | ICGLYDGMEHL | 192 | 626.3 $[M + 2H]^{2+}$ | 626.2 |
| 100 | LCGLYDGMEHL | 193 | 626.4 $[M + 2H]^{2+}$ | 626.2 |
| 101 | KCGLYDGMEHL | 194 | 633.9 $[M + 2H]^{2+}$ | 633.7 |
| 102 | MCGLYDGMEHL | 195 | 635.4 $[M + 2H]^{2+}$ | 635.2 |
| 103 | FCGLYDGMEHL | 196 | 643.4 $[M + 2H]^{2+}$ | 643.2 |

Experimental Example 6

Test of Trimming of N-Terminal Amino Acid by ERAP1

The peptides synthesized in Examples 31-49 were evaluated for N-terminal amino acid trimming efficiency using ERAP1. 50 μl of ERAP1 solution (50 μg/ml) in pH 8.0, 20 mM Tris.HCl-100 mM NaCl buffer (Tris.HCl buffer) was added to 142 μl of Tris.HCl buffer. 10 mM peptide solution in DMSO (2.0 μl) and 6.0 μL of DMSO were added to the aforementioned ERAP1 solution, and the mixture was blended well and stood at 30° C. 1.0 hr later, 50 μl of the mixture was injected into UFLC (under the analysis conditions shown below), and AUC of the peptide of interest was determined. The peptide to be obtained by trimming was chemically synthesized separately, and analyzed under similar conditions in the absence of the enzyme. The formation ratio of the peptide [HER2/neu$_{369-377}$ peptide (KIFGSLAFL) (SEQ ID NO: 53)] obtained by trimming was determined based on the obtained AUC, and is shown in Table 33.

Analysis Conditions
pump: UFLC manufactured by Shimadzu
column: Shim-pack XR-ODS 3.0 mmi.d.×75 mm
solution: 0.05% TFA H$_2$O(A)-0.05% TFA CH$_3$CN(B)
oven temperature: 40° C.
flow rate: 1.0 ml/min
detection wavelength: λ=220 nm
gradient: Concentration of SOLUTION B was raised from 10% to 70% from 0.0 min to 5.0 min

TABLE 33

| Example | amino acid sequence | SEQ ID NO: | formation rate of KIFGSLAFL (SEQ ID NO: 53) (%) |
|---|---|---|---|
| 31 | ACKIFGSLAFL | 124 | 6.6 |
| 32 | RCKIFGSLAFL | 125 | 0.0 |
| 33 | NCKIFGSLAFL | 126 | 5.8 |
| 34 | DCKIFGSLAFL | 127 | 7.6 |
| 35 | QCKIFGSLAFL | 128 | 12.3 |
| 36 | ECKIFGSLAFL | 129 | 20.1 |
| 37 | GCKIFGSLAFL | 130 | 11.2 |
| 38 | HCKIFGSLAFL | 131 | 0.0 |
| 39 | ICKIFGSLAFL | 132 | 4.8 |
| 40 | LCKIFGSLAFL | 133 | 4.8 |
| 41 | KCKIFGSLAFL | 134 | 0.0 |
| 42 | MCKIFGSLAFL | 135 | 4.5 |
| 43 | FCKIFGSLAFL | 136 | 2.6 |
| 44 | PCKIFGSLAFL | 137 | 4.3 |
| 45 | SCKIFGSLAFL | 138 | 19.6 |
| 46 | TCKIFGSLAFL | 139 | 15.9 |
| 47 | WCKIFGSLAFL | 140 | 0.9 |
| 48 | YCKIFGSLAFL | 141 | 5.5 |
| 49 | VCKIFGSLAFL | 142 | 5.1 |

Experimental Example 7

Measurement of Solubility
Step 1. Preparation of Isotonic Buffer
1. 75% aqueous solution of disodium hydrogen phosphate and 5.53% aqueous solution of citric acid were mixed to prepare buffers of pH 6.0 and 7.4.

Step 2. Preparation of Test Solution

To prepare a test solution, about 1 mg of a test product was measured and the isotonic buffer (0.5 mL) was added thereto. The prepared solution was shaken at room temperature for 90 min (shaking conditions: RECIPRO SHAKER SR-1N manufactured by TAITEC, Speed=8), centrifuged (15000 rpm, 5 min, room temperature), and the supernatant after centrifugation was used as a test solution.

Step 3. Preparation of Standard Solution

About 1 mg of the test product was accurately measured, dissolved in 0.1% TFA water/acetonitrile=1/1, made the total amount 10 mL, and this was used as a standard solution of the test product.

Step 4. Measurement of Concentration of Test Product

The standard solution of the test product and the test solution are analyzed by HPLC (under the analysis conditions described in Table 34), and the solubility of the test product is calculated from the ratio of peak area compared to the standard solution.

HPLC Measurement Conditions
column: Chemcopack Quicksorb (4.6 mmφ×150 mm, 5 μm) manufactured by Chemco Scientific Co., Ltd.
mobile phase: SOLUTION A; 0.1% TFA water, SOLUTION B;
0.1% TFA acetonitrile solution
column temperature: room temperature
flow rate: 1 mL/min
detection wavelength: UV 254 nm, 230 nm (2 wavelength detection)
sample injection volume: 10

TABLE 34

| gradient analysis conditions | | |
|---|---|---|
| time (min) | SOLUTION A (%) | SOLUTION B (%) |
| 0.00 | 80 | 20 |
| 10.00 | 0 | 100 |
| 15.00 | 0 | 100 |
| 15.01 | 80 | 20 |
| 25.00 | 80 | 20 |
| 25.01 | STOP | |

The respective peptides consisting of the amino acid sequences of SEQ ID NOs: 19, 87 and 53 and the compound represented by the formula (4) (conjugate) synthesized in Example 29 were subjected to the above-mentioned solubility measurement. Each solubility is shown in Table 35.

TABLE 35

| Ex. No | amino acid sequence or structural formula | SEQ ID NO: or formula No. | pH 6.0 (mg/mL) | pH 7.4 (mg/mL) |
|---|---|---|---|---|
| — | GLYDGMEHL | SEQ ID NO: 19 | >1.0 | >1.0 |
| — | VYGFVRACL | SEQ ID NO: 87 | >1.0 | >1.0 |
| — | KIFGSLAFL | SEQ ID NO: 53 | 0.1 | 0.123 |
| 29 | CGLYDGMEHL<br>\|<br>CKIFGSLAFL | formula (4) | 0.17 | >1.0 |

Examples 104-105

By a method similar to that in Example 1, respective peptides consisting of the amino acid sequences of SEQ ID NOs: 197 and 198 were synthesized. Table 36 shows the result of mass spectrometry of each synthesized peptide.

All of the peptides in Table 36 are the compounds of the present invention of the formula (2) wherein $X^b$ is a single bond, $Y^b$ is a single bond, and cancer antigen peptide B is an HLA-DR-restricted universal cancer antigen peptide (SEQ ID NO: 101 or 102).

TABLE 36

| Ex. No. | amino acid sequence | SEQ ID NO: | mass spectrometry: LC-ESI/ MS m/z | mass spectrometry: Calculated |
|---|---|---|---|---|
| 104 | CAKFVAAWT LKAAA | 197 | 726.5 $[M + 2H]^{2+}$ | 726.4 |
| 105 | CaKFVAAWT LKAAa | 198 | 726.4 $[M + 2H]^{2+}$ | 726.4 |

Examples 106 and 107

By a method similar to that in Example 1, respective peptides consisting of the amino acid sequences of SEQ ID NOs: 199 and 200 were synthesized. Table 37 shows the result of mass spectrometry of each synthesized peptide.

All of the peptides in Table 37 are the compounds of the present invention of the formula (3) wherein $X^c$ is a single bond, $Y^c$ is a single bond, and cancer antigen peptide C is an HLA-DR-restricted universal cancer antigen peptide (SEQ ID NO: 101 or 102).

TABLE 37

| Ex. No. | amino acid sequence | SEQ ID NO: | mass spectrometry: LC-ESI/ MS m/z | mass spectrometry: Calculated |
|---|---|---|---|---|
| 106 | AKFVAAWTL KAAAC | 199 | 726.5 $[M + 2H]^{2+}$ | 726.4 |
| 107 | aKFVAAWTL KAAaC | 200 | 726.5 $[M + 2H]^{2+}$ | 726.4 |

Example 108

Synthesis of the Compound Represented by the Formula (14):

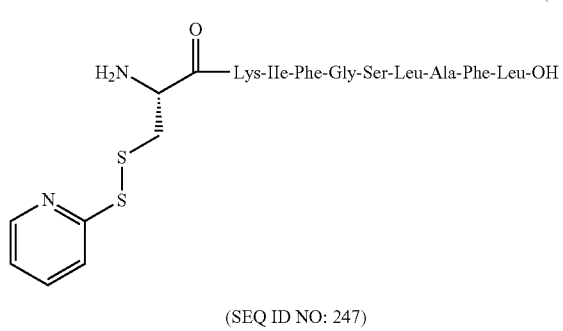

(14)

(SEQ ID NO: 247)

By using the synthesis method described in step 1 of Example 29, H-Cys(Pys)-Lys-Ile-Phe-Gly-Ser-Leu-Ala-Phe-Leu-OH (SEQ ID NO: 247), i.e., the compound represented by the formula (14) was synthesized.
mass spectrometry: LC-ESI/MS m/z=1208.1[M+H]⁺ (Calculated=1208.5)

Examples 109-113

By using the synthesis method described in step 2 of Example 29 and the synthesis method described in Example 108, the compound (conjugate) represented by any of the formulas (5), (11) and (15)-(17) was synthesized. The results of mass spectrometry are shown in Table 38, wherein the bond between C and C is a disulfide bond.

TABLE 38

| Ex. No. | structural formula | formula No. | mass spectrometry: LC-ESI/ MS m/z | mass spectrometry: Calculated |
|---|---|---|---|---|
| 109 | CGLYDGMEHL<br>\|<br>SLLMWITQC | 11 | 1115.9 $[M + 2H]^{2+}$ | 1115.8 |
| 110 | CGLYDGMEHL<br>\|<br>CVLQELNVTV | 5 | 1127.2 $[M + 2H]^{2+}$ | 1127.0 |
| 111 | CKIFGSLAFL<br>\|<br>CAKFVAAWTLKAAA | 15 | 1274.5 $[M + 2H]^{2+}$ | 1274.6 |
| 112 | CKIFGSLAFL<br>\|<br>CaKFVAAWTLKAAa | 16 | 850.0 $[M + 3H]^{3+}$ | 850.1 |
| 113 | CKIFGSLAFL<br>\|<br>aKFVAAWTLKAAaC | 17 | 1274.3 $[M + 2H]^{2+}$ | 1274.6 |

Examples 114-143

By a method similar to that in Example 1, peptides consisting of the amino acid sequences of SEQ ID NOs: 201-230 were synthesized. Tables 39-41 show the result of mass spectrometry of each synthesized peptide.

All of the peptides in Tables 39-41 are the compounds of the present invention of the formula (1) wherein $R^1$ is a hydrogen atom, $X^a$ is a single bond, $Y^a$ is a single bond, and cancer antigen peptide A is an MHC class I-restricted cancer antigen peptide shown in Tables 1-9.

TABLE 39

| Ex. No. | amino acid sequence | SEQ ID NO: | mass spectrometry: LC-ESI/ MS m/z | mass spectrometry: Calculated |
|---|---|---|---|---|
| 114 | CGYDQIMPKI | 201 | 584.8 $[M + 2H]^{2+}$ | 584.7 |
| 115 | CGYDQIMPKK | 202 | 592.3 $[M + 2H]^{2+}$ | 592.2 |
| 116 | CSLLMWITQCFL | 203 | 729.8 $[M + 2H]^{2+}$ | 729.9 |
| 117 | CEYLQLVFGI | 204 | 593.3 $[M + 2H]^{2+}$ | 593.2 |
| 118 | CLIYRRRLMK | 205 | 677.1 $[M + 2H]^{2+}$ | 676.8 |
| 119 | CAFLPWHRLF | 206 | 645.8 $[M + 2H]^{2+}$ | 645.9 |

TABLE 39-continued

| Ex. No. | amino acid sequence | SEQ ID NO: | mass spectrometry: LC-ESI/ MS m/z | mass spectrometry: Calculated |
|---|---|---|---|---|
| 120 | CYMDGTMSQV | 207 | 1135.3 $[M + H]^{+}$ | 1134.6 |
| 121 | CAAGIGILTV | 208 | 918.1 $[M + H]^{+}$ | 917.7 |
| 122 | CFLWGPRALV | 209 | 581.7 $[M + 2H]^{2+}$ | 581.6 |
| 123 | CAYACNTSTL | 210 | 1047.2 $[M + H]^{+}$ | 1046.6 |

TABLE 40

| Ex. No. | amino acid sequence | SEQ ID NO: | mass spectrometry: LC-ESI/ MS m/z | mass spectrometry: Calculated |
|---|---|---|---|---|
| 124 | CKWFPSCQFLL | 211 | 686.8 $[M + 2H]^{2+}$ | 686.9 |
| 125 | CNYKHCFPEI | 212 | 627.7 $[M + 2H]^{2+}$ | 627.8 |
| 126 | CYLSGANLNL | 213 | 534.6 $[M + 2H]^{2+}$ | 534.6 |
| 127 | CAYIDFEMKI | 214 | 617.2 $[M + 2H]^{2+}$ | 617.1 |
| 128 | CQLSLLMWIT | 215 | 604.8 $[M + 2H]^{2+}$ | 604.9 |
| 129 | CAEEAAGIGIL | 216 | 524.1 $[M + 2H]^{2+}$ | 524.1 |
| 130 | CSNDGPTLI | 217 | 920.0 $[M + H]^{+}$ | 919.5 |
| 131 | CKCDICTDEY | 218 | 597.2 $[M + 2H]^{2+}$ | 597.2 |
| 132 | CHLFGYSWYK | 219 | 652.7 $[M + 2H]^{2+}$ | 652.8 |
| 133 | CWQYFFPVIF | 220 | 675.8 $[M + 2H]^{2+}$ | 675.8 |

TABLE 41

| Ex. No. | amino acid sequence | SEQ ID NO: | mass spectrometry: LC-ESI/ MS m/z | mass spectrometry: Calculated |
|---|---|---|---|---|
| 134 | CKTWGQYWQV | 221 | 650.2 [M + 2H]$^{2+}$ | 650.3 |
| 135 | CSEIWRDIDF | 222 | 642.7 [M + 2H]$^{2+}$ | 642.6 |
| 136 | CVLRENTSPK | 223 | 574.2 [M + 2H]$^{2+}$ | 574.2 |
| 137 | CSTAPPAHGV | 224 | 470.5 [M + 2H]$^{2+}$ | 470.5 |
| 138 | CSTAPPVHNV | 225 | 513.1 [M + 2H]$^{2+}$ | 513.1 |
| 139 | CVYFFLPDHL | 226 | 627.7 [M + 2H]$^{2+}$ | 627.9 |
| 140 | CASGPGGGAPR | 227 | 465.5 [M + 2H]$^{2+}$ | 465.5 |
| 141 | CMEVDPIGHLY | 228 | 639.2 [M + 2H]$^{2+}$ | 639.4 |
| 142 | CTFPDLESEF | 229 | 1188.3 [M + H]$^{+}$ | 1187.7 |
| 143 | CEADPIGHLY | 230 | 559.6 [M + 2H]$^{2+}$ | 559.8 |

Experimental Example 8

The compounds represented by the formulas (5), (11) and (15)-(17) (conjugates) synthesized in Examples 109-113 were subjected to the solubility measurement shown in Experimental Example 7. Each solubility is shown in Table 42.

TABLE 42

| Ex. No. | amino acid sequence or structural formula | SEQ ID NO: or formula No. | pH 6.0 (mg/mL) | pH 7.4 (mg/mL) |
|---|---|---|---|---|
| 109 | CGLYDGMEHL<br>\|<br>SLLMWITQC | 11 | 0.079 | 0.7 |
| 110 | CGLYDGMEHL<br>\|<br>CVLQELNVTV | 5 | 0.511 | >1.0 |
| 111 | CKIFGSLAFL<br>\|<br>CAKFVAAWTLKAAA | 15 | <0.001 | <0.001 |
| 112 | CKIFGSLAFL<br>\|<br>CaKFVAAWTLKAAa | 16 | <0.001 | 0.002 |
| 113 | CKIFGSLAFL<br>\|<br>aKFVAAWTLKAAaC | 17 | <0.001 | 0.002 |

Experimental Example 9

Test of Trimming of N-Terminal Amino Acid by ERAP1

The peptides synthesized in Examples 69-84 were evaluated for N-terminal amino acid trimming efficiency using ERAP1. 50 μl of ERAP1 solution (10 μg/ml) in pH 8.0, 20 mM Tris.HCl-100 mM NaCl buffer (Tris.HCl buffer) was added to 142 μl of Tris.HCl buffer. 10 mM peptide solution in DMSO (2.0 μl) and 6.0 μL of DMSO were added to the aforementioned ERAP1 solution, and the mixture was blended well and stood at 30° C. 1.0 hr later, 50 μl of the mixture was injected into UFLC (under the analysis conditions shown below), and AUC of the peptide of interest was determined. The peptide obtained by trimming was chemically synthesized separately, and analyzed under similar conditions in the absence of the enzyme. The formation ratio of the peptide [MAGE-A10$_{254-262}$ peptide (GLYDGMEHL) (SEQ ID NO: 19)] obtained by trimming was determined based on the obtained AUC, and is shown in Tables 43 and 44.

Analysis Conditions pump: UFLC manufactured by Shimadzu
column: Kinetex 2.6 u C18 100 A 3.0 mmi.d.×75 mm
solution: 0.1% TFA H$_2$O(A)-0.1% TFA CH$_3$CN(B)
oven temperature: 40° C.
flow rate: 1.0 ml/min
detection wavelength: λ=220 nm
gradient: concentration of SOLUTION B was raised from 10% to 50% from 0.0 min to 8.5 min

TABLE 43

| Ex. No. | amino acid sequence | SEQ ID NO: | formation rate of GLYDGMEHL (SEQ ID NO: 19) (%) |
|---|---|---|---|
| 69 | CQGLYDGMEHL | 162 | 56.9 |
| 70 | CEGLYDGMEHL | 163 | 6.2 |
| 71 | CGGLYDGMEHL | 164 | 0.0 |
| 72 | CHGLYDGMEHL | 165 | 0.0 |
| 73 | CIGLYDGMEHL | 166 | 0.4 |

TABLE 43-continued

| Ex. No. | amino acid sequence | SEQ ID NO: | formation rate of GLYDGMEHL (SEQ ID NO: 19) (%) |
|---|---|---|---|
| 74 | CKGLYDGMEHL | 167 | 0.0 |
| 75 | CFGLYDGMEHL | 168 | 0.0 |
| 76 | CPGLYDGMEHL | 169 | 0.0 |

TABLE 44

| Ex. No. | amino acid sequence | SEQ ID NO: | formation rate of GLYDGMEHL (SEQ ID NO: 19) (%) |
|---|---|---|---|
| 77 | CTGLYDGMEHL | 170 | 89.4 |
| 78 | CWGLYDGMEHL | 171 | 0.0 |
| 79 | CYGLYDGMEHL | 172 | 0.0 |
| 80 | CVGLYDGMEHL | 173 | 0.0 |
| 81 | CRGLYDGMEHL | 174 | 0.0 |
| 82 | CNGLYDGMEHL | 175 | 82.2 |
| 83 | CDGLYDGMEHL | 176 | 25.0 |
| 84 | CSGLYDGMEHL | 177 | 1.1 |

Experimental Example 10

Test of Trimming of N-Terminal Amino Acid by ERAP1

The peptides synthesized in Examples 85-103 were evaluated for N-terminal amino acid trimming efficiency using ERAP1. 50 μl of ERAP1 solution (10 μg/ml) in pH 8.0, 20 mM Tris.HCl-100 mM NaCl buffer (Tris.HCl buffer) was added to 142 μl of Tris.HCl buffer. 10 mM peptide solution in DMSO (2.0 μl) and 6.0 μL of DMSO were added to the aforementioned ERAP1 solution, and the mixture was blended well and stood at 30° C. 1.0 hr later, 50 μl of the mixture was injected into UFLC (under the analysis conditions shown below), and AUC of the peptide of interest was determined. The peptide to be obtained by trimming was chemically synthesized separately, and analyzed under similar conditions in the absence of the enzyme. The formation ratio of the peptide [MAGE-A10$_{254-262}$ peptide (GLYDGMEHL) (SEQ ID NO: 19)] obtained by trimming was determined based on the obtained AUC, and is shown in Tables 45 and 46.

Analysis Conditions
pump: UFLC manufactured by Shimadzu
column: Kinetex 2.6 u C18 100 A 3.0 mmi.d.×75 mm
solution: 0.1% TFA H$_2$O(A)-0.1% TFA CH$_3$CN(B)
oven temperature: 40° C.
flow rate: 1.0 ml/min
detection wavelength: λ=220 nm
gradient: concentration of SOLUTION B was raised from 10% to 50% from 0.0 min to 8.5 min

TABLE 45

| Ex. No. | amino acid sequence | SEQ ID NO: | formation rate of GLYDGMEHL (SEQ ID NO: 19) (%) |
|---|---|---|---|
| 85 | QCGLYDGMEHL | 178 | 3.6 |
| 86 | PCGLYDGMEHL | 179 | 19.2 |
| 87 | SCGLYDGMEHL | 180 | 22.2 |
| 88 | TCGLYDGMEHL | 181 | 7.3 |
| 89 | WCGLYDGMEHL | 182 | 0.0 |
| 90 | YCGLYDGMEHL | 183 | 5.7 |
| 91 | VCGLYDGMEHL | 184 | 2.4 |
| 92 | ACGLYDGMEHL | 185 | 5.2 |
| 93 | RCGLYDGMEHL | 186 | 0.0 |

TABLE 46

| Ex. No. | amino acid sequence | SEQ ID NO: | formation rate of GLYDGMEHL (SEQ ID NO: 19) (%) |
|---|---|---|---|
| 94 | NCGLYDGMEHL | 187 | 18.2 |
| 95 | DCGLYDGMEHL | 188 | 3.2 |
| 96 | ECGLYDGMEHL | 189 | 2.9 |
| 97 | GCGLYDGMEHL | 190 | 10.4 |
| 98 | HCGLYDGMEHL | 191 | 0.0 |
| 99 | ICGLYDGMEHL | 192 | 0.0 |
| 100 | LCGLYDGMEHL | 193 | 0.0 |
| 101 | KCGLYDGMEHL | 194 | 0.0 |
| 102 | MCGLYDGMEHL | 195 | 5.8 |
| 103 | FCGLYDGMEHL | 196 | 17.6 |

Experimental Example 11

Test of Trimming of N-Terminal Amino Acid by ERAP1

The peptides synthesized in Examples 50, 56, 64 and 67 were evaluated for N-terminal amino acid trimming efficiency using ERAP1. 50 μl of ERAP1 solution (10 μg/ml) in pH 8.0, 20 mM Tris.HCl-100 mM NaCl buffer (Tris.HCl buffer) was added to 142 μl of Tris.HCl buffer. 10 mM peptide solution in DMSO (2.0 μl) and 6.0 μL of DMSO were added to the aforementioned ERAP1 solution, and the mixture was blended well and stood at 30° C. 1.0 hr later, 50 μl of the mixture was injected into UFLC (under the analysis conditions shown below), and AUC of the peptide of interest was determined. The peptide to be obtained by trimming was chemically synthesized separately, and analyzed under similar conditions in the absence of the enzyme. The formation ratio of the peptide [Proteinase-3$_{169-177}$ peptide (VLQELNVTV) (SEQ ID NO: 43)] obtained by trimming was determined based on the obtained AUC, and is shown in Table 47.

Analysis Conditions
pump: UFLC manufactured by Shimadzu
column: Kinetex 2.6 u C18 100 A 3.0 mmi.d.×75 mm
solution: 0.1% TFA H$_2$O(A)-0.1% TFA CH$_3$CN(B)
oven temperature: 40° C.
flow rate: 1.0 ml/min
detection wavelength: λ=220 nm
gradient: concentration of SOLUTION B was raised from 10% to 50% from 0.0 min to 8.5 min

TABLE 47

| Ex. No. | amino acid sequence | SEQ ID NO: | formation rate of VLQELNVTV (SEQ ID NO: 43) (%) |
|---|---|---|---|
| 50 | ACVLQELNVTV | 143 | 1.8 |
| 56 | GCVLQELNVTV | 149 | 1.1 |
| 64 | SCVLQELNVTV | 157 | 1.3 |
| 67 | YCVLQELNVTV | 160 | 0.7 |

Experimental Example 12

Test of Trimming of N-Terminal Amino Acid by ERAP1

The peptides synthesized in Examples 114, 115, 118-122, 126, 129, 132, 137, 139 and 141-143 were evaluated for N-terminal amino acid trimming efficiency using ERAP1. 50 µl of ERAP1 solution (10 µg/ml) in pH 8.0, 20 mM Tris.HCl-100 mM NaCl buffer (Tris.HCl buffer) was added to 142 µl of Tris.HCl buffer. 10 mM peptide solution in DMSO (2.0 µl) and 6.0 µL of DMSO were added to the aforementioned ERAP1 solution, and the mixture was blended well and stood at 30° C. 1.0 hr later, 50 µl of the mixture was injected into UFLC (under the analysis conditions shown below), and AUC of the peptide of interest was determined. The peptide to be obtained by trimming was chemically synthesized separately, and analyzed under similar conditions in the absence of the enzyme. The formation ratio of the peptide obtained by trimming was determined based on the obtained AUC, and is shown in Tables 48 and 49.

Analysis Conditions
pump: UFLC manufactured by Shimadzu
column: Kinetex 2.6 u C18 100 A 3.0 mmi.d.×75 mm
solution: 0.1% TFA H₂O(A)-0.1% TFA CH₃CN(B)
oven temperature: 40° C.
flow rate: 1.0 ml/min
detection wavelength: λ=220 nm
gradient: concentration of SOLUTION B was raised from 10% to 50% from 0.0 min to 8.5 min

TABLE 48

| Ex. No. | amino acid sequence | SEQ ID NO: | sequence to be formed | formation rate (%) |
|---|---|---|---|---|
| 114 | CGYDQIMPKI | 201 | GYDQIMPKI | 6.4 |
| 115 | CGYDQIMPKK | 202 | GYDQIMPKK | 1.1 |
| 118 | CLIYRRRLMK | 205 | LIYRRRLMK | 3.0 |
| 119 | CAFLPWHRLF | 206 | AFLPWHRLF | 7.8 |
| 120 | CYMDGTMSQV | 207 | YMDGTMSQV | 21.5 |
| 121 | CAAGIGILTV | 208 | AAGIGILTV | 7.2 |
| 122 | CFLWGPRALV | 209 | FLWGPRALV | 2.8 |

TABLE 49

| Ex. No. | amino acid sequence | SEQ ID NO: | sequence to be formed | formation rate (%) |
|---|---|---|---|---|
| 126 | CYLSGANLNL | 213 | YLSGANLNL | 15.2 |
| 129 | CAEEAAGIGIL | 216 | AEEAAGIGIL | 5.2 |
| 132 | CHLFGYSWYK | 219 | HLFGYSWYK | 1.4 |
| 137 | CSTAPPAHGV | 224 | STAPPAHGV | 6.9 |
| 139 | CVYFFLPDHL | 226 | VYFFLPDHL | 5.6 |
| 141 | CMEVDPIGHLY | 228 | MEVDPIGHLY | 20.6 |
| 142 | CTFPDLESEF | 229 | TFPDLESEF | 16.8 |
| 143 | CEADPIGHLY | 230 | EADPIGHLY | 1.7 |

Examples 144-146

By a method similar to that in Example 29, the compound (conjugate) represented by any of the formulas (7)-(9) was synthesized. The results of mass spectrometry are shown in Table 50, wherein the bond between C and C is a disulfide bond.

TABLE 50

| Ex. No. | structural formula | formula No. | mass spectrometry: LC-ESI/ MS m/z | mass spectrometry: Calculated |
|---|---|---|---|---|
| 144 | CGLYDGMEHL<br>\|<br>aKFVAAWTLKAAaC | 9 | 1293.9 $[M + 2H]^{2+}$ | 1294.0 |
| 145 | CGLYDGMEHL<br>\|<br>AKFVAAWTLKAAAC | 8 | 1293.7 $[M + 2H]^{2+}$ | 1294.0 |
| 146 | CGLYDGMEHL<br>\|<br>CaKFVAAWTLKAAa | 7 | 1293.6 $[M + 2H]^{2+}$ | 1294.0 |

Experimental Example 13

Evaluation of In Vivo CTL Induction Ability Using HLA-A0201 Transgenic Mouse

The compound represented by the formula (11) synthesized in Example 109 was evaluated for the CTL induction ability by an in vivo CTL induction test using an HLA-A0201 transgenic mouse. The compound represented by the formula (11):

(11)

wherein the bond between C and C is a disulfide bond, is, in particular, a compound of the aforementioned formula (1) wherein cancer antigen peptide A is GLYDGMEHL (SEQ ID NO: 19) and cancer antigen peptide D is SLLMWITQC (SEQ ID NO: 88). GLYDGMEHL (SEQ ID NO: 19) and SLLMWITQC (SEQ ID NO: 88) are HLA-A0201-restricted cancer antigen peptides.

The HLA-A0201 transgenic mouse is as described in Experimental Example 4.

To evaluate whether CTLs to each of the peptides (SEQ ID NOs: 19 and 88) endogenously presented by cancer cells was induced, the compound represented by the formula (11) was administered to the HLA-A0201 transgenic mouse. That is, it was determined whether IFNγ production was observed by re-stimulation, with the peptide (SEQ ID NO: 19 or 88), of the splenocyte derived from the above-mentioned mouse administered with the compound represented by the formula (11).

Specifically, the compound represented by the formula (11) was dissolved in dimethyl sulfoxide (DMSO) at 80 mg/mL, further diluted with water for injection to 10 mg/mL, and emulsified by mixing with an equal amount of incomplete Freund's adjuvant (IFA). The emulsified compound was intradermally administered to 2 sites at the base of tail of the mouse at 250 μg/site. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated at $0.25 \times 10^6$ cells/well on the blocked ELISPOT plate. Each of the peptide (SEQ ID NO: 19 and 88) was dissolved in DMSO at 40 mg/mL, and further diluted with RPMI1640 medium containing 10% FBS to 40 μg/mL. The HLA-A0201 transgenic mouse-derived splenocytes were pulsed with the diluted peptide represented by SEQ ID NO: 19 or SEQ ID NO: 88 (final concentration: 10 μg/mL), and cultivated for 17 hr at 37° C., 5% $CO_2$, whereby peptide re-stimulation in vitro was performed. After the culture, the supernatant was removed, and the ELISPOT plate was allowed to develop color according to the attached protocol. The number of spots that developed color was measured by ImmunoSpot Analyzer (manufactured by C.T.L.).

Figure 11:
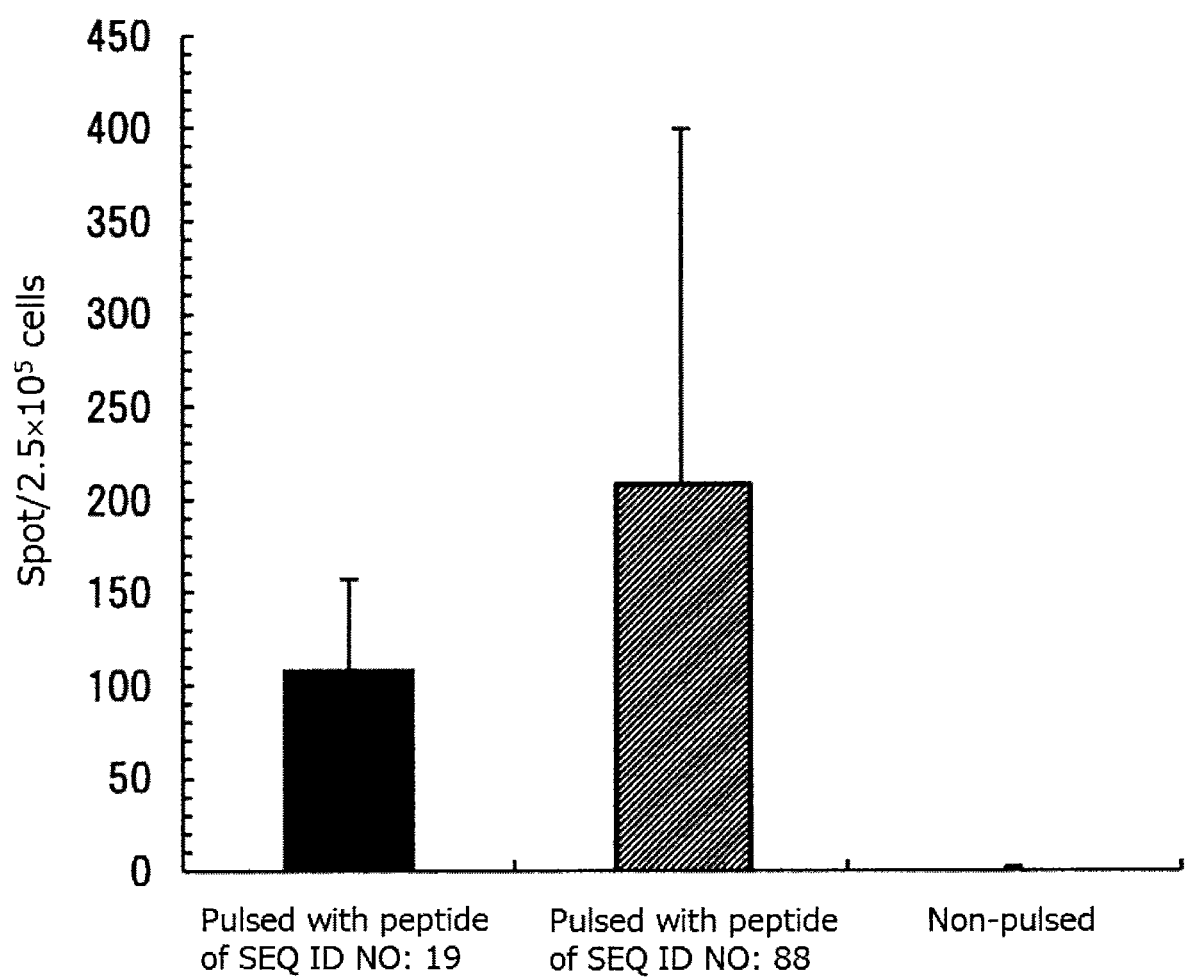
FIG. 11 is a Figure showing the test results of Experimental Example 13 that examined the in vivo CTL induction ability of a compound represented by the formula (11) synthesized in Example 109, by IFNγ ELISPOT assay using HLA-A0201 transgenic mouse.

The results of IFNγ ELISPOT assay using the HLA-A0201 transgenic mouse are shown in FIG. 11.

In FIG. 11, the vertical axis shows the number of cells that responded among the plated cells. In FIG. 11, the black bar and the shaded bar show the results of culture of HLA-A0201 transgenic mouse-derived splenocytes while being pulsed with the peptides shown by SEQ ID NOs: 87 and 88, respectively, and the white bar show the result of culture without pulsing. That is, the difference in the values of the black or shaded bar and the white bar shows the number of peptide-specific CTLs, and that the administration of the compound represented by the formula (11) resulted in the induction of CTLs specific to each of the peptides shown by SEQ ID NOs: 19 and 88 in vivo in the mouse.

In FIG. 11, the value of the white bar is not detected. This means that the splenocytes of the HLA-A0201 transgenic mouse did not react at all in the absence of pulsing with the peptide of interest. As a result of this test, IFNγ production specific to each of the peptides shown by SEQ ID NOs: 19 and 88 was detected in the HLA-A0201 transgenic mouse-derived splenocytes.

From the above, it was demonstrated that the compound represented by the formula (11) can induce CTLs specific to each of the peptided shown by SEQ ID NOs: 19 and 88. It was strongly suggested that the compound represented by the formula (11) undergoes cleavage of disulfide bond and appropriate trimming by ERAP-1 in mice in vivo and is indeed processed into the peptides shown by SEQ ID NOs: 19 and 88.

That is, it was demonstrated that the compound represented by the formula (11), which is one embodiment of the compound of the present invention, is a conjugate wherein two different peptides form a composite via the disulfide bond shown in the formula (1), and is a cancer antigen peptide conjugate vaccine that indeed can induce different two types of CTLs in vivo.

Experimental Example 14

Evaluation of In Vivo CTL Induction Ability Using HLA-A0201 Transgenic Mouse

The compound represented by the formula (5) synthesized in Example 110 was evaluated for the CTL induction ability by an in vivo CTL induction test using HLA-A0201 transgenic mouse. The compound represented by the formula (5):

(5)

wherein the bond between C and C is a disulfide bond, is, in particular, a compound of the aforementioned formula (1) wherein cancer antigen peptide A is GLYDGMEHL (SEQ ID NO: 19) and cancer antigen peptide A is VLQELNVTV (SEQ ID NO: 43). GLYDGMEHL (SEQ ID NO: 19) and VLQELNVTV (SEQ ID NO: 43) are HLA-A0201-restricted cancer antigen peptides.

The HLA-A0201 transgenic mouse is as described in Experimental Example 4.

To evaluate whether CTLs to each of the peptides (SEQ ID NOs: 19 and 43) endogenously presented by cancer cells was induced, the compound represented by the formula (5) was administered to the HLA-A0201 transgenic mouse. That is, it was determined whether IFNγ production was observed by re-stimulation, with the peptide (SEQ ID NO: 19 or 43), of the splenocyte derived from the above-mentioned mouse administered with the compound represented by the formula (5).

Specifically, the compound represented by the formula (5) was dissolved in dimethyl sulfoxide (DMSO) at 80 mg/mL, further diluted with water for injection to 10 mg/mL, and emulsified by mixing with an equal amount of incomplete Freund's adjuvant (IFA). The emulsified compound was intradermally administered to 2 sites at the base of tail of the mouse at 250 μg/site. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated at $0.25 \times 10^6$ cells/well on the blocked ELISPOT plate. Each of the peptide (SEQ ID NO: 19 or 43) was dissolved in DMSO at 40 mg/mL, and further diluted with RPMI1640 medium containing 10% FBS to 40 μg/mL. The HLA-A0201 transgenic mouse-derived splenocytes were pulsed with the diluted peptide represented by SEQ ID NO: 19 or SEQ ID NO: 43 (final concentration: 10 μg/mL), and cultivated for 17 hr at 37° C., 5% $CO_2$, whereby peptide re-stimulation in vitro was performed. After the culture, the supernatant was removed, and the ELISPOT plate was allowed to develop color according to the attached protocol. The number of spots that developed color was measured by ImmunoSpot Analyzer (manufactured by C.T.L.).

Figure 12:
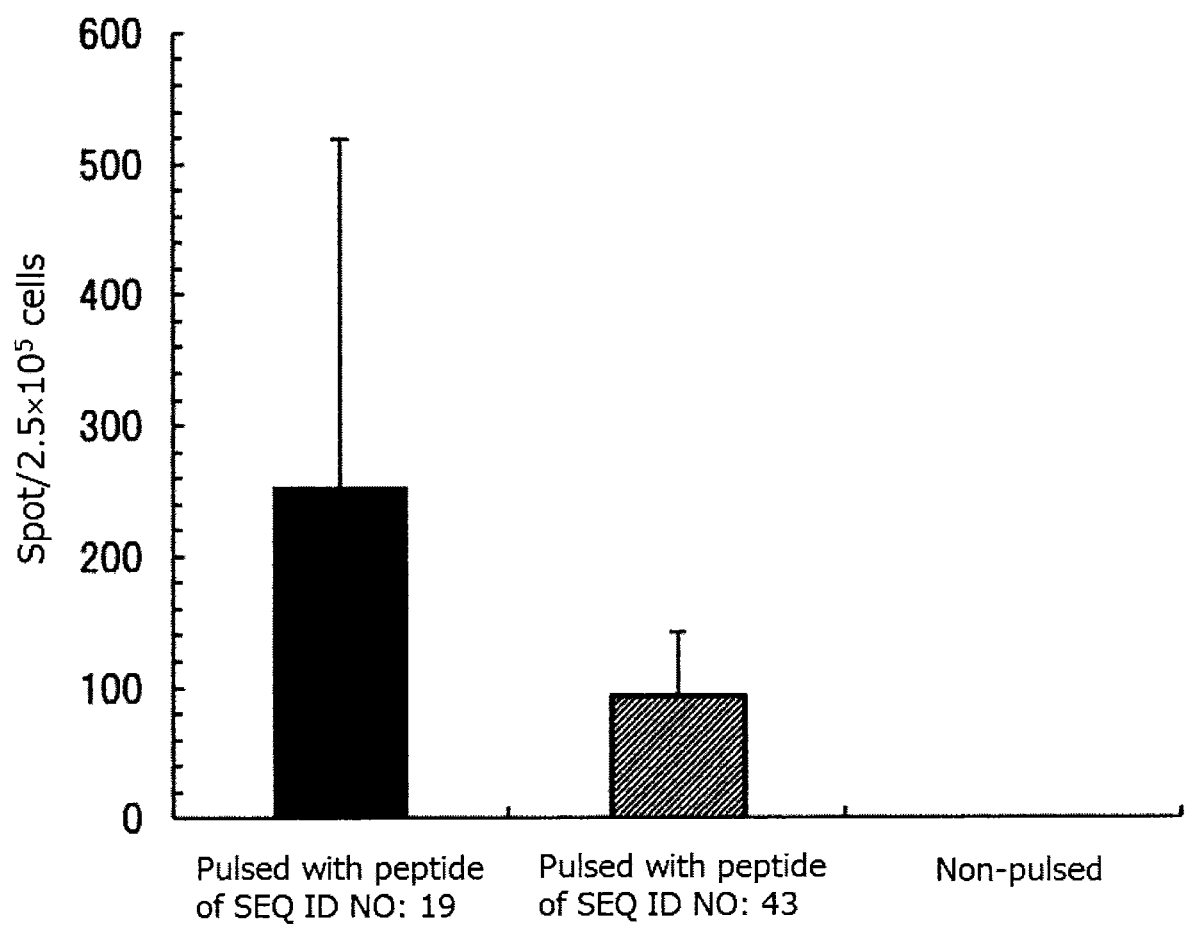
FIG. 12 is a Figure showing the test results of Experimental Example 14 that examined the in vivo CTL induction ability of a compound represented by the formula (5) synthesized in Example 110, by IFNγ ELISPOT assay using HLA-A0201 transgenic mouse.

The results of IFNγ ELISPOT assay using the HLA-A0201 transgenic mouse are shown in FIG. 12.

In FIG. 12, the vertical axis shows the number of cells that responded among the plated cells. In FIG. 12, the black bar and the shaded bar show the results of culture of HLA-A0201 transgenic mouse-derived splenocytes while being pulsed with the peptides shown by SEQ ID NOs: 19 and 43, respectively, and the white bar show the result of culture without pulsing. That is, the difference in the values of the black or shaded bar and the white bar shows the number of peptide-specific CTLs, and that the administration of the compound represented by the formula (5) resulted in the induction of CTLs specific to each of the peptides shown by SEQ ID NO: 19 and 43 in vivo in the mouse.

In FIG. 12, the value of the white bar is not detected. This means that the splenocytes of the HLA-A0201 transgenic mouse did not react in the absence of pulsing with the peptide of interest. As a result of this test, IFNγ production specific to each of the peptides shown by SEQ ID NOs: 19 and 43 was detected in the HLA-A0201 transgenic mouse-derived splenocytes.

From the above, it was demonstrated that the compound represented by the formula (5) can induce CTLs specific to each of the peptides shown by SEQ ID NOs: 19 and 43. It was strongly suggested that the compound represented by the formula (5) undergoes cleavage of disulfide bond and appropriate trimming by ERAP-1 in mice in vivo and is indeed processed into the peptides shown by SEQ ID NOs: 19 and 43.

That is, it was demonstrated that the compound represented by the formula (5), which is one embodiment of the compound of the present invention, is a conjugate wherein two different peptides form a composite via the disulfide bond shown in the formula (1), and is a cancer antigen peptide conjugate vaccine that indeed can induce different two types of CTLs in vivo.

Experimental Example 15

Test of Trimming of N-Terminal Amino Acid by ERAP1

The peptides synthesized in Examples 123-125, 130, 134, 135 and 138 were evaluated for N-terminal amino acid trimming efficiency using ERAP1. 50 μl of ERAP1 solution (50 μg/ml) in pH 8.0, 20 mM Tris.HCl-100 mM NaCl buffer (Tris.HCl buffer) was added to 142 μl of Tris.HCl buffer. 10 mM peptide solution in DMSO (2.0 μl) and 6.0 μL of DMSO were added to the aforementioned ERAP1 solution, and the mixture was blended well and stood at 30° C. 1.0 hr later, 50 μl of the mixture was injected into UFLC (under the analysis conditions shown below), and AUC of the peptide of interest was determined. The peptide to be obtained by trimming was chemically synthesized separately, and analyzed under similar conditions in the absence of the enzyme. The formation ratio of the peptide obtained by trimming was determined based on the obtained AUC, and is shown in Table 51.

Analysis Conditions pump: UFLC manufactured by Shimadzu
column: Kinetex 2.6 u C18 100 A 3.0 mmi.d.×75 mm
solution: 0.1% TFA $H_2O$(A)-0.1% TFA $CH_3CN$(B)
oven temperature: 40° C.
flow rate: 1.0 ml/min
detection wavelength: λ=220 nm
gradient: concentration of SOLUTION B was raised from 10% to 50% from 0.0 min to 8.5 min

TABLE 51

| Ex. No. | amino acid sequence | SEQ ID NO: | sequence to be formed | formation rate (%) |
|---|---|---|---|---|
| 123 | CAYACNTSTL | 210 | AYACNTSTL | 21.8 |
| 124 | CKWFPSCQFLL | 211 | KWFPSCQFLL | 4.0 |
| 125 | CNYKHCFPEI | 212 | NYKHCFPEI | 13.9 |
| 130 | CSNDGPTLI | 217 | SNDGPTLI | 26.0 |
| 134 | CKTWGQYWQV | 221 | KTWGQYWQV | 5.8 |
| 135 | CSEIWRDIDF | 222 | SEIWRDIDF | 3.6 |
| 138 | CSTAPPVHNV | 225 | STAPPVHNV | 71.2 |

Experimental Example 16

Test of Trimming of N-Terminal Amino Acid by ERAP1

The peptides synthesized in Example 140 were evaluated for N-terminal amino acid trimming efficiency using ERAP1. 50 μl of ERAP1 solution (50 μg/ml) in pH 8.0, 20 mM Tris.HCl-100 mM NaCl buffer (Tris.HCl buffer) was added to 142 μl of Tris.HCl buffer. 10 mM peptide solution in DMSO (2.0 μl) and 6.0 μL of DMSO were added to the aforementioned ERAP1 solution, and the mixture was blended well and stood at 30° C. 1.0 hr later, 50 μl of the mixture was injected into UFLC (under the analysis conditions shown below), and AUC of the peptide of interest was determined. The peptide to be obtained by trimming was chemically synthesized separately, and analyzed under similar conditions in the absence of the enzyme. The formation ratio of the peptide obtained by trimming was determined based on the obtained AUC, and is shown in Table 52.

Analysis Conditions pump: UFLC manufactured by Shimadzu
column: Kinetex 2.6 u C18 100 A 3.0 mmi.d.×75 mm
solution: 0.1% TFA $H_2O$(A)-0.1% TFA $CH_3CN$(B)
oven temperature: 40° C.
flow rate: 1.0 ml/min
detection wavelength: λ=220 nm
gradient: concentration of SOLUTION B was raised from 1% to 30% from 0.0 min to 8.5 min

TABLE 52

| Ex. No. | amino acid sequence | SEQ ID NO: | sequence to be formed | formation rate (%) |
|---|---|---|---|---|
| 140 | CASGPGGGAPR | 227 | ASGPGGGAPR | 11.0 |

Experimental Example 17

Test of Trimming of N-Terminal Amino Acid by ERAP1

The peptides synthesized in Example 131 were evaluated for N-terminal amino acid trimming efficiency using ERAP1. 50 μl of ERAP1 solution (100 μg/ml) in pH 8.0, 20 mM Tris.HCl-100 mM NaCl buffer (Tris.HCl buffer) was added to 142 μl of Tris.HCl buffer. 10 mM peptide solution in DMSO (8.0 μl) was added to the aforementioned ERAP1 solution, and the mixture was blended well and stood at 30° C. 1.0 hr later, 10 μl of the mixture was injected into UFLC (under the analysis conditions shown below), and AUC of the peptide of interest was determined. The peptide to be obtained by trimming was chemically synthesized separately, and analyzed under similar conditions in the absence of the enzyme. The formation ratio of the peptide obtained by trimming was determined based on the obtained AUC, and is shown in Table 53.

Analysis Conditions
pump: UFLC manufactured by Shimadzu
column: Kinetex 2.6 u C18 100 A 3.0 mmi.d.×75 mm
solution: 0.1% TFA $H_2O$(A)-0.1% TFA $CH_3CN$(B)
oven temperature: 40° C.
flow rate: 1.0 ml/min
detection wavelength: λ=220 nm
gradient: concentration of SOLUTION B was raised from 10% to 50% from 0.0 min to 8.5 min

TABLE 53

| Ex. No. | amino acid sequence | SEQ ID NO: | sequence to be formed | formation rate (%) |
|---|---|---|---|---|
| 131 | CKCDICTDEY | 218 | KCDICTDEY | 13.2 |

Experimental Example 18

Test of Trimming of N-Terminal Amino Acid by ERAP1

The peptides synthesized in Example 136 were evaluated for N-terminal amino acid trimming efficiency using ERAP1. 50 μl of ERAP1 solution (100 μg/ml) in pH 8.0, 20 mM Tris.HCl-100 mM NaCl buffer (Tris.HCl buffer) was added to 142 μl of Tris.HCl buffer. 10 mM peptide solution in DMSO (8.0 μl) was added to the aforementioned ERAP1 solution, and the mixture was blended well and stood at 30° C. 1.0 hr later, 10 μl of the mixture was injected into UFLC (under the analysis conditions shown below), and AUC of the peptide of interest was determined. The peptide to be obtained by trimming was chemically synthesized separately, and analyzed under similar conditions in the absence of the enzyme. The formation ratio of the peptide obtained by trimming was determined based on the obtained AUC, and is shown in Table 54.

Analysis Conditions
pump: UFLC manufactured by Shimadzu
column: Kinetex 2.6 u C18 100 A 3.0 mmi.d.×75 mm
solution: 0.1% TFA $H_2O$(A)-0.1% TFA $CH_3CN$(B)
oven temperature: 40° C.
flow rate: 1.0 ml/min
detection wavelength: λ=220 nm
gradient: concentration of SOLUTION B was raised from 1% to 30% from 0.0 min to 8.5 min

TABLE 54

| Ex. No. | amino acid sequence | SEQ ID NO: | sequence to be formed | formation rate (%) |
|---|---|---|---|---|
| 136 | CVLRENTSPK | 223 | VLRENTSPK | 20.8 |

Examples 147-148

By a method similar to that in Example 29, the compound (conjugate) represented by any of the formulas (12) and (18) was synthesized. The results of mass spectrometry are shown in Table 55, wherein the bond between C and C is a disulfide bond.

TABLE 55

| Ex. No. | structural formula | formula No. | mass spectrometry: LC-ESI/ MS m/z | mass spectrometry: Calculated |
|---|---|---|---|---|
| 147 | CKIFGSLAFL<br>\|<br>AKFVAAWTLKAAAC | 18 | 637.5<br>$[M + 3H]^{3+}$ | 637.8 |
| 148 | CGLYDGMEHL<br>\|<br>aK-Cha-VAAWTLKAAa-Ahx-C | 12 | 677.0<br>$[M + 3H]^{3+}$ | 677.3 |

Reference Examples 2-9

By a method similar to that in Example 1, peptides consisting of the amino acid sequences of SEQ ID NOs: 231-238 were synthesized. Table 56 shows the result of mass spectrometry of each synthesized peptide.

The compounds of SEQ ID NOs: 231-238 were not the compounds of the present invention and were therefore described as Reference Example.

TABLE 56

| Ref. Ex. No. | amino acid sequence | SEQ ID NO: | mass spectrometry: LC-ESI/ MS m/z | mass spectrometry: Calculated |
|---|---|---|---|---|
| 2 | GLYDGMEHLKIFGSLAFL | 231 | 1006.4<br>$[M + 2H]^{2+}$ | 1007.2 |

TABLE 56-continued

| Ref. Ex. No. | amino acid sequence | SEQ ID NO: | mass spectrometry: LC-ESI/ MS m/z | mass spectrometry: Calculated |
|---|---|---|---|---|
| 3 | KIFGSLAFLGLYDGM EHL | 232 | 671.3 [M + 3H]³⁺ | 671.5 |
| 4 | GLYDGMEHLGGGGGG KIFGSLAFL | 233 | 785.3 [M + 3H]³⁺ | 785.6 |
| 5 | KIFGSLAFLGGGGGG GLYDGMEHL | 234 | 785.3 [M + 3H]³⁺ | 785.6 |
| 6 | VYGFVRACLGLYDGM EHL | 235 | 681.9 [M + 3H]³⁺ | 682.1 |
| 7 | GLYDGMEHLVYGFVR ACL | 236 | 681.9 [M + 3H]³⁺ | 682.1 |
| 8 | VYGFVRACLGGGGGG GLYDGMEHL | 237 | 796.0 [M + 3H]³⁺ | 796.2 |
| 9 | GLYDGMEHLGGGGGG VYGFVRACL | 238 | 796.0 [M + 3H]³⁺ | 796.2 |

The peptides represented by SEQ ID NOs: 233, 234, 237 and 238 shown in Table 56 were synthesized by referring to the non-patent document, Cancer Science January 2012, Vol. 103, no. 1, 150-153.

Example 149

Synthesis of the Compound Represented by the Formula (19):

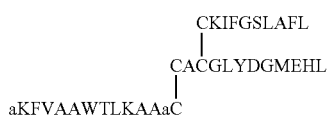

wherein the bond between C and C is a disulfide bond
Step 1. Synthesis of Fmoc-Cys(Mmt)-Ala-SBn (Mmt is 4 Methoxytrityl)
(Synthesis of Fmoc-C(Mmt)A-SBn)
A solution of Fmoc-Cys(Mmt)-OH (4.80 g), N,N-diisopropylethylamine (2.56 mL), hexafluorophosphoric acid (benzotriazol-1-yloxy)tripyrrolidinophosphonium (4.50 g) and H-Ala-SBn synthesized by a known method (for example, Journal of Organic Chemistry, Vol. 64, No. 24 8761-8769) in chloroform (20 ml) was stirred at room temperature for 1 hr. The reaction mixture was purified by column chromatography (elution solvent, hexane/ethyl acetate) to give the desired compound, Fmoc-C(Mmt)A-SBn (2.80 g).
NMR: ¹H NMR (CDCl₃) δ 7.72 (t, J=7.6 Hz, 2H), 7.54 (d, J=7.2 Hz, 1H), 7.38-7.34 (m, 7H), 7.29-7.25 (m, 6H), 7.23-7.15 (m, 7H), 6.76 (d, J=8.8 Hz, 2H), 6.15 (d, J=8.0 Hz, 1H), 4.95 (d, J=7.2 Hz, 1H), 4.57 (quin, J=7.6 Hz, 1H), 4.35 (d, J=6.8 Hz, 2H) 4.19-4.17 (m, 1H), 4.04 (s, 2H), 3.73 (s, 3H), 2.72 (dd, J=13.2, 8.4 Hz, 1H), 2.61 (d, J=9.6 Hz, 1H), 1.31 (d, J=7.2 Hz, 3H).
Step 2. Synthesis of H-Cys(Mmt)-Ala-Cys-Gly-Leu-Tyr-Asp-Gly-Met-Glu-His-Leu-OH (Synthesis of C(Mmt)ACG-LYDGMEHL) (SEQ ID NO: 248)
A solution of Fmoc-Cys(Mmt)-Ala-SBn(11 mg) obtained in step 1, H-Cys-Gly-Leu-Tyr-Asp-Gly-Met-Glu-His-Leu-OH (SEQ ID NO: 98) (16 mg) synthesized in Example 25, N,N-diisopropylethylamine (200 μL), 3,3',3"-Phosphanetriyl tripropanoic acid hydrochloride (1 mg), 4-mercaptophenylacetic acid (1 mg) and 0.1M sodium phosphate buffer (pH 7.5, 200 μL) in DMF (400 μL) was stirred at room temperature for 4 hr. To the reaction mixture was added diethylamine (200 μL) and the mixture was further stirred for 15 min. The reaction mixture was purified by reversed-phase HPLC to give the desired compound, C(Mmt)ACG-LYDGMEHL (SEQ ID NO: 248) (6 mg).
mass spectrometry: LC-ESI/MS m/z=792.7 [M+2H]²⁺ (Calculated=792.9)
Step 3. Synthesis of (H-Cys(Mmt)-Ala-Cys-Gly-Leu-Tyr-Asp-Gly-Met-Glu-His-Leu-OH) (H-Cys-Lys-Ile-Phe-Gly-Ser-Leu-Ala-Phe-Leu-OH) disulfide bond
[i.e., synthesis of the compound represented by the formula (20):

wherein the bond between C and C is a disulfide bond.
A solution of H-Cys(Mmt)-Ala-Cys-Gly-Leu-Tyr-Asp-Gly-Met-Glu-His-Leu-OH (SEQ ID NO: 248) (19 mg) obtained in step 2 and (H-Cys(Pys)-Lys-Ile-Phe-Gly-Ser-Leu-Ala-Phe-Leu-OH) (SEQ ID NO: 247) (15 mg) obtained in Example 108 in DMF (1 mL) was stirred at room temperature for 2 hr. The reaction mixture was purified by reversed-phase HPLC to give 19 mg of the desired compound, (H-Cys(Mmt)-Ala-Cys-Gly-Leu-Tyr-Asp-Gly-Met-Glu-His-Leu-OH) (H-Cys-Lys-Ile-Phe-Gly-Ser-Leu-Ala-Phe-Leu-OH) disulfide bond [i.e., a compound represented by the formula (20)].
mass spectrometry: LC-ESI/MS m/z=803.3 [M-Mmt+3]²⁺ (Calculated=803.3)
Step 4.
Synthesis of aKFVAAWTLKAAaC(Pys) (SEQ ID NO: 249)
aKFVAAWTLKAAaC (SEQ ID NO: 200) (138 mg) obtained in Example 107 and 2,2'-dipyridyl bisulfide (0.2 M isopropanol solution, 718 μL) in (20% (w/w) aqueous acetic acid solution)/(acetonitrile)=1/1 (5 mL) solution were stirred at room temperature for 2 hr. 2,2'-Dipyridyl bisulfide (0.2 M isopropanol solution, 350 μL) was further added, and the mixture was stirred for 2 hr. The reaction mixture was purified by reversed-phase HPLC to give 34 mg of the desired compound, aKFVAAWTLKAAaC(Pys) (SEQ ID NO: 249).
mass spectrometry: LC-ESI/MS m/z=520.5 [M+3H]³⁺ (Calculated=521.0)
Step 5. Synthesis of a Compound Represented by the Formula (19):

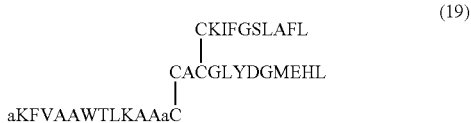

wherein the bond between C and C is a disulfide bond
A solution of (H-Cys(Mmt)-Ala-Cys-Gly-Leu-Tyr-Asp-Gly-Met-Glu-His-Leu-OH)(H-Cys-Lys-Ile-Phe-Gly-Ser-Leu-Ala-Phe-Leu-OH) disulfide bond obtained in step 3 [i.e., a compound represented by the formula (20)] (40 mg), aKFVAAWTLKAAaC (Pys) (35 mg) obtained in step 4 and triisopropylsilane (30 μL) in trifluoroacetic acid (570 μL) was stirred at room temperature for 30 min. The reaction mixture was purified by reversed-phase HPLC to give the desired compound, a compound represented by the formula (19) (5 mg).

mass spectrometry: LC-ESI/MS m/z=1285.8 $[M+3H]^{3+}$ (Calculated=1286.5)

Experimental Example 19

Evaluation of In Vivo CTL Induction Ability Using HLA-A0201 Transgenic Mouse

The compound represented by the formula (16) synthesized in Example 112 was evaluated for the CTL induction ability by an in vivo CTL induction test using an HLA-A0201 transgenic mouse. The compound represented by the formula (16):

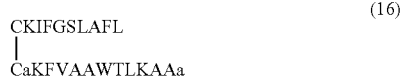

(16)

wherein the bond between C and C is a disulfide bond, is, in particular, a compound of the aforementioned formula (1) wherein cancer antigen peptide A is KIFGSLAFL (SEQ ID NO: 53) and cancer antigen peptide B is aKFVAAWTLKAAa (SEQ ID NO: 102). KIFGSLAFL (SEQ ID NO: 53) is an HLA-A0201-restricted cancer antigen peptide, and aKFVAAWTLKAAa (SEQ ID NO: 102) is an HLA-DR-restricted universal cancer antigen peptide (i.e., helper peptide).

The HLA-A0201 transgenic mouse is as described in Experimental Example 4. Using this mouse, peptides capable of inducing CTLs in HLA-A02 positive humans can be selected, and also the activity of helper peptides capable of inducing helper T cells by binding to human HLA-DRB1*0101 to enhance CTL induction can be evaluated.

Whether the administration of the compound represented by the formula (16) results in the induction of CTLs specific to the peptide of interest (SEQ ID NO: 53) was determined based on the measurement of IFNγ production by re-stimulation, with the peptide (SEQ ID NO: 53), of the splenocytes derived from the above-mentioned mouse administered with the compound represented by the formula (16). Whether the helper peptide (SEQ ID NO: 102) works in the living body was determined by comparison of the numbers of IFNγ-producing cells obtained by re-stimulating the splenocytes derived from the mouse administered with the compound represented by the formula (16) and those derived from the mouse administered with the compound represented by SEQ ID NO: 53 with the peptide (SEQ ID NO: 53).

Specifically, the compound represented by the formula (16) was dissolved in dimethyl sulfoxide (DMSO) at 80 mg/mL, further diluted with water for injection to 5.1 mg/mL, and emulsified by mixing with an equal amount of incomplete Freund's adjuvant (IFA). The emulsified compound was intradermally administered to 2 sites at the base of tail of the mouse at 130 μg/site. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day.

The prepared HLA-A0201 transgenic mouse-derived splenocytes were plated at $0.125 \times 10^6$ cells/well on the blocked ELISPOT plate. The peptide (SEQ ID NO: 53) was dissolved in DMSO at 40 mg/mL, and further diluted with RPMI1640 medium containing 10% FBS to 40 μg/mL. The HLA-A0201 transgenic mouse-derived splenocytes were pulsed with the diluted peptide represented by SEQ ID NO: 53 (final concentration: 10 μg/mL), and cultivated for 19 hr at 37° C., 5% $CO_2$, whereby peptide re-stimulation in vitro was performed. After the culture, the supernatant was removed, and the ELISPOT plate was allowed to develop color according to the attached protocol. The number of spots that developed color was measured by ImmunoSpot Analyzer (manufactured by C.T.L.).

Figure 13:
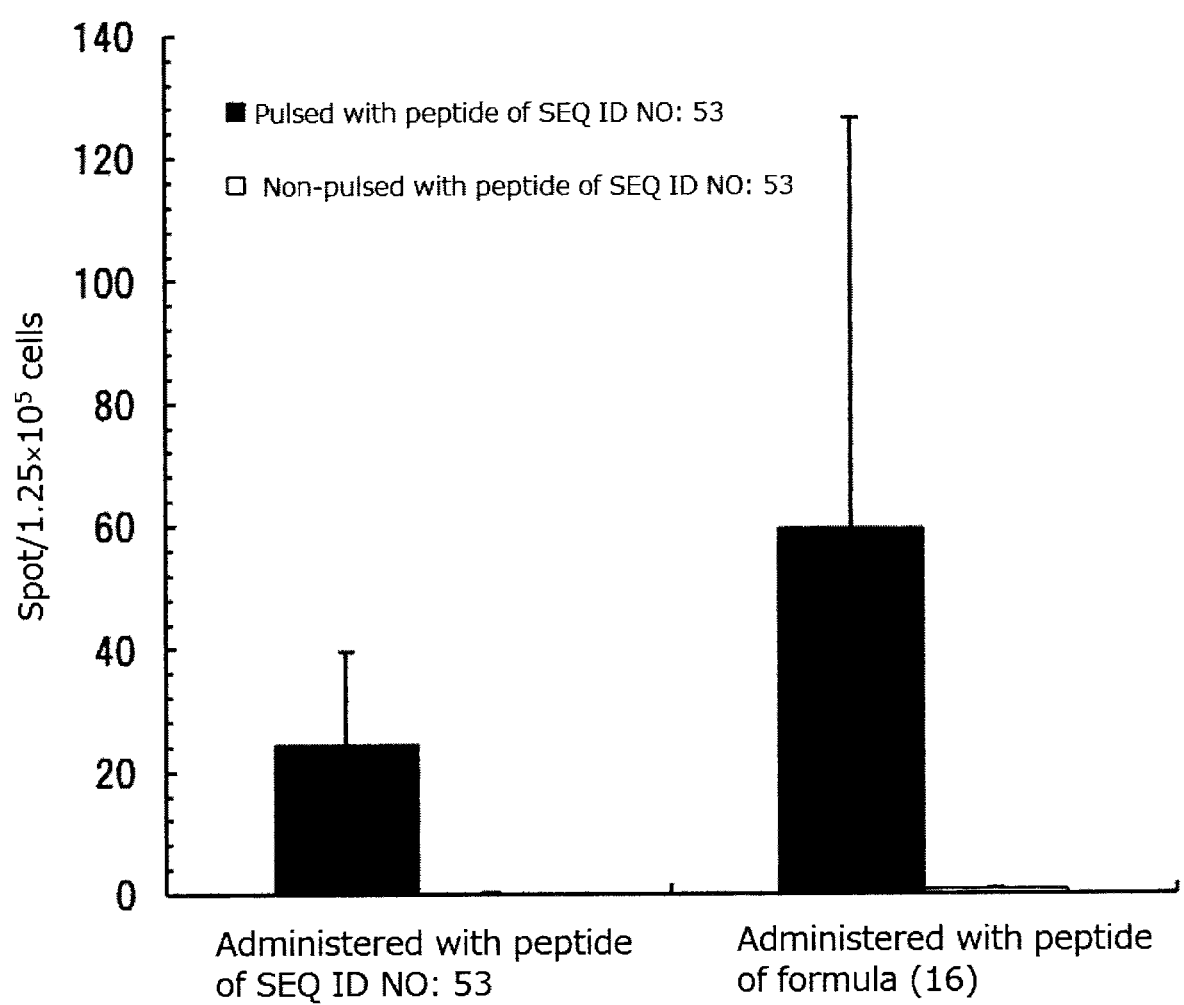
FIG. 13 is a Figure showing the test results of Experimental Example 19 that examined the in vivo CTL induction ability of a compound represented by the formula (16) synthesized in Example 112, by IFNγ ELISPOT assay using HLA-A0201 transgenic mouse.

The results of IFNγ ELISPOT assay using the HLA-A0201 transgenic mouse are shown in FIG. 13. In FIG. 13, the vertical axis shows the number of cells that responded among the plated cells, and the horizontal axis shows the compound or peptide administered to the mouse. In FIG. 13, the black bar shows the result of culture of HLA-A0201 transgenic mouse-derived splenocytes while being pulsed with the peptide shown by SEQ ID NO: 53, and the white bar shows the results of culture without pulsing. That is, the difference in the values of the black bar and the white bar shows the number of peptide-specific CTLs, and that the administration of the peptide shown by SEQ ID NO: 53 or the compound represented by the formula (16) resulted in the induction of CTLs specific to the peptide shown by SEQ ID NO: 53 in vivo in the mouse. In FIG. 13, the value of the white bar is not detected. This means that the splenocytes of the HLA-A0201 transgenic mouse did not react at all in the absence of pulsing with the peptide of interest. As a result of this test, IFNγ production specific to the peptide shown by SEQ ID NO: 53 was detected in the HLA-A0201 transgenic mouse-derived splenocytes. Moreover, in FIG. 13, the number of IFNγ-producing cells specific to the peptide shown by SEQ ID NO: 53 induced by the administration of the compound represented by the formula (16) was higher than that induced by the administration of the peptide shown by SEQ ID NO: 53.

From the above, it was demonstrated that the compound represented by the formula (16) can induce CTLs specific to the peptide shown by SEQ ID NO: 53. Administration of the compound represented by the formula (16) induced more IFNγ producing cells specific to the peptide shown by SEQ ID NO: 53 than the administration of the peptide shown by SEQ ID NO: 53. It was assumed that induction of cells reactive with the helper peptide shown by SEQ ID NO: 102 produced from the compound represented by the formula (16) enhanced induction of CTLs specific to the peptide shown by SEQ ID NO: 53. Therefore, it was strongly suggested that the compound represented by the formula (16) undergoes cleavage of disulfide bond and appropriate trimming by ERAP-1 in mice in vivo and is indeed processed into the peptides shown by SEQ ID NOs: 53 and 102.

That is, it was demonstrated that the compound represented by the formula (16), which is one embodiment of the compound of the present invention, is a conjugate wherein two different peptides form a composite via the disulfide bond shown in the formula (1), and is a cancer antigen peptide conjugate vaccine that indeed can induce CTLs and helper peptide reactive cells in vivo.

Experimental Example 20

Evaluation of In Vivo CTL Induction Ability Using HLA-A0201 Transgenic Mouse

The compound represented by the formula (17) synthesized in Example 113 was evaluated for the CTL induction ability by an in vivo CTL induction test using HLA-A0201 transgenic mouse. The compound represented by the formula (17):

(17)

wherein the bond between C and C is a disulfide bond, is, in particular, a compound of the aforementioned formula (1) wherein cancer antigen peptide A is KIFGSLAFL (SEQ ID NO: 53) and cancer antigen peptide C is aKFVAAWTL-KAAa (SEQ ID NO: 102). KIFGSLAFL (SEQ ID NO: 53) is an HLA-A0201-restricted cancer antigen peptide, and aKFVAAWTLKAAa (SEQ ID NO: 102) is an HLA-DR-restricted universal cancer antigen peptide (i.e., helper peptide).

The HLA-A0201 transgenic mouse is as described in Experimental Examples 4 and 19.

Whether the administration of the compound represented by the formula (17) results in the induction of CTLs specific to the peptide of interest (SEQ ID NO: 53) was determined based on the measurement of IFNγ production by re-stimulation, with the peptide (SEQ ID NO: 53), of the splenocyte derived from the above-mentioned mouse administered with a compound represented by the formula (17). Whether the helper peptide (SEQ ID NO: 102) works in the living body was determined by comparison of the numbers of IFNγ-producing cells obtained by re-stimulating the splenocytes derived from the mouse administered with the compound represented by the formula (17) and those derived from the mouse administered with the compound represented by SEQ ID NO: 53 with the peptide (SEQ ID NO: 53).

By a method similar to that in Experimental Example 19, CTL induction test was performed.

Figure 14:
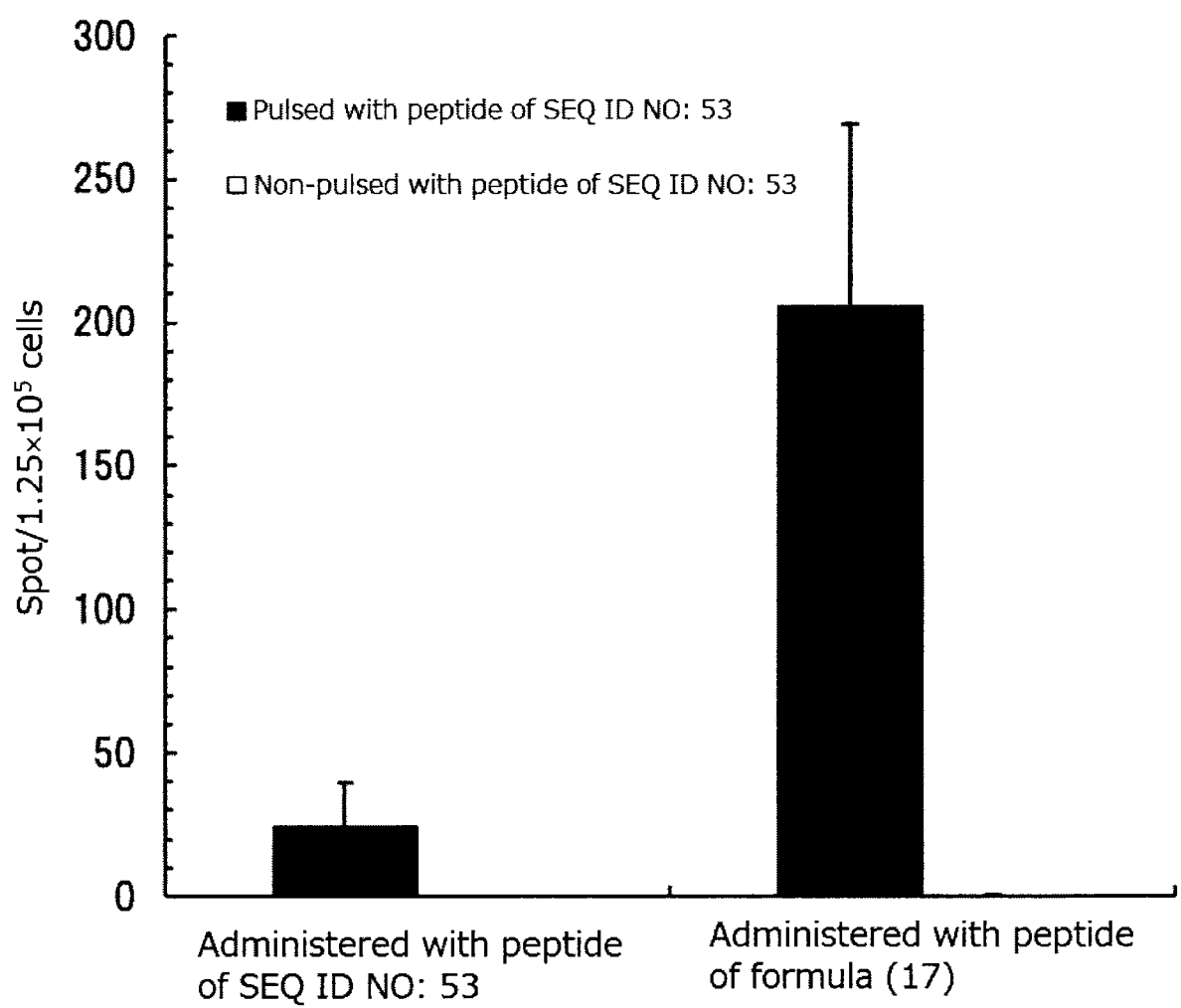
FIG. 14 is a Figure showing the test results of Experimental Example 20 that examined the in vivo CTL induction ability of a compound represented by the formula (17) synthesized in Example 113, by IFNγ ELISPOT assay using HLA-A0201 transgenic mouse.

The results of IFNγ ELISPOT assay using the HLA-A0201 transgenic mouse are shown in FIG. 14. In FIG. 14, the vertical axis shows the number of cells that responded among the plated cells, and the horizontal axis shows the compound or peptide administered to the mouse. In FIG. 14, the black bar shows the result of culture of HLA-A0201 transgenic mouse-derived splenocytes while being pulsed with the peptide shown by SEQ ID NO: 53, and the white bar shows the results of culture without pulsing. That is, the difference in the values of the black bar and the white bar shows the number of peptide-specific CTLs, and that the administration of the peptide shown by SEQ ID NO: 53 or the compound represented by the formula (17) resulted in the induction of CTLs specific to the peptide shown by SEQ ID NO: 53 in vivo in the mouse. In FIG. 14, the value of the white bar is not detected. This means that the splenocytes of the HLA-A0201 transgenic mouse did not react at all in the absence of pulsing with the peptide of interest. As a result of this test, IFNγ production specific to the peptide shown by SEQ ID NO: 53 was detected in the HLA-A0201 transgenic mouse-derived splenocytes. Moreover, in FIG. 14, the number of IFNγ-producing cells specific to the peptide shown by SEQ ID NO: 53 induced by the administration of a compound represented by the formula (17) was higher than that induced by the administration of the peptide shown by SEQ ID NO: 53.

From the above, it was demonstrated that the compound represented by the formula (17) can induce CTLs specific to the peptide shown by SEQ ID NO: 53. Administration of the compound represented by the formula (17) induced more IFNγ producing cells specific to the peptide shown by SEQ ID NO: 53 than administration of the peptide shown by SEQ ID NO: 53. It was assumed that the induction of cells reactive with the helper peptide shown by SEQ ID NO: 102 produced from the compound represented by the formula (17) enhanced induction of CTLs specific to the peptide shown by SEQ ID NO: 53. Therefore, it was strongly suggested that the compound represented by the formula (17) undergoes cleavage of disulfide bond and appropriate trimming by ERAP-1 in mice in vivo and is indeed processed into the peptides shown by SEQ ID NOs: 53 and 102.

That is, it was demonstrated that the compound represented by the formula (17), which is one embodiment of the compound of the present invention, is a conjugate wherein two different peptides form a composite via the disulfide bond shown in the formula (1), and is a cancer antigen peptide conjugate vaccine that indeed can induce CTLs and helper peptide reactive cells in vivo.

Experimental Example 21

Evaluation of In Vivo CTL Induction Ability Using HLA-A0201 Transgenic Mouse

The compound represented by the formula (18) synthesized in Example 147 was evaluated for the CTL induction ability by an in vivo CTL induction test using an HLA-A0201 transgenic mouse. The compound represented by the formula (18):

(18)

wherein the bond between C and C is a disulfide bond, is, in particular, a compound of the aforementioned formula (1) wherein cancer antigen peptide A is KIFGSLAFL (SEQ ID NO: 53) and cancer antigen peptide C is AKFVAAWTL-KAAA (SEQ ID NO: 101). KIFGSLAFL (SEQ ID NO: 53) is an HLA-A0201-restricted cancer antigen peptide, and AKFVAAWTLKAAA (SEQ ID NO: 101) is an HLA-DR-restricted universal cancer antigen peptide (i.e., helper peptide).

The HLA-A0201 transgenic mouse is as described in Experimental Examples 4 and 19.

Whether the administration of the compound represented by the formula (18) results in the induction of CTLs specific to the peptide of interest (SEQ ID NO: 53) was determined based on the measurement of IFNγ production by re-stimulation, with the peptide (SEQ ID NO: 53), of the splenocyte derived from the above-mentioned mouse administered with a compound represented by the formula (18). Whether the helper peptide (SEQ ID NO: 101) works in the living body was determined by comparison of the numbers of IFNγ-producing cells obtained by re-stimulating the splenocytes derived from the mouse administered with the compound represented by the formula (18) and those derived from the mouse administered with the compound shown by SEQ ID NO: 53 with the peptide (SEQ ID NO: 53).

By a method similar to that in Experimental Example 19, CTL induction test was performed.

Figure 15:
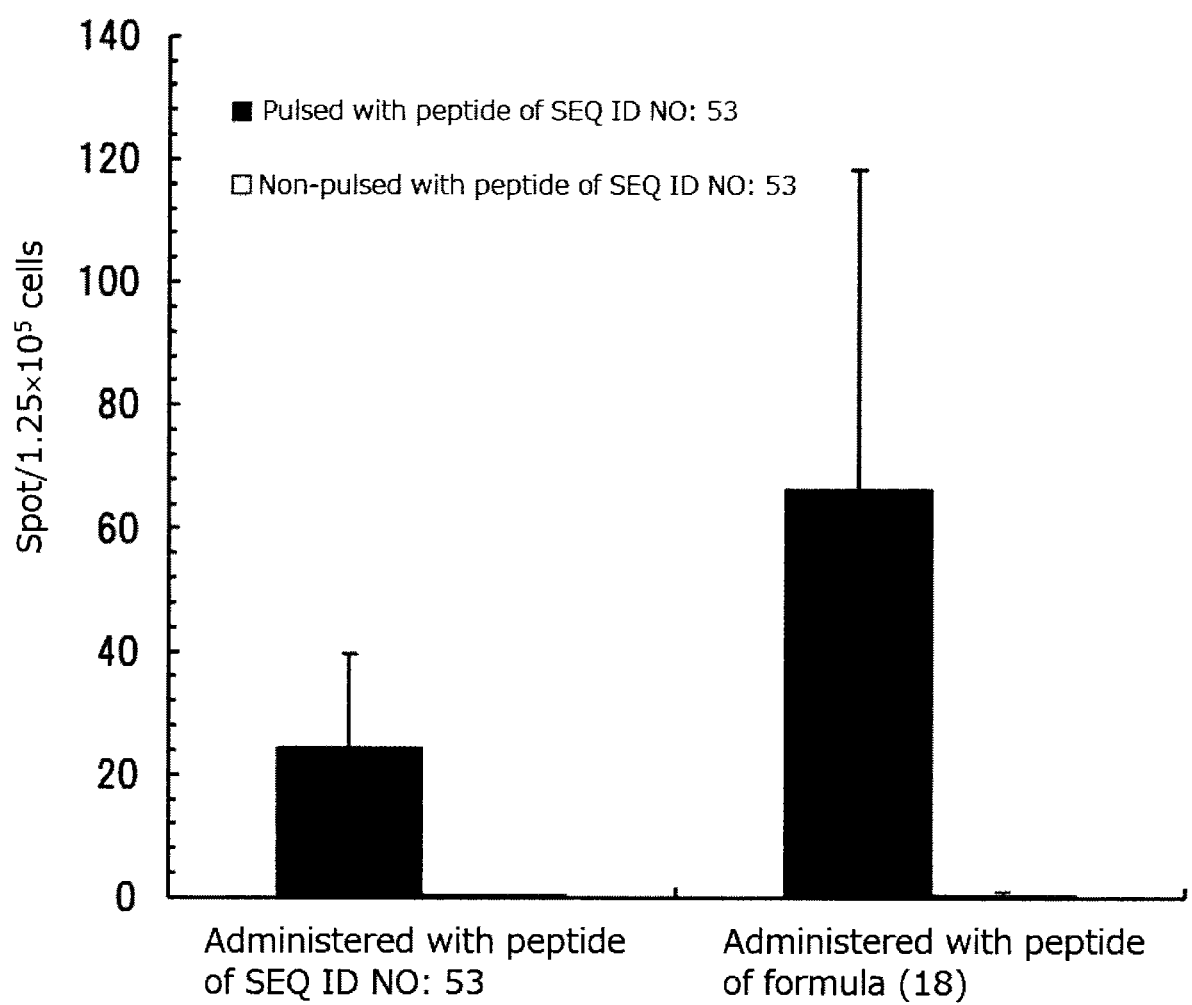
FIG. 15 is a Figure showing the test results of Experimental Example 21 that examined the in vivo CTL induction ability of a compound represented by the formula (18) synthesized in Example 147, by IFNγ ELISPOT assay using HLA-A0201 transgenic mouse.

The results of IFNγ ELISPOT assay using the HLA-A0201 transgenic mouse are shown in FIG. 15. In FIG. 15, the vertical axis shows the number of cells that responded among the plated cells, and the horizontal axis shows the compound or peptide administered to the mouse. In FIG. 15, the black bar shows the result of culture of HLA-A0201 transgenic mouse-derived splenocytes while being pulsed with the peptide shown by SEQ ID NO: 53, and the white bar shows the result of culture without pulsing. That is, the difference in the values of the black bar and the white bar shows the number of peptide-specific CTLs, and that the administration of the peptide shown by SEQ ID NO: 53 or the compound represented by the formula (18) resulted in the induction of CTLs specific to the peptide shown by SEQ ID NO: 53 in vivo in the mouse. In FIG. 15, the value of the white bar is not detected. This means that the splenocytes of the HLA-A0201 transgenic mouse did not react at all in the absence of pulsing with the peptide of interest. As a result of this test, IFNγ production specific to the peptide shown by SEQ ID NO: 53 was detected in the HLA-A0201 transgenic mouse-derived splenocytes. Moreover, in FIG. 15, the number of IFNγ-producing cells specific to the peptide shown by SEQ ID NO: 53 induced by the administration of a compound represented by the formula (18) was higher than that induced by the administration of the peptide shown by SEQ ID NO: 53.

From the above, it was demonstrated that the compound represented by the formula (18) can induce CTLs specific to the peptide shown by SEQ ID NO: 53. Administration of the compound represented by the formula (18) induced more IFNγ producing cells specific to the peptide shown by SEQ ID NO: 53 than administration of the peptide shown by SEQ ID NO: 53. It was assumed that induction of cells reactive with the helper peptide shown by SEQ ID NO: 101 produced from the compound represented by the formula (18) enhanced induction of CTLs specific to the peptide shown by SEQ ID NO: 53. Therefore, it was strongly suggested that the compound represented by the formula (18) undergoes cleavage of disulfide bond and appropriate trimming by ERAP-1 in mice in vivo and is indeed processed into the peptides shown by SEQ ID NOs: 53 and 101.

That is, it was demonstrated that the compound represented by the formula (18), which is one embodiment of the compound of the present invention, is a conjugate wherein two different peptides form a composite via the disulfide bond shown in the formula (1), and is a cancer antigen peptide conjugate vaccine that indeed can induce CTLs and helper peptide reactive cells in vivo.

Experimental Example 22

Evaluation of In Vivo CTL Induction Ability Using HLA-A0201 Transgenic Mouse

The compound represented by the formula (15) synthesized in Example 111 was evaluated for the CTL induction ability by an in vivo CTL induction test using HLA-A0201 transgenic mouse. The compound represented by the formula (15):

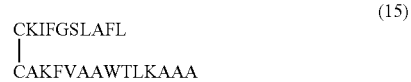

(15)

wherein the bond between C and C is a disulfide bond, is, in particular, a compound of the aforementioned formula (1) wherein cancer antigen peptide A is KIFGSLAFL (SEQ ID NO: 53) and cancer antigen peptide B is AKFVAAWTLKAAA (SEQ ID NO: 101). KIFGSLAFL (SEQ ID NO: 53) is an HLA-A0201-restricted cancer antigen peptide, and AKFVAAWTLKAAA (SEQ ID NO: 101) is an HLA-DR-restricted universal cancer antigen peptide (i.e., helper peptide).

The HLA-A0201 transgenic mouse is as described in Experimental Examples 4 and 19.

Whether the administration of the compound represented by the formula (15) results in the induction of CTLs specific to the peptide of interest (SEQ ID NO: 53) was determined based on the measurement of IFNγ production by re-stimulation, with the peptide (SEQ ID NO: 53), of the splenocytes derived from the above-mentioned mouse administered with a compound represented by the formula (15). Whether the helper peptide (SEQ ID NO: 101) works in the living body was determined by comparison of the numbers of IFNγ-producing cells obtained by re-stimulating the splenocytes derived from the mouse administered with the compound represented by the formula (15) and those derived from the mouse administered with the compound shown by SEQ ID NO: 53 with the peptide (SEQ ID NO: 53).

By a method similar to that in Experimental Example 19, CTL induction test was performed.

Figure 16:
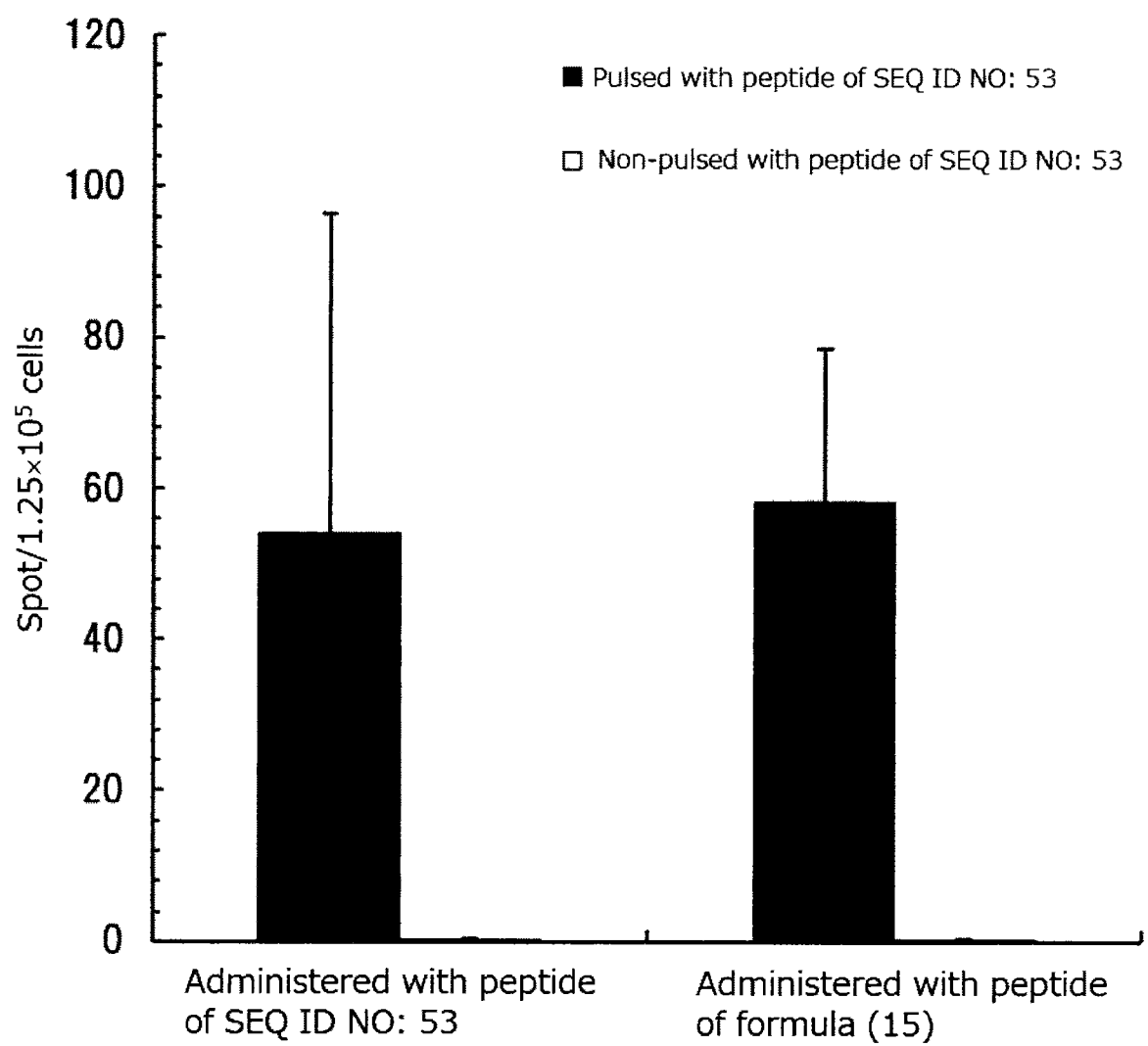
FIG. 16 is a Figure showing the test results of Experimental Example 22 that examined the in vivo CTL induction ability of a compound represented by the formula (15) synthesized in Example 111, by IFNγ ELISPOT assay using HLA-A0201 transgenic mouse.

The results of IFNγ ELISPOT assay using the HLA-A0201 transgenic mouse are shown in FIG. 16. In FIG. 16, the vertical axis shows the number of cells that responded among the plated cells, and the horizontal axis shows the compound or peptide administered to the mouse. In FIG. 16, the black bar shows the result of culture of HLA-A0201 transgenic mouse-derived splenocytes while being pulsed with the peptide shown by SEQ ID NO: 53, and the white bar shows the result of culture without pulsing. That is, the difference in the values of the black bar and the white bar shows the number of peptide-specific CTLs, and that the administration of the peptide shown by SEQ ID NO: 53 or the compound represented by the formula (15) resulted in the induction of CTLs specific to the peptide shown by SEQ ID NO: 53 in vivo in the mouse. In FIG. 16, the value of the white bar is not detected. This means that the splenocytes of the HLA-A0201 transgenic mouse did not react at all in the absence of pulsing with the peptide of interest. As a result of this test, IFNγ production specific to the peptide shown by SEQ ID NO: 53 was detected in the HLA-A0201 transgenic mouse-derived splenocytes. Meanwhile, in FIG. 16, the number of IFNγ-producing cells specific to the peptide shown by SEQ ID NO: 53 induced by the administration of the compound represented by the formula (15) was comparable to that induced by the administration of the peptide shown by SEQ ID NO: 53.

The results of Experimental Example 21 and Experimental Example 22 suggest that, when AKFVAAWTLKAAA (SEQ ID NO: 101) is used as an MHC class II-restricted peptide, an embodiment of the invention using AKFVAAWTLKAAA (SEQ ID NO: 101) as a cancer antigen peptide C is more preferable than that using AKFVAAWTLKAAA (SEQ ID NO: 101) as a cancer antigen peptide B in the aforementioned formula (1).

Experimental Example 23

Evaluation of In Vivo CTL Induction Ability Using HLA-A0201 Transgenic Mouse

The CTL induction ability of the compound represented by the formula (19) synthesized in Example 149 was evaluated by an in vivo CTL induction test using an HLA-A0201 transgenic mouse. KIFGSLAFL (SEQ ID NO: 53) and GLYDGMEHL (SEQ ID NO: 19) contained in the compound represented by the formula (19):

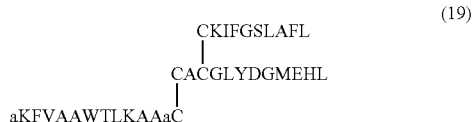

(19)

wherein the bond between C and C is a disulfide bond, are HLA-A0201-restricted cancer antigen peptides, and aKFVAAWTLKAAa (SEQ ID NO: 102) is an HLA-DR-restricted universal cancer antigen peptide (i.e., helper peptide).

The HLA-A0201 transgenic mouse is as described in Experimental Examples 4 and 19.

Whether the administration of the compound represented by the formula (19) results in the induction of CTLs specific to the peptide of interest (SEQ ID NO: 19 or 53) was determined based on the measurement of IFNγ production by re-stimulation, with the peptide (SEQ ID NO: 19 or 53), of the splenocyte derived from the above-mentioned mouse administered with the compound represented by the formula (19). Whether the helper peptide (SEQ ID NO: 102) works in the living body was determined by comparison of the numbers of IFNγ-producing cells obtained by re-stimulating the splenocytes derived from the mouse administered with the compound represented by the formula (19) and those derived from the mouse administered with the compound represented by the formula (4) with the peptide (SEQ ID NO: 19 or 53).

Specifically, the compound represented by the formula (4) was dissolved in dimethyl sulfoxide (DMSO) at 80 mg/mL, further diluted with water for injection to 2 mg/mL, and emulsified by mixing with an equal amount of incomplete Freund's adjuvant (IFA). The emulsified compound was intradermally administered to 2 sites at the base of tail of the mouse at 100 μg/site. In addition, the compound represented by the formula (19) was dissolved in dimethyl sulfoxide (DMSO) at 80 mg/mL, further diluted with water for injection to 3.45 mg/mL, and emulsified by mixing with an equal amount of incomplete Freund's adjuvant (IFA). The emulsified compound was intradermally administered to 2 sites at the base of tail of the mouse at 173 μg/site. The mole number of the compound represented by the formula (4) contained in the dosage amount of the compound represented by the formula (19) per mouse was controlled to be equal to the mole number contained in the dosage amount of the compound represented by the formula (4) per mouse. In addition, the concentration of DMSO contained in each emulsion was also set to the same level. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated at $0.25 \times 10^6$ cells/well, on the blocked ELISPOT plate. Each of the peptides (SEQ ID NOs: 19 and 53) was dissolved in DMSO at 40 mg/mL, and further diluted with RPMI1640 medium containing 10% FBS to 40 μg/mL. The diluted peptide (SEQ ID NO: 19 or 53) was added to the HLA-A0201 transgenic mouse-derived splenocytes at a final concentration of 10 μg/mL. The splenocytes added with the peptide were cultivated for 18 hr at 37° C., 5% $CO_2$, whereby peptide re-stimulation in vitro was performed. After the culture, the supernatant was removed, and the ELISPOT plate was allowed to develop color according to the attached protocol. The number of spots that developed color was measured by ImmunoSpot Analyzer (manufactured by C.T.L.).

Figure 17:
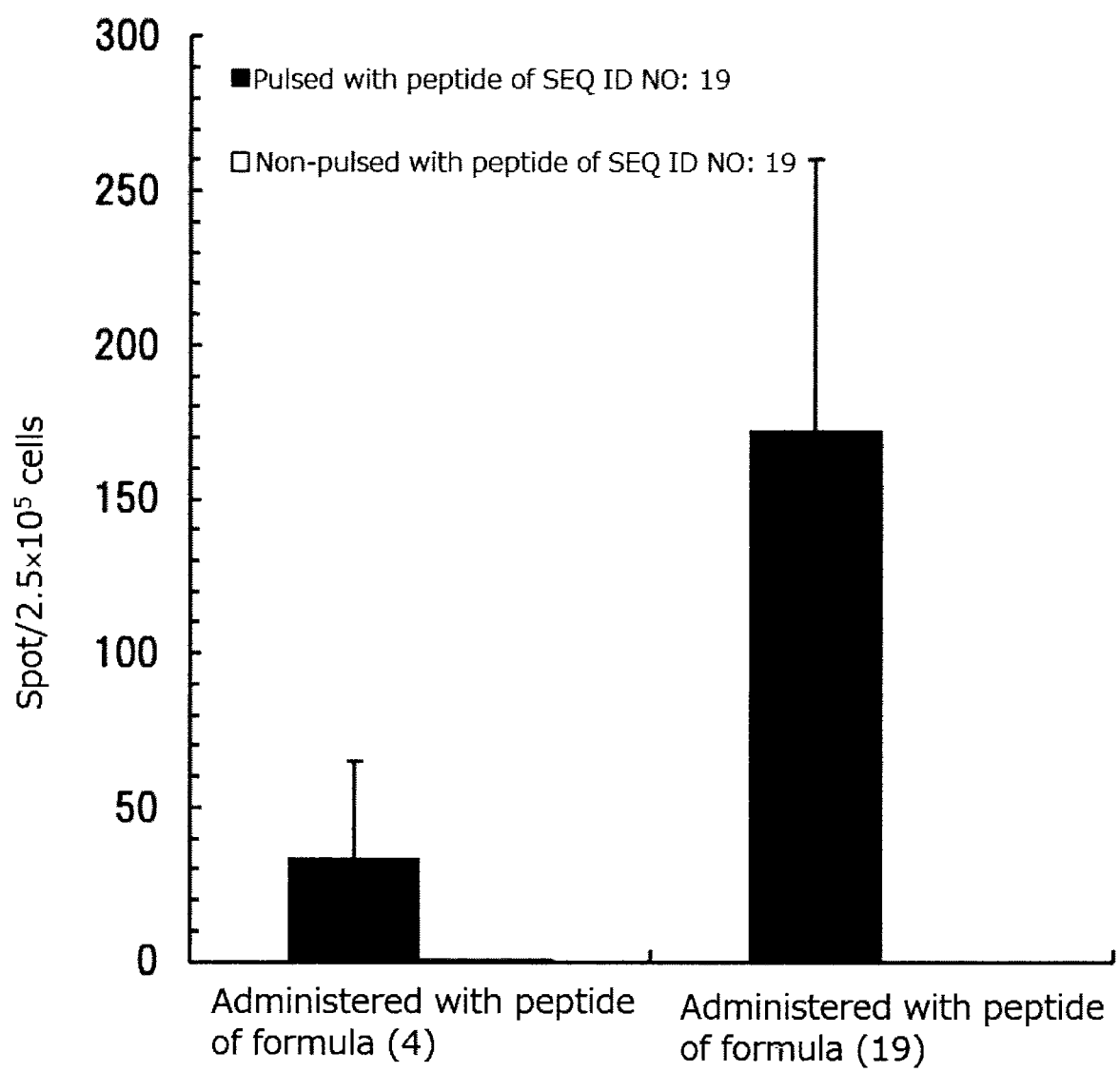
FIG. 17 is a Figure showing the test results of Experimental Example 23 that examined the in vivo CTL induction ability of a compound represented by the formula (19) synthesized in Example 149 in the pulsed or non-pulsed state with peptide of SEQ ID NO: 19, by IFNγ ELISPOT assay using HLA-A0201 transgenic mouse.
Figure 18:
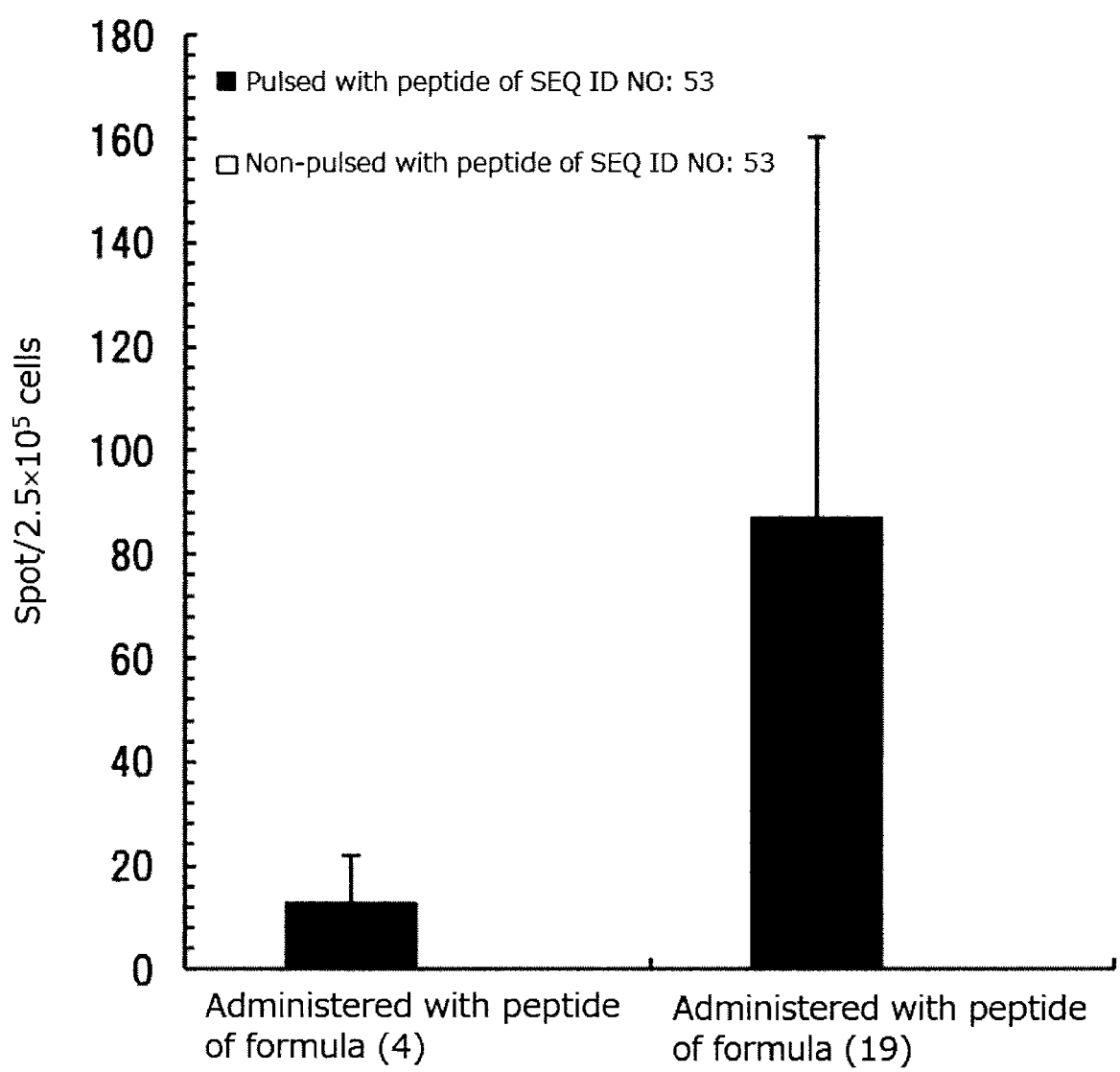
FIG. 18 is a Figure showing the test results of Experimental Example 23 that examined the in vivo CTL induction ability of a compound represented by the formula (19) synthesized in Example 149 in the pulsed or non-pulsed state with peptide of SEQ ID NO: 53, by IFNγ ELISPOT assay using HLA-A0201 transgenic mouse.

The results of IFNγ ELISPOT assay using the HLA-A0201 transgenic mouse are shown in FIG. 17 and FIG. 18. In each Figure, the vertical axis shows the number of cells that responded among the plated cells. In FIG. 17, the black bar and the white bar show the results of culture of HLA-A0201 transgenic mouse-derived splenocytes in the presence and absence of the peptide of interest represented by SEQ ID NO: 19, respectively, and in FIG. 18, the black bar and the white bar show the results of culture of HLA-A0201 transgenic mouse-derived splenocytes in the presence and absence of the peptide of interest represented by SEQ ID NO: 53, respectively. That is, the difference in the values of the black bar and the white bar shows the number of CTLs specific to the peptide of interest induced in the mouse in vivo by the administration of the compound represented by the formula (4) or formula (19).

In each Figure, the value of the white bar is not detected. This means that the splenocytes of respective transgenic mice did not react in the absence of the peptide of interest. As a result of this test, IFNγ production specific to the peptide of interest shown by SEQ ID NO: 19 or 53 was detected in the HLA-A0201 transgenic mouse-derived splenocytes administered with the compound represented by the formula (4) or formula (19). In each Figure, the number of the IFNγ-producing cells specific to the peptide shown by SEQ ID NO: 19 or 53 induced by the administration of the compound represented by the formula (19) was higher than that induced by the administration of the compound represented by the formula (4).

From the above, it was demonstrated that the compound represented by the formula (19) can induce CTLs specific to each of the peptides shown by SEQ ID NOs: 19 and 53. Administration of the compound represented by the formula (19) induced more IFNγ producing cells specific to the peptide shown by SEQ ID NOs: 19 or 53 than administration of the compound represented by the formula (4). It was assumed that induction of cells reactive with the helper peptide shown by SEQ ID NO: 102 produced from the compound represented by the formula (19) enhanced induction of CTLs specific to the peptide shown by SEQ ID NOs: 19 or 53. Accordingly, it was strongly suggested that the compound represented by the formula (19) undergoes cleavage of disulfide bond and appropriate trimming by ERAP-1 in mice in vivo and is indeed processed into the peptides shown by SEQ ID NOs: 19, 53 and 102.

That is, it was demonstrated that the compound represented by the formula (19), which is one embodiment of the compound of the present invention, is a conjugate wherein three different peptides form a composite via the disulfide bond, and is a cancer antigen peptide conjugate vaccine that indeed can induce CTLs and helper peptide reactive cells in vivo.

Comparative Example 1

Evaluation of In Vivo CTL Induction Ability Using HLA-A0201 Transgenic Mouse

The CTL induction abilities of the compound represented by the formula (4) synthesized in Example 29 and the peptides shown by SEQ ID NOs: 231 and 232 synthesized in Reference Examples 2 and 3 were evaluated by an in vivo CTL induction test using an HLA-A0201 transgenic mouse. The compound represented by the formula (4):

(4)

wherein the bond between C and C is a disulfide bond, is as described in Experimental Example 4. The peptides shown by SEQ ID NOs: 231 and 232 are long chain peptides wherein GLYDGMEHL (SEQ ID NO: 19), which is the HLA-A0201-restricted cancer antigen peptide A, and KIFGSLAFL (SEQ ID NO: 53), which is the cancer antigen peptide B, are linked by an amide bond.

The HLA-A0201 transgenic mouse is as described in Experimental Example 4.

Whether the administration of the compound represented by the formula (4) or the peptide shown by SEQ ID NO: 231 or 232 results in the induction of CTLs specific to the peptide of interest (SEQ ID NO: 19 or 53) was determined based on the measurement of IFNγ production by re-stimulation, with the peptide (SEQ ID NO: 19 or 53), of the splenocyte derived from the above-mentioned mouse administered with the compound represented by the formula (4) or the peptide shown by SEQ ID NO: 231 or 232.

Specifically, the compound represented by the formula (4) was dissolved in dimethyl sulfoxide (DMSO) at 80 mg/mL, further diluted with water for injection to 10 mg/mL, and emulsified by mixing with an equal amount of incomplete Freund's adjuvant (IFA). The emulsified compound was intradermally administered to 2 sites at the base of tail of the mouse at 250 μg/site. Also, the peptide shown by SEQ ID NO: 231 or 232 was dissolved in dimethyl sulfoxide (DMSO) at 80 mg/mL, further diluted with water for injection to 9 mg/mL, and emulsified by mixing with an equal amount of incomplete Freund's adjuvant (IFA). The emulsified compound was intradermally administered to 2 sites at the base of tail of the mouse at 225 μg/site. One week later, the mouse was euthanized with $CO_2$ gas, the spleen was isolated, and splenocytes were prepared. IFNγ ELISPOT assay kit was used for the measurement of IFNγ production. On the previous day of splenocyte preparation, an ELISPOT plate was treated with an anti-mouse IFNγ antibody, and blocked with RPMI1640 medium containing 10% FBS the next day. The prepared HLA-A0201 transgenic mouse-derived splenocytes were plated at $0.25 \times 10^6$ cells/well on the blocked ELISPOT plate. Each of the peptides (SEQ ID NOs: 19 and 53) was dissolved in DMSO at 40 mg/mL, and further diluted with RPMI1640 medium containing 10% FBS to 40 μg/mL. The diluted peptide (SEQ ID NO: 19 or 53) was added to the HLA-A0201 transgenic mouse-derived splenocytes at a final concentration of 10 μg/mL. The splenocytes added with the peptide were cultured for 18 hr at 37° C., 5% $CO_2$, whereby peptide re-stimulation in vitro was performed. After the culture, the supernatant was removed, and the ELISPOT plate was allowed to develop color according to the attached protocol. The number of spots that developed color was measured by ImmunoSpot Analyzer (manufactured by C.T.L.).

Figure 19:
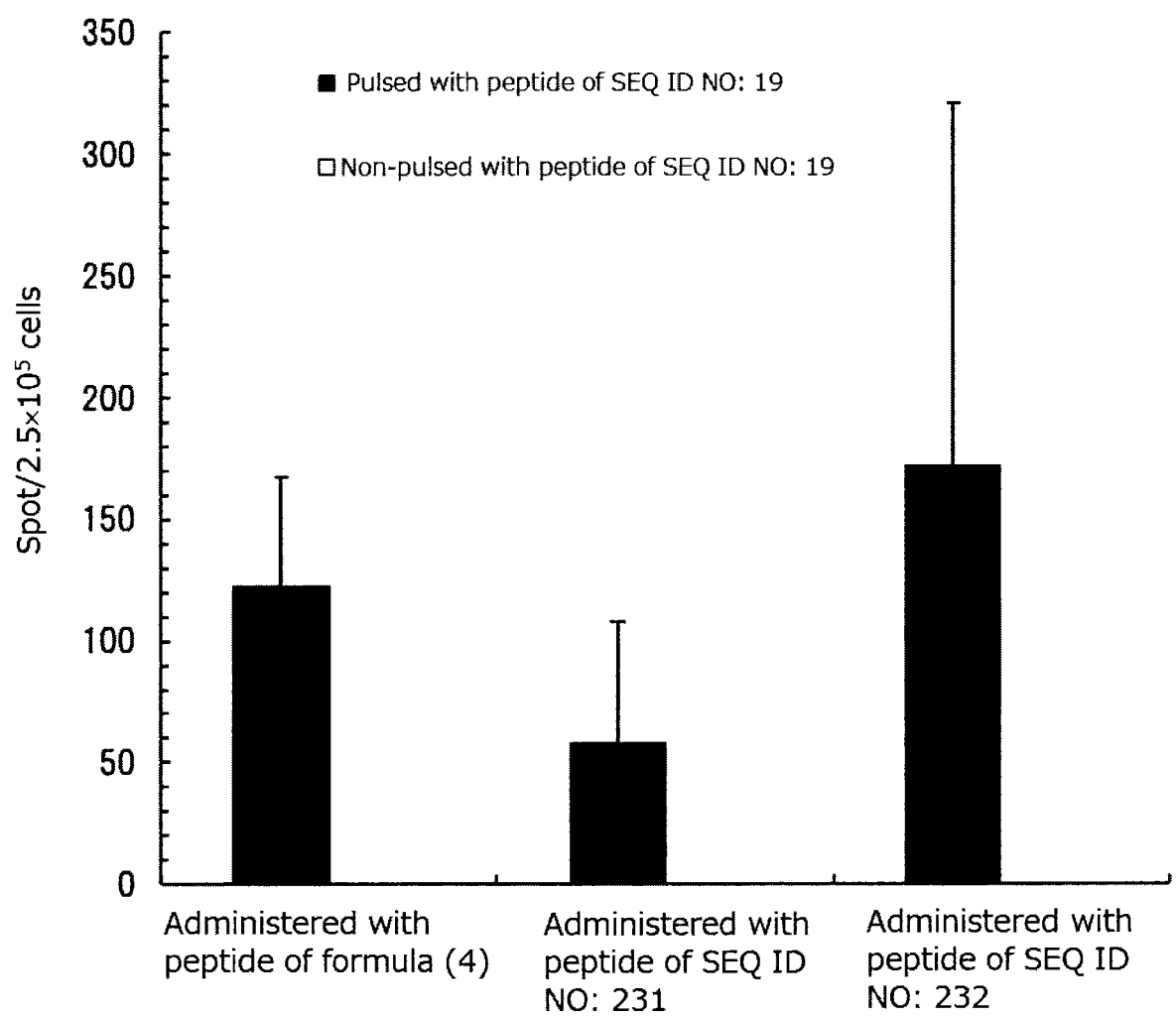
FIG. 19 is a Figure showing the test results of Comparative Example 1 that examined the in vivo CTL induction ability of peptides shown by SEQ ID NOs: 231 and 232 synthesized in Reference Examples 2 and 3 in the pulsed or non-pulsed state with peptide of SEQ ID NO: 19, by IFNγ ELISPOT assay using HLA-A0201 transgenic mouse.
Figure 20:
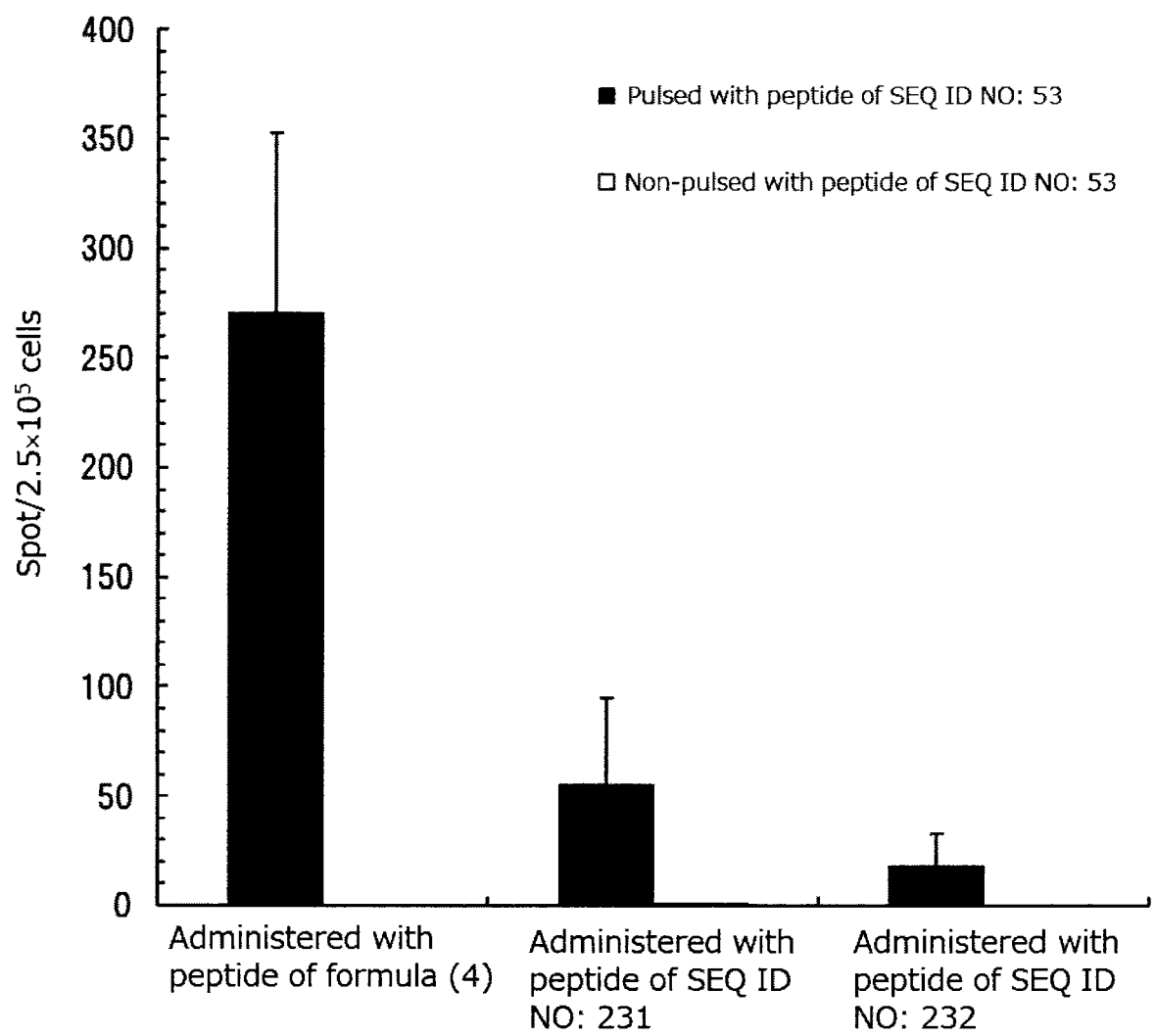
FIG. 20 is a Figure showing the test results of Comparative Example 1 that examined the in vivo CTL induction ability of peptides shown by SEQ ID NOs: 231 and 232 synthesized in Reference Examples 2 and 3 in the pulsed or non-pulsed state with peptide of SEQ ID NO: 53, by IFNγ ELISPOT assay using HLA-A0201 transgenic mouse.

The results of IFNγ ELISPOT assay using the HLA-A0201 transgenic mouse are shown in FIGS. 19 and 20. In each Figure, the vertical axis shows the number of cells that responded among the plated cells. In FIG. 19, the black bar and the white bar show the results of culture of HLA-A0201 transgenic mouse-derived splenocytes in the presence and absence of the peptide of interest represented by SEQ ID NO: 19, respectively, and in FIG. 20, the black bar and the white bar show the results of culture of HLA-A0201 transgenic mouse-derived splenocytes in the presence and absence of the peptide of interest represented by SEQ ID NO: 53, respectively. That is, the difference in the values of the black bar and the white bar show the number of CTLs specific to the peptide of interest induced in the mouse in vivo by the administration of the compound represented by the formula (4) or the peptide shown by SEQ ID NO: 231 or 232.

In each Figure, the value of the white bar is not detected. This means that the splenocytes of respective transgenic mice did not react at all in the absence of the peptide of interest. As a result of this test, IFNγ production specific to the peptide of interest shown by SEQ ID NO: 19 or 53 was detected in the splenocytes derived from the HLA-A0201 transgenic mouse administered with the compound represented by the formula (4). On the other hand, while IFNγ production specific to the peptide of interest shown by SEQ ID NO: 19 was detected in the splenocytes derived from the mouse administered with the peptide shown by SEQ ID NO: 231, the number of cells that responded was small compared to that in the splenocytes derived from mouse administered with the compound represented by the formula (4). IFNγ production specific to the peptide of interest shown by SEQ ID NO: 19 was detected in the splenocytes derived from the mouse administered with the peptide shown by SEQ ID NO: 232. Further, while IFNγ production specific to the peptide of interest shown by SEQ ID NO: 53 was detected in the splenocytes derived from the mouse administered with the peptide shown by SEQ ID NO: 231 or 232, the number of cells that responded was very small compared to that in the splenocytes derived from the mouse administered with the compound represented by the formula (4).

Therefrom, it was demonstrated that the compound represented by the formula (4) of the present invention can efficiently induce both of CTLs specific to the peptide shown by SEQ ID NO: 19 and those specific to the peptide shown by SEQ ID NO: 53. On the other hand, the long chain peptides shown by SEQ ID NOs: 231 and 232 could not efficiently induce both of the CTLs.

Comparative Example 2

Evaluation of In Vivo CTL Induction Ability Using HLA-A0201 Transgenic Mouse

The CTL induction abilities of the compound represented by the formula (4) synthesized in Example 29 and the peptides shown by SEQ ID NOs: 233 and 234 synthesized in Reference Examples 4 and 5 were evaluated by an in vivo CTL induction test using an HLA-A0201 transgenic mouse. The compound represented by the formula (4):

(4)

wherein the bond between C and C is a disulfide bond, is as described in Experimental Example 4. The peptide shown by SEQ ID NO: 233 or 234 is a long chain peptide wherein GLYDGMEHL (SEQ ID NO: 19), which is the HLA-A0201-restricted cancer antigen peptide A, and KIFG-SLAFL (SEQ ID NO: 53), which is the cancer antigen peptide B, are linked by an amide bond via 6 glycines as a peptide spacer.

The HLA-A0201 transgenic mouse is as described in Experimental Example 4.

Whether the administration of the compound represented by the formula (4) or the peptide shown by SEQ ID NO: 233 or 234 results in the induction of CTLs specific to the peptide of interest (SEQ ID NO: 19 or 53) was determined based on the measurement of IFNγ production by re-stimulation, with the peptide (SEQ ID NO: 19 or 53), of the splenocyte derived from the above-mentioned mouse administered with the compound represented by the formula (4) or the peptide shown by SEQ ID NO: 233 or 234.

Specifically, the compound represented by the formula (4) was dissolved in dimethyl sulfoxide (DMSO) at 80 mg/mL, further diluted with water for injection to 10 mg/mL, and emulsified by mixing with an equal amount of incomplete Freund's adjuvant (IFA). The emulsified compound was intradermally administered to 2 sites at the base of tail of the mouse at 250 μg/site. Also, the peptide shown in SEQ ID NOs: 233 or 234 was dissolved in dimethyl sulfoxide (DMSO) at 80 mg/mL, further diluted with water for injection to 10.5 mg/mL, and emulsified by mixing with an equal amount of incomplete Freund's adjuvant (IFA). The emulsified compound was intradermally administered to 2 sites at the base of tail of the mouse at 265 μg/site. Subsequently, similar processes to those in Comparative Example 1 were performed.

Figure 21:
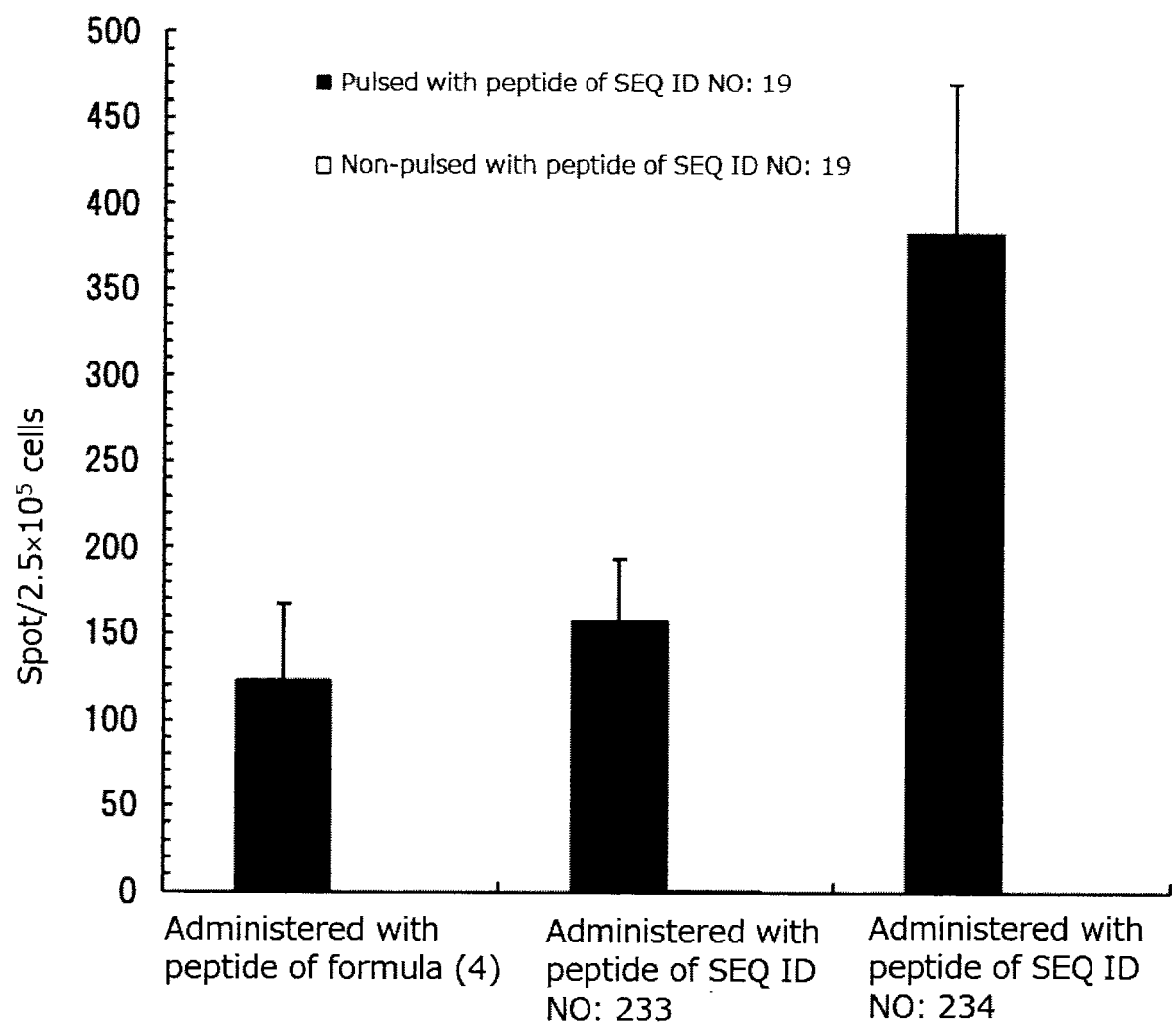
FIG. 21 is a Figure showing the test results of Comparative Example 2 that examined the in vivo CTL induction ability of peptides shown by SEQ ID NOs: 233 and 234 synthesized in Reference Examples 4 and 5 in the pulsed or non-pulsed state with peptide of SEQ ID NO: 19, by IFNγ ELISPOT assay using HLA-A0201 transgenic mouse.
Figure 22:
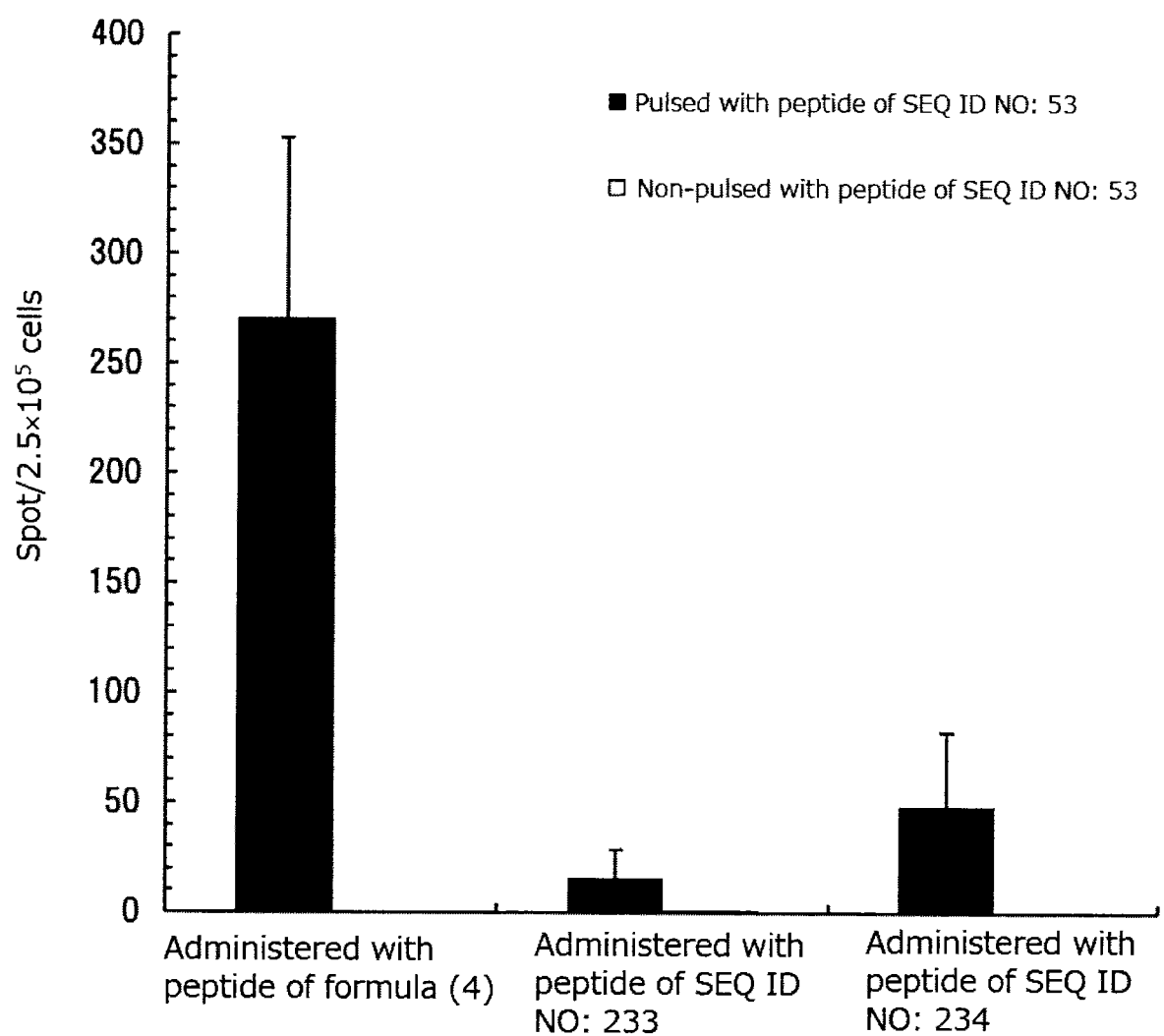
FIG. 22 is a Figure showing the test results of Comparative Example 2 that examined the in vivo CTL induction ability of peptides shown by SEQ ID NOs: 233 and 234 synthesized in Reference Examples 4 and 5 in the pulsed or non-pulsed state with peptide of SEQ ID NO: 53, by IFNγ ELISPOT assay using HLA-A0201 transgenic mouse.

The results of IFNγ ELISPOT assay using the HLA-A0201 transgenic mouse are shown in FIGS. 21 and 22. In each Figure, the vertical axis shows the number of cells that responded among the plated cells. In FIG. 21, the black bar and the white bar show the results of culture of HLA-A0201 transgenic mouse-derived splenocytes in the presence and absence of the peptide of interest represented by SEQ ID NO: 19, respectively, and in FIG. 22, the black bar and the white bar show the results of culture of HLA-A0201 transgenic mouse-derived splenocytes in the presence and absence of the peptide of interest represented by SEQ ID NO: 53, respectively. That is, the difference in the values of the black bar and the white bar shows the number of CTLs specific to the peptide of interest induced in the mouse in vivo by the administration of the compound represented by the formula (4) or the peptide shown by SEQ ID NO: 233 or 234.

In each Figure, the value of the white bar is not detected. This means that the splenocytes of respective transgenic mice did not react at all in the absence of the peptide of interest. As a result of this test, IFNγ production specific to the peptide of interest shown by SEQ ID NOs: 19 or 53 was detected in the splenocytes derived from HLA-A0201 transgenic mouse administered with the compound represented by the formula (4). IFNγ production specific to the peptide of interest shown by SEQ ID NO: 19 was detected in the splenocytes derived from the mouse administered with the peptide shown by SEQ ID NO: 233 or 234. However, while IFNγ production specific to the peptide of interest shown by SEQ ID NO: 53 was detected in the splenocytes derived from the mouse administered with the peptide shown by SEQ ID NO: 233 or 234, the number of cells that responded was very small compared to that in the splenocytes derived from the mouse administered with the compound represented by the formula (4).

Therefrom, it was demonstrated that the compound represented by the formula (4) of the present invention can efficiently induce both CTLs specific to the peptide shown by SEQ ID NO: 19 and those specific to the peptide shown by SEQ ID NO: 53. On the other hand, the long chain peptides shown by SEQ ID NOs: 233 and 234 could not efficiently induce both of the CTLs.

An example of a vaccine containing two antigen peptides is a cocktail vaccine containing the two different peptides in a single preparation. When a cocktail vaccine is produced, physical properties of cancer antigen peptides to be mixed would become one problem. As shown in Table 35 and Table 42, production of a cocktail of two antigen peptides requires processing of two peptides having different solubilities, namely, different physical properties, into one preparation. In contrast, the conjugate of the present invention is a compound wherein two antigen peptides are bonded via a disulfide bond, and shows a single solubility, namely, a single physical property. This means that the conjugate of the present invention has a single physical property and also responds to the two antigen peptides as shown in Experimental Example 4. In this regard, it has been shown that the conjugate of the present invention is a compound capable of inducing responses to the two antigen peptides without the need to consider factors such as interaction between the two antigen peptides, unlike cocktail vaccines.

Reference Example 10

By a method similar to that in Example 1, peptides consisting of the amino acid sequences of SEQ ID NOs: 239-242 were synthesized. Table 57 shows the result of mass spectrometry of each synthesized peptide.

The compounds of SEQ ID NOs: 239-242 were not the compounds of the present invention and were therefore described as Reference Examples.

TABLE 57

| Ref. Ex. No. | amino acid sequence | SEQ ID NO: | mass spectrometry: LC-ESI/ MS m/z | mass spectrometry: Calculated |
|---|---|---|---|---|
| 10 | KIFGSLAFLaKFVAA WTLKAAa | 239 | 466.2 $[M + 5H]^{5+}$ | 466.0 |
| 11 | KIFGSLAFLGGGGGG aKFVAAWTLKAAa | 240 | 667.8 $[M + 4H]^{4+}$ | 667.8 |
| 12 | aKFVAAWTLKAAaKI FGSLAFL | 241 | 775.7 $[M + 3H]^{3+}$ | 776.0 |
| 13 | aKFVAAWTLKAAaGG GGGGKIFGSLAFL | 242 | 667.5 $[M + 4H]^{4+}$ | 667.8 |

The peptides represented by SEQ ID NOs: 241 and 242 shown in Table 57 were synthesized by referring to the non-patent document, Cancer Science January 2012, Vol. 103, no. 1, 150-153.

Experimental Example 24

Evaluation of In Vivo CTL Induction Ability Using HLA-A2401 Transgenic Mouse after Filter Filtration A homodimer of SEQ ID NO: 4 formed via a disulfide bond and the compound represented by the formula (5) are dissolved in water for injection at 3-10 mg/mL. The pharmacological activity of each compound is evaluated using an HLA-A2402 transgenic mouse (C57BL/6CrHLA-A2402/K$^b$) with the CTL induction activity as an index. For administration to the HLA-A2402 transgenic mouse, the compound is dissolved in water for injection, sterilized by filtration using a low protein-binding filter (a membrane filter of the grade aiming at sterilization for injection) and mixed with incomplete Freund's adjuvant to give an emulsion.

The emulsified compound is intradermally administered to the base of tail of the HLA-A2402 transgenic mouse. One week later, the mouse is euthanized with $CO_2$ gas, the spleen or inguinal lymph node is isolated, and splenocytes or lymph node cells are prepared. IFNγ ELISPOT assay kit is used for the measurement of IFNγ production. On the previous day of cell preparation, an ELISPOT plate is treated with an anti-mouse IFNγ antibody, and blocked with RPMI1640 medium containing 10% FBS the next day. The prepared cells derived from the mouse are plated on the blocked ELISPOT plate. A peptide (SEQ ID NO: 4) is dissolved in DMSO at 40 mg/mL, and further diluted with RPMI1640 medium containing 10% FBS to 40 μg/mL. The diluted peptide (SEQ ID NO: 4) is added to the HLA-A2402 transgenic mouse-derived splenocytes or lymph node cells at a final concentration of 10 μg/mL. The cells added with the peptide are cultivated for 16-20 hr at 37° C., 5% $CO_2$, whereby peptide re-stimulation in vitro is performed. After the culture, the supernatant is removed, and the ELISPOT plate is allowed to develop color according to the attached protocol. The number of spots that developed color is measured by ImmunoSpot Analyzer (manufactured by C.T.L.).

INDUSTRIAL APPLICABILITY

The compound of the present invention is useful as an active ingredient of a cancer vaccine that efficiently induces CTLs and is easy to produce. The present application is based on the patent application No. 2013-074441 (filing date: Mar. 29, 2013) and the patent application No. 2013-158386 (filing date: Jul. 31, 2013) filed in Japan, and the whole contents of the patent applications are herein incorporated.

The invention claimed is:

1. A compound represented by formula (1):

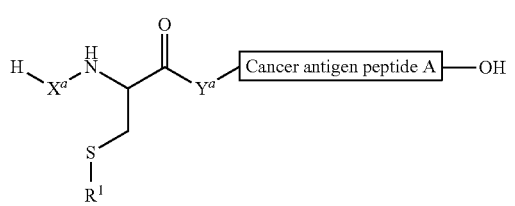

or a pharmaceutically acceptable salt thereof,
wherein $X^a$ and $Y^a$ are each independently a single bond,
cancer antigen peptide A is an MHC class I-restricted cancer antigen peptide consisting of an amino acid sequence selected from the group consisting of

EADPTGHYS, (SEQ ID NO: 1)

SLFRAVITK, (SEQ ID NO: 2)

NYKHCFPEI, (SEQ ID NO: 3)

EVYDGREHSA, (SEQ ID NO: 4)

REPVTKAEML, (SEQ ID NO: 5)

DPARYEFLW, (SEQ ID NO: 6)

SAFPTTINF, (SEQ ID NO: 7)

SAYGEPRKL, (SEQ ID NO: 8)

SAYGEPRKL, (SEQ ID NO: 9)

KMVELVHFL, (SEQ ID NO: 10)

EYLQLVFGI, (SEQ ID NO: 11)

-continued

EADPIGHLY, (SEQ ID NO: 12)

FLWGPRALV, (SEQ ID NO: 13)

TFPDLESEF, (SEQ ID NO: 14)

MEVDPIGHLY, (SEQ ID NO: 15)

WQYFFPVIF, (SEQ ID NO: 16)

GVYDGREHTV, (SEQ ID NO: 17)

MVKISGGPR, (SEQ ID NO: 18)

GLYDGMEHL, (SEQ ID NO: 19)

VRIGHLYIL, (SEQ ID NO: 20)

AARAVFLAL, (SEQ ID NO: 21)

FLWGPRAYA, (SEQ ID NO: 22)

YRPRPRRY, (SEQ ID NO: 23)

YYWPRPRRY, (SEQ ID NO: 24)

MTQGQHFLQKV, (SEQ ID NO: 25)

SLLMWITQCFL, (SEQ ID NO: 26)

QLSLLMWIT, (SEQ ID NO: 27)

ASGPGGGAPR, (SEQ ID NO: 28)

AAGIGILTV, (SEQ ID NO: 29)

AEEAAGIGIL, (SEQ ID NO: 30)

TILLGIFFL, (SEQ ID NO: 31)

KTWGQYWQV, (SEQ ID NO: 32)

LIYRRRLMK, (SEQ ID NO: 33)

VYFFLPDHL, (SEQ ID NO: 34)

SNDGPTLI, (SEQ ID NO: 35)

VSHSFPHPLY, (SEQ ID NO: 36)

FLTPKKLQCV, (SEQ ID NO: 37)

HSTNGVTRIY, (SEQ ID NO: 38)

-continued

KCDICTDEY, (SEQ ID NO: 39)

YMDGTMSQV, (SEQ ID NO: 40)

AFLPWHRLF, (SEQ ID NO: 41)

SEIWRDIDF, (SEQ ID NO: 42)

VLQELNVTV, (SEQ ID NO: 43)

MSLQRQFLR, (SEQ ID NO: 44)

SVYDFFVWL, (SEQ ID NO: 45)

LLGPGRPYR, (SEQ ID NO: 46)

ANDPIFVVL, (SEQ ID NO: 47)

AFLRHAAL, (SEQ ID NO: 48)

MLMAQEALAFL, (SEQ ID NO: 49)

YLSGANLNL, (SEQ ID NO: 50)

HLFGYSWYK, (SEQ ID NO: 51)

KFHRVIKDF, (SEQ ID NO: 52)

KIFGSLAFL, (SEQ ID NO: 53)

VLRENTSPK, (SEQ ID NO: 54)

ILAKFLHWL, (SEQ ID NO: 55)

SPRWWPTCL, (SEQ ID NO: 56)

STAPPAHGV, (SEQ ID NO: 57)

STAPPVHNV, (SEQ ID NO: 58)

LLNQLQVNL, (SEQ ID NO: 59)

LYVDSLFFL, (SEQ ID NO: 60)

AYGLDFYIL, (SEQ ID NO: 61)

VPYGSFKHV, (SEQ ID NO: 62)

LPRWPPPQL, (SEQ ID NO: 63)

EYRGFTQDF, (SEQ ID NO: 64)

DYSARWNEI, (SEQ ID NO: 65)

-continued

AYIDFEMKI, (SEQ ID NO: 66)

GVALQTMKQ, (SEQ ID NO: 67)

SYLDSGIHF, (SEQ ID NO: 68)

FPSDSWCYF, (SEQ ID NO: 69)

ACDPHSGHFV, (SEQ ID NO: 70)

ETVSEQSNV, (SEQ ID NO: 71)

VLPDVFIRC, (SEQ ID NO: 72)

HLSTAFARV, (SEQ ID NO: 73)

SLFEGIDIY, (SEQ ID NO: 74)

YSWMDISCWI, (SEQ ID NO: 75)

EEKLIVVLF, (SEQ ID NO: 76)

SELFRSGLDY, (SEQ ID NO: 77)

FRSGLDSYV, (SEQ ID NO: 78)

EAFIQPITR, (SEQ ID NO: 79)

KINKNPKYK, (SEQ ID NO: 80)

SPSSNRIRNT, (SEQ ID NO: 81)

RVAALARDA, (SEQ ID NO: 82)

AYACNTSTL, (SEQ ID NO: 83)

KWFPSCQFLL, (SEQ ID NO: 84)

GYDQIMPKK, (SEQ ID NO: 85)

VYGFVRACL (SEQ ID NO: 87)
and

SLLMWITQC, (SEQ ID NO: 88)

or a peptide comprising an amino acid sequence which is one of SEQ ID NOs: 1-85, 87 and 88 where an amino acid is deleted from, substituted in, or added to the original amino acid sequence, and having a CTL induction activity, an amino group of an N-terminal amino acid of the cancer antigen peptide A binds to $Y^a$ in the formula (I), and a carbonyl group of a C-terminal amino acid of the cancer antigen peptide A binds to a hydroxyl group in the formula (1), and $R^1$ is a group represented by formula (2):

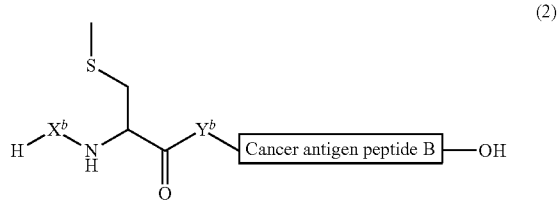

wherein $X^b$ and $Y^b$ are each independently a single bond, cancer antigen peptide B is different from the cancer antigen peptide A, and is an MHC class I-restricted cancer antigen peptide consisting of an amino acid sequence selected from the group consisting of

EADPTGHYS, (SEQ ID NO: 1)

SLFRAVITK, (SEQ ID NO: 2)

NYKHCFPEI, (SEQ ID NO: 3)

EVYDGREHSA, (SEQ ID NO: 4)

REPVTKAEML, (SEQ ID NO: 5)

DPARYEFLW, (SEQ ID NO: 6)

SAFPTTINF, (SEQ ID NO: 7)

SAYGEPRKL, (SEQ ID NO: 8)

SAYGEPRKL, (SEQ ID NO: 9)

KMVELVHFL, (SEQ ID NO: 10)

EYLQLVFGI, (SEQ ID NO: 11)

EADPIGHLY, (SEQ ID NO: 12)

FLWGPRALV, (SEQ ID NO: 13)

TFPDLESEF, (SEQ ID NO: 14)

MEVDPIGHLY, (SEQ ID NO: 15)

WQYFFPVIF, (SEQ ID NO: 16)

GVYDGREHTV, (SEQ ID NO: 17)

MVKISGGPR, (SEQ ID NO: 18)

GLYDGMEHL, (SEQ ID NO: 19)

-continued

VRIGHLYIL, (SEQ ID NO: 20)

AARAVFLAL, (SEQ ID NO: 21)

FLWGPRAYA, (SEQ ID NO: 22)

YRPRPRRY, (SEQ ID NO: 23)

YYWPRPRRY, (SEQ ID NO: 24)

MTQGQHFLQKV, (SEQ ID NO: 25)

SLLMWITQCFL, (SEQ ID NO: 26)

QLSLLMWIT, (SEQ ID NO: 27)

ASGPGGGAPR, (SEQ ID NO: 28)

AAGIGILTV, (SEQ ID NO: 29)

AEEAAGIGIL, (SEQ ID NO: 30)

TILLGIFFL, (SEQ ID NO: 31)

KTWGQYWQV, (SEQ ID NO: 32)

LIYRRRLMK, (SEQ ID NO: 33)

VYFFLPDHL, (SEQ ID NO: 34)

SNDGPTLI, (SEQ ID NO: 35)

VSHSFPHPLY, (SEQ ID NO: 36)

FLTPKKLQCV, (SEQ ID NO: 37)

HSTNGVTRIY, (SEQ ID NO: 38)

KCDICTDEY, (SEQ ID NO: 39)

YMDGTMSQV, (SEQ ID NO: 40)

AFLPWHRLF, (SEQ ID NO: 41)

SEIWRDIDF, (SEQ ID NO: 42)

VLQELNVTV, (SEQ ID NO: 43)

MSLQRQFLR, (SEQ ID NO: 44)

SVYDFFVWL, (SEQ ID NO: 45)

LLGPGRPYR, (SEQ ID NO: 46)

-continued

ANDPIFVVL, (SEQ ID NO: 47)

AFLRHAAL, (SEQ ID NO: 48)

MLMAQEALAFL, (SEQ ID NO: 49)

YLSGANLNL, (SEQ ID NO: 50)

HLFGYSWYK, (SEQ ID NO: 51)

KFHRVIKDF, (SEQ ID NO: 52)

KIFGSLAFL, (SEQ ID NO: 53)

VLRENTSPK, (SEQ ID NO: 54)

ILAKFLHWL, (SEQ ID NO: 55)

SPRWWPTCL, (SEQ ID NO: 56)

STAPPAHGV, (SEQ ID NO: 57)

STAPPVHNV, (SEQ ID NO: 58)

LLNQLQVNL, (SEQ ID NO: 59)

LYVDSLFFL, (SEQ ID NO: 60)

AYGLDFYIL, (SEQ ID NO: 61)

VPYGSFKHV, (SEQ ID NO: 62)

LPRWPPPQL, (SEQ ID NO: 63)

EYRGFTQDF, (SEQ ID NO: 64)

DYSARWNEI, (SEQ ID NO: 65)

AYIDFEMKI, (SEQ ID NO: 66)

GVALQTMKQ, (SEQ ID NO: 67)

SYLDSGIHF, (SEQ ID NO: 68)

FPSDSWCYF, (SEQ ID NO: 69)

ACDPHSGHFV, (SEQ ID NO: 70)

ETVSEQSNV, (SEQ ID NO: 71)

VLPDVFIRC, (SEQ ID NO: 72)

HLSTAFARV, (SEQ ID NO: 73)

-continued

SLFEGIDIY, (SEQ ID NO: 74)

YSWMDISCWI, (SEQ ID NO: 75)

EEKLIVVLF, (SEQ ID NO: 76)

SELFRSGLDY, (SEQ ID NO: 77)

FRSGLDSYV, (SEQ ID NO: 78)

EAFIQPITR, (SEQ ID NO: 79)

KINKNPKYK, (SEQ ID NO: 80)

SPSSNRIRNT, (SEQ ID NO: 81)

RVAALARDA, (SEQ ID NO: 82)

AYACNTSTL, (SEQ ID NO: 83)

KWFPSCQFLL, (SEQ ID NO: 84)

GYDQIMPKK, (SEQ ID NO: 85)

VYGFVRACL (SEQ ID NO: 87)
and

SLLMWITQC, (SEQ ID NO: 88)

or a peptide comprising an amino acid sequence which is one of SEQ ID NOs: 1-85, 87 and 88 where an amino acid is deleted from, substituted in, or added to the original amino acid sequence, and having a CTL induction activity, or an MHC class II-restricted cancer antigen peptide consisting of an amino acid sequence selected from the group consisting of AKFVAAWTLKAAA (SEQ ID NO: 101)
and aKFVAAWTLKAAa, (SEQ ID NO: 102)

or a peptide comprising an amino acid sequence which is one of SEQ ID NOs: 101 and 102 where an amino acid is deleted from, substituted in, or added to the original amino acid sequence, and having a helper T cell induction activity, an amino group of an N-terminal amino acid of the cancer antigen peptide B binds to $Y^b$ in the formula (2), and a carbonyl group of a C-terminal amino acid of the cancer antigen peptide B binds to a hydroxyl group in the formula (2), and a thioether group in the formula (2) binds to a thioether group in the formula (1).

2. The compound of claim 1, wherein the cancer antigen peptide A is a peptide consisting of an amino acid sequence selected from the following amino acid sequences:

GLYDGMEHL, (SEQ ID NO: 19)

VLQELNVTV (SEQ ID NO: 43)
and

KIFGSLAFL, (SEQ ID NO: 53)

or a pharmaceutically acceptable salt thereof.

3. The compound of claim 1, wherein the cancer antigen peptide B is a peptide consisting of an amino acid sequence selected from the following amino acid sequences:

GLYDGMEHL, (SEQ ID NO: 19)

VLQELNVTV (SEQ ID NO: 43)
and

KIFGSLAFL, (SEQ ID NO: 53)

or a pharmaceutically acceptable salt thereof.

4. The compound of claim 1, wherein the cancer antigen peptide B is a peptide consisting of an amino acid sequence selected from the following amino acid sequences:

AKFVAAWTLKAAA (SEQ ID NO: 101)
and aKFVAAWTLKAAa, (SEQ ID NO: 102)

or a pharmaceutically acceptable salt thereof.

5. A pharmaceutical composition comprising the compound of claim 1, or a pharmaceutically acceptable salt thereof, and a pharmaceutically acceptable carrier.

6. The compound of claim 1, wherein the cancer antigen peptide A is a peptide consisting of an amino acid sequence which is one of SEQ ID NOs: 1-85, 87 and 88, the cancer antigen peptide B is a peptide consisting of an amino acid sequence which is one of SEQ ID NOs: 1-85, 87 and 88, or a pharmaceutically acceptable salt thereof.

7. The compound of claim 1, wherein the cancer antigen peptide A is a peptide consisting of an amino acid sequence which is one of SEQ ID NOs: 3, 11, 13, 19, 26, 27, 29, 33, 40, 41, 43, 50, 53, 66, 83, 84, 85, 87 and 88, or a pharmaceutically acceptable salt thereof.

8. The compound of claim 1, wherein the cancer antigen peptide B is a peptide consisting of an amino acid sequence which is one of SEQ ID NOs: 3, 11, 13, 19, 26, 27, 29, 33, 40, 41, 43, 50, 53, 66, 83, 84, 85, 87 and 88, or a pharmaceutically acceptable salt thereof.

* * * * *